US010865414B2

(12) United States Patent
Freier

(10) Patent No.: US 10,865,414 B2
(45) Date of Patent: Dec. 15, 2020

(54) MODULATORS OF DNM2 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 16/248,549

(22) Filed: Jan. 15, 2019

(65) Prior Publication Data

US 2019/0241896 A1    Aug. 8, 2019

Related U.S. Application Data

(60) Provisional application No. 62/617,411, filed on Jan. 15, 2018.

(51) Int. Cl.
*C12N 15/113*    (2010.01)

(52) U.S. Cl.
CPC ........ *C12N 15/1137* (2013.01); *C12N 15/113* (2013.01); *C12N 2310/11* (2013.01); *C12N 2310/14* (2013.01); *C12N 2310/315* (2013.01); *C12N 2310/3231* (2013.01); *C12N 2310/334* (2013.01); *C12N 2310/3341* (2013.01); *C12N 2310/341* (2013.01); *C12N 2310/346* (2013.01); *C12N 2310/351* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |

(Continued)

FOREIGN PATENT DOCUMENTS

| WO | WO 2016/170162 | 10/1916 |
|---|---|---|
| WO | 2012058268 A2 | 5/2012 |

(Continued)

OTHER PUBLICATIONS

International Search Report and Written Opinion for International Application No. PCT/US2019/013689, dated May 2, 2019.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

(Continued)

*Primary Examiner* — Tracy Vivlemore

(74) *Attorney, Agent, or Firm* — Lathrop GPM LLP; James H. Velema, Esq.; Laura A. Labeots, Esq.

(57) ABSTRACT

The present embodiments provide methods, compounds, and compositions useful for inhibiting DNM2 expression, which may be useful for treating, preventing, or ameliorating a disease associated with DNM2.

49 Claims, No Drawings

Specification includes a Sequence Listing.

(56) References Cited

U.S. PATENT DOCUMENTS

| | | |
|---|---|---|
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2013/0130378 A1 | 5/2013 | Manoharan et al. |
| 2014/0107330 A1 | 4/2014 | Freier et al. |
| 2014/0161894 A1* | 6/2014 | MacLachlan ........ C12N 15/113 424/498 |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |

FOREIGN PATENT DOCUMENTS

| | | | |
|---|---|---|---|
| WO | WO 2015/055859 | 4/2015 | |
| WO | WO-2015107425 A2 * | 7/2015 | ........... C12N 15/113 |

OTHER PUBLICATIONS

Cowling et al., "Reducing dynamin 2 expression rescues X-linked centronuclear myopathy" J. Clin. Invest. (2014) 124: 1350-1363.

(56) References Cited

OTHER PUBLICATIONS

Crooke et al., "Basic Principles of Antisense Therapeutics" Antisense Research and Application (1998) Chapter 1:1-50.
Crooke, ST., et al., "Antisense Drug Technology" Second Edition, CRC Press (2008) Chapters 1-28.
Durieux et al., "Dynamin 2 and human diseases" J Mol Med (2010) 88: 339-350.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Gautschi et al., "Activity of a novel bcl-2/bcl-xLbispecific antisense oligonucleotide against tumors of diverse histologic origins" J. Natl. Cancer Inst. (2001) 93:463-471.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals " J Med Chem (2009) 52:10-13.
Tasfaout et al. "Antisense oligonucleotide-mediated Dnm2 knockdown prevents and reverts myotubular myopathy in mice" Nat. Commun. (2017) 8: 15661.
Woolf et al., "Specificity of antisense oligonucleotides in vivo" PNAS (1992) 89: 7305-7309.

* cited by examiner

MODULATORS OF DNM2 EXPRESSION

SEQUENCE LISTING

The present application is being filed along with a Sequence Listing in electronic format. The Sequence Listing is provided as a file entitled BIOL0322USSEQ_ST25.txt created Jan. 14, 2019 which is 784 kb in size. The information in the electronic format of the sequence listing is incorporated herein by reference in its entirety.

FIELD

The present embodiments provide methods, compounds, and compositions useful for inhibiting DNM2 expression, which can be useful for treating, preventing, or ameliorating a disease associated with DNM2.

BACKGROUND

Dynamin 2 (DNM2) is a large GTPase that is involved in membrane trafficking and microtubule dynamics (See, e.g., Durieux et al. *J Mol Med,* 88, 339 (2010)). Mutations in DNM2 are associated with several diseases, including centronuclear myopathy (CNM) and Charcot-Marie-Tooth disease. DNM2 is also associated with Duchenne's Muscular Dystrophy (See, e.g., WO 2015/055859 and WO 2016/170162). CNM and CNM-like myopathy are also associated with mutations in MTM1, BIN1, RYR1, TTN, CCDC78, and MTMR14

SUMMARY

Certain embodiments provided herein are directed to potent and tolerable compounds and compositions useful for inhibiting DNM2 expression, which can be useful for treating, preventing, ameliorating, or slowing progression of diseases, such as centronuclear myopathy (CNM), Charcot-Marie-Tooth disease (CMT), and Duchenne's Muscular Dystrophy (DMD). Certain embodiments provided herein comprise modified oligonucleotides complementary to a DNM2 nucleic acid that potently reduce DNM2 expression in animals.

One object of the present invention is a compound comprising a modified oligonucleotide 8 to 50 linked nucleosides in length having a nucleobase sequence comprising at least 8 contiguous nucleobases of any of the nucleobase sequences of SEQ ID NOs: 7-3134. Another object of the present invention is a compound comprising a modified oligonucleotide 9 to 50 linked nucleosides in length having a nucleobase sequence comprising at least 9 contiguous nucleobases of any of the nucleobase sequences of SEQ ID NOs: 7-3134. Another object of the present invention is a compound comprising a modified oligonucleotide 10 to 50 linked nucleosides in length having a nucleobase sequence comprising at least 10 contiguous nucleobases of any of the nucleobase sequences of SEQ ID NOs: 7-3134. Another object of the present invention is a compound comprising a modified oligonucleotide 11 to 50 linked nucleosides in length having a nucleobase sequence comprising at least 11 contiguous nucleobases of any of the nucleobase sequences of SEQ ID NOs: 7-3134. Another object of the present invention is a compound comprising a modified oligonucleotide 12 to 50 linked nucleosides in length having a nucleobase sequence comprising at least 12, at least 13, at least 14, or at least 15 contiguous nucleobases of any of the nucleobase sequences of SEQ ID NOs: 7-3134. Another object of the present invention is a compound comprising a modified oligonucleotide 16 to 50 linked nucleosides in length having a nucleobase sequence comprising the nucleobase sequence of any of SEQ ID NOs: 7-3134. Another object of the present invention is a compound comprising a modified oligonucleotide having a nucleobase sequence consisting of any one of SEQ ID NOs: 7-3134. Another object of the present invention is a compound comprising a modified oligonucleotide 8 to 50 linked nucleosides in length complementary within nucleobases 3,404-44,737; 83,573-87,287; 87,359-90,915; 90,968-97,263; 97,378-104,979; 81,061-81,199; or 116,048-116,903 of SEQ ID NO: 1, wherein said modified oligonucleotide is at least 85%, 90%, 95%, or 100% complementary to SEQ ID NO: 1. Another object of the present invention is a compound comprising a modified oligonucleotide 8 to 50 linked nucleosides in length having a nucleobase sequence comprising a portion of at least 8 contiguous nucleobases 100% complementary to an equal length portion of nucleobases 3,404-44,737; 83,573-87,287; 87,359-90,915; 90,968-97,263; 97,378-104,979; 81,061-81,199; or 116,048-116,903 of SEQ ID NO: 1, wherein the nucleobase sequence of the modified oligonucleotide is at least 85%, 90%, 95%, or 100% complementary to SEQ ID NO: 1. Another object of the present invention is a compound comprising a modified oligonucleotide 8 to 50 linked nucleosides in length complementary within nucleobases 83,573-87,287 or 87,359-90,915 of SEQ ID NO: 1, wherein said modified oligonucleotide is at least 85%, 90%, 95%, or 100% complementary to SEQ ID NO: 1. Another object of the present invention is a compound comprising a modified oligonucleotide complementary to intron 1 of a human DNM2 pre-mRNA. Another object of the present invention is a compound comprising a modified oligonucleotide complementary to intron 11 of a human DNM2 pre-mRNA. Another object of the present invention is a compound comprising a modified oligonucleotide complementary to intron 12 of a human DNM2 pre-mRNA. Another object of the present invention is a compound comprising a modified oligonucleotide complementary to intron 13 of a human DNM2 pre-mRNA. Another object of the present invention is a compound comprising a modified oligonucleotide complementary to intron 14 of a human DNM2 pre-mRNA. Another object of the present invention is a compound comprising a modified oligonucleotide complementary to exon 10 of a human DNM2 pre-mRNA or human DNM2 mRNA. Another object of the present invention is a compound comprising a modified oligonucleotide complementary to the 3'-UTR of a human DNM2 pre-mRNA or human DNM2 mRNA. Another object of the present invention is a compound comprising a modified oligonucleotide 16 to 50 linked nucleosides in length having a nucleobase sequence comprising any of SEQ ID NOs: 2879, 3056, 2123, 2189, 2453, 2160, or 2232. Another object of the present invention is a compound comprising a modified oligonucleotide having a nucleobase sequence consisting of any one of SEQ ID NOs: 2879, 3056, 2123, 2189, 2453, 2160, or 2232. Another object of the present invention is a compound comprising a modified oligonucleotide having a nucleobase sequence comprising SEQ ID NO: 2879.

Another object of the present invention is a compound comprising a modified oligonucleotide 16 to 50 linked nucleosides in length having a nucleobase sequence comprising any of SEQ ID NOs: 2879, 3056, 2123, 2189, 2453, 2160, or 2232, wherein the modified oligonucleotide comprises:

a gap segment consisting of 8-12 linked 2'-deoxynucleosides;
a 5' wing segment consisting of 1-7 linked nucleosides; and
a 3' wing segment consisting of 1-7 linked nucleosides;
wherein the gap segment is positioned between the 5' wing segment and the 3' wing segment and wherein each terminal wing nucleoside comprises a modified sugar.

Another object of the present invention is a compound comprising a modified oligonucleotide 16 linked nucleosides in length having a nucleobase sequence consisting of the sequence recited in SEQ ID NO: 2879, 3056, 2123, 2189, 2453, 2160, or 2232, wherein the modified oligonucleotide comprises
a gap segment consisting of 10 linked 2'-deoxynucleosides;
a 5' wing segment consisting of 3 linked nucleosides; and
a 3' wing segment consisting of 3 linked nucleosides;
wherein the gap segment is positioned between the 5' wing segment and the 3' wing segment; wherein each nucleoside of each wing segment comprises a cEt sugar moiety; wherein each internucleoside linkage is a phosphorothioate linkage; and wherein each cytosine is a 5-methylcytosine.

In one embodiment, the oligonucleotide is at least 80%, 85%, 90%, 95% or 100% complementary to any of SEQ ID NO: 1, 2, 3, or 3135. In one embodiment, the modified oligonucleotide comprises at least one modified internucleoside linkage. In one embodiment, the at least one modified internucleoside linkage is a phosphorothioate internucleoside linkage. In one embodiment, the modified oligonucleotide comprises at least one bicyclic sugar. In one embodiment, the at least one bicyclic sugar is selected from the group consisting of LNA, ENA, and cEt. In one embodiment, the at least one bicyclic sugar moiety is a cEt sugar moiety.

In one embodiment, the modified oligonucleotide comprises at least one 5-methylcytosine. In one embodiment, the modified oligonucleotide comprises:

a gap segment consisting of linked 2'-deoxynucleosides;
a 5' wing segment consisting of linked nucleosides; and
a 3' wing segment consisting of linked nucleosides;
wherein the gap segment is positioned immediately adjacent to and between the 5' wing segment and the 3' wing segment and wherein each nucleoside of each wing segment comprises a modified sugar moiety.

In one embodiment, the compound is single-stranded. In one embodiment, the compound is double-stranded.

In one embodiment, the compound comprises at least one unmodified ribosyl sugar moiety. In one embodiment, the compound comprises at least one unmodified 2'-deoxyribosyl sugar moiety.

In one embodiment, the modified oligonucleotide consists of 10 to 30 linked nucleosides. In one embodiment, the modified oligonucleotide consists of 12 to 30 linked nucleosides. In one embodiment, the modified oligonucleotide consists of 15 to 30 linked nucleosides. In one embodiment, the modified oligonucleotide consists of 16 to 20 linked nucleosides.

Another object of the present invention is a compound comprising a modified oligonucleotide according to the following formula: Gks Tks Tks Tds Ads Tds Tds Ads Tds Ads Gds Gds Gds mCks Tks Tk; wherein,
A=an adenine,
mC=a 5-methylcytosine
G=a guanine,
T=a thymine,
k=a cEt sugar moiety,
d=a 2'-deoxyribosyl sugar moiety, and
s=a phosphorothioate internucleoside linkage.

In one embodiment, the compound of the invention comprises a conjugate group. In one embodiment, the compound of the invention consists of the modified oligonucleotide and the conjugate group.

Another object of the present invention is a compound according to the following formula:

[SEQ ID NO: 2879]

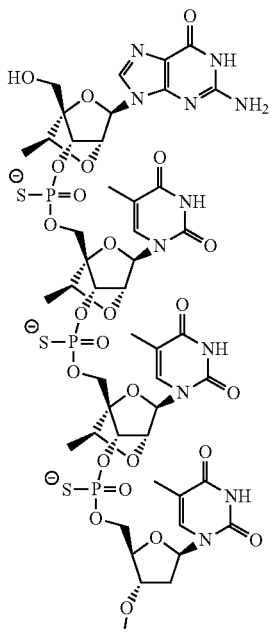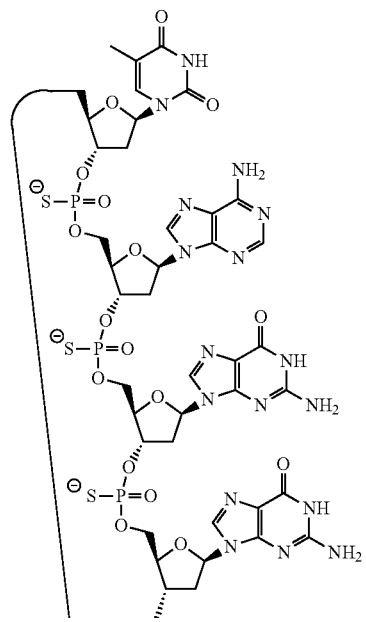

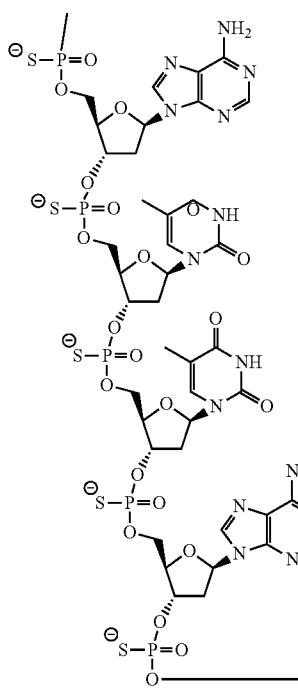
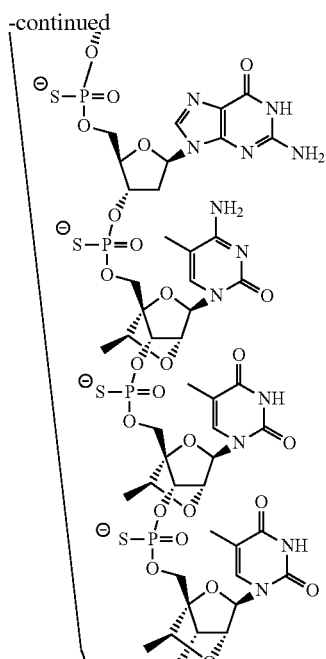

or a salt thereof.

In one embodiment, the compound consists of the modified oligonucleotide.

The present invention further relates to a compound consisting of a pharmaceutically acceptable salt form of any one of the compounds described herein. In one embodiment, the pharmaceutically acceptable salt is a sodium salt. In one embodiment, the pharmaceutically acceptable salt is a potassium salt.

The present invention also relates to a pharmaceutical composition comprising a compound as described herein and at least one pharmaceutically acceptable carrier or diluent.

The present invention further relates to a chirally enriched population of the compounds described herein, wherein the population is enriched for modified oligonucleotides comprising at least one particular phosphorothioate internucleoside linkage having a particular stereochemical configuration. In one embodiment, the population is enriched for modified oligonucleotides comprising at least one particular phosphorothioate internucleoside linkage having the (Sp) configuration. In one embodiment, the population is enriched for modified oligonucleotides comprising at least one particular phosphorothioate internucleoside linkage having the (Rp) configuration. In one embodiment, the population is enriched for modified oligonucleotides having a particular, independently selected stereochemical configuration at each phosphorothioate internucleoside linkage. In one embodiment, the population is enriched for modified oligonucleotides having the (Sp) configuration at each phosphorothioate internucleoside linkage. In one embodiment, the population is enriched for modified oligonucleotides having the (Rp) configuration at each phosphorothioate internucleoside linkage. In one embodiment, the population is enriched for modified oligonucleotides having the (Rp) configuration at one particular phosphorothioate internucleoside linkage and the (Sp) configuration at each of the remaining phosphorothioate internucleoside linkages. In one embodiment, the population is enriched for modified oligonucleotides having at least 3 contiguous phosphorothioate internucleoside linkages in the Sp, Sp, and Rp configurations, in the 5' to 3' direction. In one embodiment, all of the phosphorothioate internucleoside linkages of the modified oligonucleotide are stereorandom.

The present invention further relates to a pharmaceutical composition comprising the population of compounds described herein and at least one pharmaceutically acceptable diluent or carrier.

The present invention further relates to a compound described herein, a pharmaceutical composition comprising said compound and at least one pharmaceutically acceptable carrier or diluent, or a pharmaceutical composition comprising the population of compounds described herein and at least one pharmaceutically acceptable carrier or diluent, for use in therapy.

The present invention further relates to a compound described herein, a pharmaceutical composition comprising said compound and at least one pharmaceutically acceptable carrier or diluent, or a pharmaceutical composition comprising the population of compounds described herein and at least one pharmaceutically acceptable carrier or diluent, for use in treating, preventing, or ameliorating centronuclear myopathy, Duchenne Muscular Dystrophy, or Charcot-Marie Tooth disease.

The present invention also relates to a method of treating, preventing, or ameliorating a disease associated with DNM2 in an individual comprising administering to the individual a compound or composition described herein, thereby treating, preventing, or ameliorating the disease.

The present invention also relates to a method of treating, preventing, or ameliorating a disease associated with DNM2 in an individual comprising administering to the individual a compound comprising a modified oligonucleotide 100% complementary to an exon 10, an intron, or the 3'-UTR of a DNM2 nucleic acid transcript, thereby treating, preventing, or ameliorating the disease.

In one embodiment, the disease is centronuclear myopathy, Duchenne Muscular Dystrophy, or Charcot-Marie Tooth disease. In one embodiment, the compound is single-stranded. In one embodiment, the DNM2 nucleic acid transcript is a pre-mRNA. In one embodiment, the disease is X-linked myotubular myopathy, autosomal recessive centronuclear myopathy, or autosomal dominant centronuclear myopathy. In one embodiment, the individual has at least one mutation in at least one gene selected from among MTM1, BIN1, and DNM2. In one embodiment, the administering increases body weight or muscle strength.

The present invention further relates to a method of inhibiting expression of DNM2 in a cell comprising contacting the cell with a single-stranded compound comprising a modified oligonucleotide 100% complementary to exon 10, an intron, or the 3'-UTR of a DNM2 nucleic acid transcript, thereby inhibiting expression of DNM2 in the cell. In one embodiment, the method is an in vitro method. In one embodiment, the cell is in the muscle of an individual. In one embodiment, the individual has, or is at risk of having, a centronuclear myopathy, Duchenne Muscular Dystrophy, or Charcot-Marie Tooth disease. The present invention further relates to a method of increasing body weight or muscle strength in an individual having, or at risk of having, a disease associated with DNM2 comprising administering a single-stranded compound comprising a modified oligonucleotide 100% complementary to a DNM2 nucleic acid transcript to the individual, thereby increasing body weight or muscle strength in the individual. In one embodiment, the individual has, or is at risk of having, centronuclear myopathy, Duchenne Muscular Dystrophy, or Charcot-Marie Tooth disease.

In one embodiment, the compound is a compound as described herein. In one embodiment, the compound is a member of the chirally enriched population described herein. In one embodiment, the compound is a component of the pharmaceutical composition described herein.

In one embodiment, the compound is administered to the individual via subcutaneous injection. In one embodiment, the compound is administered to the individual via intramuscular injection. In one embodiment, the compound is administered to the individual via intravenous injection.

The present invention further relates to the use of a single-stranded compound comprising a modified oligonucleotide 100% complementary to exon 10, intron 1, intron 11, intron, 12, intron 13, intron 14, or the 3'-UTR of a DNM2 nucleic acid transcript for treating, preventing, or ameliorating a disease associated with DNM2. In one embodiment, the disease is centronuclear myopathy, Duchenne Muscular Dystrophy, or Charcot-Marie Tooth disease.

The present invention further relates to the use of the compound described herein or the composition described herein for treating, preventing, or ameliorating a disease associated with DNM2.

The present invention further relates to the use of the compound described herein or the composition described herein in the manufacture of a medicament for treating, preventing, or ameliorating a disease associated with DNM2.

In one embodiment, the disease is centronuclear myopathy, Duchenne Muscular Dystrophy, or Charcot-Marie Tooth disease. In one embodiment, the disease is X-linked myotubular myopathy, autosomal recessive centronuclear myopathy, or autosomal dominant centronuclear myopathy. In one embodiment, the disease is associated with a mutation in at least one gene selected from among MTM1, BIN1, and DNM2.

The present invention further relates to the use of the compound described herein or the composition described herein in the preparation of a medicament for treating, preventing, or ameliorating a disease associated with DNM2. In one embodiment, the disease is centronuclear myopathy, Duchenne Muscular Dystrophy, or Charcot-Marie Tooth disease. In one embodiment, the disease is X-linked myotubular myopathy, autosomal recessive centronuclear myopathy, or autosomal dominant centronuclear myopathy. In one embodiment, the disease is associated with a mutation in at least one gene selected from among MTM1, BIN1, and DNM2.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase.

As used herein, "2'-deoxynucleoside" means a nucleoside comprising 2'-H(H) ribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" or "2-modified nucleoside" means a nucleoside comprising a 2'-substituted or 2'-modified sugar moiety. As used herein, "2'-substituted" or "2-modified" in reference to a furanosyl sugar moiety means a sugar moiety comprising at least one 2'-substituent group other than H or OH.

As used herein, "administration" or "administering" refers to routes of introducing a compound or composition provided herein to an individual to perform its intended function. An example of a route of administration that can be used includes, but is not limited to, administration by inhalation.

As used herein, "administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

As used herein, "animal" refers to a human or non-human animal, including, but not limited to, mice, rats, rabbits, dogs, cats, pigs, and non-human primates, including, but not limited to, monkeys and chimpanzees.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is at least partially complementary to a target nucleic acid.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cEt" or "constrained ethyl" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-CH($CH_3$)—O-2', and the methyl group of the bridge is in the S configuration. A cEt bicyclic sugar moiety is in the β-D configuration.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more sterorandom chiral centers. In certain embodiments, the molecules are modified oligonucleotides. In certain embodiments, the molecules are compounds comprising modified oligonucleotides.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases are nucleobase pairs that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

As used herein, "efficacy" means the ability to produce a desired effect.

As used herein "DNM2" means any Dynamin 2 nucleic acid or protein. "DNM2 nucleic acid" means any nucleic acid encoding DNM2. For example, in certain embodiments, a DNM2 nucleic acid includes a DNA chromosomal region encoding DNM2, an RNA transcribed from DNA encoding DNM2 (e.g., a pre-mRNA transcript), and an mRNA transcript encoding DNM2.

As used herein, "expression" includes all the functions by which a gene's coded information is converted into structures present and operating in a cell. Such structures include, but are not limited to, the products of transcription and translation. Methods for measuring expression levels (such as a transcription level or a translation level) are well-known in the field and include, but are not limited to, RT-PCR, RT-qPCR, Northern Blot, hybridization techniques such as, for example, use of microarrays, and combinations thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like, immunohistochemistry, Multiplex methods (Luminex), western blot, enzyme-linked immunosorbent assay (ELISA), sandwich ELISA, multiplex ELISA, electrochemiluminescence (ECL) (Elecsys®, Roche Diagnostics), enzyme-linked fluorescent assay (ELFA) (such as VIDAS®, Biomerieux), fluorescent-linked immunosorbent assay (FLISA), enzyme immunoassay (ETA), radioimmunoassay (RIA), flow cytometry (FACS), surface plasmon resonance (SPR), biolayer interferometry (BLI), immunochromatographic assay (ICA) (such as NEXUS IB10, Sphingotech) and mass spectrometry-based approaches.

As used herein, "gapmer" means an oligonucleotide, such as an antisense oligonucleotide, comprising an internal segment having a plurality of nucleosides that support RNase H cleavage positioned between external segments, each having one or more nucleosides, wherein the nucleosides comprising the internal segment are chemically distinct from the immediately adjacent nucleoside or nucleosides comprising the external segments. The internal segment may be referred to as the "gap" or "gap segment" and the external segments may be referred to as the "wings" or "wing segments".

As used herein, "hybridization" means the pairing or annealing of complementary oligonucleotides and/or nucleic acids. While not limited to a particular mechanism, the most common mechanism of hybridization involves hydrogen bonding, which may be, for example, Watson-Crick, Hoogsteen or reversed Hoogsteen hydrogen bonding, between complementary nucleobases.

As used herein, "individual" means a human or non-human animal selected for treatment or therapy.

As used herein, "inhibiting the expression or activity" refers to a reduction or blockade of the expression or activity relative to the expression or activity in an untreated or control sample and does not necessarily indicate a total elimination of expression or activity. In one embodiment, inhibiting the expression or activity refers to a reduction or blockade of the expression or activity relative to the expression or activity in an untreated or control sample of at least about 40%, at least about 50%, at least about 60%, at least about 70%, at least about 80%, or at least about 90%. In one embodiment, inhibiting the expression or activity refers to a reduction or blockade of the expression or activity relative to the expression or activity in an untreated or control sample of at least 50%, 55%, 60%, 65%, 70%, 75%, 80%, 85%, 90%, 91%, 92%, 93%, 94%, 95%, 96%, 97%, 98% or 99%.

As used herein, the term "about" preceding a figure means plus or less 10% of the value of said figure.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage. Modified internucleoside linkages include linkages that comprise abasic nucleosides. As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar" or "non-bicyclic modified sugar moiety" means a modified sugar moiety that comprises a modification, such as a substituent, that does not form a bridge between two atoms of the sugar to form a second ring.

As used herein, "linked nucleosides" are nucleosides that are connected in a continuous sequence (i.e. no additional nucleosides are present between those that are linked).

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulating" refers to changing or adjusting a feature in a cell, tissue, organ or organism. For example, modulating DNM2 expression can mean to increase or decrease the level of an DNM2 RNA and/or a DNM2 protein in a cell, tissue, organ or organism. A "modulator" effects the change in the cell, tissue, organ or organism. For example, a compound that modulates DNM2 expression can be a modulator that decreases the amount of a DNM2 RNA and/or a DNM2 protein in a cell, tissue, organ or organism.

As used herein, "MOE" means methoxyethyl. "2'-MOE" or "2'-O-methoxyethyl" means a 2'-OCH$_2$CH$_2$OCH$_3$ group in place of the 2'-OH group of a ribosyl ring.

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), and guanine (G). As used herein, a modified nucleobase is a group of atoms capable of pairing with at least one unmodified nucleobase. A universal base is a nucleobase that can pair with any one of the five unmodified nucleobases.

As used herein, "nucleobase sequence" means the order of contiguous nucleobases in a nucleic acid or oligonucleotide independent of any sugar or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, liquids, powders, or suspensions that can be aerosolized or otherwise dispersed for inhalation by a subject. In certain embodiments, a pharmaceutically acceptable carrier or diluent is sterile water; sterile saline; or sterile buffer solution. In one embodiment, the pharmaceutically acceptable carrier or diluent does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and an aqueous solution.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, "standard cell assay" means any of the assays described in Examples 1-9, and reasonable variations thereof.

As used herein, "standard in vivo experiment" means the procedure described in Example 10 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) moiety, as found in DNA (an "unmodified DNA sugar moiety"). As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid," "target RNA," "target RNA transcript" and "nucleic acid target" mean a nucleic acid that an antisense compound is designed to affect.

As used herein, "target region" means a portion of a target nucleic acid to which an antisense compound is designed to hybridize.

As used herein, "terminal group" means a chemical group or group of atoms that is covalently linked to a terminus of an oligonucleotide.

As used herein, "terminal wing nucleoside" means a nucleoside that is located at the terminus of a wing segment of a gapmer. Any wing segment that comprises or consists of at least two nucleosides has two termini: one that is immediately adjacent to the gap segment; and one that is at the end opposite the gap segment. Thus, any wing segment that comprises or consists of at least two nucleosides has two terminal nucleosides, one at each terminus.

As used herein, "therapeutically effective amount" means an amount of a compound, pharmaceutical agent, or composition that provides a therapeutic benefit to an individual. In certain embodiments, the therapeutically effective amount refers to the level or amount of a compound that treats or ameliorates symptoms of a disease associated with DNM2. In certain embodiments, the therapeutically effective amount may be administered prior to the onset of the disease associated with DNM2 or may be administered after initiation of the disease associated with DNM2.

As used herein, "treat" refers to administering a compound or pharmaceutical composition to an animal in order to effect an alteration or improvement of a disease, disorder, or condition in the animal. In one embodiment, a subject is successfully treated if, after receiving a therapeutically effective amount of a compound according to the present invention, the subject shows observable and/or measurable reduction or relief to some extent of one or more of the symptoms associated with the specific disease associated with DNM2, such as but not limited to reduced morbidity and mortality, improvement in quality of life issues, increased body weight, preservation or increase in muscle strength, decrease in time taken to rise from the floor, decrease in nine-meter walking time, decrease in time taken to climb four stairs, increased ability to lift weight, increased distance of a 6 minute walk, increased leg function grade, improved pulmonary function and/or cardiac function. Parameters for assessing successful treatment and improvement in the disease are readily measurable by routine procedures familiar to a physician.

Certain Embodiments

Certain embodiments provide methods, compounds and compositions for inhibiting DNM2 expression.

Certain embodiments provide methods, compounds and compositions for inhibiting DNM2 expression as compared to an untreated or control sample. In one embodiment, said inhibition is an inhibition of DNM2 expression of at least about 40%, at least about 50%, at least about 60%, at least about 70%, at least about 80%, or at least about 90%. In one embodiment, inhibiting the expression or activity refers to a reduction or blockade of the expression or activity relative to the expression or activity in an untreated or control sample of at least 50%, 55%, 60%, 65%, 70%, 75%, 80%, 85%, 90%, 91%, 92%, 93%, 94%, 95%, 96%, 97%, 98% or 99% as compared to an untreated or control sample.

Certain embodiments provide compounds comprising or consisting of oligonucleotides complementary to a DNM2 nucleic acid. In certain embodiments, the DNM2 nucleic acid has the sequence set forth in RefSeq or GenBank Accession No. NC_000019.10 truncated from nucleosides 10715001 to 10835000 (disclosed herein as SEQ ID NO: 1), NM_004945.3 (disclosed herein as SEQ ID NO: 2), NM_001005361.2 (disclosed herein as SEQ ID NO: 3), or NM_001005360.2 (disclosed herein as SEQ ID NO: 3135). In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 8 to 50 linked nucleosides in length and having a nucleobase sequence comprising at least 8 contiguous nucleobases of any of the nucleobase sequences of SEQ ID NOs: 7-3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134.

As used herein, the term "identity" refers to the subunit sequence identity between two nucleic acid molecules, such as, two DNA molecules or two RNA molecules. When a subunit position in both of the two molecules is occupied by the same monomeric subunit; e.g., if a position in each of two DNA molecules is occupied by adenine, then they are identical (or homologous) at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Thus, the term "homologous" or "identical", when used in a relationship between the sequences of two or more nucleic acid molecules, refers to the degree of sequence relatedness between nucleic acid molecules, as determined by the number of matches between strings of two or more nucleotide residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 8 to 50 linked nucleosides in length and having a nucleobase sequence comprising at least 8 contiguous nucleobases of any of the nucleobase sequences of SEQ ID NOs: 2879, 3056, 2123, 2189, 2453, 2160, or 2232 or at least 8 contiguous nucleobases of a sequence having at least 70% identity with any of the nucleobase sequences of SEQ ID NOs: 2879, 3056, 2123, 2189, 2453, 2160, or 2232. In certain embodiments, the nucleobase sequence of the modified oligonucleotide comprises or consists of SEQ ID NO: 2879 or a sequence having at least 70% identity with SEQ ID NO: 2879. In certain embodiments, the nucleobase sequence of the modified oligonucleotide comprises or consists of SEQ ID NO: 3056 or a sequence having at least 70% identity with SEQ ID NO: 3056. In certain embodiments, the nucleobase sequence of the modified oligonucleotide comprises or consists of SEQ ID NO: 2123 or a sequence having at least 70% identity with SEQ ID NO: 2123. In certain embodiments, the nucleobase sequence of the modified oligonucleotide comprises or consists of SEQ ID NO: 2189 or a sequence having at least 70% identity with SEQ ID NO: 2189. In certain embodiments, the nucleobase sequence of the modified oligonucleotide comprises or consists of SEQ ID NO: 2453 or a sequence having at least 70% identity with SEQ ID NO: 2453. In certain embodiments, the nucleobase sequence of the modified oligonucleotide comprises or consists of SEQ ID NO: 2160 or a sequence having at least 70% identity with SEQ ID NO: 2160. In certain embodiments, the nucleobase sequence of the modified oligonucleotide comprises or consists of SEQ ID NO: 2232 or a sequence having at least 70% identity with SEQ ID NO: 2232. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length. In certain embodiments, the modified oligonucleotide has a nucleobase sequence comprising at least 12 contiguous nucleobases of any of SEQ ID Numbers from 7 to 3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134.

Certain embodiments provide a compound comprising a modified oligonucleotide 10 to 50 linked nucleosides in length and having a nucleobase sequence comprising at least 10 contiguous nucleobases of any of the nucleobase sequences of SEQ ID NOs: 7-3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 11 to 50 linked nucleosides in length and having a nucleobase sequence comprising at least 11 contiguous nucleobases of any of the nucleobase sequences of SEQ ID NOs: 7-3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134. In certain embodiments, the compound is an antisense compound or oligomeric compound. In certain embodiments, the compound is single-stranded. In certain embodiments, the compound is double-stranded. In certain embodiments, the modified oligonucleotide is 11 to 30 linked nucleosides in length.

Certain embodiments provide a compound comprising a modified oligonucleotide 12 to 50 linked nucleosides in length and having a nucleobase sequence comprising at least 12 contiguous nucleobases of any of the nucleobase sequences of SEQ ID NOs: 7-3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

In certain embodiments, the compound comprises a modified oligonucleotide 16 linked nucleosides in length. In certain embodiments, the compound is an antisense compound or oligomeric compound.

Certain embodiments provide a compound comprising a modified oligonucleotide 16 to 50 linked nucleosides in length and having a nucleobase sequence comprising the nucleobase sequence of any one of SEQ ID NOs: 7-3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

Certain embodiments provide a compound comprising a modified oligonucleotide consisting of the nucleobase sequence of any one of SEQ ID NOs: 7-3134 or of any sequence having at least about 70% identity with any of the nucleobase sequences of SEQ ID NOs: 7-3134, such as, for example, at least about 75%, 80%, 85%, 90%, 91%, 92%, 93%, 94%, 95%, 96%, 97%, 98%, 99% identity or more with any of the nucleobase sequences of SEQ ID NOs: 7-3134. In certain embodiments, the compound is an antisense compound or oligomeric compound. In certain embodiments, the compound is single-stranded. In certain embodiments, the compound is double-stranded.

In certain embodiments, compounds comprise or consist of modified oligonucleotides complementary to an intron of a DNM2 nucleic acid transcript. In certain embodiments, modified oligonucleotides are complementary to intron 1, intron 2, intron 3, intron 4, intron 5, intron 6, intron 7, intron 8, intron 9, intron 9-10a, intron 10, intron 10a-11, intron 11, intron 12, intron 13, intron 14, intron 15, intron 16, intron 17, intron 18, intron 19, or intron 19-20a of a DNM2 nucleic acid transcript. In certain such embodiments, modified oligonucleotides are complementary to a sequence within nucleotides 3404-44,737; 44,812-57,478; 57,629-60,702; 60,907-62,117; 62,217-67,959; 68,121-71,563; 71,707-78,719; 78,856-80,371; 80,440-81,060; 80,440-82,379; 81,200-83,485; 82,519-83,485; 83,573-87,287; 87,359-90,915; 90,968-97,263; 97,378-104,979; 105,090-108,787; 108,990-110,056; 110,222-114,035; 114,269-115,126; 115,379-115,977; or 115,379-115,980 of SEQ ID NO: 1. In certain embodiments, compounds comprise or consist of oligonucleotides having at least an 8, 9, 10, 11, 12, 13, 14, 15, or 16 contiguous nucleobase portion complementary to an equal length portion of intron 1, intron 2, intron 3, intron 4, intron 5, intron 6, intron 7, intron 8, intron 9, intron 9-10a, intron 10, intron 10a-11, intron 11, intron 12, intron 13, intron 14, intron 15, intron 16, intron 17, intron 18, intron 19, or intron 19-20a of a DNM2 nucleic acid transcript. In certain embodiments, such oligonucleotides have at least an 8, 9, 10, 11, 12, 13, 14, 15, or 16 contiguous nucleobase portion complementary to an equal length portion within nucleotides 3404-44,737; 44,812-57,478; 57,629-60,702; 60,907-62,117; 62,217-67,959; 68,121-71,563; 71,707-78,719; 78,856-80,371; 80,440-81,060; 80,440-82,379; 81,200-

83,485; 82,519-83,485; 83,573-87,287; 87,359-90,915; 90,968-97,263; 97,378-104,979; 105,090-108,787; 108,990-110,056; 110,222-114,035; 114,269-115,126; 115,379-115,977; or 115,379-115,980 of SEQ ID NO: 1. In certain embodiments, these compounds are antisense compounds or oligomeric compounds. Compounds comprising a modified oligonucleotide complementary to certain introns of a DNM2 nucleic acid transcript, e.g., intron 1, intron 11, intron 12, intron 13, or intron 14 of a DNM2 pre-mRNA, are generally especially potent and tolerable. Thus, such certain introns can be considered hot spot regions for targeting a DNM2 nucleic acid transcript.

In certain embodiments, compounds comprise or consist of modified oligonucleotides complementary to intron 1, intron 11, intron 12, intron 13, intron 14, exon 10, or the 3'-UTR of a DNM2 nucleic acid transcript. In certain embodiments, modified oligonucleotides are complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, compounds comprise or consist of oligonucleotides having at least an 8, 9, 10, 11, 12, 13, 14, 15, or 16 contiguous nucleobase portion complementary to an equal length portion of intron 1, intron 11, intron 12, intron 13, intron 14, exon 10, or the 3'-UTR of a DNM2 nucleic acid transcript. In certain embodiments, such oligonucleotides have at least an 8, 9, 10, 11, 12, 13, 14, 15, or 16 contiguous nucleobase portion complementary to an equal length portion within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, these compounds are antisense compounds or oligomeric compounds.

In certain embodiments, a compound comprises a modified oligonucleotide 8 to 50 linked nucleosides in length and having at least an 8, 9, 10, 11, 12, 13, 14, 15, or 16 contiguous nucleobase portion complementary to an equal length portion within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the modified oligonucleotide is 10 to 30 linked nucleosides in length.

In certain embodiments, compounds comprise or consist of modified oligonucleotides complementary to intron 1, intron 11, intron 12, intron 13, or intron 14 of a DNM2 nucleic acid transcript. In certain embodiments, modified oligonucleotides are complementary to a sequence within nucleotides 3,404-44,737; 83,573-87,287; 87,359-90,915; 90,968-97,263; or 97,378-104,979 of SEQ ID NO: 1. In certain embodiments, compounds comprise or consist of oligonucleotides having at least an 8, 9, 10, 11, 12, 13, 14, 15, or 16 contiguous nucleobase portion complementary to an equal length portion of intron 1, intron 11, intron 12, intron 13, or intron 14 of a DNM2 nucleic acid transcript. In certain embodiments, such oligonucleotides have at least an 8, 9, 10, 11, 12, 13, 14, 15, or 16 contiguous nucleobase portion complementary to an equal length portion within nucleotides 3,404-44,737; 83,573-87,287; 87,359-90,915; 90,968-97,263; or 97,378-104,979 of SEQ ID NO: 1. In certain embodiments, these compounds are antisense compounds or oligomeric compounds.

In certain embodiments, a compound comprises a modified oligonucleotide 8 to 50 linked nucleosides in length and having at least an 8, 9, 10, 11, 12, 13, 14, 15, or 16 contiguous nucleobase portion complementary to an equal length portion within nucleotides 3,404-44,737; 83,573-87,287; 87,359-90,915; 90,968-97,263; or 97,378-104,979 of SEQ ID NO: 1. In certain embodiments, the modified oligonucleotide is 10 to 30 linked nucleosides in length.

In certain embodiments, a compound comprises a modified oligonucleotide 8 to 50 linked nucleosides in length and complementary within nucleotides 89,722-89,737; 83,880-83,895; 90,081-90,096; 94,450-94,465; 11,960-11,975; 93,322-93,337; or 97,855-97,870 of SEQ ID NO: 1. In certain embodiments, the modified oligonucleotide is 10 to 30 linked nucleosides in length.

In certain embodiments, a compound comprises a modified oligonucleotide 8 to 50 linked nucleosides in length and having a nucleobase sequence comprising at least an 8, 9, 10, 11, 12, 13, 14, 15, or 16 contiguous nucleobase portion of the nucleobase sequence of any one of compound numbers 951799, 949935, 950023, 950089, 951372, 950060, or 950132 (SEQ ID NOs: 2879, 3056, 2123, 2189, 2453, 2160, or 2232). In certain embodiments, the modified oligonucleotide is 10 to 30 linked nucleosides in length. In certain embodiments, the nucleobase sequence of the modified oligonucleotide comprises or consists of SEQ ID NO: 2879 or of a sequence having at least 70% identity with SEQ ID NO: 2879. In certain embodiments, the nucleobase sequence of the modified oligonucleotide comprises or consists of SEQ ID NO: 3056 or of a sequence having at least 70% identity with SEQ ID NO: 3056. In certain embodiments, the nucleobase sequence of the modified oligonucleotide comprises or consists of SEQ ID NO: 2123 or of a sequence having at least 70% identity with SEQ ID NO: 2123. In certain embodiments, the nucleobase sequence of the modified oligonucleotide comprises or consists of SEQ ID NO: 2189 or of a sequence having at least 70% identity with SEQ ID NO: 2189. In certain embodiments, the nucleobase sequence of the modified oligonucleotide comprises or consists of SEQ ID NO: 2453 or of a sequence having at least 70% identity with SEQ ID NO: 2453. In certain embodiments, the nucleobase sequence of the modified oligonucleotide comprises or consists of SEQ ID NO: 2160 or of a sequence having at least 70% identity with SEQ ID NO: 2160. In certain embodiments, the nucleobase sequence of the modified oligonucleotide comprises or consists of SEQ ID NO: 2232 or of a sequence having at least 70% identity with SEQ ID NO: 2232.

In certain embodiments, a compound comprises or consists of a modified oligonucleotide 8 to 50 linked nucleosides in length and having a nucleobase sequence comprising the nucleobase sequence of any one of compound numbers 951799, 949935, 950023, 950089, 951372, 950060, or 950132 (SEQ ID NOs: 2879, 3056, 2123, 2189, 2453, 2160, or 2232). In certain embodiments, the modified oligonucleotide is 10 to 30 linked nucleosides in length.

In certain embodiments, a compound comprises or consists of a modified oligonucleotide having a nucleobase sequence consisting of the nucleobase sequence of any one of compound numbers 951799, 949935, 950023, 950089, 951372, 950060, or 950132 (SEQ ID NOs: 2879, 3056, 2123, 2189, 2453, 2160, or 2232).

In certain embodiments, a compound comprises or consists of a modified oligonucleotide 8 to 50 linked nucleosides in length and having a nucleobase sequence comprising the nucleobase sequence of the compound number 951799 (SEQ ID NO: 2879). In certain embodiments, the modified oligonucleotide is 10 to 30 linked nucleosides in length.

In certain embodiments, a compound comprising or consisting of a modified oligonucleotide complementary to DNM2 is compound number 951799. Out of the over 3,000 compounds that were screened as described in the Examples section below, compound numbers 951799, 949935, 950023, 950089, 951372, 950060, and 950132 emerged as the top lead compounds. In particular, compound number 951799 exhibited the best combination of properties in terms of potency and tolerability out of over 3,000 compounds.

In certain embodiments, any of the foregoing oligonucleotides is a modified oligonucleotide comprising at least one modified internucleoside linkage, at least one modified sugar, and/or at least one modified nucleobase.

In certain embodiments, any of the foregoing modified oligonucleotides comprises at least one modified sugar. In certain embodiments, at least one modified sugar is a bicyclic sugar, such as a cEt bicyclic sugar, an LNA bicyclic sugar, or an ENA bicyclic sugar.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:
a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar. In certain embodiments, the modified oligonucleotide is 16 to 50 linked nucleosides in length having a nucleobase sequence comprising the sequence recited in any one of SEQ ID NOs: 2879, 3056, 2123, 2189, 2453, 2160, or 2232 or a sequence having at least 70% identity with any one of SEQ ID NOs: 2879, 3056, 2123, 2189, 2453, 2160, or 2232. In certain embodiments, the modified oligonucleotide is 16 to 50 linked nucleosides in length having a nucleobase sequence comprising the sequence recited in SEQ ID NO: 2879 or a sequence having at least 70% identity with SEQ ID NO: 2879. In certain embodiments, the modified oligonucleotide is 10 to 30 linked nucleosides in length having a nucleobase sequence comprising the sequence recited in any one of SEQ ID NOs: 2879, 3056, 2123, 2189, 2453, 2160, or 2232 or a sequence having at least 70% identity with any one of SEQ ID NOs: 2879, 3056, 2123, 2189, 2453, 2160, or 2232. In certain embodiments, the modified oligonucleotide is 10 to 30 linked nucleosides in length having a nucleobase sequence comprising the sequence recited in SEQ ID NO: 2879 or a sequence having at least 70% identity with SEQ ID NO: 2879. In certain embodiments, the modified oligonucleotide is 16 linked nucleosides in length having a nucleobase sequence consisting of the sequence recited in any one of SEQ ID NOs: 2879, 3056, 2123, 2189, 2453, 2160, or 2232 or a sequence having at least 70% identity with any one of SEQ ID NOs: 2879, 3056, 2123, 2189, 2453, 2160, or 2232. In certain embodiments, the modified oligonucleotide is 16 linked nucleosides in length having a nucleobase sequence consisting of the sequence recited in SEQ ID NO: 2879 or a sequence having at least 70% identity with SEQ ID NO: 2879.

In certain embodiments, a compound comprises or consists of a modified oligonucleotide 20-50 linked nucleobases in length having a nucleobase sequence comprising the sequence recited in any one of SEQ ID NOs: 2879, 3056, 2123, 2189, 2453, 2160, or 2232 or a sequence having at least 70% identity with any one of SEQ ID NOs: 2879, 3056, 2123, 2189, 2453, 2160, or 2232, wherein the modified oligonucleotide comprises a gap segment consisting of ten linked 2'-deoxynucleosides;

a 5' wing segment consisting of three linked nucleosides; and a 3' wing segment consisting of three linked nucleosides;

wherein the gap segment is positioned between the 5' wing segment and the 3' wing segment; wherein the nucleosides of the 5' wing segment each comprise a cEt bicyclic sugar; wherein the nucleosides of the 3' wing segment each comprises a cEt bicyclic sugar; wherein each internucleoside linkage is a phosphorothioate linkage; and wherein each cytosine is a 5-methylcytosine. In certain embodiments, the modified oligonucleotide is 16-80 linked nucleosides in length. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide according to one of the following formulas:

(SEQ ID NO: 2879)
Gks Tks Tks Tds Ads Tds Tds Ads Tds Ads Gds Gds

Gds mCks Tks Tk;

(SEQ ID NO: 3056)
Gks Gks Aks Tds Tds Tds Tds Ads Gds Gds Ads Gds

Gds Tks Gks Ak;

(SEQ ID NO: 2123)
Gks mCks Aks Tds Ads Gds Ads mCds Ads Ads Ads Tds mCds mCks mCks Ak;

(SEQ ID NO: 2189)
Gks mCks Aks Ads Ads Tds Ads Tds Gds Ads Tds Tds mCds Aks Tks mCk;

(SEQ ID NO: 2453)
Gks Gks Tks mCds Ads Tds Tds Ads Ads Ads Gds Ads

Tds Tks mCks Tk;

(SEQ ID NO: 2160)
Aks Tks Gks Tds Ads Tds Tds Ads mCds mCds Tds Ads mCds Gks Gks mCk;
or (SEQ ID NO: 2232)
Gks Tks Aks mCds Ads Ads Tds Gds Tds Ads Ads Gds mCds mCks Tks Tk wherein A=an adenine, mC=a 5-methylcytosine, G=a guanine, T=a thymine, k=a cEt sugar moiety, d=a 2'-deoxyribosyl sugar moiety, and s=a phosphorothioate internucleoside linkage.
In certain embodiments, a compound comprises or consists of compound 951799, or salt thereof, a modified oligonucleotide having the following chemical structure:
[SEQ ID NO: 2879]
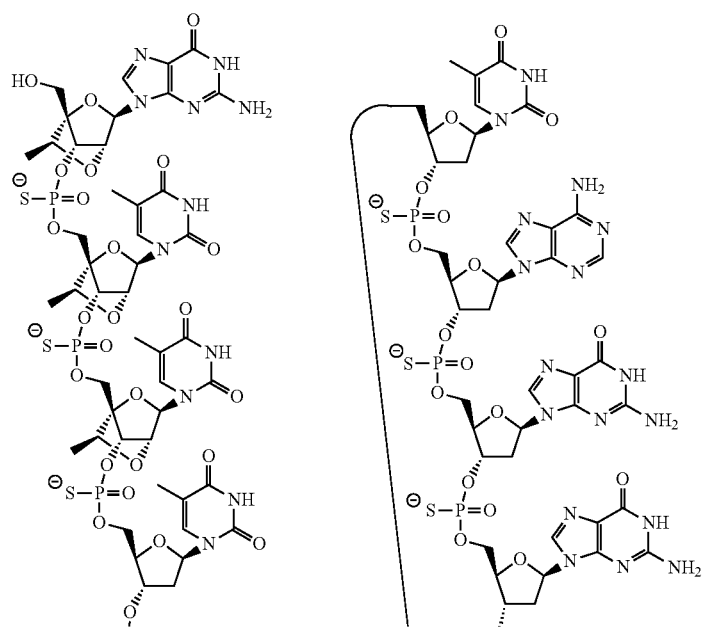
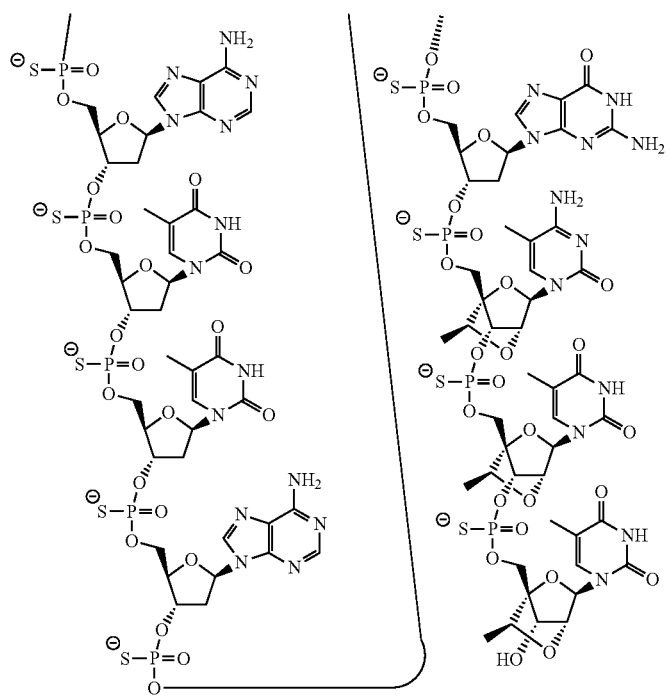

In certain embodiments, a compound comprises or consists of the sodium salt of compound 951799 having the following chemical structure:

[SEQ ID NO: 2879]

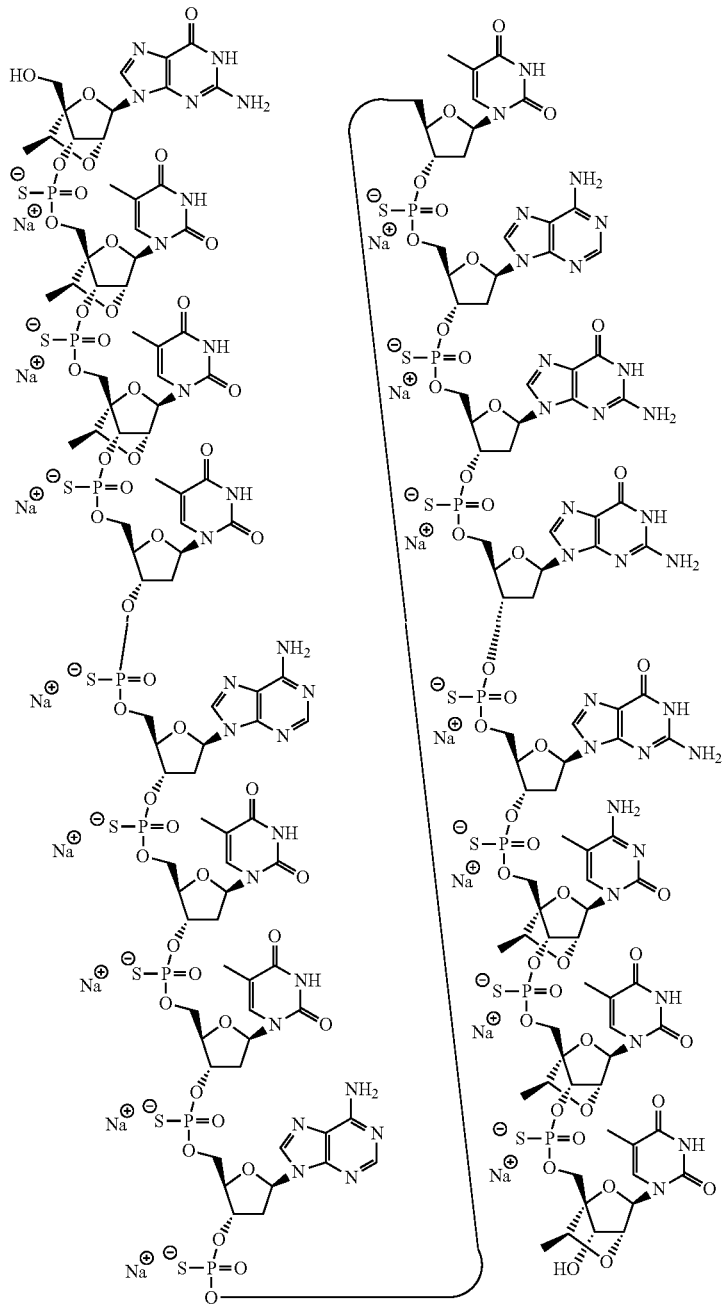

In any of the foregoing embodiments, the compound or oligonucleotide can be at least 85%, at least 90%, at least 95%, at least 98%, at least 99%, or 100% complementary to a nucleic acid encoding DNM2.

In any of the foregoing embodiments, the compound can be single-stranded. In certain embodiments, the compound comprises 2'-deoxyribonucleosides. In certain embodiments, the compound is double-stranded. In certain embodiments, the compound is double-stranded and comprises ribonucleosides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

The present invention thus relates to a modified oligonucleotide or compounds comprising modified oligonucleotides complementary to a DNM2 nucleic acid as described hereinabove.

In certain embodiments, a compound comprises a modified oligonucleotide described herein and a conjugate group. In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide.

In certain embodiments, compounds or compositions provided herein comprise a salt of the modified oligonucleotide. In certain embodiments, the salt is a sodium salt. In certain embodiments, the salt is a potassium salt.

In certain embodiments, the compounds or compositions as described herein are active by virtue of having at least one of an in vitro $IC_{50}$ of less than 300 nM, 200 nM, 100 nM, 80 nM, 50 nM, or 30 nM in a standard cell assay. Standard cell assays are described in the Examples.

In certain embodiments, the compounds or compositions as described herein are highly tolerable as demonstrated by having at least one of an increase an alanine transaminase (ALT) or aspartate transaminase (AST) value of no more than 4 fold, 3 fold, 2 fold, or 1.5 fold over saline treated animals or an increase in liver, spleen, or kidney weight of no more than 30%, 20%, 15%, 12%, 10%, 5%, or 2% compared to control treated animals. In certain embodiments, the compounds or compositions as described herein are highly tolerable as demonstrated by having no increase of ALT or AST over control treated animals. In certain embodiments, the compounds or compositions as described herein are highly tolerable as demonstrated by having no increase in liver, spleen, or kidney weight over control animals.

Certain embodiments provide a composition comprising or consisting essentially of the compound of any of the aforementioned embodiments or salt thereof.

Certain embodiments provide a composition comprising or consisting essentially of the compound of any of the aforementioned embodiments or salt thereof and at least one of a pharmaceutically acceptable carrier or diluent. Therefore, in one embodiment, the composition of the invention is a pharmaceutical composition.

Certain embodiments provide a medicament comprising or consisting essentially of the compound of any of the aforementioned embodiments or salt thereof. Therefore, in one embodiment, the composition of the invention is a medicament.

As used herein, the term "consists essentially of", with reference to a composition, pharmaceutical composition or medicament, means that the compound of the invention is the only active ingredient, therapeutic agent or agent with a biologic activity within said pharmaceutical composition or medicament.

In certain embodiments, the composition has a viscosity less than about 40 centipoise (cP), less than about 30 cP, less than about 20 cP, less than about 15 cP, less than about 10 cP, less than about 5 cP, or less than about 3 cP, or less than about 1.5 cP. In certain embodiments, the composition having any of the aforementioned viscosities comprises a compound provided herein at a concentration of about 15 mg/mL, 20 mg/mL, 25 mg/mL, 50 mg/mL, 100 mg/mL, 150 mg/mL, or about 200 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

Embodiment 1

A compound comprising a modified oligonucleotide 8 to 50 linked nucleosides in length having a nucleobase sequence comprising at least 8 contiguous nucleobases of any of the nucleobase sequences of SEQ ID NOs: 7-3134.

Embodiment 2

A compound comprising a modified oligonucleotide 9 to 50 linked nucleosides in length having a nucleobase sequence comprising at least 9 contiguous nucleobases of any of the nucleobase sequences of SEQ ID NOs: 7-3134.

Embodiment 3

A compound comprising a modified oligonucleotide 10 to 50 linked nucleosides in length having a nucleobase sequence comprising at least 10 contiguous nucleobases of any of the nucleobase sequences of SEQ ID NOs: 7-3134.

Embodiment 4

A compound comprising a modified oligonucleotide 11 to 50 linked nucleosides in length having a nucleobase sequence comprising at least 11 contiguous nucleobases of any of the nucleobase sequences of SEQ ID NOs: 7-3134.

Embodiment 5

A compound comprising a modified oligonucleotide 12 to 50 linked nucleosides in length having a nucleobase sequence comprising at least 12, at least 13, at least 14, or at least 15 contiguous nucleobases of any of the nucleobase sequences of SEQ ID NOs: 7-3134.

Embodiment 6

A compound comprising a modified oligonucleotide 16 to 50 linked nucleosides in length having a nucleobase sequence comprising the nucleobase sequence of any of SEQ ID NOs: 7-3134.

Embodiment 7

A compound comprising a modified oligonucleotide having a nucleobase sequence consisting of any one of SEQ ID NOs: 7-3134.

Embodiment 8

A compound comprising a modified oligonucleotide 8 to 50 linked nucleosides in length complementary within nucleobases 3,404-44,737; 83,573-87,287; 87,359-90,915; 90,968-97,263; 97,378-104,979; 81,061-81,199; or 116,048-116,903 of SEQ ID NO: 1, wherein said modified oligonucleotide is at least 85%, 90%, 95%, or 100% complementary to SEQ ID NO: 1.

Embodiment 9

A compound comprising a modified oligonucleotide 8 to 50 linked nucleosides in length having a nucleobase sequence comprising a portion of at least 8 contiguous nucleobases 100% complementary to an equal length portion of nucleobases 3,404-44,737; 83,573-87,287; 87,359-90,915; 90,968-97,263; 97,378-104,979; 81,061-81,199; or 116,048-116,903 of SEQ ID NO: 1, wherein the nucleobase sequence of the modified oligonucleotide is at least 85%, 90%, 95%, or 100% complementary to SEQ ID NO: 1.

Embodiment 10

A compound comprising a modified oligonucleotide 8 to 50 linked nucleosides in length complementary within nucleobases 83,573-87,287 or 87,359-90,915 of SEQ ID NO: 1, wherein said modified oligonucleotide is at least 85%, 90%, 95%, or 100% complementary to SEQ ID NO: 1.

Embodiment 11

A compound comprising a modified oligonucleotide complementary to intron 1 of a human DNM2 pre-mRNA.

Embodiment 12

A compound comprising a modified oligonucleotide complementary to intron 11 of a human DNM2 pre-mRNA.

Embodiment 13

A compound comprising a modified oligonucleotide complementary to intron 12 of a human DNM2 pre-mRNA.

Embodiment 14

A compound comprising a modified oligonucleotide complementary to intron 13 of a human DNM2 pre-mRNA.

Embodiment 15

A compound comprising a modified oligonucleotide complementary to intron 14 of a human DNM2 pre-mRNA.

Embodiment 16

A compound comprising a modified oligonucleotide complementary to exon 10 of a human DNM2 pre-mRNA or human DNM2 mRNA.

Embodiment 17

A compound comprising a modified oligonucleotide complementary to the 3'-UTR of a human DNM2 pre-mRNA or human DNM2 mRNA.

Embodiment 18

A compound comprising a modified oligonucleotide 16 to 50 linked nucleosides in length having a nucleobase sequence comprising any of SEQ ID NOs: 2879, 3056, 2123, 2189, 2453, 2160, or 2232.

Embodiment 19

A compound comprising a modified oligonucleotide having a nucleobase sequence consisting of any one of SEQ ID NOs: 2879, 3056, 2123, 2189, 2453, 2160, or 2232.

Embodiment 20

A compound comprising a modified oligonucleotide having a nucleobase sequence comprising SEQ ID NO: 2879.

Embodiment 21

A compound comprising a modified oligonucleotide 16 to 50 linked nucleosides in length having a nucleobase sequence comprising any of SEQ ID NOs: 2879, 3056, 2123, 2189, 2453, 2160, or 2232, wherein the modified oligonucleotide comprises:
 a gap segment consisting of 8-12 linked 2'-deoxynucleosides;
 a 5' wing segment consisting of 1-7 linked nucleosides; and
 a 3' wing segment consisting of 1-7 linked nucleosides;
 wherein the gap segment is positioned between the 5' wing segment and the 3' wing segment and wherein each terminal wing nucleoside comprises a modified sugar.

Embodiment 22

A compound comprising a modified oligonucleotide 16 linked nucleosides in length having a nucleobase sequence consisting of the sequence recited in SEQ ID NO: 2879, 3056, 2123, 2189, 2453, 2160, or 2232, wherein the modified oligonucleotide comprises
 a gap segment consisting of 10 linked 2'-deoxynucleosides;
 a 5' wing segment consisting of 3 linked nucleosides; and
 a 3' wing segment consisting of 3 linked nucleosides;
 wherein the gap segment is positioned between the 5' wing segment and the 3' wing segment; wherein each nucleoside of each wing segment comprises a cEt sugar moiety; wherein each internucleoside linkage is a phosphorothioate linkage; and wherein each cytosine is a 5-methylcytosine.

Embodiment 23

The compound of any one of embodiments 1-22, wherein the oligonucleotide is at least 80%, 85%, 90%, 95% or 100% complementary to any of SEQ ID NO: 1, 2, 3, or 3135.

Embodiment 24

The compound of any one of embodiments 1-23, wherein the modified oligonucleotide comprises at least one modified internucleoside linkage.

Embodiment 25

The compound of embodiments 24, wherein the at least one modified internucleoside linkage is a phosphorothioate internucleoside linkage.

Embodiment 26

The compound of any one of embodiments 1-21 or 23-25, wherein the modified oligonucleotide comprises at least one bicyclic sugar.

Embodiment 27

The compound of Embodiments 26, wherein the at least one bicyclic sugar is selected from the group consisting of LNA, ENA, and cEt.

Embodiment 28

The compound of embodiment 27, wherein the at least one bicyclic sugar moiety is a cEt sugar moiety.

Embodiment 29

The compound of any one of embodiments 1-28, wherein the modified oligonucleotide comprises at least one 5-methylcytosine.

Embodiment 30

The compound of any one of embodiments 1-29, wherein the modified oligonucleotide comprises:
 a gap segment consisting of linked 2'-deoxynucleosides;
 a 5' wing segment consisting of linked nucleosides; and
 a 3' wing segment consisting of linked nucleosides;
 wherein the gap segment is positioned immediately adjacent to and between the 5' wing segment and the 3' wing segment and wherein each nucleoside of each wing segment comprises a modified sugar moiety.

Embodiment 31

The compound of any one of embodiments 1-30, wherein the compound is single-stranded.

Embodiment 32

The compound of any one of embodiments 1-30, wherein the compound is double-stranded.

Embodiment 33

The compound of any one of embodiments 1-32, wherein the compound comprises at least one unmodified ribosyl sugar moiety.

Embodiment 34

The compound of any one of embodiments 1-33, wherein the compound comprises at least one unmodified 2'-deoxyribosyl sugar moiety.

Embodiment 35

The compound of any one of embodiments 1-34, wherein the modified oligonucleotide consists of 10 to 30 linked nucleosides.

Embodiment 36

The compound of any one of embodiments 1-34, wherein the modified oligonucleotide consists of 12 to 30 linked nucleosides.

Embodiment 37

The compound of any one of embodiments 1-34, wherein the modified oligonucleotide consists of 15 to 30 linked nucleosides.

Embodiment 38

The compound of any one of embodiments 1-34, wherein the modified oligonucleotide consists of 16 to 20 linked nucleosides.

Embodiment 39

A compound comprising a modified oligonucleotide according to the following formula: Gks Tks Tks Tds Ads Tds Tds Ads Tds Ads Gds Gds Gds mCks Tks Tk; wherein,
 A=an adenine,
 mC=a 5-methylcytosine
 G=a guanine,
 T=a thymine,
 k=a cEt sugar moiety,
 d=a 2'-deoxyribosyl sugar moiety, and
 s=a phosphorothioate internucleoside linkage.

Embodiment 40

The compound of any one of embodiments 1-39 comprising a conjugate group.

Embodiment 41

The compound of embodiment 40, wherein the compound consists of the modified oligonucleotide and the conjugate group.

Embodiment 42
A compound according to the following formula:
[SEQ ID NO: 2879]
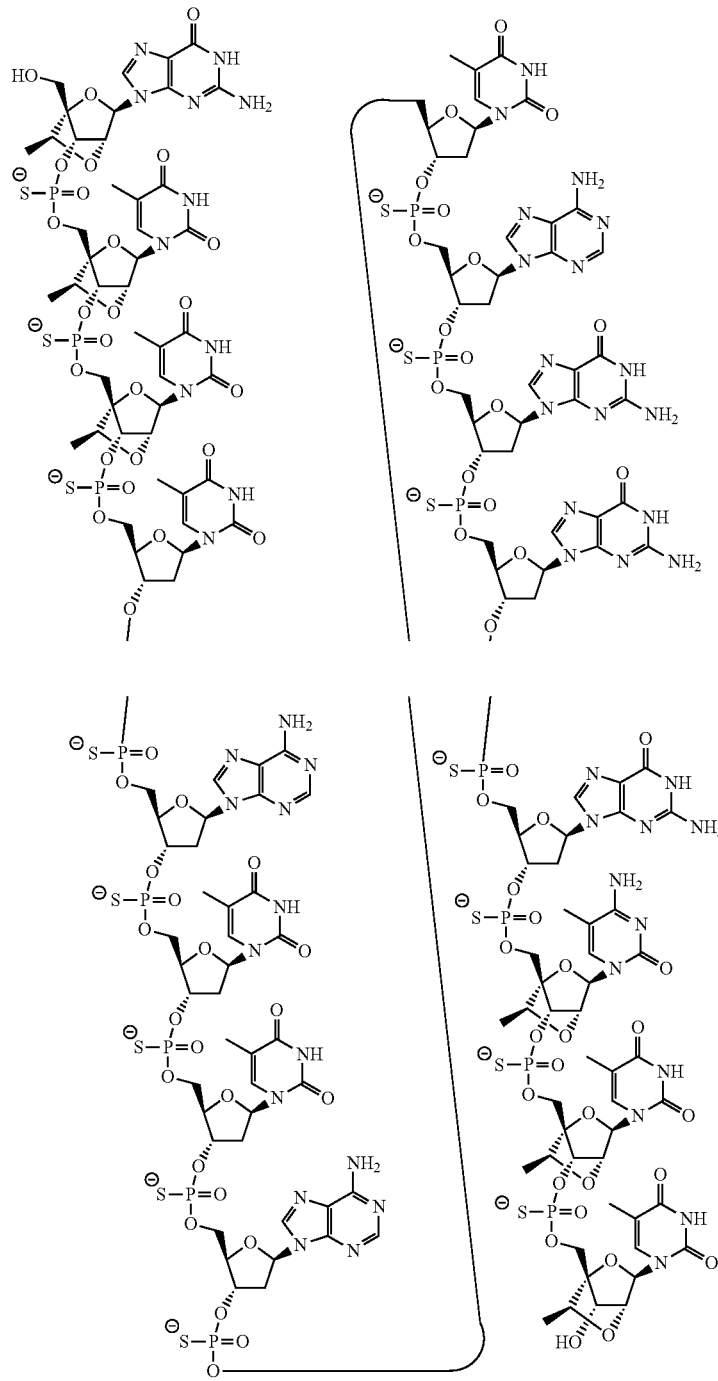
or a salt thereof.
Embodiment 43
The compound of any one of embodiments 1-39 or 42, wherein the compound consists of the modified oligonucleotide.

Embodiment 44

A compound consisting of a pharmaceutically acceptable salt form of any one of the compounds of embodiments 1-43.

Embodiment 45

The compound of embodiment 44, wherein the pharmaceutically acceptable salt is a sodium salt.

Embodiment 46

The compound of embodiment 44, wherein the pharmaceutically acceptable salt is a potassium salt.

Embodiment 47

A pharmaceutical composition comprising the compound of any one of embodiments 1-44 and at least one pharmaceutically acceptable carrier or diluent.

Embodiment 48

A chirally enriched population of the compounds of any one of embodiments 1-46, wherein the population is enriched for modified oligonucleotides comprising at least one particular phosphorothioate internucleoside linkage having a particular stereochemical configuration.

Embodiment 49

The chirally enriched population of embodiment 48, wherein the population is enriched for modified oligonucleotides comprising at least one particular phosphorothioate internucleoside linkage having the (Sp) configuration.

Embodiment 50

The chirally enriched population of embodiment 48, wherein the population is enriched for modified oligonucleotides comprising at least one particular phosphorothioate internucleoside linkage having the (Rp) configuration.

Embodiment 51

The chirally enriched population of embodiment 48, wherein the population is enriched for modified oligonucleotides having a particular, independently selected stereochemical configuration at each phosphorothioate internucleoside linkage

Embodiment 52

The chirally enriched population of embodiment 51, wherein the population is enriched for modified oligonucleotides having the (Sp) configuration at each phosphorothioate internucleoside linkage.

Embodiment 53

The chirally enriched population of embodiment 51, wherein the population is enriched for modified oligonucleotides having the (Rp) configuration at each phosphorothioate internucleoside linkage.

Embodiment 54

The chirally enriched population of embodiment 51, wherein the population is enriched for modified oligonucleotides having the (Rp) configuration at one particular phosphorothioate internucleoside linkage and the (Sp) configuration at each of the remaining phosphorothioate internucleoside linkages.

Embodiment 55

The chirally enriched population of embodiment 48 or embodiment 51, wherein the population is enriched for modified oligonucleotides having at least 3 contiguous phosphorothioate internucleoside linkages in the Sp, Sp, and Rp configurations, in the 5' to 3' direction.

Embodiment 56

A chirally enriched population of the compounds of any one of embodiments 1-46, wherein all of the phosphorothioate internucleoside linkages of the modified oligonucleotide are stereorandom.

Embodiment 57

A pharmaceutical composition comprising the population of compounds of any one of embodiments 48-56 and at least one pharmaceutically acceptable diluent or carrier.

Embodiment 58

The compound of any one of embodiments 1-46, a pharmaceutical composition comprising the compound of any one of embodiments 1-46 and at least one pharmaceutically acceptable carrier or diluent, or a pharmaceutical composition comprising the population of compounds of any one of embodiments 48-56 and at least one pharmaceutically acceptable carrier or diluent, for use in therapy.

Embodiment 59

The compound or composition of embodiment 58, for use in treating, preventing, or ameliorating centronuclear myopathy, Duchenne Muscular Dystrophy, or Charcot-Marie Tooth disease.

Embodiment 60

A method of treating, preventing, or ameliorating a disease associated with DNM2 in an individual comprising administering to the individual any of the compounds or compositions of embodiment 1-59, thereby treating, preventing, or ameliorating the disease.

Embodiment 61

A method of treating, preventing, or ameliorating a disease associated with DNM2 in an individual comprising administering to the individual a compound comprising a modified oligonucleotide 100% complementary to an exon 10, an intron, or the 3'-UTR of a DNM2 nucleic acid transcript, thereby treating, preventing, or ameliorating the disease.

Embodiment 62

The method of embodiment 60 or 61, wherein the disease is centronuclear myopathy, Duchenne Muscular Dystrophy, or Charcot-Marie Tooth disease.

Embodiment 63

The method of any one of embodiments 60-62, wherein the compound is single-stranded.

Embodiment 64

The method of any one of embodiments 60-63, wherein the DNM2 nucleic acid transcript is a pre-mRNA.

Embodiment 65

The method of any one of embodiments 60-64, wherein the disease is X-linked myotubular myopathy, autosomal recessive centronuclear myopathy, or autosomal dominant centronuclear myopathy.

Embodiment 66

The method of embodiment 65, wherein the individual has at least one mutation in at least one gene selected from among MTM1, BIN1, and DNM2.

Embodiment 67

The method of any one of embodiments 60-66, wherein the administering increases body weight or muscle strength.

Embodiment 68

A method of inhibiting expression of DNM2 in a cell comprising contacting the cell with a single-stranded compound comprising a modified oligonucleotide 100% complementary to exon 10, an intron, or the 3'-UTR of a DNM2 nucleic acid transcript, thereby inhibiting expression of DNM2 in the cell.

Embodiment 69

The method of embodiment 68, wherein the cell is in the muscle of an individual.

Embodiment 70

The method of embodiment 69, wherein the individual has, or is at risk of having, a centronuclear myopathy, Duchenne Muscular Dystrophy, or Charcot-Marie Tooth disease.

Embodiment 71

A method of increasing body weight or muscle strength in an individual having, or at risk of having, a disease associated with DNM2 comprising administering a single-stranded compound comprising a modified oligonucleotide 100% complementary to a DNM2 nucleic acid transcript to the individual, thereby increasing body weight or muscle strength in the individual.

Embodiment 72

The method of embodiment 71, wherein the individual has, or is at risk of having, centronuclear myopathy, Duchenne Muscular Dystrophy, or Charcot-Marie Tooth disease.

Embodiment 73

The method of any one of embodiments 60-72, wherein the compound is the compound of any one of embodiments 1-46.

Embodiment 74

The method of any one of embodiments 60-72, wherein the compound is a member of the chirally enriched population of any one of embodiments 48-56.

Embodiment 75

The method of any one of embodiments 60-72, wherein the compound is a component of the pharmaceutical composition of embodiment 57.

Embodiment 76

The method any one of embodiments 60-67 or 69-75, wherein the compound is administered to the individual via subcutaneous injection.

Embodiment 77

The method any one of embodiments 60-67 or 69-75, wherein the compound is administered to the individual via intramuscular injection.

Embodiment 78

The method of any one of embodiments 60-67 or 69-77, wherein the compound is administered to the individual via intravenous injection.

Embodiment 79

Use of a single-stranded compound comprising a modified oligonucleotide 100% complementary to exon 10, intron 1, intron 11, intron, 12, intron 13, intron 14, or the 3'-UTR of a DNM2 nucleic acid transcript for treating, preventing, or ameliorating a disease associated with DNM2.

Embodiment 80

The use of embodiment 79, wherein the disease is centronuclear myopathy, Duchenne Muscular Dystrophy, or Charcot-Marie Tooth disease.

Embodiment 81

Use of the compound of any one of embodiments 1-46 or the composition of embodiment 57 for treating, preventing, or ameliorating a disease associated with DNM2.

Embodiment 82

Use of the compound of any one of embodiments 1-46 or the composition of embodiment 57 in the manufacture of a medicament for treating, preventing, or ameliorating a disease associated with DNM2.

Embodiment 83

The use of embodiment 81 or 82, wherein the disease is centronuclear myopathy, Duchenne Muscular Dystrophy, or Charcot-Marie Tooth disease.

Embodiment 84

The use of embodiment 80 or 83, wherein the disease is X-linked myotubular myopathy, autosomal recessive centronuclear myopathy, or autosomal dominant centronuclear myopathy.

Embodiment 85

The use of embodiment 84, wherein the disease is associated with a mutation in at least one gene selected from among MTM1, BIN1, and DNM2.

Embodiment 86

Use of the compound of any one of embodiments 1-46 or the composition of embodiment 57 in the preparation of a medicament for treating, preventing, or ameliorating a disease associated with DNM2.

Embodiment 87

The use of embodiment 86, wherein the disease is centronuclear myopathy, Duchenne Muscular Dystrophy, or Charcot-Marie Tooth disease.

Embodiment 88

The use of embodiment 87, wherein the disease is X-linked myotubular myopathy, autosomal recessive centronuclear myopathy, or autosomal dominant centronuclear myopathy.

Embodiment 89

The use of embodiment 88, wherein the disease is associated with a mutation in at least one gene selected from among MTM1, BIN1, and DNM2.

Certain Indications

Certain embodiments provided herein relate to methods of inhibiting DNM2 expression, which can be useful for treating, preventing, or ameliorating a disease associated with DNM2 in an individual, by administration of a compound that targets DNM2, such as the compound described herein. In certain diseases associated with DNM2, modest or partial inhibition of DNM2 expression is sufficient to treat, prevent, or ameliorate the disease (See, e.g., Cowling et al. *J. Clin. Invest.* 124, 1350-1363 (2014) and Tasfaout et al. *Nat. Commun.* June 7; 8:15661 (2017).) In certain embodiments, the compound can be an antisense compound, oligomeric compound, or oligonucleotide complementary to DNM2, such as the ones described herein.

Examples of diseases associated with DNM2 that are treatable, preventable, and/or ameliorable with the methods provided herein include centronuclear myopathy (CNM), Charcot-Marie-Tooth disease (CMT), and Duchenne's Muscular Dystrophy (DMD). Centronuclear myopathy includes X-linked CNM (XLCNM), autosomal dominant CNM (ADCNM) and autosomal recessive CNM (ARCNM). Mutations in several genes are associated with CNM, including mutations in MTM1, BIN1, and DNM2. Other genes have been linked to a CNM-like myopathy: RYR1 encoding for the ryanodine receptor, TTN encoding Titin, CCDC78 (OMIM 614807) and the phosphoinositides phosphatase MTMR14 (called hJUMPY; OMIM 160150).

In certain embodiments, a method of treating, preventing, or ameliorating a disease associated with DNM2 in an individual comprises administering to the individual a compound comprising an antisense compound targeted to DNM2, thereby treating, preventing, or ameliorating the disease. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound. In certain embodiments, the compound is administered to the individual subcutaneously, intradermally, intranodally, intramedullary, intramuscularly, intrasternally, by intravenous (i.v.) injection, by infusion techniques or intraperitoneally. In certain embodiments, the compound is administered to the individual via subcutaneous injection. In certain embodiments, administering the compound increases or preserves body weight or muscle strength.

In certain embodiments, a method of treating, preventing, or ameliorating CNM, DMD, or CMT comprises administering to the individual a compound comprising a modified oligonucleotide complementary to a DNM2 nucleic acid, thereby treating, preventing, or ameliorating CNM, DMD, or CMT. In certain embodiments, the compound is a compound as described herein. In certain embodiments, the compound is an antisense compound targeted to DNM2. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound. In certain embodiments, the compound is administered to the individual subcutaneously, intradermally, intratumorally, intranodally, intramedullary, intramuscularly, intrasternally, by intravenous (i.v.) injection, by infusion techniques or intraperitoneally. In certain embodiments, the compound is administered to the individual systemically, e.g., via subcutaneous or intramuscular injection. In certain embodiments, administering the compound increases or preserves body weight or muscle strength. In certain such embodiments, time taken to rise from the floor, nine-meter walking time, or time taken to climb four stairs is decreased. In certain embodiments, ability to lift weight, distance of a 6 minute walk, or leg function grade is increased. In certain embodiments, pulmonary function or cardiac function is improved. In certain embodiments, the individual is identified as having or at risk of having a disease associated with DNM2. Examples of factors of risk of having a disease associated with DNM2 include, but are not limited to, genetic predisposition, such as, for example, a mutation in at least one gene selected from among MTM1, BIN1, and DNM2.

In certain embodiments, a method of inhibiting expression of DNM2 in an individual having, or at risk of having, a disease associated with DNM2 comprises administering to the individual a compound comprising a modified oligonucleotide complementary to a DNM2 nucleic acid, thereby inhibiting expression of DNM2 in the individual. In certain embodiments, administering the compound inhibits expression of DNM2 in skeletal muscle. In certain embodiments, the individual has, or is at risk of having CNM, DMD, or CMT. In certain embodiments, the compound comprises an antisense compound targeted to DNM2. In certain embodiments, the antisense compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound. In certain embodiments, the compound is administered to the individual subcutaneously, intradermally, intranodally, intramedullary, intramuscularly, intrasternally, by intravenous (i.v.) injection, by infusion techniques or intraperitoneally. In certain embodiments, the compound is administered to the individual systemically, e.g., via subcutaneous or intramuscular injection. In certain embodiments, administering the compound increases or preserves body weight or muscle strength. In certain embodiments, the individual is identified as having or at risk of having a disease associated with DNM2.

In certain embodiments, a method of inhibiting expression of DNM2 in a cell comprises contacting the cell with a compound comprising an antisense compound targeted to DNM2, thereby inhibiting expression of DNM2 in the cell. In one embodiment, the expression of DNM2 is inhibited by at least about 40%, at least about 50%, at least about 60%, at least about 70%, at least about 80%, or at least about 90%. In one embodiment, the expression of DNM2 is inhibited by at least 50%, 55%, 60%, 65%, 70%, 75%, 80%, 85%, 90%, 91%, 92%, 93%, 94%, 95%, 96%, 97%, 98% or 99% as compared to an untreated or control sample. In one embodiment, the method is an in vitro method. In certain embodiments, the cell is a muscle cell. In certain embodiments, the cell is a skeletal muscle cell. In certain embodiments, the muscle cell is in an individual who has, or is at risk of having CNM, DMD, or CMT. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound.

In certain embodiments, a method of increasing or preserving body weight or muscle strength of an individual having, or at risk of having, a disease associated with DNM2 comprises administering to the individual a compound comprising an antisense compound targeted to DNM2, increasing or preserving body weight or muscle strength of the individual. In certain such embodiments, time taken to rise from the floor, nine-meter walking time, or time taken to climb four stairs is decreased. In certain embodiments, ability to lift weight, distance of a 6 minute walk, or leg function grade is increased. In certain embodiments, pulmonary function or cardiac function is improved. In certain embodiments, the individual has, or is at risk of having, CNM, DMD, or CMT. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound. In certain embodiments, the compound is administered to the individual subcutaneously, intradermally, intranodally, intramedullary, intramuscularly, intrasternally, by intravenous (i.v.) injection, by infusion techniques or intraperitoneally. In certain embodiments, the compound is administered to the individual systemically, e.g., via subcutaneous or intramuscular injection. In certain embodiments, the individual is identified as having or at risk of having a disease associated with DNM2.

Certain embodiments are drawn to a compound comprising an antisense compound targeted to DNM2 for use in treating a disease associated with DNM2. In certain embodiments, the disease is CNM, DMD, or CMT. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound. In certain embodiments, the compound is administered to the individual subcutaneously, intradermally, intranodally, intramedullary, intramuscularly, intrasternally, by intravenous (i.v.) injection, by infusion techniques or intraperitoneally. In certain embodiments, the compound is to be administered to the individual systemically, e.g., via subcutaneous or intramuscular injection.

Certain embodiments are drawn to a compound comprising an antisense compound targeted to DNM2 for use in increasing or preserving body weight or muscle strength of an individual having or at risk of having CNM, DMD, or CMT. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound.

Certain embodiments are drawn to use of the compound comprising an antisense compound targeted to DNM2 for the manufacture or preparation of a medicament for treating a disease associated with DNM2. Certain embodiments are drawn to use of the compound comprising an antisense compound targeted to DNM2 for the preparation of a medicament for treating a disease associated with DNM2. In certain embodiments, the disease is CNM, DMD, or CMT. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound.

Certain embodiments are drawn to use of a compound comprising an antisense compound targeted to DNM2 for the manufacture or preparation of a medicament for increasing or preserving body weight or muscle strength of an individual having or at risk of having CNM, DMD, or CMT. In certain embodiments, the compound comprises an oligonucleotide complementary to a DNM2 nucleic acid transcript. In certain embodiments, the compound is a compound as described herein. In certain embodiments, the compound comprises or consists of a modified oligonucleotide complementary to intron 1, intron 11, intron 12, intron 13, intron 14, exon 10, or the 3'-UTR of a DNM2 nucleic acid transcript. In certain embodiments, the modified oligonucleotide is complementary to a sequence within nucleotides 3,404-44,737; 83,573-87,287; 87,359-90,915; 90,968-97,263; 97,378-104,979; 81,061-81,199; or 116,048-116,903 of SEQ ID NO: 1. In certain embodiments, the compound comprises or consists of a modified oligonucleotide complementary to intron 1, intron 11, intron 12, intron 13, or intron 14 of a DNM2 nucleic acid transcript. In certain embodiments, the modified oligonucleotide is complementary to a sequence within nucleotides 3,404-44,737; 83,573-87,287; 87,359-90,915; 90,968-97,263; or 97,378-104,979 of SEQ ID NO: 1. In certain embodiments, the compound comprises a modified oligonucleotide 8 to 50 linked nucleosides in length and having a nucleobase sequence comprising at least 8 contiguous nucleobases of any of the nucleobase sequences of SEQ ID NOs: 7-3134. In certain embodiments, the compound comprises a modified oligonucleotide 12 to 50 linked nucleosides in length and having a nucleobase sequence comprising the nucleobase sequence of any one of SEQ ID NOs: 7-3134. In certain embodiments, the compound comprises a modified oligonucleotide consisting of the nucleobase sequence of any one of SEQ ID NOs: 7-3134. In certain embodiments, the compound comprises a modified oligonucleotide 16 to 50 linked nucleosides in length having a nucleobase sequence comprising any one of SEQ ID NOs: 2879, 3056, 2123, 2189, 2453, 2160, or 2232. In certain embodiments, the compound comprises a modified oligonucleotide having a nucleobase sequence consisting of any one of SEQ ID NOs: 2879, 3056, 2123, 2189, 2453, 2160, or 2232. In any of the foregoing embodiments, the modified oligonucleotide can be 10 to 30 linked nucleosides in length. In certain embodiments, the compound is compound number 951799, 949935, 950023, 950089, 951372, 950060, or 950132. In any of the foregoing embodiments, the compound can be single-stranded or double-stranded. In any of the foregoing embodiments, the compound can be an antisense compound or oligomeric compound.

In any of the foregoing methods or uses, the compound can be targeted to a DNM2 nucleic acid transcript. In certain embodiments, the compound comprises or consists of a modified oligonucleotide, for example a modified oligonucleotide 8 to 50 linked nucleosides in length, 10 to 30 linked nucleosides in length, 12 to 30 linked nucleosides in length, or 20 linked nucleosides in length. In certain embodiments, the modified oligonucleotide is at least 80%, 85%, 90%, 95% or 100% complementary to any of the nucleobase sequences recited in SEQ ID NOs: 1, 2, 3, or 3135. In certain embodiments, the modified oligonucleotide comprises at least one modified internucleoside linkage, at least one modified sugar, and at least one modified nucleobase. In certain such embodiments, the at least one modified internucleoside linkage is a phosphorothioate internucleoside linkage, the at least one modified sugar is a bicyclic sugar, and the at least one modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each terminal wing nucleoside comprises a modified sugar.

In any of the foregoing embodiments, the modified oligonucleotide may be 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides in length. In certain embodiments, the modified oligonucleotide is at least 80%, 85%, 90%, 95% or 100% complementary to any of the nucleobase sequences recited in SEQ ID NOs: 1, 2, 3, or 3135. In certain embodiments, the modified oligonucleotide comprises at least one modified internucleoside linkage, at least one modified sugar, and at least one modified nucleobase. In certain embodiments, the at least one modified internucleoside linkage is a phosphorothioate internucleoside linkage, the at least one modified sugar is a bicyclic sugar, and the at least one modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each terminal wing nucleoside comprises a modified sugar.

In any of the foregoing methods or uses, the compound may comprise or consist of a modified oligonucleotide 16 to 30 linked nucleosides in length and having a nucleobase sequence comprising any one of SEQ ID NOs: 2879, 3056, 2123, 2189, 2453, 2160, or 2232, wherein the modified oligonucleotide comprises:

a gap segment consisting of linked 2'-deoxynucleosides;
a 5' wing segment consisting of linked nucleosides; and
a 3' wing segment consisting of linked nucleosides;

wherein the gap segment is positioned between the 5' wing segment and the 3' wing segment and wherein each nucleoside of each wing segment comprises a modified sugar.

In any of the foregoing methods or uses, the compound may comprise or consist of a modified oligonucleotide 16 to 30 linked nucleosides in length and having a nucleobase sequence comprising any one of SEQ ID NOs: 2879, 3056, 2123, 2189, 2453, 2160, or 2232, wherein the modified oligonucleotide comprises:

a gap segment consisting of linked 2'-deoxynucleosides;
a 5' wing segment consisting of linked nucleosides; and
a 3' wing segment consisting of linked nucleosides;

wherein the gap segment is positioned between the 5' wing segment and the 3' wing segment, wherein each terminal wing nucleoside comprises a modified sugar.

49

In any of the foregoing methods or uses, the compound may comprise or consist of a modified oligonucleotide 16 to 50 linked nucleobases in length having a nucleobase sequence comprising or consisting of the sequence recited in any one of SEQ ID NOs: 2879, 3056, 2123, 2189, 2453, 2160, or 2232, wherein the modified oligonucleotide comprises:
  a gap segment consisting of 10 linked 2'-deoxynucleosides;
  a 5' wing segment consisting of 3 linked nucleosides; and
  a 3' wing segment consisting of 3 linked nucleosides;

50 wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In one embodiment, in any of the foregoing methods or uses, the compound has the following chemical structure:

[SEQ ID NO: 2879]

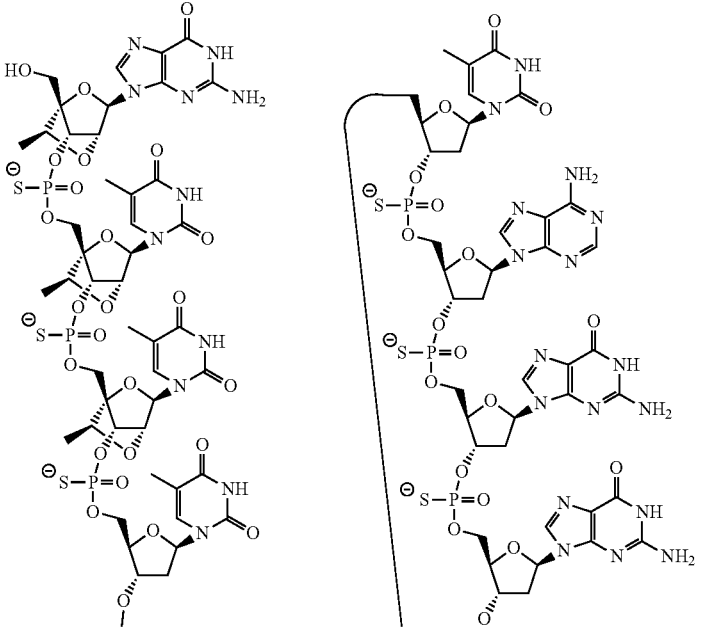

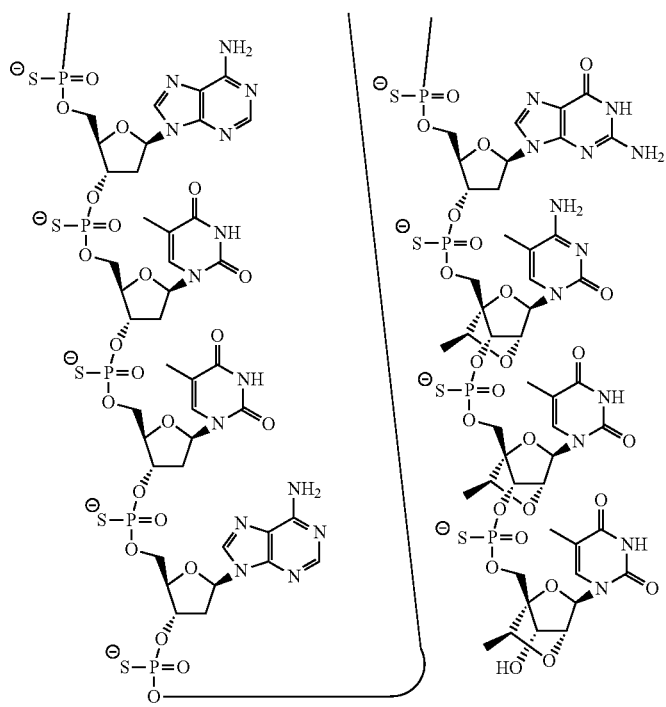

In one embodiment, in any of the foregoing methods or uses, the compound can be administered systemically. In certain embodiments, the compound of any of the foregoing methods or uses can be administered through injection or infusion. In certain embodiments, the compound of any of the foregoing methods or uses can be administered via subcutaneous administration, intravenous administration, intramuscular administration, intraarterial administration, intraperitoneal administration, or intracranial administration, e.g. intrathecal or intracerebroventricular administration. In certain embodiments, the compound is administered to the individual intradermally, intranodally, intramedullary or intrasternally. In certain embodiments, the compound of any of the foregoing methods or uses can be administered orally.

Certain Combinations and Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more secondary agents. In certain embodiments, one or more compounds or compositions provided herein and one or more secondary agents, are administered at different times. In certain embodiments, one or more compounds or compositions provided herein and one or more secondary agents, are prepared together in a single formulation. In certain embodiments, one or more compounds or compositions provided herein and one or more secondary agents, are prepared separately.

Certain embodiments are directed to the use of a compound comprising a modified oligonucleotide complementary to a DNM2 nucleic acid transcript as described herein in combination with a secondary agent. In particular embodiments such use is in a method of treating a patient suffering from CNM, DMD, or CMT, or in the preparation or manufacture of a medicament for treating CNM, DMD, or CMT.

In certain embodiments the compound comprising a modified oligonucleotide complementary to a DNM2 nucleic acid transcript as described herein and the secondary agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

Certain Compounds

In certain embodiments, compounds described herein can be antisense compounds. In certain embodiments, the antisense compound comprises or consists of an oligomeric compound. In certain embodiments, the oligomeric compound comprises or consists of a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, a compound or antisense compound is double-stranded. Such double-stranded compounds comprise a first oligomeric compound comprising or consisting of a first modified oligonucleotide having a region complementary to a target nucleic acid and a second oligomeric compound comprising or consisting of a second oligonucleotide having a region complementary to the first modified oligonucleotide. In certain embodiments, the first oligonucleotide is 100% complementary to the second oligonucleotide. In certain embodiments, the first and second oligonucleotides include non-complementary, overhanging nucleosides. In certain embodiments, the first modified oligonucleotide comprises unmodified ribosyl sugar moieties as those found in RNA. In such embodiments, thymine nucleobases in the first and/or second oligonucleotide are replaced by uracil nucleobases. In certain embodiments, the first and/or second oligomeric compound comprises a conjugate group. In certain embodiments, the first modified oligonucleotide is 12-30 linked nucleosides in length and the second oligonucleotide is 12-30 linked nucleosides in length. In certain embodiments, the second oligonucleotide is modified. In certain embodiments, the first modified oligonucleotide has a nucleobase sequence comprising at least 8 contiguous nucleobases of any of SEQ ID NOs: 7-3134.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a DNM2 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. *Proc. Natl. Acad. Sci. USA* 1992, 89:7305-7309; Gautschi et al. *J. Natl. Cancer Inst*. March 2001, 93:463-471; Maher and Dolnick *Nuc. Acid. Res.* 1998, 16:3341-3358). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics.

In certain embodiments, a compound described herein can comprise any of the oligonucleotide sequences targeted to a DNM2 nucleic acid transcript described herein. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 7-3134 and a second strand. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 2879, 3056, 2123, 2189, 2453, 2160, or 2232 and a second strand. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of SEQ ID NO: 2879 and a second strand. In certain embodiments, the compound comprises a first strand comprising the nucleobase sequence of any one of SEQ ID NOs: 7-3134 and a second strand. In certain embodiments, the compound comprises a first strand comprising the nucleobase sequence of any one of SEQ ID NOs: 2879, 3056, 2123, 2189, 2453, 2160, or 2232 and a second strand. In certain embodiments, the compound comprises a first strand comprising the nucleobase sequence of SEQ ID NO: 2879 and a second strand. In certain embodiments, the compound comprises ribonucleotides in which the first strand has uracil (U) in place of thymine (T) in any one of SEQ ID NOs: 7-3134. In certain embodiments, the compound comprises (i) a first strand comprising a nucleobase sequence complementary to the site on a DNM2 nucleic acid to which any of SEQ ID NOs: 7-3134 is complementary, and (ii) a second strand. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to a DNM2 nucleic acid described herein. In certain embodiments, the compound is single-stranded. In certain embodiments, such a compound is a single-stranded RNAi (ssRNAi) compound. In certain embodiments, the compound comprises at least an 8, 9, 10, 11, 12, 13, 14, 15, 16, 17, 18, 19, or 20 contiguous nucleobase portion of any one of SEQ ID NOs: 7-3134. In certain embodiments, the compound comprises at least an 8, 9, 10, 11, 12, 13, 14, 15, 16, 17, 18, 19, or 20 contiguous nucleobase portion of any one of SEQ ID NOs: 2879, 3056, 2123, 2189, 2453, 2160, or 2232. In certain embodiments, the compound comprises at least an 8, 9, 10, 11, 12, 13, 14, 15, 16, 17, 18, 19, or 20 contiguous nucleobase portion of SEQ ID NO: 2879. In certain embodiments, the compound comprises the nucleobase sequence of any one of SEQ ID NOs: 7-3134. In certain embodiments, the compound comprises the nucleobase sequence of any one of SEQ ID NOs: 2879, 3056, 2123, 2189, 2453, 2160, or 2232. In certain embodiments, the compound comprises the nucleobase sequence of SEQ ID NO: 2879. In certain embodiments, the compound comprises ribonucleotides in which uracil (U) is in place of thymine (T) in any of SEQ ID NOs: 7-3134. In certain embodiments, the compound comprises a nucleobase sequence complementary to the site on DNM2 to which any of SEQ ID NOs: 7-3134 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 13, such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a DNM2 target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain embodiments, a pre-mRNA and corresponding mRNA are both target nucleic acids of a single compound. In certain such embodiments, the target region is entirely within an intron of a target pre-mRNA. In certain embodiments, the target region spans an intron/exon junction. In certain embodiments, the target region is at least 50% within an intron. Target nucleic acid sequences that encode DNM2 include, without limitation, the following: RefSeq or GenBank Accession No. NC_000019.10 truncated from nucleosides 10715001 to 10835000, NM_004945.3, NM_001005361.2, or NM_001005360.2 (SEQ ID Nos: 1, 2, 3, and 3135, respectively).

Hybridization

In some embodiments, hybridization occurs between a compound disclosed herein and a DNM2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a DNM2 nucleic acid.

Complementarity

In certain embodiments, compounds described herein comprise or consist of modified oligonucleotides. In certain embodiments, compounds described herein are antisense compounds. In certain embodiments, compounds comprise oligomeric compounds. In certain embodiments, oligonucleotides complementary to a DNM2 nucleic acid comprise nucleobase that are non-complementary with the DNM2 nucleic acid, yet may be tolerated provided that the compound remains able to specifically hybridize to a target nucleic acid. Moreover, a compound may hybridize over one or more segments of a DNM2 nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a DNM2 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a DNM2 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be 100% complementary to a DNM2 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap segment. In certain such embodiments, the mismatch is at position 9, 8, 7, 6, 5, 4, 3, 2, 1 from the 3'-end of the gap segment. In certain such embodiments, the mismatch is at position 1, 2, 3, or 4 from the 5'-end of the wing segment. In certain such embodiments, the mismatch is at position 4, 3, 2, or 1 from the 3'-end of the wing segment. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 1, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e., linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a DNM2 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a DNM2 nucleic acid, or specified portion thereof.

In certain embodiments, compounds described herein also include those which are complementary to a portion (a defined number of contiguous nucleobases within a region or segment) of a target nucleic acid. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Certain Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

I. Modifications

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-C—H(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al.,; Wengel et a., U.S. Pat. No. 7,053,207; Imanishi et al., U.S. Pat. No. 6,268,490; Imanishi et al. U.S. Pat. No. 6,770,748; Imanishi et al., U.S. Pat. No. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

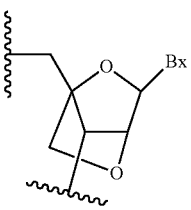

LNA (β-D-configuration)
bridge = 4'-CH$_2$——O-2'

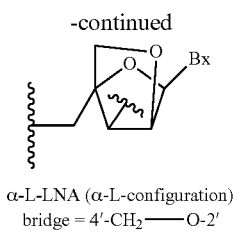

α-L-LNA (α-L-configuration)
bridge = 4'-CH$_2$——O-2'

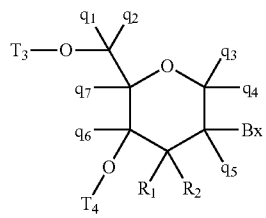

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

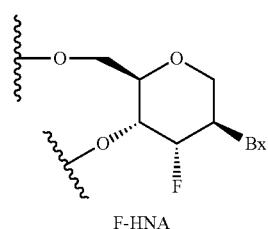

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

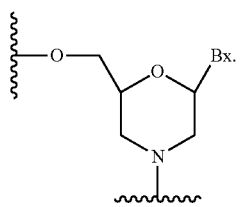

In certain embodiments, morpholinos may be modified, for example by adding or altering various substituent groups from the above morpholino structure. Such sugar surrogates are refered to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Modified Nucleobases

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds comprise or consist of a modified oligonucleotide complementary to an α-DNM2 nucleic acid comprising one or more modified nucleobases. In certain embodiments, the modified nucleobase is 5-methylcytosine. In certain embodiments, each cytosine is a 5-methylcytosine.

B. Modified Internucleoside Linkages

In certain embodiments, compounds described herein having one or more modified internucleoside linkages are selected over compounds having only phosphodiester internucleoside linkages because of desirable properties such as, for example, enhanced cellular uptake, enhanced affinity for target nucleic acids, and increased stability in the presence of nucleases.

In certain embodiments, compounds comprise or consist of a modified oligonucleotide complementary to a DNM2 nucleic acid comprising one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS-P═S"). Representative non-phosphorus containing internucleoside linking groups include but are not limited to methylenemethylimino (—CH$_2$—N(CH$_3$)—O—CH$_2$—), thiodiester, thionocarbamate (—O—C(═O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

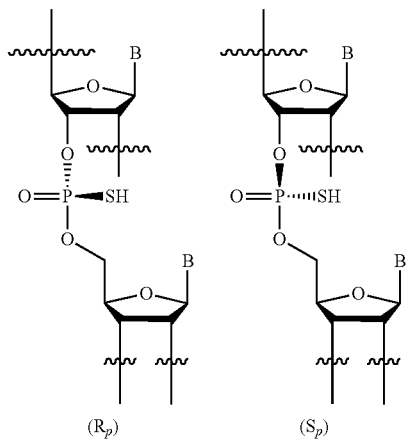

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—$N(CH_3)$—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

II. Certain Motifs

In certain embodiments, compounds described herein comprise or consist of oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, compounds described herein comprise or consist of oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external segments or "wings" and a central or internal segment or "gap." The three segments of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are immediately adjacent to the gap (the 3'-terminal wing nucleoside of the 5'-wing and the 5'-terminal wing nucleoside of the 3'-wing) differ from the sugar moiety of the adjacent gap nucleosides. In certain embodiments, the sugar moieties within the gap are the same as one another. In certain embodiments, the gap includes one or more nucleoside having a sugar moiety that differs from the sugar moiety of one or more other nucleosides of the gap.

In certain embodiments, the wings of a gapmer each comprise 1-5 nucleosides. In certain embodiments, the wings of a gapmer each comprise 2-5 nucleosides. In certain embodiments, the wings of a gapmer each comprise 3-5 nucleosides. In certain embodiments, the nucleosides of the wings of a gapmer are all modified nucleosides. In certain such embodiments, the sugar moieties of the wings of a gapmer are all modified sugar moieties.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiments, each nucleoside of the gap of a gapmer is a 2'-deoxynucleoside.

In certain embodiments, the gapmer is a deoxy gapmer. In such embodiments, the nucleosides on the gap side of each wing/gap junction are 2'-deoxynucleosides and the terminal wing nucleosides immediately adjacent to the gap comprise modified sugar moieties. In certain such embodiments, each nucleoside of the gap is a 2'-deoxynucleoside. In certain such embodiments, each nucleoside of each wing comprises a modified sugar moiety.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

B. Certain Nucleobase Motifs

In certain embodiments, compounds described herein comprise or consist of oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

C. Certain Internucleoside Linkage Motifs

In certain embodiments, compounds described herein comprise or consist of oligonucleotides. In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are phosphorothioate internucleoside linkages. In certain embodiments, all of the internucleoside linkages of the oligonucleotide are phosphorothioate internucleoside linkages. In certain embodiments, each internucleoside linkage of the oligonucleotide is selected from phosphodiester or phophate and phosphorothioate. In certain embodiments, each internucleoside linkage of the oligonucleotide is selected from phosphodiester or phosphate and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the gap of an oligonucleotide having a gapmer sugar motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

III. Certain Modified Oligonucleotides

In certain embodiments, compounds described herein comprise or consist of modified oligonucleotides. In certain embodiments, the above modifications (sugar, nucleobase, internucleoside linkage) are incorporated into a modified oligonucleotide. In certain embodiments, modified oligonucleotides are characterized by their modifications, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions or segments, A, B, and C, wherein region or segment A consists of 2-6 linked nucleosides having a specified sugar motif, region or segment B consists of 6-10 linked nucleosides having a specified sugar motif, and region or segment C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of 20 for the overall length of the modified oligonucleotide. Unless otherwise indicated, all modifications are independent of nucleobase sequence except that the modified nucleobase 5-methylcytosine is necessarily a "C" in an oligonucleotide sequence.

In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker that links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.* 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic, a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, i, 923-937), a tocopherol group (Nishina et al., *Molecular Therapy Nucleic Acids*, 2015, 4, e220; doi:10.1038/mtna.2014.72 and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

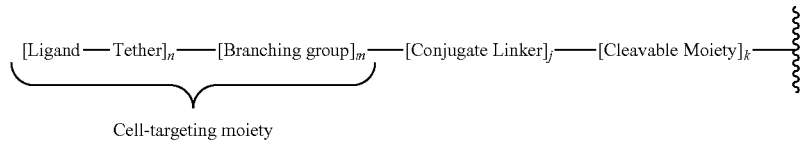

Cell-targeting moiety wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," Bioconjugate Chemistry, 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," J. Med. Chem. 2004, 47, 5798-5808, which are incorporated herein by reference in their entirety).

In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments compounds described herein comprise a conjugate group found in any of the following references: Lee, Carbohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycobiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromb Vasc Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Compositions and Methods for Formulating Pharmaceutical Compositions

Compounds described herein may be admixed with pharmaceutically acceptable active or inert substances for the preparation of pharmaceutical compositions. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. Certain embodiments provide pharmaceutical compositions comprising one or more compounds described herein or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises or consists of one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein complementary to a DNM2 nucleic acid can be utilized in pharmaceutical compositions by combining the compound with a suitable pharmaceutically acceptable diluent or carrier and/or additional components such that the pharmaceutical composition is suitable for injection. In certain embodiments, a pharmaceutically acceptable diluent is phosphate buffered saline. Accordingly, in one embodiment, employed in the methods described herein is a pharmaceutical composition comprising a compound complementary to a DNM2 nucleic acid and a pharmaceutically acceptable diluent. In certain embodiments, the pharmaceutically acceptable diluent is phosphate buffered saline. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

EXAMPLES

The Examples below describe the screening process used to identify lead compounds targeted to DNM2. Out of over 3,000 oligonucleotides that were screened, many potent and tolerable oligonucleotides were identified, and compounds 951799, 949935, 950023, 950089, 951372, 950060, and 950132 emerged as the top lead compounds. In particular, compound 951799 exhibited the best combination of properties in terms of potency and tolerability.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine nucleobase could be described as a DNA having an RNA sugar, or as an RNA having a DNA nucleobase.

Accordingly, nucleic acid sequences provided herein, including, but not limited to those in the sequence listing, are intended to encompass nucleic acids containing any combination of unmodified or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Effect of Modified Oligonucleotides Complementary to Dynamin 2 In Vitro Modified oligonucleotides complementary to one or more dynamin 2 (DNM2) nucleic acids were designed and tested for their effect on dynamin 2 mRNA expression in vitro. The modified oligonucleotides were tested in a series of experiments that had similar culture conditions.

A431 cells were cultured at a density of 10,000 cells per well and treated with 4,000 nM modified oligonucleotide via free uptake or no modified oligonucleotide for untreated controls. After approximately 24 hours, RNA was isolated from the cells and DNM2 mRNA levels were measured by quantitative real-time PCR. Human primer probe set RTS36027 (forward sequence GACCTCATGCCAAAGAC-CAT, designated herein as SEQ ID NO: 4; reverse sequence GTCTGCCGAGGAGTATAGGTA, designated herein as SEQ ID NO: 5; probe sequence CCTTCATCCAC-CACGAGCTGCT, designated herein as SEQ ID: 6) was used to measure mRNA levels. DNM2 mRNA levels were normalized to total RNA content, as measured by RIBOGREEN®. Results are presented in the tables below as normalized DNM2 mRNA level, relative to untreated control cells.

The modified oligonucleotides in the tables below each have a 3-10-3 cEt gapmer motif, wherein the central gap segment contains ten 2'-deoxynucleosides and is flanked by wing segments on the 3' and 5' ends, each containing three cEt nucleosides. All cytosine residues throughout each modified oligonucleotide are 5-methyl cytosines. All internucleoside linkages are phosphorothioate internucleoside linkages.

Each modified oligonucleotide listed in the table below is 100% complementary to human DNM2 nucleic acid sequence GENBANK Number NC_000019.10, truncated from 10715001 to 1083500 (designated herein as SEQ ID NO: 1) and/or GENBANK Number NM_004945.3 (designated herein as SEQ ID NO: 2). "Start Site" indicates the 5'-most nucleoside of the DNM2 nucleic acid to which the oligonucleotide is complementary. "Stop Site" indicates the 3'-most nucleoside of the DNM2 nucleic acid to which the oligonucleotide is complementary. 'N/A' indicates that the modified oligonucleotide is not 100% complementary to the particular nucleic acid. Several oligonucleotides match two or more sites on a nucleic acid, as shown in the table below.

As shown below, modified oligonucleotides complementary to human DNM2 inhibited human DNM2 mRNA expression.

TABLE 1

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 694793 | 3066 | 3081 | CTCAGGCGACACCCGA | 96 | 14 | 29 | 7 |
| 694833 | 60707 | 60722 | GATGAGGGTCAAGTTC | 20 | 580 | 595 | 8 |
| 694838 | 60773 | 60788 | CTTGATCTGGTACTCG | 5 | 646 | 661 | 9 |
| 694852 | N/A | N/A | GTCCGTAGGCCTTGGG | 46 | 774 | 789 | 10 |
| 694853 | 62119 | 62134 | ACCGATGGTCCGTAGG | 76 | 781 | 796 | 11 |
| 695014 | 115999 | 116014 | AATGGTGGGCCGGCTG | 99 | N/A | N/A | 12 |
| 695171 | 82451 | 82466 | ACACACTTCAAACTCG | 7 | N/A | N/A | 13 |
| 695171 | 82451 | 82466 | ACACACTTCAAACTCG | 9 | N/A | N/A | 13 |
| 695171 | 82451 | 82466 | ACACACTTCAAACTCG | 5 | N/A | N/A | 13 |
| 695171 | 82451 | 82466 | ACACACTTCAAACTCG | 6 | N/A | N/A | 13 |
| 695171 | 82451 | 82466 | ACACACTTCAAACTCG | 7 | N/A | N/A | 13 |
| 695171 | 82451 | 82466 | ACACACTTCAAACTCG | 8 | N/A | N/A | 13 |
| 695171 | 82451 | 82466 | ACACACTTCAAACTCG | 6 | N/A | N/A | 13 |
| 695171 | 82451 | 82466 | ACACACTTCAAACTCG | 6 | N/A | N/A | 13 |
| 907925 | 3055 | 3070 | CCCGACCCGAGCGACC | 96 | 3 | 18 | 14 |
| 907926 | 3057 | 3072 | CACCCGACCCGAGCGA | 77 | 5 | 20 | 15 |
| 907927 | 3059 | 3074 | GACACCCGACCCGAGC | 115 | 7 | 22 | 16 |
| 907928 | 3062 | 3077 | GGCGACACCCGACCCG | 96 | 10 | 25 | 17 |
| 907929 | 3069 | 3084 | GTTCTCAGGCGACACC | 101 | 17 | 32 | 18 |
| 907930 | 3072 | 3087 | CCGGTTCTCAGGCGAC | 95 | 20 | 35 | 19 |
| 907931 | 3075 | 3090 | CATCCGGTTCTCAGGC | 58 | 23 | 38 | 20 |
| 907932 | 3078 | 3093 | CCTCATCCGGTTCTCA | 47 | 26 | 41 | 21 |
| 907933 | 3083 | 3098 | CGCCGCCTCATCCGGT | 69 | 31 | 46 | 22 |
| 907934 | 3086 | 3101 | GGTCGCCGCCTCATCC | 65 | 34 | 49 | 23 |
| 907935 | 3089 | 3104 | CACGGTCGCCGCCTCA | 29 | 37 | 52 | 24 |
| 907936 | 3091 | 3106 | CTCACGGTCGCCGCCT | 42 | 39 | 54 | 25 |
| 907937 | 3093 | 3108 | GCCTCACGGTCGCCGC | 65 | 41 | 56 | 26 |
| 907938 | 3095 | 3110 | CGGCCTCACGGTCGCC | 106 | 43 | 58 | 27 |
| 907939 | 3098 | 3113 | GCTCGGCCTCACGGTC | 44 | 46 | 61 | 28 |
| 907940 | 3101 | 3116 | CCGGCTCGGCCTCACG | 87 | 49 | 64 | 29 |
| 907941 | 3111 | 3126 | ACGCCCGCTCCCGGCT | 100 | 59 | 74 | 30 |
| 907942 | 3123 | 3138 | GGCCTCGGCAAGACGC | 96 | 71 | 86 | 31 |
| 907943 | 3126 | 3141 | CCGGGCCTCGGCAAGA | 97 | 74 | 89 | 32 |
| 907944 | 3129 | 3144 | CGCCCGGGCCTCGGCA | 84 | 77 | 92 | 33 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 907945 | 3144 | 3159 | CCGTTGCTCCCCGCCC | 5 | 92 | 107 | 34 |
| 907946 | 3146 | 3161 | AGCCGTTGCTCCCCGC | 12 | 94 | 109 | 35 |
| 907947 | 3149 | 3164 | TGTAGCCGTTGCTCCC | 10 | 97 | 112 | 36 |
| 907948 | 3153 | 3168 | CGTCTGTAGCCGTTGC | 8 | 101 | 116 | 37 |
| 907949 | 3171 | 3186 | AACGACCTGGCCCCGC | 12 | 119 | 134 | 38 |
| 907950 | 3177 | 3192 | ACCCTCAACGACCTGG | 41 | 125 | 140 | 39 |
| 907951 | 3180 | 3195 | CCGACCCTCAACGACC | 26 | 128 | 143 | 40 |
| 907952 | 3182 | 3197 | CGCCGACCCTCAACGA | 54 | 130 | 145 | 41 |
| 907953 | 3186 | 3201 | CCGCCGCCGACCCTCA | 35 | 134 | 149 | 42 |
| 907954 | 3190 | 3205 | TCGCCCGCCGCCGACC | 61 | 138 | 153 | 43 |
| 907955 | 3196 | 3211 | CGCTCCTCGCCCGCCG | 52 | 144 | 159 | 44 |
| 907956 | 3198 | 3213 | TGCGCTCCTCGCCCGC | 120 | 146 | 161 | 45 |
| 907957 | 3201 | 3216 | CCCTGCGCTCCTCGCC | 32 | 149 | 164 | 46 |
| 907958 | 3204 | 3219 | GCGCCCTGCGCTCCTC | 105 | 152 | 167 | 47 |
| 907959 | 3220 | 3235 | GCGGCCCCCGGCCCGA | 90 | 168 | 183 | 48 |
| 907960 | 3302 | 3317 | CTGGCCGATGGAGCTG | 129 | 250 | 265 | 49 |
| 907961 | 3304 | 3319 | CTCTGGCCGATGGAGC | 70 | 252 | 267 | 50 |
| 907962 | 3308 | 3323 | GCAGCTCTGGCCGATG | 46 | 256 | 271 | 51 |
| 907963 | N/A | N/A | GGGAAGGAAGTCCCGG | 97 | 349 | 364 | 52 |
| 907964 | 44749 | 44764 | ATTCCTGAACCGCGGG | 89 | 363 | 378 | 53 |
| 907965 | 44751 | 44766 | CGATTCCTGAACCGCG | 47 | 365 | 380 | 54 |
| 907966 | 44753 | 44768 | GACGATTCCTGAACCG | 11 | 367 | 382 | 55 |
| 907967 | 57491 | 57506 | GACTTGCAGTGCAAAA | 6 | 438 | 453 | 56 |
| 907968 | 57493 | 57508 | TGGACTTGCAGTGCAA | 15 | 440 | 455 | 57 |
| 907969 | 57495 | 57510 | TTTGGACTTGCAGTGC | 2 | 442 | 457 | 58 |
| 907970 | 57499 | 57514 | ACTTTTGGACTTGCA | 5 | 446 | 461 | 59 |
| 907971 | 57526 | 57541 | CCTGCCGGACTTCATC | 17 | 473 | 488 | 60 |
| 907972 | 57529 | 57544 | TCTCCTGCCGGACTTC | 13 | 476 | 491 | 61 |
| 907973 | 57532 | 57547 | CAATCTCCTGCCGGAC | 20 | 479 | 494 | 62 |
| 907974 | 57534 | 57549 | TTCAATCTCCTGCCGG | 25 | 481 | 496 | 63 |
| 907975 | 60711 | 60726 | GGTCGATGAGGGTCAA | 8 | 584 | 599 | 64 |
| 907976 | 60716 | 60731 | CGGGAGGTCGATGAGG | 66 | 589 | 604 | 65 |
| 907977 | 60718 | 60733 | CCCGGGAGGTCGATGA | 117 | 591 | 606 | 66 |
| 907978 | 60722 | 60737 | GATACCCGGGAGGTCG | 55 | 595 | 610 | 67 |
| 907979 | 60724 | 60739 | GTGATACCCGGGAGGT | 11 | 597 | 612 | 68 |
| 907980 | 60728 | 60743 | CTTGGTGATACCCGGG | 57 | 601 | 616 | 69 |
| 907981 | 60734 | 60749 | AGGCACCTTGGTGATA | 40 | 607 | 622 | 70 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 907982 | 60776 | 60791 | GTCCTTGATCTGGTAC | 28 | 649 | 664 | 71 |
| 907983 | 60778 | 60793 | ATGTCCTTGATCTGGT | 8 | 651 | 666 | 72 |
| 907984 | 60784 | 60799 | AGGATCATGTCCTTGA | 58 | 657 | 672 | 73 |
| 907985 | 60788 | 60803 | CTGCAGGATCATGTCC | 35 | 661 | 676 | 74 |
| 907986 | 60798 | 60813 | GGCTGATGAACTGCAG | 56 | 671 | 686 | 75 |
| 907987 | 60806 | 60821 | GCTCTCCCGGCTGATG | 40 | 679 | 694 | 76 |
| 907988 | 60809 | 60824 | GCTGCTCTCCCGGCTG | 68 | 682 | 697 | 77 |
| 907989 | 60826 | 60841 | GTGACAGCCAGAATGA | 26 | 699 | 714 | 78 |
| 907990 | 60842 | 60857 | GTCCATGTTGGCGGGC | 66 | 715 | 730 | 79 |
| 907991 | 60882 | 60897 | CGACTTCCTTGGCCAG | 68 | 755 | 770 | 80 |
| 907992 | 60884 | 60899 | ATCGACTTCCTTGGCC | 99 | 757 | 772 | 81 |
| 907993 | N/A | N/A | TGGTCCGTAGGCCTTG | 72 | 776 | 791 | 82 |
| 907994 | 62116 | 62131 | GATGGTCCGTAGGCCT | 68 | 778 | 793 | 83 |
| 907995 | 62195 | 62210 | TCAACGGGAGCAACTT | 18 | 857 | 872 | 84 |
| 907996 | N/A | N/A | GCCTCTTCTCAACGGG | 105 | 865 | 880 | 85 |
| 907997 | N/A | N/A | TAGCCTCTTCTCAACG | 17 | 867 | 882 | 86 |
| 907998 | 68005 | 68020 | GCACGGATGTCCTTCT | 8 | 924 | 939 | 87 |
| 907999 | 68008 | 68023 | GCTGCACGGATGTCCT | 25 | 927 | 942 | 88 |
| 908000 | 68013 | 68028 | CCAGTGCTGCACGGAT | 17 | 932 | 947 | 89 |
| 908001 | 68057 | 68072 | GTGCCGGTAGGCCGGG | 91 | 976 | 991 | 90 |
| 908002 | 68059 | 68074 | ATGTGCCGGTAGGCCG | 83 | 978 | 993 | 91 |
| 908003 | 68062 | 68077 | GCCATGTGCCGGTAGG | 77 | 981 | 996 | 92 |
| 908004 | 68064 | 68079 | CGGCCATGTGCCGGTA | 90 | 983 | 998 | 93 |
| 908005 | 68096 | 68111 | CGTCTTCTGCAGATGT | 26 | 1015 | 1030 | 94 |
| 908006 | 71583 | 71598 | GCCGGCAGCGACTCCC | 107 | 1059 | 1074 | 95 |
| 908007 | 71586 | 71601 | AGGGCCGGCAGCGACT | 64 | 1062 | 1077 | 96 |
| 908008 | 71589 | 71604 | CGTAGGGCCGGCAGCG | 67 | 1065 | 1080 | 97 |
| 908009 | 71603 | 71618 | TCTGTAGTTTGCTACG | 34 | 1079 | 1094 | 98 |
| 908010 | 71605 | 71620 | GCTCTGTAGTTTGCTA | 42 | 1081 | 1096 | 99 |
| 908011 | 71659 | 71674 | GTCGGGCCGAAAGTTC | 15 | 1135 | 1150 | 100 |
| 908012 | 71681 | 71696 | CTTTGGTTTTGCGGGT | 36 | 1157 | 1172 | 101 |
| 908013 | 78772 | 78787 | GAGTGTCCACCTGATC | 11 | 1235 | 1250 | 102 |
| 908014 | 78786 | 78801 | CCCGGAGAGCTCCAGA | 58 | 1249 | 1264 | 103 |
| 908015 | 78789 | 78804 | GCCCCCGGAGAGCTCC | 71 | 1252 | 1267 | 104 |
| 908016 | 78791 | 78806 | GCGCCCCGGAGAGCT | 129 | 1254 | 1269 | 105 |
| 908017 | 78804 | 78819 | GCGATTGATTCGGGCG | 50 | 1267 | 1282 | 106 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908018 | 78808 | 78823 | AGATGCGATTGATTCG | 14 | 1271 | 1286 | 107 |
| 908019 | 80422 | 80437 | GACTCCATGGATGTTC | 91 | 1369 | 1384 | 108 |
| 908020 | N/A | N/A | GCCCGGTCCTGACTCC | 54 | 1379 | 1394 | 109 |
| 908021 | N/A | N/A | AAGCCCGGTCCTGACT | 81 | 1381 | 1396 | 110 |
| 908022 | 81058 | 81073 | GAAAAGCCCGGTCCTG | 35 | 1384 | 1399 | 111 |
| 908023 | 81061 | 81076 | GGTGAAAAGCCCGGTC | 58 | 1387 | 1402 | 112 |
| 908024 | 81076 | 81091 | GAATGCCAAGTCCGGG | 43 | 1402 | 1417 | 113 |
| 908025 | 81079 | 81094 | CTCGAATGCCAAGTCC | 8 | 1405 | 1420 | 114 |
| 908026 | 81082 | 81097 | GGCCTCGAATGCCAAG | 169 | 1408 | 1423 | 115 |
| 908027 | 81103 | 81118 | GACGACCTGCTTTTTC | 4 | 1429 | 1444 | 116 |
| 908028 | 81106 | 81121 | CTTGACGACCTGCTTT | 13 | 1432 | 1447 | 117 |
| 908029 | 81107 | 81122 | GCTTGACGACCTGCTT | 14 | 1433 | 1448 | 118 |
| 908030 | 81109 | 81124 | CAGCTTGACGACCTGC | 33 | 1435 | 1450 | 119 |
| 908031 | 81111 | 81126 | TTCAGCTTGACGACCT | 5 | 1437 | 1452 | 120 |
| 908032 | 81113 | 81128 | CTTTCAGCTTGACGAC | 22 | 1439 | 1454 | 121 |
| 908033 | 81115 | 81130 | CTCTTTCAGCTTGACG | 7 | 1441 | 1456 | 122 |
| 908034 | 81137 | 81152 | GGTCGACACATTTCAG | 13 | 1463 | 1478 | 123 |
| 908035 | 81139 | 81154 | CAGGTCGACACATTTC | 2 | 1465 | 1480 | 124 |
| 908036 | 81147 | 81162 | TGGATAACCAGGTCGA | 14 | 1473 | 1488 | 125 |
| 908037 | 81160 | 81175 | ATTGATTAGCTCCTGG | 2 | 1486 | 1501 | 126 |
| 908038 | 81170 | 81185 | GCCTAACTGTATTGAT | 22 | 1496 | 1511 | 127 |
| 908039 | 81172 | 81187 | CTGCCTAACTGTATTG | 28 | 1498 | 1513 | 128 |
| 908040 | 81175 | 81190 | ACACTGCCTAACTGTA | 54 | 1501 | 1516 | 129 |
| 908041 | 81182 | 81197 | TACTGGTACACTGCCT | 4 | 1508 | 1523 | 130 |
| 908042 | N/A | N/A | CTGAGCTTACTGGTAC | 19 | 1515 | 1530 | 131 |
| 908043 | N/A | N/A | GAACTGAGCTTACTGG | 10 | 1518 | 1533 | 132 |
| 908044 | N/A | N/A | GGTAGGAACTGAGCTT | 8 | 1523 | 1538 | 133 |
| 908045 | 83499 | 83514 | TCCTCTCGCAACCGGG | 46 | 1539 | 1554 | 134 |
| 908046 | 83502 | 83517 | GTCTCCTCTCGCAACC | 34 | 1542 | 1557 | 135 |
| 908047 | 83505 | 83520 | TCTGTCTCCTCTCGCA | 11 | 1545 | 1560 | 136 |
| 908048 | 83517 | 83532 | GTGACGATTCGCTCTG | 48 | 1557 | 1572 | 137 |
| 908049 | 83522 | 83537 | AAGTGGTGACGATTCG | 5 | 1562 | 1577 | 138 |
| 908050 | 83524 | 83539 | GTAAGTGGTGACGATT | 17 | 1564 | 1579 | 139 |
| 908051 | 83536 | 83551 | CCGTTCCCGGATGTAA | 86 | 1576 | 1591 | 140 |
| 908052 | 83548 | 83563 | CGTTCTCCCCTCCCGT | 9 | 1588 | 1603 | 141 |
| 908053 | N/A | N/A | CAGAAGAATCTGGTCC | 33 | 1606 | 1621 | 142 |
| 908054 | 87290 | 87305 | GTCGATCAGCAGAAGA | 33 | 1615 | 1630 | 143 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908055 | 87294 | 87309 | CAATGTCGATCAGCAG | 16 | 1619 | 1634 | 144 |
| 908056 | 87296 | 87311 | CTCAATGTCGATCAGC | 10 | 1621 | 1636 | 145 |
| 908057 | 87299 | 87314 | CTGCTCAATGTCGATC | 18 | 1624 | 1639 | 146 |
| 908058 | 87302 | 87317 | GGACTGCTCAATGTCG | 58 | 1627 | 1642 | 147 |
| 908059 | 87304 | 87319 | TAGGACTGCTCAATGT | 3 | 1629 | 1644 | 148 |
| 908060 | 87308 | 87323 | GATGTAGGACTGCTCA | 19 | 1633 | 1648 | 149 |
| 908061 | 87311 | 87326 | GTTGATGTAGGACTGC | 3 | 1636 | 1651 | 150 |
| 908062 | 97288 | 97303 | GGCTGATGTTGTTGAT | 31 | 1760 | 1775 | 151 |
| 908063 | 97290 | 97305 | CAGGCTGATGTTGTTG | 36 | 1762 | 1777 | 152 |
| 908064 | 97294 | 97309 | TCATCAGGCTGATGTT | 100 | 1766 | 1781 | 153 |
| 908065 | 97299 | 97314 | GCCTTTCATCAGGCTG | 89 | 1771 | 1786 | 154 |
| 908066 | 97338 | 97353 | TGACTCGGCAGTCAGC | 86 | 1810 | 1825 | 155 |
| 908067 | 97341 | 97356 | CAGTGACTCGGCAGTC | 24 | 1813 | 1828 | 156 |
| 908068 | 97345 | 97360 | AGGACAGTGACTCGGC | 17 | 1817 | 1832 | 157 |
| 908069 | 105015 | 105030 | ATCACGGATCTTGAGG | 40 | 1885 | 1900 | 158 |
| 908070 | 105019 | 105034 | CCACATCACGGATCTT | 12 | 1889 | 1904 | 159 |
| 908071 | 105020 | 105035 | TCCACATCACGGATCT | 31 | 1890 | 1905 | 160 |
| 908072 | 105022 | 105037 | TCTCCACATCACGGAT | 72 | 1892 | 1907 | 161 |
| 908073 | 105060 | 105075 | GAAGATGGCGAAGACG | 81 | 1930 | 1945 | 162 |
| 908074 | 108791 | 108806 | CAGGTCCTTGTAGACG | 60 | 1963 | 1978 | 163 |
| 908075 | 108804 | 108819 | GCTCGATCTGCCGCAG | 55 | 1976 | 1991 | 164 |
| 908076 | 108806 | 108821 | CAGCTCGATCTGCCGC | 54 | 1978 | 1993 | 165 |
| 908077 | 108857 | 108872 | TCGGAGGAACGAGGCC | 80 | 2029 | 2044 | 166 |
| 908078 | 108859 | 108874 | GCTCGGAGGAACGAGG | 67 | 2031 | 2046 | 167 |
| 908079 | 108861 | 108876 | CAGCTCGGAGGAACGA | 59 | 2033 | 2048 | 168 |
| 908080 | 108863 | 108878 | GCCAGCTCGGAGGAAC | 93 | 2035 | 2050 | 169 |
| 908081 | N/A | N/A | GCCTGGTCCTTCTCGG | 70 | 2058 | 2073 | 170 |
| 908082 | 110075 | 110090 | AGGTGTTCTCCTGGGC | 74 | 2090 | 2105 | 171 |
| 908083 | 110077 | 110092 | GAAGGTGTTCTCCTGG | 81 | 2092 | 2107 | 172 |
| 908084 | 110080 | 110095 | GGAGAAGGTGTTCTCC | 119 | 2095 | 2110 | 173 |
| 908085 | 110160 | 110175 | ATGGACTTGTTGATGA | 11 | 2175 | 2190 | 174 |
| 908086* | 110166 | 110181 | TCGCGGATGGACTTGT | 36 | 2181 | 2196 | 175 |
| 908087* | 110168 | 110183 | GGTCGCGGATGGACTT | 58 | 2183 | 2198 | 176 |
| 908088* | 110171 | 110186 | TGAGGTCGCGGATGGA | 4 | 2186 | 2201 | 177 |
| 908089* | 114042 | 114057 | CGTGGTGGATGAAGGC | 3 | 2243 | 2258 | 178 |
| 908090* | 114069 | 114084 | CCGAGGAGTATAGGTA | 17 | 2270 | 2285 | 179 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908091* | 114072 | 114087 | CTGCCGAGGAGTATAG | 14 | 2273 | 2288 | 180 |
| 908092* | 114074 | 114089 | GTCTGCCGAGGAGTAT | 11 | 2275 | 2290 | 181 |
| 908093* | 114077 | 114092 | CTGGTCTGCCGAGGAG | 9 | 2278 | 2293 | 182 |
| 908094* | 114080 | 114095 | GCTCTGGTCTGCCGAG | 39 | 2281 | 2296 | 183 |
| 908095 | 115141 | 115156 | CTGGACACCGGTCGGC | 39 | 2484 | 2499 | 184 |
| 908096 | 115144 | 115159 | ATGCTGGACACCGGTC | 47 | 2487 | 2502 | 185 |
| 908097 | 115146 | 115161 | GTATGCTGGACACCGG | 33 | 2489 | 2504 | 186 |
| 908098 | 115150 | 115165 | GGGTGTATGCTGGACA | 11 | 2493 | 2508 | 187 |
| 908099 | 115214 | 115229 | CACGGGAACAGGAATC | 25 | 2557 | 2572 | 188 |
| 908100 | 115221 | 115236 | CTGCCCCCACGGGAAC | 80 | 2564 | 2579 | 189 |
| 908101 | 115238 | 115253 | CGCCGAGAAGGAGGCT | 97 | 2581 | 2596 | 190 |
| 908102 | 115283 | 115298 | GTTGGCAAACACGCTC | 16 | 2626 | 2641 | 191 |
| 908103 | 115285 | 115300 | CTGTTGGCAAACACGC | 30 | 2628 | 2643 | 192 |
| 908104 | 115292 | 115307 | GAGGTCACTGTTGGCA | 9 | 2635 | 2650 | 193 |
| 908105 | 115324 | 115339 | GGCCGAGATGGGATCT | 73 | 2667 | 2682 | 194 |
| 908106 | 115326 | 115341 | CTGGCCGAGATGGGAT | 45 | 2669 | 2684 | 195 |
| 908107 | 115329 | 115344 | GAACTGGCCGAGATGG | 6 | 2672 | 2687 | 196 |
| 908108 | 115332 | 115347 | TCCGAACTGGCCGAGA | 33 | 2675 | 2690 | 197 |
| 908109 | 115336 | 115351 | GGGATCCGAACTGGCC | 82 | 2679 | 2694 | 198 |
| 908110 | 116010 | 116025 | GCTGGGCGGATAATGG | 45 | 2754 | 2769 | 199 |
| 908111 | 116015 | 116030 | GCTCGGCTGGGCGGAT | 101 | 2759 | 2774 | 200 |
| 908112 | 116017 | 116032 | TGGCTCGGCTGGGCGG | 89 | 2761 | 2776 | 201 |
| 908113 | 116022 | 116037 | AGGGATGGCTCGGCTG | 75 | 2766 | 2781 | 202 |
| 908114 | 116030 | 116045 | AGTCGAGCAGGGATGG | 53 | 2774 | 2789 | 203 |
| 908115 | 116035 | 116050 | GGCCTAGTCGAGCAGG | 104 | 2779 | 2794 | 204 |
| 908116 | 116038 | 116053 | CGAGGCCTAGTCGAGC | 79 | 2782 | 2797 | 205 |
| 908117 | 116042 | 116057 | CCCTCGAGGCCTAGTC | 87 | 2786 | 2801 | 206 |
| 908118 | 116045 | 116060 | CCCCCCTCGAGGCCTA | 69 | 2789 | 2804 | 207 |
| 908119 | 116047 | 116062 | CGCCCCCTCGAGGCC | 89 | 2791 | 2806 | 208 |
| 908120 | 116057 | 116072 | CCCGAGAGCACGCCCC | 40 | 2801 | 2816 | 209 |
| 908121 | 116060 | 116075 | CCCCCCGAGAGCACGC | 38 | 2804 | 2819 | 210 |
| 908122 | 116063 | 116078 | GGCCCCCCCGAGAGCA | 95 | 2807 | 2822 | 211 |
| 908123 | 116068 | 116083 | CGTGAGGCCCCCCCGA | 67 | 2812 | 2827 | 212 |
| 908124 | 116088 | 116103 | AAGCTCCTGCGCCGCG | 55 | 2832 | 2847 | 213 |
| 908125 | 116096 | 116111 | GACCACTGAAGCTCCT | 32 | 2840 | 2855 | 214 |
| 908126 | 116098 | 116113 | CAGACCACTGAAGCTC | 38 | 2842 | 2857 | 215 |
| 908127 | 116108 | 116123 | CGGAGGGCCCCAGACC | 100 | 2852 | 2867 | 216 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908128 | 116110 | 116125 | GGCGGAGGGCCCCAGA | 91 | 2854 | 2869 | 217 |
| 908129 | 116128 | 116143 | TGGTCCCAGCATAGGG | 88 | 2872 | 2887 | 218 |
| 908130 | 116130 | 116145 | CCTGGTCCCAGCATAG | 73 | 2874 | 2889 | 219 |
| 908131 | 116138 | 116153 | ACTGGGAGCCTGGTCC | 72 | 2882 | 2897 | 220 |
| 908132 | 116164 | 116179 | CGTTAAGGAAGAGGCC | 69 | 2908 | 2923 | 221 |
| 908133 | 116209 | 116224 | GCGGTGTCCAGCCAGG | 49 | 2953 | 2968 | 222 |
| 908134 | 116211 | 116226 | GTGCGGTGTCCAGCCA | 37 | 2955 | 2970 | 223 |
| 908135 | 116215 | 116230 | CGCAGTGCGGTGTCCA | 13 | 2959 | 2974 | 224 |
| 908136 | 116218 | 116233 | TTGCGCAGTGCGGTGT | 29 | 2962 | 2977 | 225 |
| 908137 | 116220 | 116235 | CTTTGCGCAGTGCGGT | 15 | 2964 | 2979 | 226 |
| 908138 | 116223 | 116238 | CCCCTTTGCGCAGTGC | 12 | 2967 | 2982 | 227 |
| 908139 | 116226 | 116241 | GGGCCCCTTTGCGCAG | 101 | 2970 | 2985 | 228 |
| 908140 | 116228 | 116243 | CAGGGCCCCTTTGCGC | 92 | 2972 | 2987 | 229 |
| 908141 | 116260 | 116275 | TGCAACACCCCAGCGC | 78 | 3004 | 3019 | 230 |
| 908142 | 116265 | 116280 | CAAAGTGCAACACCCC | 20 | 3009 | 3024 | 231 |
| 908143 | 116268 | 116283 | CCCCAAAGTGCAACAC | 47 | 3012 | 3027 | 232 |
| 908144 | 116300 | 116315 | TGGTCCCCCCTCTGCC | 64 | 3044 | 3059 | 233 |
| 908145 | 116309 | 116324 | CAAGGGTTCTGGTCCC | 45 | 3053 | 3068 | 234 |
| 908146 | 116312 | 116327 | TGTCAAGGGTTCTGGT | 15 | 3056 | 3071 | 235 |
| 908147 | 116314 | 116329 | GGTGTCAAGGGTTCTG | 8 | 3058 | 3073 | 236 |
| 908148 | 116318 | 116333 | GGATGGTGTCAAGGGT | 7 | 3062 | 3077 | 237 |
| 908149 | 116331 | 116346 | GACCCCTCATTCAGGA | 84 | 3075 | 3090 | 238 |
| 908150 | 116333 | 116348 | TGGACCCCTCATTCAG | 64 | 3077 | 3092 | 239 |
| 908151 | 116336 | 116351 | GGCTGGACCCCTCATT | 80 | 3080 | 3095 | 240 |
| 908152 | 116348 | 116363 | GAGTCCCCCCCAGGCT | 63 | 3092 | 3107 | 241 |
| 908153 | 116352 | 116367 | GGTAGAGTCCCCCCCA | 31 | 3096 | 3111 | 242 |
| 908154 | 116356 | 116371 | CCTTGGTAGAGTCCCC | 3 | 3100 | 3115 | 243 |
| 908155 | 116359 | 116374 | AGACCTTGGTAGAGTC | 73 | 3103 | 3118 | 244 |
| 908156 | 116385 | 116400 | CCTACATGGGCTTTCC | 37 | 3129 | 3144 | 245 |
| 908157 | 116389 | 116404 | CTGCCCTACATGGGCT | 115 | 3133 | 3148 | 246 |
| 908158 | 116398 | 116413 | ATAGAAGGCCTGCCCT | 71 | 3142 | 3157 | 247 |
| 908159 | 116400 | 116415 | TTATAGAAGGCCTGCC | 41 | 3144 | 3159 | 248 |
| 908160 | 116404 | 116419 | GCACTTATAGAAGGCC | 70 | 3148 | 3163 | 249 |
| 908161 | 116408 | 116423 | GCCCGCACTTATAGAA | 45 | 3152 | 3167 | 250 |
| 908162 | 116410 | 116425 | GTGCCCGCACTTATAG | 66 | 3154 | 3169 | 251 |
| 908163 | 116418 | 116433 | CGCCCTTGGTGCCCGC | 62 | 3162 | 3177 | 252 |

TABLE 1-continued

| | | | DNM2 mRNA Expression | | | |
|---|---|---|---|---|---|---|
| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908164 | 116455 | 116470 | TATACCCCTGCACCCC | 11 | 3199 | 3214 | 253 |
| 908165 | 116464 | 116479 | GGAAGTTGATATACCC | 29 | 3208 | 3223 | 254 |
| 908166 | 116471 | 116486 | GCTAATGGGAAGTTGA | 13 | 3215 | 3230 | 255 |
| 908167 | 116474 | 116489 | CCTGCTAATGGGAAGT | 14 | 3218 | 3233 | 256 |
| 908168 | 116477 | 116492 | GCTCCTGCTAATGGGA | 139 | 3221 | 3236 | 257 |
| 908169 | 116481 | 116496 | GGGAGCTCCTGCTAAT | 102 | 3225 | 3240 | 258 |
| 908170 | 116497 | 116512 | GCCAGGCTTGCCGCTG | 80 | 3241 | 3256 | 259 |
| 908171 | 116499 | 116514 | GGGCCAGGCTTGCCGC | 87 | 3243 | 3258 | 260 |
| 908172 | 116511 | 116526 | ACCGAGCCCACTGGGC | 72 | 3255 | 3270 | 261 |
| 908173 | 116513 | 116528 | CTACCGAGCCCACTGG | 57 | 3257 | 3272 | 262 |
| 908174 | 116518 | 116533 | GGGCACTACCGAGCCC | 87 | 3262 | 3277 | 263 |
| 908175 | 116523 | 116538 | CAGCTGGGCACTACCG | 86 | 3267 | 3282 | 264 |
| 908176 | 116541 | 116556 | TGTACACCTCAGGCCT | 83 | 3285 | 3300 | 265 |
| 908177 | 116544 | 116559 | CTATGTACACCTCAGG | 10 | 3288 | 3303 | 266 |
| 908178 | 116547 | 116562 | GGACTATGTACACCTC | 7 | 3291 | 3306 | 267 |
| 908179 | 116550 | 116565 | GAAGGACTATGTACAC | 8 | 3294 | 3309 | 268 |
| 908180 | 116556 | 116571 | GGCCGGGAAGGACTAT | 51 | 3300 | 3315 | 269 |
| 908181 | 116558 | 116573 | ATGGCCGGGAAGGACT | 78 | 3302 | 3317 | 270 |
| 908182 | 116561 | 116576 | AATATGGCCGGGAAGG | 19 | 3305 | 3320 | 271 |
| 908183 | 116565 | 116580 | GGTTAATATGGCCGGG | 13 | 3309 | 3324 | 272 |
| 908184 | 116573 | 116588 | GGCTGTGTGGTTAATA | 8 | 3317 | 3332 | 273 |
| 908185 | 116603 | 116618 | CCTCTGGCAGCCGAGG | 100 | 3347 | 3362 | 274 |
| 908186 | 116606 | 116621 | GCACCTCTGGCAGCCG | 73 | 3350 | 3365 | 275 |
| 908187 | 116608 | 116623 | AGGCACCTCTGGCAGC | 61 | 3352 | 3367 | 276 |
| 908188 | 116614 | 116629 | TAGCAAAGGCACCTCT | 41 | 3358 | 3373 | 277 |
| 908189 | 116617 | 116632 | GCCTAGCAAAGGCACC | 146 | 3361 | 3376 | 278 |
| 908190 | 116621 | 116636 | CCGGGCCTAGCAAAGG | 60 | 3365 | 3380 | 279 |
| 908191 | 116624 | 116639 | GCTCCGGGCCTAGCAA | 123 | 3368 | 3383 | 280 |
| 908192 | 116626 | 116641 | CGGCTCCGGGCCTAGC | 97 | 3370 | 3385 | 281 |
| 908193 | 116630 | 116645 | CCAACGGCTCCGGGCC | 117 | 3374 | 3389 | 282 |
| 908194 | 116638 | 116653 | GGCCCGGGCCAACGGC | 109 | 3382 | 3397 | 283 |
| 908195 | 116640 | 116655 | CCGGCCCGGGCCAACG | 104 | 3384 | 3399 | 284 |
| 908196 | 116642 | 116657 | GGCCGGCCCGGGCCAA | 99 | 3386 | 3401 | 285 |
| 908197 | 116644 | 116659 | AAGGCCGGCCCGGGCC | 86 | 3388 | 3403 | 286 |
| 908198 | 116646 | 116661 | GCAAGGCCGGCCCGGG | 88 | 3390 | 3405 | 287 |
| 908199 | 116648 | 116663 | GGGCAAGGCCGGCCCG | 125 | 3392 | 3407 | 288 |
| 908200 | 116650 | 116665 | TAGGGCAAGGCCGGCC | 99 | 3394 | 3409 | 289 |

TABLE 1-continued

| | | | DNM2 mRNA Expression | | | | |
|---|---|---|---|---|---|---|---|
| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
| 908201 | 116655 | 116670 | AGGAATAGGGCAAGGC | 6 | 3399 | 3414 | 290 |
| 908202 | 116712 | 116727 | ACCACCCACATAGCCC | 31 | 3456 | 3471 | 291 |
| 908203 | 116729 | 116744 | CAAGACCCCCCGCCAC | 64 | 3473 | 3488 | 292 |
| 908204 | 116732 | 116747 | CCCCAAGACCCCCCGC | 59 | 3476 | 3491 | 293 |
| 908205 | 116738 | 116753 | AGAGGCCCCCAAGACC | 86 | 3482 | 3497 | 294 |
| 908206 | 116772 | 116787 | GGCCCACCCATCAGGG | 110 | 3516 | 3531 | 295 |
| 908207 | 116774 | 116789 | TGGGCCCACCCATCAG | 127 | 3518 | 3533 | 296 |
| 908208 | 116789 | 116804 | AGAGAGAGGCCGCCCT | 37 | 3533 | 3548 | 297 |
| 908209 | 116791 | 116806 | TCAGAGAGAGGCCGCC | 70 | 3535 | 3550 | 298 |
| 908210 | 116808 | 116823 | GAGTGGGTGAGGTCTC | 77 | 3552 | 3567 | 299 |
| 908211 | 116815 | 116830 | GAGCGAGGAGTGGGTG | 59 | 3559 | 3574 | 300 |
| 908212 | 116819 | 116834 | AACTGAGCGAGGAGTG | 55 | 3563 | 3578 | 301 |
| 908213 | 116822 | 116837 | TCAAACTGAGCGAGGA | 5 | 3566 | 3581 | 302 |
| 908214 | 116826 | 116841 | GTGGTCAAACTGAGCG | 15 | 3570 | 3585 | 303 |
| 908215 | 116832 | 116847 | CTTACAGTGGTCAAAC | 10 | 3576 | 3591 | 304 |
| 908216 | 116843 | 116858 | GAGTGCAGGCACTTAC | 48 | 3587 | 3602 | 305 |
| 908217 | 116849 | 116864 | AATACAGAGTGCAGGC | 4 | 3593 | 3608 | 306 |
| 908221 | 82462 | 82477 | CCACGAGATCAACACA | 20 | N/A | N/A | 307 |
| 908222 | 82464 | 82479 | GACCACGAGATCAACA | 88 | N/A | N/A | 308 |
| 908223 | 82465 | 82480 | AGACCACGAGATCAAC | 82 | N/A | N/A | 309 |
| 908224 | 82468 | 82483 | CTGAGACCACGAGATC | 34 | N/A | N/A | 310 |
| 908225 | 82471 | 82486 | GCTCTGAGACCACGAG | 59 | N/A | N/A | 311 |
| 908226 | 82482 | 82497 | GACCGTGGCCAGCTCT | 52 | N/A | N/A | 312 |
| 908227 | 82484 | 82499 | ATGACCGTGGCCAGCT | 54 | N/A | N/A | 313 |
| 908228 | 82485 | 82500 | TATGACCGTGGCCAGC | 31 | N/A | N/A | 314 |
| 908229 | 82487 | 82502 | TTTATGACCGTGGCCA | 64 | N/A | N/A | 315 |
| 908230 | 82488 | 82503 | TTTTATGACCGTGGCC | 102 | N/A | N/A | 316 |
| 908231 | 82498 | 82513 | CGGCACACTTTTTTAT | 37 | N/A | N/A | 317 |
| 908232 | 82502 | 82517 | TTCTCGGCACACTTTT | 4 | N/A | N/A | 318 |
| 908236 | N/A | N/A | CCCCGCCGCGGGCACG | 103 | 3506 | 3521 | 319 |
| 908237 | 4387 | 4402 | CCAAGGAGGGCCCCC | 88 | N/A | N/A | 320 |
| 908238 | 4857 | 4872 | CGCCAGCCTAGTGGCC | 142 | N/A | N/A | 321 |
| 908239 | 5585 | 5600 | TGGGACTACCACCCTA | 129 | N/A | N/A | 322 |
| 908240 | 6095 | 6110 | CTCCATACTGGCCGGC | 91 | N/A | N/A | 323 |
| 908241 | 6449 | 6464 | CTTAACGAGGCCAGCC | 56 | N/A | N/A | 324 |
| 908242 | 7057 | 7072 | ACCCATCTAGGCCCCA | 23 | N/A | N/A | 325 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908243 | 7335 | 7350 | TGGTGCACCGCAGACA | 61 | N/A | N/A | 326 |
| 908244 | 8045 | 8060 | TCAGGAGGCGAGATTG | 93 | N/A | N/A | 327 |
| 908245 | 8318 | 8333 | CGGGAAAACCCCGCCT | 123 | N/A | N/A | 328 |
| 908246 | 8813 | 8828 | AGCCACTAAGTGGCCC | 130 | N/A | N/A | 329 |
| 908247 | 9601 | 9616 | GCTAAACTGGCCTCCG | 78 | N/A | N/A | 330 |
| 908248 | 9989 | 10004 | GCCAACGGGCATCCGA | 104 | N/A | N/A | 331 |
| 908249 | 10650 | 10665 | GTCCACTCCCAGTAGG | 77 | N/A | N/A | 332 |
| 908250 | 11631 | 11646 | GGTGATCCGATGCTGG | 34 | N/A | N/A | 333 |
| 908251 | 12300 | 12315 | GGCCATCTTCCGCCCT | 102 | N/A | N/A | 334 |
| 908252 | 12662 | 12677 | CTAACCTAGGCCGGGT | 70 | N/A | N/A | 335 |
| 908253 | 12991 | 13006 | AGACGCAGGGCCACAT | 66 | N/A | N/A | 336 |
| 908254 | 13381 | 13396 | GGCTCTAGAGGGCCCA | 110 | N/A | N/A | 337 |
| 908255 | 13954 | 13969 | CCGCATACAGCCTTTT | 12 | N/A | N/A | 338 |
| 908256 | 14620 | 14635 | GCATTCCACGGGCAGC | 34 | N/A | N/A | 339 |
| 908257 | 15396 | 15411 | CACCGCTACCCTAGCT | 63 | N/A | N/A | 340 |
| 908258 | 15792 | 15807 | GGGCACCCCGCAGGTT | 102 | N/A | N/A | 341 |
| 908259 | 16235 | 16250 | TCTAGAAGGACCCTGT | 64 | N/A | N/A | 342 |
| 908260 | 16810 | 16825 | AGCCGGGCTTCCGTCT | 84 | N/A | N/A | 343 |
| 908261 | 17238 | 17253 | TTTAAGGGCGCGGTGG | 99 | N/A | N/A | 344 |
| 908262 | 17624 | 17639 | TGCACTTCCGGACAGG | 82 | N/A | N/A | 345 |
| 908263 | 18173 | 18188 | CACCAGCCCAGGCGCG | 117 | N/A | N/A | 346 |
| 908264 | 18617 | 18632 | AGCTAGGTTAATTTCT | 64 | N/A | N/A | 347 |
| 908265 | 19070 | 19085 | CAACATCCCGCCAGGC | 80 | N/A | N/A | 348 |
| 908266 | 19407 | 19422 | AGCAATCTAGCCTCCC | 39 | N/A | N/A | 349 |
| 908267 | 19819 | 19834 | TGCAATGTCCAGTCCT | 11 | N/A | N/A | 350 |
| 908268 | 20435 | 20450 | ACCTAGCAAGCCTACC | 64 | N/A | N/A | 351 |
| 908269 | 21415 | 21430 | GCTACAGCAATATAGA | 67 | N/A | N/A | 352 |
| 908270 | 21839 | 21854 | TCTTAACAGGCTCCCT | 63 | N/A | N/A | 353 |
| 908271 | 22199 | 22214 | CCTCAGGGACGACTTC | 87 | N/A | N/A | 354 |
| 908272 | 22636 | 22651 | TATACGGGCATGTTGA | 55 | N/A | N/A | 355 |
| 908273 | 22916 | 22931 | GTGCATCCCGAGAGGG | 89 | N/A | N/A | 356 |
| 908274 | 23292 | 23307 | ATGAAAGTCTCCACTT | 61 | N/A | N/A | 357 |
| 908275 | 23543 | 23558 | AACCGCTGGGATCCCC | 71 | N/A | N/A | 358 |
| 908276 | 24229 | 24244 | GTACAGGAGTTCCCCA | 90 | N/A | N/A | 359 |
| 908277 | 25038 | 25053 | AAATACACCCTAGATG | 83 | N/A | N/A | 360 |
| 908278 | 25670 | 25685 | GAAGATTTTGGCCGGG | 85 | N/A | N/A | 361 |
| 908279 | 25997 | 26012 | CTCCAGGACACACCGT | 42 | N/A | N/A | 362 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908280 | 27088 | 27103 | GGGAGTAGGCTCGACC | 51 | N/A | N/A | 363 |
| 908281 | 27400 | 27415 | CCCTATTCCACAGGAC | 85 | N/A | N/A | 364 |
| 908282 | 27746 | 27761 | GCTAAGAGCAGCCCTC | 80 | N/A | N/A | 365 |
| 908283 | 28198 | 28213 | GGCATCACGGCCGGGC | 76 | N/A | N/A | 366 |
| 908284 | 29125 | 29140 | TGTCACCCCAGCCGAA | 67 | N/A | N/A | 367 |
| 908285 | 29568 | 29583 | AGCCGGGCACCACCCA | 67 | N/A | N/A | 368 |
| 908286 | 30330 | 30345 | GGCAAGGACAGCCGAC | 94 | N/A | N/A | 369 |
| 908287 | 30334 | 30349 | GTTTGGCAAGGACAGC | 40 | N/A | N/A | 370 |
| 908288 | 30337 | 30352 | GTGGTTTGGCAAGGAC | 14 | N/A | N/A | 371 |
| 908289 | 30340 | 30355 | GCAGTGGTTTGGCAAG | 46 | N/A | N/A | 372 |
| 908290 | 30342 | 30357 | ATGCAGTGGTTTGGCA | 86 | N/A | N/A | 373 |
| 908291 | 30401 | 30416 | TCAACACCTTGAGGGC | 34 | N/A | N/A | 374 |
| 908292 | 30498 | 30513 | TGCCTAGGCGATCCTC | 88 | N/A | N/A | 375 |
| 908293 | 30928 | 30943 | GACATTGCTGTCGCAG | 78 | N/A | N/A | 376 |
| 908294 | 31347 | 31362 | TCCCAAGTGCCCCCCA | 90 | N/A | N/A | 377 |
| 908295 | 31703 | 31718 | AGCCGGCACGGTTGCT | 125 | N/A | N/A | 378 |
| 908296 | 32187 | 32202 | GAGAACATTCGCCCCA | 27 | N/A | N/A | 379 |
| 908297 | 32386 | 32401 | TGACCTGTGGCAATTC | 26 | N/A | N/A | 380 |
| 908298 | 32388 | 32403 | GGTGACCTGTGGCAAT | 44 | N/A | N/A | 381 |
| 908299 | 32689 | 32704 | TCCCGTATCGGCCCCT | 85 | N/A | N/A | 382 |
| 908300 | 33343 | 33358 | GTCCAGCCGCGAGTCC | 59 | N/A | N/A | 383 |
| 908301 | 33635 | 33650 | GGCAGACCCGCAGTCA | 73 | N/A | N/A | 384 |
| 908302 | 34108 | 34123 | GGGCAAGCCACCCCTC | 93 | N/A | N/A | 385 |
| 908303 | 34623 | 34638 | AAGTCGAGCTCCGCCC | 63 | N/A | N/A | 386 |
| 908304 | 35031 | 35046 | TGGTCCTAGCCCGTCC | 78 | N/A | N/A | 387 |
| 908305 | 35549 | 35564 | GGGTACAGGCAAACCT | 88 | N/A | N/A | 388 |
| 908306 | 36028 | 36043 | CCATACCCCCATCTGA | 102 | N/A | N/A | 389 |
| 908307 | 36712 | 36727 | GCGCAGAGGGCCTCGC | 123 | N/A | N/A | 390 |
| 908308 | 37097 | 37112 | CACTACAGACATCCCT | 64 | N/A | N/A | 391 |
| 908309 | 37538 | 37553 | AGCCAGGGCCCGGCTT | 93 | N/A | N/A | 392 |
| 908310 | 38044 | 38059 | CTCCAACTGTAGGGCT | 87 | N/A | N/A | 393 |
| 908311 | 39735 | 39750 | GCGGATGGTGGCATTC | 90 | N/A | N/A | 394 |
| 908312 | 40399 | 40414 | CAGCAGCGGCGGTGAC | 84 | N/A | N/A | 395 |
| 908313 | 41143 | 41158 | CTCTTAGCATGGCCCC | 73 | N/A | N/A | 396 |
| 908314 | 41620 | 41635 | GGCCTGGGATGCTACC | 129 | N/A | N/A | 397 |
| 908315 | 41957 | 41972 | TTAAACCCCCTCTGG | 104 | N/A | N/A | 398 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908316 | 42239 | 42254 | GCCCAAGCCCTCGGCG | 147 | N/A | N/A | 399 |
| 908317 | 42806 | 42821 | ATGCACGCGCTACCAT | 106 | N/A | N/A | 400 |
| 908318 | 43841 | 43856 | ACATATCCTGGCCGGG | 112 | N/A | N/A | 401 |
| 908319 | 44266 | 44281 | CTGGATGTGGGAACGG | 94 | N/A | N/A | 402 |
| 908320 | 44817 | 44832 | CCTCAGGCCGCCCCAT | 57 | N/A | N/A | 403 |
| 908321 | 45179 | 45194 | GGCCATGGAGGGTCAC | 111 | N/A | N/A | 404 |
| 908322 | 45544 | 45559 | GGGACAACTGGCGACA | 39 | N/A | N/A | 405 |
| 908323 | 45952 | 45967 | TGGTAGAGGGCTGGTG | 78 | N/A | N/A | 406 |
| 908324 | 46827 | 46842 | GCCCATCGGCTGCTGT | 153 | N/A | N/A | 407 |
| 908325 | 47604 | 47619 | GGGTAGGCCTGCGCTC | 119 | N/A | N/A | 408 |
| 908326 | 48030 | 48045 | TGCCATGATCAGGCGG | 109 | N/A | N/A | 409 |
| 908327 | 48530 | 48545 | ACCAAGTGGGCACCTA | 92 | N/A | N/A | 410 |
| 908328 | 49088 | 49103 | CCACAAGGCCCCGCCG | 103 | N/A | N/A | 411 |
| 908329 | 49883 | 49898 | GTGACCAGGTGCGGGT | 84 | N/A | N/A | 412 |
| 908330 | 50310 | 50325 | CTGGGCAGAGCCGATC | 95 | N/A | N/A | 413 |
| 908331 | 50840 | 50855 | GACGAGGCTGGCCCTG | 36 | N/A | N/A | 414 |
| 908332 | 51504 | 51519 | CCCCACTGTGCTAAAC | 91 | N/A | N/A | 415 |
| 908333 | 51765 | 51780 | AGTCAGCCGTCCTCGC | 58 | N/A | N/A | 416 |
| 908334 | 52587 | 52602 | CACCAGGCCGAGAGCA | 111 | N/A | N/A | 417 |
| 908335 | 53006 | 53021 | GCCCAGGCACCGACCA | 92 | N/A | N/A | 418 |
| 908336 | 53680 | 53695 | CCCCGGAACCTCAGGC | 85 | N/A | N/A | 419 |
| 908337 | 54271 | 54286 | CAGCACGCTGTGTGCA | 65 | N/A | N/A | 420 |
| 908338 | 54667 | 54682 | CACTCGGCCGCTCTTC | 80 | N/A | N/A | 421 |
| 908339 | 55325 | 55340 | GCGCACTGCCCTGTCG | 77 | N/A | N/A | 422 |
| 908340 | 56452 | 56467 | CAAGAGGGCCCCCTAC | 110 | N/A | N/A | 423 |
| 908341 | 56855 | 56870 | TATGAATCCCCCTCCC | 99 | N/A | N/A | 424 |
| 908342 | 57413 | 57428 | GCGCATGGACTGCGGG | 150 | N/A | N/A | 425 |
| 908343 | 57695 | 57710 | TGGAAGTACACAGGCT | 40 | N/A | N/A | 426 |
| 908344 | 58949 | 58964 | GTCTATGGCCCCGGGC | 102 | N/A | N/A | 427 |
| 908345 | 59713 | 59728 | GCATAGGCCAACGCAG | 88 | N/A | N/A | 428 |
| 908346 | 60635 | 60650 | AAACAGGCCCGCAGCC | 95 | N/A | N/A | 429 |
| 908347 | 61004 | 61019 | CCTACAGCGGCCATGG | 115 | N/A | N/A | 430 |
| 908348 | 61545 | 61560 | GTGCTAACCGTGTGTG | 85 | N/A | N/A | 431 |
| 908349 | 62025 | 62040 | GTCCAGTTGGCCCTGA | 84 | N/A | N/A | 432 |
| 908350 | 62964 | 62979 | AACCACCGAAGCTGGG | 125 | N/A | N/A | 433 |
| 908351 | 63324 | 63339 | GGAAGATGGCCGGGTG | 111 | N/A | N/A | 434 |
| 908352 | 63675 | 63690 | GCTACAATGCCTAGGA | 85 | N/A | N/A | 435 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908353 | 64393 | 64408 | GGTCAACGCAGGCTCA | 48 | N/A | N/A | 436 |
| 908354 | 64657 | 64672 | AGCCAGGAGCAATCGC | 78 | N/A | N/A | 437 |
| 908355 | 65114 | 65129 | GGCAACCAAGGTCTGA | 15 | N/A | N/A | 438 |
| 908356 | 65639 | 65654 | CGCCTAGCCTGGGTTC | 67 | N/A | N/A | 439 |
| 908357 | 66042 | 66057 | CACCATCACACACGGA | 44 | N/A | N/A | 440 |
| 908358 | 66433 | 66448 | GGGAGAGGTGCCGGTC | 99 | N/A | N/A | 441 |
| 908359 | 66885 | 66900 | CACCGAGAAGGAGGTA | 99 | N/A | N/A | 442 |
| 908360 | 67650 | 67665 | AAAATCTCGGCCGGGA | 101 | N/A | N/A | 443 |
| 908361 | 67903 | 67918 | GCCAAGTGGACCTGGC | 84 | N/A | N/A | 444 |
| 908362 | 68192 | 68207 | GCCTGAAACAAGTGCC | 75 | N/A | N/A | 445 |
| 908363 | 68628 | 68643 | CCCCAGGCAATGCATA | 125 | N/A | N/A | 446 |
| 908364 | 68993 | 69008 | AGAACGATAGGCCAGG | 52 | N/A | N/A | 447 |
| 908365 | 69310 | 69325 | TCTTTTCCCGGCCCCC | 48 | N/A | N/A | 448 |
| 908366 | 71364 | 71379 | CGGCACGGAGCTGCCC | 126 | N/A | N/A | 449 |
| 908367 | 71557 | 71572 | GGTCAGTTGCTGCAGG | 40 | N/A | N/A | 450 |
| 908368 | 72040 | 72055 | GGCCGGCCAATGCTCA | 118 | N/A | N/A | 451 |
| 908369 | 73315 | 73330 | TTGCACTGGCCGGGCT | 75 | N/A | N/A | 452 |
| 908370 | 73937 | 73952 | CCCTTAGCCCACGACC | 92 | N/A | N/A | 453 |
| 908371 | 74402 | 74417 | CTGCCAGTTTGTCCCC | 25 | N/A | N/A | 454 |
| 908372 | 74408 | 74423 | TGTAATCTGCCAGTTT | 53 | N/A | N/A | 455 |
| 908373 | 74410 | 74425 | CTTGTAATCTGCCAGT | 55 | N/A | N/A | 456 |
| 908374 | 74415 | 74430 | GGCACCTTGTAATCTG | 96 | N/A | N/A | 457 |
| 908375 | 74908 | 74923 | TGTGATGGGCATCCCC | 56 | N/A | N/A | 458 |
| 908376 | 75761 | 75776 | ATACATGAGGTCCGGG | 106 | N/A | N/A | 459 |
| 908377 | 76583 | 76598 | GCCCAACCCACGCTGC | 79 | N/A | N/A | 460 |
| 908378 | 77237 | 77252 | CCCCAACTGGGAGAGG | 107 | N/A | N/A | 461 |
| 908379 | 77517 | 77532 | TAGAACGGGCCTGGCC | 93 | N/A | N/A | 462 |
| 908380 | 78331 | 78346 | TCCATAGGTTCCCGCC | 89 | N/A | N/A | 463 |
| 908381 | 78849 | 78864 | GGGCACTACCTTCACC | 138 | N/A | N/A | 464 |
| 908382 | 79488 | 79503 | TCCCACGGATTATAGG | 140 | N/A | N/A | 465 |
| 908383 | 80002 | 80017 | GCCCAGGAAGGTCGAA | 105 | N/A | N/A | 466 |
| 908384 | 80333 | 80348 | ATGCATGGAGGCACCC | 93 | N/A | N/A | 467 |
| 908385 | 80626 | 80641 | TGCAATGGACGCAGGA | 37 | N/A | N/A | 468 |
| 908386 | 80968 | 80983 | GGCCGGGTCCCCAACA | 113 | N/A | N/A | 469 |
| 908387 | 81643 | 81658 | GGCCATTCCCGGAGCT | 114 | N/A | N/A | 470 |
| 908388 | 82021 | 82036 | CCTTTTCTAATCGAAG | 116 | N/A | N/A | 471 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908389 | 82046 | 82061 | ACCTGTTTGGACTGTT | 5 | N/A | N/A | 472 |
| 908390 | 82049 | 82064 | CCAACCTGTTTGGACT | 74 | N/A | N/A | 473 |
| 908391 | 82051 | 82066 | TTCCAACCTGTTTGGA | 54 | N/A | N/A | 474 |
| 908392 | 82055 | 82070 | CGTTTTCCAACCTGTT | 3 | N/A | N/A | 475 |
| 908393 | 82069 | 82084 | GGCTCTAGGACGAGCG | 55 | N/A | N/A | 476 |
| 908394 | 82072 | 82087 | CCTGGCTCTAGGACGA | 41 | N/A | N/A | 477 |
| 908395 | 82083 | 82098 | TGTCCATGACACCTGG | 66 | N/A | N/A | 478 |
| 908396 | 82086 | 82101 | TCATGTCCATGACACC | 8 | N/A | N/A | 479 |
| 908397 | 82088 | 82103 | ATTCATGTCCATGACA | 25 | N/A | N/A | 480 |
| 908398 | 82704 | 82719 | CCCCACGGGCAGCCAC | 127 | N/A | N/A | 481 |
| 908399 | 83290 | 83305 | GGGCACCGTGGACCGG | 112 | N/A | N/A | 482 |
| 908400 | 83646<br>83734<br>83822 | 83661<br>83749<br>83837 | CATATGCAGCTGTCAG | 27 | N/A<br>N/A<br>N/A | N/A<br>N/A<br>N/A | 483 |
| 908401 | 83647<br>83735<br>83823 | 83662<br>83750<br>83838 | CCATATGCAGCTGTCA | 2 | N/A<br>N/A<br>N/A | N/A<br>N/A<br>N/A | 484 |
| 908402 | 83649<br>83737<br>83825 | 83664<br>83752<br>83840 | TGCCATATGCAGCTGT | 27 | N/A<br>N/A<br>N/A | N/A<br>N/A<br>N/A | 485 |
| 908403 | 83650<br>83738<br>83826 | 83665<br>83753<br>83841 | TTGCCATATGCAGCTG | 18 | N/A<br>N/A<br>N/A | N/A<br>N/A<br>N/A | 486 |
| 908404 | 83651<br>83739<br>83827 | 83666<br>83754<br>83842 | TTTGCCATATGCAGCT | 17 | N/A<br>N/A<br>N/A | N/A<br>N/A<br>N/A | 487 |
| 908405 | 83658<br>83746<br>83834 | 83673<br>83761<br>83849 | GGGTTACTTTGCCATA | 7 | N/A<br>N/A<br>N/A | N/A<br>N/A<br>N/A | 488 |
| 908406 | 83659<br>83747<br>83835 | 83674<br>83762<br>83850 | AGGGTTACTTTGCCAT | 74 | N/A<br>N/A<br>N/A | N/A<br>N/A<br>N/A | 489 |
| 908407 | 83660<br>83748<br>83836 | 83675<br>83763<br>83851 | AAGGGTTACTTTGCCA | 7 | N/A<br>N/A<br>N/A | N/A<br>N/A<br>N/A | 490 |
| 908408 | 83661<br>83749<br>83837 | 83676<br>83764<br>83852 | TAAGGGTTACTTTGCC | 2 | N/A<br>N/A<br>N/A | N/A<br>N/A<br>N/A | 491 |
| 908409 | 83662<br>83750<br>83838 | 83677<br>83765<br>83853 | GTAAGGGTTACTTTGC | 8 | N/A<br>N/A<br>N/A | N/A<br>N/A<br>N/A | 492 |
| 908410 | 83663<br>83751<br>83839 | 83678<br>83766<br>83854 | GGTAAGGGTTACTTTG | 12 | N/A<br>N/A<br>N/A | N/A<br>N/A<br>N/A | 493 |
| 908411 | 83664<br>83752<br>83840 | 83679<br>83767<br>83855 | AGGTAAGGGTTACTTT | 17 | N/A<br>N/A<br>N/A | N/A<br>N/A<br>N/A | 494 |
| 908412 | 83665<br>83753<br>83841 | 83680<br>83768<br>83856 | GAGGTAAGGGTTACTT | 12 | N/A<br>N/A<br>N/A | N/A<br>N/A<br>N/A | 495 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID 2: Stop Site | SEQ ID NO |
|---|---|---|---|---|---|---|---|
| 908413 | 83666 | 83681 | TGAGGTAAGGGTTACT | 3 | N/A | N/A | 496 |
|  | 83754 | 83769 |  |  | N/A | N/A |  |
|  | 83842 | 83857 |  |  | N/A | N/A |  |
| 908414 | 83667 | 83682 | TTGAGGTAAGGGTTAC | 5 | N/A | N/A | 497 |
|  | 83755 | 83770 |  |  | N/A | N/A |  |
|  | 83843 | 83858 |  |  | N/A | N/A |  |
| 908415 | 83669 | 83684 | AACCCTTACCTCAATC | 3 | N/A | N/A | 498 |
|  | 83757 | 83772 |  |  | N/A | N/A |  |
|  | 83845 | 83860 |  |  | N/A | N/A |  |
| 908416 | 83670 | 83685 | TGATTGAGGTAAGGGT | 4 | N/A | N/A | 499 |
|  | 83758 | 83773 |  |  | N/A | N/A |  |
|  | 83846 | 83861 |  |  | N/A | N/A |  |
| 908417 | 83671 | 83686 | TTGATTGAGGTAAGGG | 2 | N/A | N/A | 500 |
|  | 83759 | 83774 |  |  | N/A | N/A |  |
|  | 83847 | 83862 |  |  | N/A | N/A |  |
| 908418 | 83672 | 83687 | CTTGATTGAGGTAAGG | 8 | N/A | N/A | 501 |
|  | 83760 | 83775 |  |  | N/A | N/A |  |
|  | 83848 | 83863 |  |  | N/A | N/A |  |
| 908419 | 83673 | 83688 | TCTTGATTGAGGTAAG | 5 | N/A | N/A | 502 |
|  | 83761 | 83776 |  |  | N/A | N/A |  |
|  | 83849 | 83864 |  |  | N/A | N/A |  |
| 908420 | 83674 | 83689 | ATCTTGATTGAGGTAA | 2 | N/A | N/A | 503 |
|  | 83762 | 83777 |  |  | N/A | N/A |  |
|  | 83850 | 83865 |  |  | N/A | N/A |  |
| 908421 | 83684 | 83699 | ACCGCTCTGTATCTTG | 3 | N/A | N/A | 504 |
|  | 83772 | 83787 |  |  | N/A | N/A |  |
|  | 83860 | 83875 |  |  | N/A | N/A |  |
| 908422 | 83685 | 83700 | AACCGCTCTGTATCTT | 3 | N/A | N/A | 505 |
|  | 83773 | 83788 |  |  | N/A | N/A |  |
|  | 83861 | 83876 |  |  | N/A | N/A |  |
| 908423 | 83686 | 83701 | AGATACAGAGCGGTTC | 28 | N/A | N/A | 506 |
|  | 83774 | 83789 |  |  | N/A | N/A |  |
|  | 83862 | 83877 |  |  | N/A | N/A |  |
| 908424 | 83687 | 83702 | GGAACCGCTCTGTATC | 8 | N/A | N/A | 507 |
|  | 83775 | 83790 |  |  | N/A | N/A |  |
|  | 83863 | 83878 |  |  | N/A | N/A |  |
| 908425 | 83688 | 83703 | CGGAACCGCTCTGTAT | 13 | N/A | N/A | 508 |
|  | 83776 | 83791 |  |  | N/A | N/A |  |
|  | 83864 | 83879 |  |  | N/A | N/A |  |
| 908426 | 83689 | 83704 | ACGGAACCGCTCTGTA | 47 | N/A | N/A | 509 |
|  | 83777 | 83792 |  |  | N/A | N/A |  |
|  | 83865 | 83880 |  |  | N/A | N/A |  |
| 908427 | 83690 | 83705 | GACGGAACCGCTCTGT | 21 | N/A | N/A | 510 |
|  | 83778 | 83793 |  |  | N/A | N/A |  |
|  | 83866 | 83881 |  |  | N/A | N/A |  |
| 908428 | 83691 | 83706 | TGACGGAACCGCTCTG | 33 | N/A | N/A | 511 |
|  | 83779 | 83794 |  |  | N/A | N/A |  |
|  | 83867 | 83882 |  |  | N/A | N/A |  |
| 908429 | 83692 | 83707 | GTGACGGAACCGCTCT | 44 | N/A | N/A | 512 |
|  | 83780 | 83795 |  |  | N/A | N/A |  |
|  | 83868 | 83883 |  |  | N/A | N/A |  |
| 908430 | 83693 | 83708 | GGTGACGGAACCGCTC | 27 | N/A | N/A | 513 |
|  | 83781 | 83796 |  |  | N/A | N/A |  |
|  | 83869 | 83884 |  |  | N/A | N/A |  |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908431 | 83694 | 83709 | AGCGGTTCCGTCACCT | 67 | N/A | N/A | 514 |
|  | 83782 | 83797 |  |  | N/A | N/A |  |
|  | 83870 | 83885 |  |  | N/A | N/A |  |
| 908432 | 83695 | 83710 | GAGGTGACGGAACCGC | 69 | N/A | N/A | 515 |
|  | 83783 | 83798 |  |  | N/A | N/A |  |
|  | 83871 | 83886 |  |  | N/A | N/A |  |
| 908433 | 83696 | 83711 | GGAGGTGACGGAACCG | 62 | N/A | N/A | 516 |
|  | 83784 | 83799 |  |  | N/A | N/A |  |
|  | 83872 | 83887 |  |  | N/A | N/A |  |
| 908434 | 83697 | 83712 | AGGAGGTGACGGAACC | 6 | N/A | N/A | 517 |
|  | 83785 | 83800 |  |  | N/A | N/A |  |
|  | 83873 | 83888 |  |  | N/A | N/A |  |
| 908435 | 83698 | 83713 | TAGGAGGTGACGGAAC | 16 | N/A | N/A | 518 |
|  | 83786 | 83801 |  |  | N/A | N/A |  |
|  | 83874 | 83889 |  |  | N/A | N/A |  |
| 908436 | 83699 | 83714 | TTAGGAGGTGACGGAA | 14 | N/A | N/A | 519 |
|  | 83787 | 83802 |  |  | N/A | N/A |  |
|  | 83875 | 83890 |  |  | N/A | N/A |  |
| 908437 | 83709 | 83724 | GACAGGGATTTTAGGA | 29 | N/A | N/A | 520 |
|  | 83885 | 83900 |  |  | N/A | N/A |  |
| 908438 | 83710 | 83725 | GGACAGGGATTTTAGG | 49 | N/A | N/A | 521 |
|  | 83886 | 83901 |  |  | N/A | N/A |  |
| 908439 | 83719 | 83734 | CCTGTCCCTATCATGC | 3 | N/A | N/A | 522 |
|  | 83807 | 83822 |  |  | N/A | N/A |  |
| 908440 | 83720 | 83735 | AGCATGATAGGGACAG | 4 | N/A | N/A | 523 |
|  | 83808 | 83823 |  |  | N/A | N/A |  |
| 908441 | 83721 | 83736 | CAGCATGATAGGGACA | 2 | N/A | N/A | 524 |
|  | 83809 | 83824 |  |  | N/A | N/A |  |
| 908442 | 83722 | 83737 | TCAGCATGATAGGGAC | 4 | N/A | N/A | 525 |
|  | 83810 | 83825 |  |  | N/A | N/A |  |
| 908443 | 83723 | 83738 | GTCAGCATGATAGGGA | 4 | N/A | N/A | 526 |
|  | 83811 | 83826 |  |  | N/A | N/A |  |
| 908444 | 83724 | 83739 | TGTCAGCATGATAGGG | 4 | N/A | N/A | 527 |
|  | 83812 | 83827 |  |  | N/A | N/A |  |
| 908445 | 83725 | 83740 | CTGTCAGCATGATAGG | 44 | N/A | N/A | 528 |
|  | 83813 | 83828 |  |  | N/A | N/A |  |
| 908446 | 83726 | 83741 | GCTGTCAGCATGATAG | 70 | N/A | N/A | 529 |
|  | 83814 | 83829 |  |  | N/A | N/A |  |
| 908447 | 83727 | 83742 | TATCATGCTGACAGCT | 55 | N/A | N/A | 530 |
|  | 83815 | 83830 |  |  | N/A | N/A |  |
| 908448 | 83910 | 83925 | GAGGTTGACTACAAAG | 12 | N/A | N/A | 531 |
| 908449 | 83913 | 83928 | TGAGAGGTTGACTACA | 6 | N/A | N/A | 532 |
| 908450 | 83915 | 83930 | TTTGAGAGGTTGACTA | 17 | N/A | N/A | 533 |
| 908451 | 83921 | 83936 | TGGGTTTTGAGAGGT | 9 | N/A | N/A | 534 |
| 908452 | 84177 | 84192 | GGCGATGGCACGACCA | 71 | N/A | N/A | 535 |
| 908453 | 84938 | 84953 | GTATAAGGACGGCCCA | 45 | N/A | N/A | 536 |
| 908454 | 85500 | 85515 | TCAGATCCGGCCTGGC | 191 | N/A | N/A | 537 |
| 908455 | 86165 | 86180 | GTGGTGTGGCGTGCGC | 75 | N/A | N/A | 538 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908456 | 86583 | 86598 | GAACTTACTGTCTCCC | 14 | N/A | N/A | 539 |
| 908457 | 87056 | 87071 | AGGCAGGGCCGCTGTC | 100 | N/A | N/A | 540 |
| 908458 | 87386 | 87401 | AGGATTGGTGCCGCCC | 36 | N/A | N/A | 541 |
| 908459 | 87906 | 87921 | AATCAGCGGGTGATGC | 118 | N/A | N/A | 542 |
| 908460 | 88179 | 88194 | GCCCAGTGGCCGCCCT | 70 | N/A | N/A | 543 |
| 908461 | 88831 | 88846 | CTACAGCTGGTGCGGT | 40 | N/A | N/A | 544 |
| 908462 | 89400 | 89415 | CGCCAGGCTTGGGCCC | 100 | N/A | N/A | 545 |
| 908463 | 89711 | 89726 | GCCCAGATAAGAAGCC | 38 | N/A | N/A | 546 |
| 908464 | 90096 | 90111 | GGCTAGTTCATGCCGG | 63 | N/A | N/A | 547 |
| 908465 | 90743 | 90758 | ACGGCCTGGGCACACG | 52 | N/A | N/A | 548 |
| 908466 | 90747 | 90762 | GGAAACGGCCTGGGCA | 64 | N/A | N/A | 549 |
| 908467 | 90750 | 90765 | AAGGGAAACGGCCTGG | 76 | N/A | N/A | 550 |
| 908468 | 90753 | 90768 | CGCAAGGGAAACGGCC | 108 | N/A | N/A | 551 |
| 908469 | 90755 | 90770 | TGCGCAAGGGAAACGG | 87 | N/A | N/A | 552 |
| 908470 | 90757 | 90772 | GCTGCGCAAGGGAAAC | 124 | N/A | N/A | 553 |
| 908471 | 90761 | 90776 | CCCTTGCGCAGCTCTG | 18 | N/A | N/A | 554 |
| 908472 | 90765 | 90780 | CACACAGAGCTGCGCA | 57 | N/A | N/A | 555 |
| 908473 | 90778 | 90793 | GAAGCCCCTGCACAC | 37 | N/A | N/A | 556 |
| 908474 | 90781 | 90796 | AGAGAAGCCCCTGCA | 72 | N/A | N/A | 557 |
| 908475 | 90809 | 90824 | CCAAGTGAGCAGCCAC | 9 | N/A | N/A | 558 |
| 908476 | 90811 | 90826 | GACCAAGTGAGCAGCC | 27 | N/A | N/A | 559 |
| 908477 | 90813 | 90828 | GGGACCAAGTGAGCAG | 63 | N/A | N/A | 560 |
| 908478 | 91157 | 91172 | CACTAGGCCCTGCCAG | 128 | N/A | N/A | 561 |
| 908479 | 91836 | 91851 | GAGCGGGGTCTGTGA | 58 | N/A | N/A | 562 |
| 908480 | 92802 | 92817 | CAGCACTTTGTCCGGG | 82 | N/A | N/A | 563 |
| 908481 | 93315 | 93330 | ACCTACGGCAAGCGCA | 31 | N/A | N/A | 564 |
| 908482 | 93568 | 93583 | TACCAGGATCTCCCCC | 19 | N/A | N/A | 565 |
| 908483 | 94077 | 94092 | GCTAGAGGAGCGGCAC | 74 | N/A | N/A | 566 |
| 908484 | 94531 | 94546 | GCCCATCTCACGCCCC | 71 | N/A | N/A | 567 |
| 908485 | 95058 | 95073 | CCAGAGGCCACGGCCA | 94 | N/A | N/A | 568 |
| 908486 | 95635 | 95650 | CCGCACACCCCTCGGT | 111 | N/A | N/A | 569 |
| 908487 | 96522 | 96537 | CAGGCCGCCCTGTGCG | 93 | N/A | N/A | 570 |
| 908488 | 97096 | 97111 | CCCAAGCATTTCCAGC | 37 | N/A | N/A | 571 |
| 908489 | 97109 | 97124 | AGTTCCACCCTGTCCC | 23 | N/A | N/A | 572 |
| 908490 | 97144 | 97159 | TAGAGACACCTCCAGC | 47 | N/A | N/A | 573 |
| 908491 | 97147 | 97162 | CAATAGAGACACCTCC | 44 | N/A | N/A | 574 |
| 908492 | 97150 | 97165 | CCGCAATAGAGACACC | 43 | N/A | N/A | 575 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 908493 | 97152 | 97167 | GACCGCAATAGAGACA | 64 | N/A | N/A | 576 |
| 908494 | 97154 | 97169 | GGGACCGCAATAGAGA | 94 | N/A | N/A | 577 |
| 908495 | 97157 | 97172 | CTATTGCGGTCCCTGG | 31 | N/A | N/A | 578 |
| 908496 | 97159 | 97174 | AGCCAGGGACCGCAAT | 85 | N/A | N/A | 579 |
| 908497 | 97426 | 97441 | GCCCACCCGCTCTTCC | 80 | N/A | N/A | 580 |
| 908498 | 98041 | 98056 | TGGAACCCCGGTGCCC | 119 | N/A | N/A | 581 |
| 908499 | 98971 | 98986 | CTTCACCGTTTGGCCA | 45 | N/A | N/A | 582 |
| 908500 | 100149 | 100164 | CGCGGAGCCAGGCCCT | 114 | N/A | N/A | 583 |
| 908501 | 101337 | 101352 | CCCCAGAGTCCCGCAG | 72 | N/A | N/A | 584 |
| 908502 | 101845 | 101860 | ACACGAAGGGCCCCTC | 52 | N/A | N/A | 585 |
| 908503 | 102223 | 102238 | GCAGACTGATAGGGCC | 103 | N/A | N/A | 586 |
| 908504 | 102495 | 102510 | GGATAGCCGGCCCCGC | 102 | N/A | N/A | 587 |
| 908505 | 102955 | 102970 | CGCGGCCGGAAGCTTC | 93 | N/A | N/A | 588 |
| 908506 | 103211 103249 | 103226 103264 | CAGAGCATAGGAGAGG | 7 | N/A N/A | N/A N/A | 589 |
| 908507 | 103213 103251 | 103228 103266 | AGCAGAGCATAGGAGA | 12 | N/A N/A | N/A N/A | 590 |
| 908508 | 103216 103254 | 103231 103269 | GGGAGCAGAGCATAGG | 16 | N/A N/A | N/A N/A | 591 |
| 908509 | 104082 | 104097 | GCCAGCCACGGCTGTC | 81 | N/A | N/A | 592 |
| 908510 | 104495 | 104510 | GCTGACGGCACGCACA | 65 | N/A | N/A | 593 |
| 908511 | 105108 | 105123 | TGGGGATGGCTCGGGG | 79 | N/A | N/A | 594 |
| 908512 | 105526 | 105541 | CACCAGGGCTCCGCCT | 107 | N/A | N/A | 595 |
| 908513 | 106268 | 106283 | GGCACACGGCTCAGGG | 93 | N/A | N/A | 596 |
| 908514 | 106974 | 106989 | CAGCAAGTGGCTGCCC | 107 | N/A | N/A | 597 |
| 908515 | 107645 | 107660 | TGGGAGTGGTACTGCA | 70 | N/A | N/A | 598 |
| 908516 | 108733 | 108748 | TGCCATGGGTCTGGCA | 86 | N/A | N/A | 599 |
| 908517 | 108893 | 108908 | GCTCCTCACCTGGTCC | 92 | N/A | N/A | 600 |
| 908518 | 108899 | 108914 | AGGACGGCTCCTCACC | 111 | N/A | N/A | 601 |
| 908519 | 108902 | 108917 | GAGGAGCCGTCCTGCG | 85 | N/A | N/A | 602 |
| 908520 | 108906 | 108921 | GCTGCGCAGGACGGCT | 104 | N/A | N/A | 603 |
| 908521 | 109226 | 109241 | GGGCGAACCACCCACC | 78 | N/A | N/A | 604 |
| 908522 | 109577 | 109592 | GCCCAAAGGATCTGCC | 88 | N/A | N/A | 605 |
| 908523 | 109968 | 109983 | CCCTATTGTCCCACCA | 43 | N/A | N/A | 606 |
| 908524 | 110612 | 110627 | GTGCACTCTAGGCTTA | 100 | N/A | N/A | 607 |
| 908525 | 111378 | 111393 | GGACACAGCGGCTGCC | 78 | N/A | N/A | 608 |
| 908526 | 111925 | 111940 | CCGCAGGTTTCTGTGG | 122 | N/A | N/A | 609 |
| 908527 | 112198 | 112213 | ACCGATAGGATCGGAG | 95 | N/A | N/A | 610 |

TABLE 1-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID 2: Stop Site | SEQ ID NO |
|---|---|---|---|---|---|---|---|
| 908528 | 112578 | 112593 | GGCCGTCACAACTTTT | 116 | N/A | N/A | 611 |
| 908529 | 112910 | 112925 | CTGGAACCTCCTACTG | 87 | N/A | N/A | 612 |
| 908530 | 114292 | 114307 | GGCCGAATGCTTGAGG | 97 | N/A | N/A | 613 |
| 908531 | 114921 | 114936 | TCACAGGGCCCCCTCA | 68 | N/A | N/A | 614 |
| 908532 | 115371 | 115386 | GGCCTTACCTGGGCAC | 101 | N/A | N/A | 615 |
| 908533 | 115837 | 115852 | CCGCAAGCCACCAGGG | 87 | N/A | N/A | 616 |

*Oligos with an asterisk target an amplicon region.

Each modified oligonucleotide listed in the table below is 100% complementary to human DNM2 nucleic acid sequence GENBANK Number NM_001005361.2 (designated herein as SEQ ID NO: 3). "Start Site" indicates the 5'-most nucleoside of SEQ ID No: 3 to which the oligonucleotide is complementary. "Stop Site" indicates the 3'-most nucleoside of SEQ ID No: 3 to which the modified oligonucleotide is complementary. 'N/A' indicates that the modified oligonucleotide is not 100% complementary to the particular nucleic acid. As shown below, modified oligonucleotides complementary to DNM2 reduced human DNM2 mRNA expression.

TABLE 2

DNM2 mRNA Expression

| Compound Number | SEQ ID: 3 Start Site | SEQ ID: 3 Stop Site | Sequence | Dynamin2 (% Control) | SEQ ID NO |
|---|---|---|---|---|---|
| 695118 | 1728 | 1743 | ATCTCCCCCTGATTGG | 60 | 617 |
| 908218 | 1732 | 1747 | CAGGATCTCCCCCTGA | 114 | 618 |
| 908219 | 1379 | 1394 | GCCCCGTCCTGACTCC | 61 | 619 |
| 908220 | 1381 | 1396 | GAGCCCCGTCCTGACT | 92 | 620 |
| 908233 | 1515 | 1530 | CTGAGCTTCTCGGCAC | 70 | 621 |
| 908234 | 1517 | 1532 | AACTGAGCTTCTCGGC | 85 | 622 |
| 908235 | 1519 | 1534 | GGAACTGAGCTTCTCG | 33 | 623 |

Example 2: Effect of Modified Oligonucleotides Complementary to Dynamin 2 In Vitro Modified oligonucleotides complementary to dynamin 2 (DNM2) nucleic acid were designed and tested for their effect on dynamin 2 mRNA in vitro. The modified oligonucleotides were tested in a series of experiments that had similar culture conditions.

A431 cells cultured at a density of 10,000 cells per well were treated with 2,000 nM of modified oligonucleotide via free uptake or no oligonucleotide for untreated controls. After approximately 24 hours, RNA was isolated from the cells and DNM2 mRNA levels were measured by quantitative real-time PCR as described in Example 1.

The modified oligonucleotides in the tables below each have a 3-10-3 cEt gapmer motif, wherein the central gap segment contains ten 2'-deoxynucleosides and is flanked by wing segments on the 3' and 5' ends, each containing three cEt nucleosides. All cytosine residues throughout each modified oligonucleotide are 5-methyl cytosines. All internucleoside linkages are phosphorothioate internucleoside linkages.

Each modified oligonucleotide listed in the tables below is 100% complementary to human DNM2 nucleic acid sequence GENBANK Number NC_000019.10, truncated from 10715001 to 1083500 (SEQ ID NO: 1) and/or GENBANK Number NM_004945.3 (SEQ ID NO: 2). As shown below, modified oligonucleotides complementary to human DNM2 inhibited human DNM2 mRNA expression.

TABLE 3

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 694792 | 3060 | 3075 | CGACACCCGACCCGAG | 26 | N/A | N/A | 624 |
| 694812 | 3317 | 3332 | GTCCAGGTGGCAGCTC | 37 | 265 | 280 | 625 |
| 694826 | 57522 | 57537 | CCGGACTTCATCAAAG | 82 | 469 | 484 | 626 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 694999 | 115263 | 115278 | GTCCAGGCCGGGATGG | 92 | 2606 | N/A | 627 |
| 695015 | 116005 | 116020 | GCGGATAATGGTGGGC | 12 | 2749 | N/A | 628 |
| 695016 | 116011 | 116026 | GGCTGGGCGGATAATG | 76 | 2755 | N/A | 629 |
| 695170 | 82446 | 82461 | CTTCAAACTCGGCTCT | 9 | N/A | N/A | 630 |
| 695171 | 82451 | 82466 | ACACACTTCAAACTCG | 7 | N/A | N/A | 13 |
| 695171 | 82451 | 82466 | ACACACTTCAAACTCG | 12 | N/A | N/A | 13 |
| 695171 | 82451 | 82466 | ACACACTTCAAACTCG | 9 | N/A | N/A | 13 |
| 695171 | 82451 | 82466 | ACACACTTCAAACTCG | 8 | N/A | N/A | 13 |
| 695171 | 82451 | 82466 | ACACACTTCAAACTCG | 11 | N/A | N/A | 13 |
| 695171 | 82451 | 82466 | ACACACTTCAAACTCG | 7 | N/A | N/A | 13 |
| 695171 | 82451 | 82466 | ACACACTTCAAACTCG | 121 | N/A | N/A | 13 |
| 695171 | 82451 | 82466 | ACACACTTCAAACTCG | 14 | N/A | N/A | 13 |
| 695171 | 82451 | 82466 | ACACACTTCAAACTCG | 8 | N/A | N/A | 13 |
| 695171 | 82451 | 82466 | ACACACTTCAAACTCG | 6 | N/A | N/A | 13 |
| 695171 | 82451 | 82466 | ACACACTTCAAACTCG | 31 | N/A | N/A | 13 |
| 695171 | 82451 | 82466 | ACACACTTCAAACTCG | 8 | N/A | N/A | 13 |
| 695171 | 82451 | 82466 | ACACACTTCAAACTCG | 6 | N/A | N/A | 13 |
| 695171 | 82451 | 82466 | ACACACTTCAAACTCG | 10 | N/A | N/A | 13 |
| 695171 | 82451 | 82466 | ACACACTTCAAACTCG | 8 | N/A | N/A | 13 |
| 695171 | 82451 | 82466 | ACACACTTCAAACTCG | 12 | N/A | N/A | 13 |
| 695171 | 82451 | 82466 | ACACACTTCAAACTCG | 11 | N/A | N/A | 13 |
| 695171 | 82451 | 82466 | ACACACTTCAAACTCG | 11 | N/A | N/A | 13 |
| 695171 | 82451 | 82466 | ACACACTTCAAACTCG | 5 | N/A | N/A | 13 |
| 695171 | 82451 | 82466 | ACACACTTCAAACTCG | 12 | N/A | N/A | 13 |
| 695171 | 82451 | 82466 | ACACACTTCAAACTCG | 7 | N/A | N/A | 13 |
| 695171 | 82451 | 82466 | ACACACTTCAAACTCG | 120 | N/A | N/A | 13 |
| 695171 | 82451 | 82466 | ACACACTTCAAACTCG | 6 | N/A | N/A | 13 |
| 695171 | 82451 | 82466 | ACACACTTCAAACTCG | 8 | N/A | N/A | 13 |
| 695171 | 82451 | 82466 | ACACACTTCAAACTCG | 9 | N/A | N/A | 13 |
| 695171 | 82451 | 82466 | ACACACTTCAAACTCG | 7 | N/A | N/A | 13 |
| 695171 | 82451 | 82466 | ACACACTTCAAACTCG | 10 | N/A | N/A | 13 |
| 695171 | 82451 | 82466 | ACACACTTCAAACTCG | 9 | N/A | N/A | 13 |
| 695171 | 82451 | 82466 | ACACACTTCAAACTCG | 9 | N/A | N/A | 13 |
| 695171 | 82451 | 82466 | ACACACTTCAAACTCG | 9 | N/A | N/A | 13 |
| 695171 | 82451 | 82466 | ACACACTTCAAACTCG | 10 | N/A | N/A | 13 |
| 695171 | 82451 | 82466 | ACACACTTCAAACTCG | 7 | N/A | N/A | 13 |
| 948484 | 82379 | 82394 | GTGAAGAGCCCCGTCC | 42 | N/A | N/A | 631 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
| --- | --- | --- | --- | --- | --- | --- | --- |
| 948485 | 82380 | 82395 | GGTGAAGAGCCCCGTC | 103 | N/A | N/A | 632 |
| 948486 | 82443 | 82458 | CAAACTCGGCTCTTTG | 99 | N/A | N/A | 633 |
| 948487 | 82444 | 82459 | TCAAACTCGGCTCTTT | 15 | N/A | N/A | 634 |
| 948488 | 82445 | 82460 | TTCAAACTCGGCTCTT | 5 | N/A | N/A | 635 |
| 948489 | 82448 | 82463 | CACTTCAAACTCGGCT | 3 | N/A | N/A | 636 |
| 948490 | 82449 | 82464 | ACACTTCAAACTCGGC | 1 | N/A | N/A | 637 |
| 948491 | 82450 | 82465 | CACACTTCAAACTCGG | 25 | N/A | N/A | 638 |
| 948492 | 82452 | 82467 | AACACACTTCAAACTC | 11 | N/A | N/A | 639 |
| 948493 | 82453 | 82468 | CAACACACTTCAAACT | 51 | N/A | N/A | 640 |
| 948494 | 82454 | 82469 | TCAACACACTTCAAAC | 30 | N/A | N/A | 641 |
| 948495 | 82458 | 82473 | GAGATCAACACACTTC | 19 | N/A | N/A | 642 |
| 948496 | 82460 | 82475 | ACGAGATCAACACACT | 5 | N/A | N/A | 643 |
| 948497 | 82461 | 82476 | CACGAGATCAACACAC | 28 | N/A | N/A | 644 |
| 948498 | 82463 | 82478 | ACCACGAGATCAACAC | 50 | N/A | N/A | 645 |
| 948499 | 82467 | 82482 | TGAGACCACGAGATCA | 55 | N/A | N/A | 646 |
| 948500 | 82469 | 82484 | TCTGAGACCACGAGAT | 107 | N/A | N/A | 647 |
| 948501 | 82470 | 82485 | CTCTGAGACCACGAGA | 119 | N/A | N/A | 648 |
| 948502 | 82490 | 82505 | TTTTTTATGACCGTGG | 18 | N/A | N/A | 649 |
| 948503 | 82496 | 82511 | GCACACTTTTTTATGA | 17 | N/A | N/A | 650 |
| 948504 | 82497 | 82512 | GGCACACTTTTTTATG | 54 | N/A | N/A | 651 |
| 948505 | 82499 | 82514 | TCGGCACACTTTTTTA | 10 | N/A | N/A | 652 |
| 948506 | 82500 | 82515 | CTCGGCACACTTTTTT | 3 | N/A | N/A | 653 |
| 948507 | 82501 | 82516 | TCTCGGCACACTTTTT | 3 | N/A | N/A | 654 |
| 948508 | 82503 | 82518 | CTTCTCGGCACACTTT | 3 | N/A | N/A | 655 |
| 948514 | 3056 | 3071 | ACCCGACCCGAGCGAC | 81 | 4 | 19 | 656 |
| 948515 | 3067 | 3082 | TCTCAGGCGACACCCG | 88 | 15 | 30 | 657 |
| 948516 | 3092 | 3107 | CCTCACGGTCGCCGCC | 56 | 40 | 55 | 658 |
| 948517 | 3094 | 3109 | GGCCTCACGGTCGCCG | 98 | 42 | 57 | 659 |
| 948518 | 3103 | 3118 | TCCCGGCTCGGCCTCA | 48 | 51 | 66 | 660 |
| 948519 | 3139 | 3154 | GCTCCCCGCCCGCCCG | 71 | 87 | 102 | 661 |
| 948520 | 3141 | 3156 | TTGCTCCCCGCCCGCC | 23 | 89 | 104 | 662 |
| 948521 | 3142 | 3157 | GTTGCTCCCCGCCCGC | 10 | 90 | 105 | 663 |
| 948522 | 3143 | 3158 | CGTTGCTCCCCGCCCG | 50 | 91 | 106 | 664 |
| 948523 | 3145 | 3160 | GCCGTTGCTCCCCGCC | 53 | 93 | 108 | 665 |
| 948524 | 3147 | 3162 | TAGCCGTTGCTCCCCG | 17 | 95 | 110 | 666 |
| 948525 | 3148 | 3163 | GTAGCCGTTGCTCCCC | 14 | 96 | 111 | 667 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948526 | 3150 | 3165 | CTGTAGCCGTTGCTCC | 10 | 98 | 113 | 668 |
| 948527 | 3151 | 3166 | TCTGTAGCCGTTGCTC | 9 | 99 | 114 | 669 |
| 948528 | 3152 | 3167 | GTCTGTAGCCGTTGCT | 13 | 100 | 115 | 670 |
| 948529 | 3168 | 3183 | GACCTGGCCCCGCGGC | 76 | 116 | 131 | 671 |
| 948530 | 3169 | 3184 | CGACCTGGCCCCGCGG | 83 | 117 | 132 | 672 |
| 948531 | 3170 | 3185 | ACGACCTGGCCCCGCG | 36 | 118 | 133 | 673 |
| 948532 | 3172 | 3187 | CAACGACCTGGCCCCG | 17 | 120 | 135 | 674 |
| 948533 | 3173 | 3188 | TCAACGACCTGGCCCC | 20 | 121 | 136 | 675 |
| 948534 | 3174 | 3189 | CTCAACGACCTGGCCC | 30 | 122 | 137 | 676 |
| 948535 | 3175 | 3190 | CCTCAACGACCTGGCC | 101 | 123 | 138 | 677 |
| 948536 | 3176 | 3191 | CCCTCAACGACCTGGC | 57 | 124 | 139 | 678 |
| 948537 | 3278 | 3293 | CTGCAGTTTGTTGACC | 45 | 226 | 241 | 679 |
| 948538 | 3299 | 3314 | GCCGATGGAGCTGAAG | 7 | 247 | 262 | 680 |
| 948539 | 3300 | 3315 | GGCCGATGGAGCTGAA | 104 | 248 | 263 | 681 |
| 948540 | N/A | N/A | AAGGAAGTCCCGGCCC | 81 | 346 | 361 | 682 |
| 948541 | N/A | N/A | GAAGGAAGTCCCGGCC | 101 | 347 | 362 | 683 |
| 948542 | 44750 | 44765 | GATTCCTGAACCGCGG | 106 | 364 | 379 | 684 |
| 948543 | 44752 | 44767 | ACGATTCCTGAACCGC | 38 | 366 | 381 | 685 |
| 948544 | 44754 | 44769 | TGACGATTCCTGAACC | 18 | 368 | 383 | 686 |
| 948545 | 44755 | 44770 | GTGACGATTCCTGAAC | 40 | 369 | 384 | 687 |
| 948546 | 44756 | 44771 | GGTGACGATTCCTGAA | 42 | 370 | 385 | 688 |
| 948547 | 44758 | 44773 | CGGGTGACGATTCCTG | 111 | 372 | 387 | 689 |
| 948548 | 44761 | 44776 | CGCCGGGTGACGATTC | 44 | 375 | 390 | 690 |
| 948549 | 44769 | 44784 | TGAGAGGCCGCCGGGT | 11 | 383 | 398 | 691 |
| 948550 | 44771 | 44786 | AATGAGAGGCCGCCGG | 76 | 385 | 400 | 692 |
| 948551 | 44772 | 44787 | GAATGAGAGGCCGCCG | 67 | 386 | 401 | 693 |
| 948552 | 44775 | 44790 | GCAGAATGAGAGGCCG | 99 | 389 | 404 | 694 |
| 948553 | 57480 | 57495 | CAAAAACTCGGCATGT | 20 | 427 | 442 | 695 |
| 948554 | 57481 | 57496 | GCAAAAACTCGGCATG | 15 | 428 | 443 | 696 |
| 948555 | 57490 | 57505 | ACTTGCAGTGCAAAAA | 15 | 437 | 452 | 697 |
| 948556 | 57492 | 57507 | GGACTTGCAGTGCAAA | 7 | 439 | 454 | 698 |
| 948557 | 57494 | 57509 | TTGGACTTGCAGTGCA | 3 | 441 | 456 | 699 |
| 948558 | 57497 | 57512 | TTTTTGGACTTGCAGT | 10 | 444 | 459 | 700 |
| 948559 | 57498 | 57513 | CTTTTTGGACTTGCAG | 6 | 445 | 460 | 701 |
| 948560 | 57500 | 57515 | AACTTTTTGGACTTGC | 3 | 447 | 462 | 702 |
| 948561 | 57501 | 57516 | AAACTTTTTGGACTTG | 92 | 448 | 463 | 703 |
| 948562 | 57502 | 57517 | TAAACTTTTTGGACTT | 8 | 449 | 464 | 704 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948563 | 57503 | 57518 | GTAAACTTTTTGGACT | 26 | 450 | 465 | 705 |
| 948564 | 57504 | 57519 | TGTAAACTTTTTGGAC | 15 | 451 | 466 | 706 |
| 948565 | 57524 | 57539 | TGCCGGACTTCATCAA | 31 | 471 | 486 | 707 |
| 948566 | 57525 | 57540 | CTGCCGGACTTCATCA | 24 | 472 | 487 | 708 |
| 948567 | 57527 | 57542 | TCCTGCCGGACTTCAT | 26 | 474 | 489 | 709 |
| 948568 | 57530 | 57545 | ATCTCCTGCCGGACTT | 14 | 477 | 492 | 710 |
| 948569 | 57531 | 57546 | AATCTCCTGCCGGACT | 18 | 478 | 493 | 711 |
| 948570 | 57535 | 57550 | CTTCAATCTCCTGCCG | 29 | 482 | 497 | 712 |
| 948571 | 57597 | 57612 | TCGAAGGTTGATGGGC | 89 | 544 | 559 | 713 |
| 948572 | 57598 | 57613 | CTCGAAGGTTGATGGG | 88 | 545 | 560 | 714 |
| 948573 | 57599 | 57614 | ACTCGAAGGTTGATGG | 75 | 546 | 561 | 715 |
| 948574 | 60706 | 60721 | ATGAGGGTCAAGTTCA | 52 | 579 | 594 | 716 |
| 948575 | 60708 | 60723 | CGATGAGGGTCAAGTT | 15 | 581 | 596 | 717 |
| 948576 | 60709 | 60724 | TCGATGAGGGTCAAGT | 28 | 582 | 597 | 718 |
| 948577 | 60710 | 60725 | GTCGATGAGGGTCAAG | 22 | 583 | 598 | 719 |
| 948578 | 60712 | 60727 | AGGTCGATGAGGGTCA | 15 | 585 | 600 | 720 |
| 948579 | 60714 | 60729 | GGAGGTCGATGAGGGT | 53 | 587 | 602 | 721 |
| 948580 | 60717 | 60732 | CCGGGAGGTCGATGAG | 93 | 590 | 605 | 722 |
| 948581 | 60721 | 60736 | ATACCCGGGAGGTCGA | 32 | 594 | 609 | 723 |
| 948582 | 60723 | 60738 | TGATACCCGGGAGGTC | 34 | 596 | 611 | 724 |
| 948583 | 60725 | 60740 | GGTGATACCCGGGAGG | 32 | 598 | 613 | 725 |
| 948584 | 60726 | 60741 | TGGTGATACCCGGGAG | 79 | 599 | 614 | 726 |
| 948585 | 60727 | 60742 | TTGGTGATACCCGGGA | 27 | 600 | 615 | 727 |
| 948586 | 60729 | 60744 | CCTTGGTGATACCCGG | 44 | 602 | 617 | 728 |
| 948587 | 60774 | 60789 | CCTTGATCTGGTACTC | 6 | 647 | 662 | 729 |
| 948588 | 60775 | 60790 | TCCTTGATCTGGTACT | 20 | 648 | 663 | 730 |
| 948589 | 60777 | 60792 | TGTCCTTGATCTGGTA | 12 | 650 | 665 | 731 |
| 948590 | 60779 | 60794 | CATGTCCTTGATCTGG | 13 | 652 | 667 | 732 |
| 948591 | 60781 | 60796 | ATCATGTCCTTGATCT | 34 | 654 | 669 | 733 |
| 948592 | 60782 | 60797 | GATCATGTCCTTGATC | 57 | 655 | 670 | 734 |
| 948593 | 60783 | 60798 | GGATCATGTCCTTGAT | 38 | 656 | 671 | 735 |
| 948594 | 60815 | 60830 | AATGAGGCTGCTCTCC | 42 | 688 | 703 | 736 |
| 948595 | 60820 | 60835 | GCCAGAATGAGGCTGC | 92 | 693 | 708 | 737 |
| 948596 | 60848 | 60863 | GGCCAGGTCCATGTTG | 92 | 721 | 736 | 738 |
| 948597 | N/A | N/A | GGTCCGTAGGCCTTGG | 45 | 775 | 790 | 739 |
| 948598 | 62120 | 62135 | CACCGATGGTCCGTAG | 49 | 782 | 797 | 740 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948599 | 62192 | 62207 | ACGGGAGCAACTTGTT | 76 | 854 | 869 | 741 |
| 948600 | 62196 | 62211 | CTCAACGGGAGCAACT | 48 | 858 | 873 | 742 |
| 948601 | 62197 | 62212 | TCTCAACGGGAGCAAC | 45 | 859 | 874 | 743 |
| 948602 | 68004 | 68019 | CACGGATGTCCTTCTT | 8 | 923 | 938 | 744 |
| 948603 | 68006 | 68021 | TGCACGGATGTCCTTC | 25 | 925 | 940 | 745 |
| 948604 | 68007 | 68022 | CTGCACGGATGTCCTT | 5 | 926 | 941 | 746 |
| 948605 | 68009 | 68024 | TGCTGCACGGATGTCC | 16 | 928 | 943 | 747 |
| 948606 | 68010 | 68025 | GTGCTGCACGGATGTC | 20 | 929 | 944 | 748 |
| 948607 | 68011 | 68026 | AGTGCTGCACGGATGT | 22 | 930 | 945 | 749 |
| 948608 | 68012 | 68027 | CAGTGCTGCACGGATG | 8 | 931 | 946 | 750 |
| 948609 | 68014 | 68029 | GCCAGTGCTGCACGGA | 37 | 933 | 948 | 751 |
| 948610 | 68015 | 68030 | TGCCAGTGCTGCACGG | 50 | 934 | 949 | 752 |
| 948611 | 68016 | 68031 | CTGCCAGTGCTGCACG | 27 | 935 | 950 | 753 |
| 948612 | 68018 | 68033 | AGCTGCCAGTGCTGCA | 107 | 937 | 952 | 754 |
| 948613 | 68056 | 68071 | TGCCGGTAGGCCGGGT | 122 | 975 | 990 | 755 |
| 948614 | 71653 | 71668 | CCGAAAGTTCTTGTAC | 31 | 1129 | 1144 | 756 |
| 948615 | 71656 | 71671 | GGGCCGAAAGTTCTTG | 88 | 1132 | 1147 | 757 |
| 948616 | 71657 | 71672 | CGGGCCGAAAGTTCTT | 75 | 1133 | 1148 | 758 |
| 948617 | 71658 | 71673 | TCGGGCCGAAAGTTCT | 42 | 1134 | 1149 | 759 |
| 948618 | 71660 | 71675 | CGTCGGGCCGAAAGTT | 20 | 1136 | 1151 | 760 |
| 948619 | 71683 | 71698 | GGCTTTGGTTTTGCGG | 80 | 1159 | 1174 | 761 |
| 948620 | 78729 | 78744 | ATCCACCCCAAACTGC | 45 | 1192 | 1207 | 762 |
| 948621 | 78771 | 78786 | AGTGTCCACCTGATCT | 27 | 1234 | 1249 | 763 |
| 948622 | 78773 | 78788 | AGAGTGTCCACCTGAT | 11 | 1236 | 1251 | 764 |
| 948623 | 78774 | 78789 | CAGAGTGTCCACCTGA | 88 | 1237 | 1252 | 765 |
| 948624 | 78775 | 78790 | CCAGAGTGTCCACCTG | 74 | 1238 | 1253 | 766 |
| 948625 | 78777 | 78792 | CTCCAGAGTGTCCACC | 51 | 1240 | 1255 | 767 |
| 948626 | 78785 | 78800 | CCGGAGAGCTCCAGAG | 98 | 1248 | 1263 | 768 |
| 948627 | 78787 | 78802 | CCCCGGAGAGCTCCAG | 44 | 1250 | 1265 | 769 |
| 948628 | 78805 | 78820 | TGCGATTGATTCGGGC | 11 | 1268 | 1283 | 770 |
| 948629 | 78806 | 78821 | ATGCGATTGATTCGGG | 3 | 1269 | 1284 | 771 |
| 948630 | 78810 | 78825 | GAAGATGCGATTGATT | 10 | 1273 | 1288 | 772 |
| 948631 | 78811 | 78826 | GGAAGATGCGATTGAT | 3 | 1274 | 1289 | 773 |
| 948632 | 78812 | 78827 | TGGAAGATGCGATTGA | 9 | 1275 | 1290 | 774 |
| 948633 | 78813 | 78828 | GTGGAAGATGCGATTG | 8 | 1276 | 1291 | 775 |
| 948634 | 78829 | 78844 | CAAATGGGAACCGCTC | 60 | 1292 | 1307 | 776 |
| 948635 | 78830 | 78845 | TCAAATGGGAACCGCT | 65 | 1293 | 1308 | 777 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948636 | 78831 | 78846 | CTCAAATGGGAACCGC | 81 | 1294 | 1309 | 778 |
| 948637 | 78832 | 78847 | GCTCAAATGGGAACCG | 58 | 1295 | 1310 | 779 |
| 948638 | 78833 | 78848 | AGCTCAAATGGGAACC | 43 | 1296 | 1311 | 780 |
| 948639 | 78837 | 78852 | CACCAGCTCAAATGGG | 70 | 1300 | 1315 | 781 |
| 948640 | 80420 | 80435 | CTCCATGGATGTTCTT | 42 | 1367 | 1382 | 782 |
| 948641 | 81059 | 81074 | TGAAAAGCCCGGTCCT | 38 | 1385 | 1400 | 783 |
| 948642 | 81060 | 81075 | GTGAAAAGCCCGGTCC | 37 | 1386 | 1401 | 784 |
| 948643 | 81062 | 81077 | GGGTGAAAAGCCCGGT | 120 | 1388 | 1403 | 785 |
| 948644 | 81077 | 81092 | CGAATGCCAAGTCCGG | 84 | 1403 | 1418 | 786 |
| 948645 | 81078 | 81093 | TCGAATGCCAAGTCCG | 28 | 1404 | 1419 | 787 |
| 948646 | 81080 | 81095 | CCTCGAATGCCAAGTC | 13 | 1406 | 1421 | 788 |
| 948647 | 81081 | 81096 | GCCTCGAATGCCAAGT | 73 | 1407 | 1422 | 789 |
| 948648 | 81084 | 81099 | ATGGCCTCGAATGCCA | 94 | 1410 | 1425 | 790 |
| 948649 | 81088 | 81103 | CACAATGGCCTCGAAT | 35 | 1414 | 1429 | 791 |
| 948650 | 81104 | 81119 | TGACGACCTGCTTTTT | 15 | 1430 | 1445 | 792 |
| 948651 | 81105 | 81120 | TTGACGACCTGCTTTT | 21 | 1431 | 1446 | 793 |
| 948652 | 81108 | 81123 | AGCTTGACGACCTGCT | 84 | 1434 | 1449 | 794 |
| 948653 | 81110 | 81125 | TCAGCTTGACGACCTG | 61 | 1436 | 1451 | 795 |
| 948654 | 81112 | 81127 | TTTCAGCTTGACGACC | 11 | 1438 | 1453 | 796 |
| 948655 | 81114 | 81129 | TCTTTCAGCTTGACGA | 27 | 1440 | 1455 | 797 |
| 948656 | 81116 | 81131 | GCTCTTTCAGCTTGAC | 3 | 1442 | 1457 | 798 |
| 948657 | 81117 | 81132 | GGCTCTTTCAGCTTGA | 59 | 1443 | 1458 | 799 |
| 948658 | 81118 | 81133 | GGGCTCTTTCAGCTTG | 73 | 1444 | 1459 | 800 |
| 948659 | 81120 | 81135 | CAGGGCTCTTTCAGCT | 75 | 1446 | 1461 | 801 |
| 948660 | 81132 | 81147 | ACACATTTCAGACAGG | 3 | 1458 | 1473 | 802 |
| 948661 | 81134 | 81149 | CGACACATTTCAGACA | 7 | 1460 | 1475 | 803 |
| 948662 | 81135 | 81150 | TCGACACATTTCAGAC | 10 | 1461 | 1476 | 804 |
| 948663 | 81136 | 81151 | GTCGACACATTTCAGA | 51 | 1462 | 1477 | 805 |
| 948664 | 81138 | 81153 | AGGTCGACACATTTCA | 3 | 1464 | 1479 | 806 |
| 948665 | 81140 | 81155 | CCAGGTCGACACATTT | 6 | 1466 | 1481 | 807 |
| 948666 | 81141 | 81156 | ACCAGGTCGACACATT | 8 | 1467 | 1482 | 808 |
| 948667 | 81142 | 81157 | AACCAGGTCGACACAT | 34 | 1468 | 1483 | 809 |
| 948668 | 81146 | 81161 | GGATAACCAGGTCGAC | 34 | 1472 | 1487 | 810 |
| 948669 | 81148 | 81163 | CTGGATAACCAGGTCG | 43 | 1474 | 1489 | 811 |
| 948670 | 81149 | 81164 | CCTGGATAACCAGGTC | 111 | 1475 | 1490 | 812 |
| 948671 | 81150 | 81165 | TCCTGGATAACCAGGT | 100 | 1476 | 1491 | 813 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948672 | 81152 | 81167 | GCTCCTGGATAACCAG | 51 | 1478 | 1493 | 814 |
| 948673 | 81159 | 81174 | TTGATTAGCTCCTGGA | 2 | 1485 | 1500 | 815 |
| 948674 | 81161 | 81176 | TATTGATTAGCTCCTG | 8 | 1487 | 1502 | 816 |
| 948675 | 81162 | 81177 | GTATTGATTAGCTCCT | 2 | 1488 | 1503 | 817 |
| 948676 | 81163 | 81178 | TGTATTGATTAGCTCC | 1 | 1489 | 1504 | 818 |
| 948677 | 81164 | 81179 | CTGTATTGATTAGCTC | 2 | 1490 | 1505 | 819 |
| 948678 | 81165 | 81180 | ACTGTATTGATTAGCT | 7 | 1491 | 1506 | 820 |
| 948679 | 81168 | 81183 | CTAACTGTATTGATTA | 56 | 1494 | 1509 | 821 |
| 948680 | 81169 | 81184 | CCTAACTGTATTGATT | 44 | 1495 | 1510 | 822 |
| 948681 | 81171 | 81186 | TGCCTAACTGTATTGA | 25 | 1497 | 1512 | 823 |
| 948682 | 81177 | 81192 | GTACACTGCCTAACTG | 23 | 1503 | 1518 | 824 |
| 948683 | 81180 | 81195 | CTGGTACACTGCCTAA | 14 | 1506 | 1521 | 825 |
| 948684 | 81181 | 81196 | ACTGGTACACTGCCTA | 8 | 1507 | 1522 | 826 |
| 948685 | 81183 | 81198 | TTACTGGTACACTGCC | 2 | 1509 | 1524 | 827 |
| 948686 | 81184 | 81199 | CTTACTGGTACACTGC | 1 | 1510 | 1525 | 828 |
| 948687 | N/A | N/A | GCTTACTGGTACACTG | 6 | 1511 | 1526 | 829 |
| 948688 | N/A | N/A | AGCTTACTGGTACACT | 26 | 1512 | 1527 | 830 |
| 948689 | N/A | N/A | GAGCTTACTGGTACAC | 12 | 1513 | 1528 | 831 |
| 948690 | N/A | N/A | ACTGAGCTTACTGGTA | 47 | 1516 | 1531 | 832 |
| 948691 | N/A | N/A | AACTGAGCTTACTGGT | 24 | 1517 | 1532 | 833 |
| 948692 | N/A | N/A | GGAACTGAGCTTACTG | 10 | 1519 | 1534 | 834 |
| 948693 | N/A | N/A | AGGAACTGAGCTTACT | 12 | 1520 | 1535 | 835 |
| 948694 | N/A | N/A | TAGGAACTGAGCTTAC | 17 | 1521 | 1536 | 836 |
| 948695 | N/A | N/A | GTAGGAACTGAGCTTA | 15 | 1522 | 1537 | 837 |
| 948696 | 83484 | 83499 | GGGTAGGAACTGAGCT | 28 | 1524 | 1539 | 838 |
| 948697 | 83500 | 83515 | CTCCTCTCGCAACCGG | 56 | 1540 | 1555 | 839 |
| 948698 | 83503 | 83518 | TGTCTCCTCTCGCAAC | 44 | 1543 | 1558 | 840 |
| 948699 | 83504 | 83519 | CTGTCTCCTCTCGCAA | 27 | 1544 | 1559 | 841 |
| 948700 | 83506 | 83521 | CTCTGTCTCCTCTCGC | 5 | 1546 | 1561 | 842 |
| 948701 | 83507 | 83522 | GCTCTGTCTCCTCTCG | 8 | 1547 | 1562 | 843 |
| 948702 | 83508 | 83523 | CGCTCTGTCTCCTCTC | 5 | 1548 | 1563 | 844 |
| 948703 | 83510 | 83525 | TTCGCTCTGTCTCCTC | 5 | 1550 | 1565 | 845 |
| 948704 | 83514 | 83529 | ACGATTCGCTCTGTCT | 69 | 1554 | 1569 | 846 |
| 948705 | 83515 | 83530 | GACGATTCGCTCTGTC | 91 | 1555 | 1570 | 847 |
| 948706 | 83516 | 83531 | TGACGATTCGCTCTGT | 37 | 1556 | 1571 | 848 |
| 948707 | 83521 | 83536 | AGTGGTGACGATTCGC | 5 | 1561 | 1576 | 849 |
| 948708 | 83523 | 83538 | TAAGTGGTGACGATTC | 25 | 1563 | 1578 | 850 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948709 | 83525 | 83540 | TGTAAGTGGTGACGAT | 21 | 1565 | 1580 | 851 |
| 948710 | 83526 | 83541 | ATGTAAGTGGTGACGA | 27 | 1566 | 1581 | 852 |
| 948711 | 83527 | 83542 | GATGTAAGTGGTGACG | 37 | 1567 | 1582 | 853 |
| 948712 | 83530 | 83545 | CCGGATGTAAGTGGTG | 60 | 1570 | 1585 | 854 |
| 948713 | 83543 | 83558 | TCCCCTCCCGTTCCCG | 40 | 1583 | 1598 | 855 |
| 948714 | 83545 | 83560 | TCTCCCCTCCCGTTCC | 30 | 1585 | 1600 | 856 |
| 948715 | 83546 | 83561 | TTCTCCCCTCCCGTTC | 43 | 1586 | 1601 | 857 |
| 948716 | 83547 | 83562 | GTTCTCCCCTCCCGTT | 14 | 1587 | 1602 | 858 |
| 948717 | N/A | N/A | GCAGAAGAATCTGGTC | 27 | 1607 | 1622 | 859 |
| 948718 | 87287 | 87302 | GATCAGCAGAAGAATC | 126 | 1612 | 1627 | 860 |
| 948719 | 87289 | 87304 | TCGATCAGCAGAAGAA | 70 | 1614 | 1629 | 861 |
| 948720 | 87291 | 87306 | TGTCGATCAGCAGAAG | 27 | 1616 | 1631 | 862 |
| 948721 | 87292 | 87307 | ATGTCGATCAGCAGAA | 51 | 1617 | 1632 | 863 |
| 948722 | 87293 | 87308 | AATGTCGATCAGCAGA | 41 | 1618 | 1633 | 864 |
| 948723 | 87295 | 87310 | TCAATGTCGATCAGCA | 17 | 1620 | 1635 | 865 |
| 948724 | 87297 | 87312 | GCTCAATGTCGATCAG | 14 | 1622 | 1637 | 866 |
| 948725 | 87298 | 87313 | TGCTCAATGTCGATCA | 41 | 1623 | 1638 | 867 |
| 948726 | 87301 | 87316 | GACTGCTCAATGTCGA | 91 | 1626 | 1641 | 868 |
| 948727 | 87303 | 87318 | AGGACTGCTCAATGTC | 28 | 1628 | 1643 | 869 |
| 948728 | 87305 | 87320 | GTAGGACTGCTCAATG | 136 | 1630 | 1645 | 870 |
| 948729 | 87306 | 87321 | TGTAGGACTGCTCAAT | 2 | 1631 | 1646 | 871 |
| 948730 | 87307 | 87322 | ATGTAGGACTGCTCAA | 18 | 1632 | 1647 | 872 |
| 948731 | 87309 | 87324 | TGATGTAGGACTGCTC | 6 | 1634 | 1649 | 873 |
| 948732 | 87310 | 87325 | TTGATGTAGGACTGCT | 13 | 1635 | 1650 | 874 |
| 948733 | 87312 | 87327 | TGTTGATGTAGGACTG | 39 | 1637 | 1652 | 875 |
| 948734 | 87313 | 87328 | GTGTTGATGTAGGACT | 22 | 1638 | 1653 | 876 |
| 948735 | 87314 | 87329 | CGTGTTGATGTAGGAC | 3 | 1639 | 1654 | 877 |
| 948736 | N/A | N/A | GGCATTGGCAAACCCG | 106 | 1672 | 1687 | 878 |
| 948737 | 97293 | 97308 | CATCAGGCTGATGTTG | 43 | 1765 | 1780 | 879 |
| 948738 | 97296 | 97311 | TTTCATCAGGCTGATG | 90 | 1768 | 1783 | 880 |
| 948739 | 97340 | 97355 | AGTGACTCGGCAGTCA | 100 | 1812 | 1827 | 881 |
| 948740 | 97342 | 97357 | ACAGTGACTCGGCAGT | 25 | 1814 | 1829 | 882 |
| 948741 | 97343 | 97358 | GACAGTGACTCGGCAG | 13 | 1815 | 1830 | 883 |
| 948742 | 97344 | 97359 | GGACAGTGACTCGGCA | 33 | 1816 | 1831 | 884 |
| 948743 | 97346 | 97361 | CAGGACAGTGACTCGG | 23 | 1818 | 1833 | 885 |
| 948744 | 97347 | 97362 | CCAGGACAGTGACTCG | 36 | 1819 | 1834 | 886 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948745 | 97348 | 97363 | ACCAGGACAGTGACTC | 23 | 1820 | 1835 | 887 |
| 948746 | 97349 | 97364 | TACCAGGACAGTGACT | 93 | 1821 | 1836 | 888 |
| 948747 | 105014 | 105029 | TCACGGATCTTGAGGT | 27 | 1884 | 1899 | 889 |
| 948748 | 105016 | 105031 | CATCACGGATCTTGAG | 52 | 1886 | 1901 | 890 |
| 948749 | 105017 | 105032 | ACATCACGGATCTTGA | 43 | 1887 | 1902 | 891 |
| 948750 | 105018 | 105033 | CACATCACGGATCTTG | 19 | 1888 | 1903 | 892 |
| 948751 | 105021 | 105036 | CTCCACATCACGGATC | 60 | 1891 | 1906 | 893 |
| 948752 | 105024 | 105039 | CTTCTCCACATCACGG | 4 | 1894 | 1909 | 894 |
| 948753 | 105061 | 105076 | TGAAGATGGCGAAGAC | 52 | 1931 | 1946 | 895 |
| 948754 | 105062 | 105077 | TTGAAGATGGCGAAGA | 101 | 1932 | 1947 | 896 |
| 948755 | 105063 | 105078 | GTTGAAGATGGCGAAG | 83 | 1933 | 1948 | 897 |
| 948756 | 108794 | 108809 | CCGCAGGTCCTTGTAG | 60 | 1966 | 1981 | 898 |
| 948757 | 108796 | 108811 | TGCCGCAGGTCCTTGT | 42 | 1968 | 1983 | 899 |
| 948758 | 108809 | 108824 | GGCCAGCTCGATCTGC | 85 | 1981 | 1996 | 900 |
| 948759 | 108855 | 108870 | GGAGGAACGAGGCCTT | 80 | 2027 | 2042 | 901 |
| 948760 | 108856 | 108871 | CGGAGGAACGAGGCCT | 107 | 2028 | 2043 | 902 |
| 948761 | 108858 | 108873 | CTCGGAGGAACGAGGC | 111 | 2030 | 2045 | 903 |
| 948762 | 108864 | 108879 | CGCCAGCTCGGAGGAA | 125 | 2036 | 2051 | 904 |
| 948763 | 110079 | 110094 | GAGAAGGTGTTCTCCT | 98 | 2094 | 2109 | 905 |
| 948764 | 110082 | 110097 | ATGGAGAAGGTGTTCT | 112 | 2097 | 2112 | 906 |
| 948765 | 110158 | 110173 | GGACTTGTTGATGATG | 9 | 2173 | 2188 | 907 |
| 948766 | 110159 | 110174 | TGGACTTGTTGATGAT | 10 | 2174 | 2189 | 908 |
| 948767 | 110161 | 110176 | GATGGACTTGTTGATG | 12 | 2176 | 2191 | 909 |
| 948768 | 110162 | 110177 | GGATGGACTTGTTGAT | 8 | 2177 | 2192 | 910 |
| 948769 | 110163 | 110178 | CGGATGGACTTGTTGA | 10 | 2178 | 2193 | 911 |
| 948770 | 110164 | 110179 | GCGGATGGACTTGTTG | 36 | 2179 | 2194 | 912 |
| 948771 | 110165 | 110180 | CGCGGATGGACTTGTT | 78 | 2180 | 2195 | 913 |
| 948772 | 110173 | 110188 | CATGAGGTCGCGGATG | 25 | 2188 | 2203 | 914 |
| 948773 | 110174 | 110189 | GCATGAGGTCGCGGAT | 4 | 2189 | 2204 | 915 |
| 948774 | 110176 | 110191 | TGGCATGAGGTCGCGG | 9 | 2191 | 2206 | 916 |
| 948775 | 114037 | 114052 | TGGATGAAGGCCTTCG | 6 | 2238 | 2253 | 917 |
| 948776 | 114065 | 114080 | GGAGTATAGGTAGGCC | 15 | 2266 | 2281 | 918 |
| 948777 | 114067 | 114082 | GAGGAGTATAGGTAGG | 7 | 2268 | 2283 | 919 |
| 948778 | 114070 | 114085 | GCCGAGGAGTATAGGT | 51 | 2271 | 2286 | 920 |
| 948779 | 114071 | 114086 | TGCCGAGGAGTATAGG | 17 | 2272 | 2287 | 921 |
| 948780 | 114152 | 114167 | CTTGAGGGCATGGTAC | 48 | 2353 | 2368 | 922 |
| 948781 | 114225 | 114240 | TGTCATCGACAGGCGG | 32 | 2426 | 2441 | 923 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948782 | 115139 | 115154 | GGACACCGGTCGGCGC | 103 | 2482 | 2497 | 924 |
| 948783 | 115140 | 115155 | TGGACACCGGTCGGCG | 43 | 2483 | 2498 | 925 |
| 948784 | 115145 | 115160 | TATGCTGGACACCGGT | 33 | 2488 | 2503 | 926 |
| 948785 | 115147 | 115162 | TGTATGCTGGACACCG | 22 | 2490 | 2505 | 927 |
| 948786 | 115148 | 115163 | GTGTATGCTGGACACC | 78 | 2491 | 2506 | 928 |
| 948787 | 115149 | 115164 | GGTGTATGCTGGACAC | 79 | 2492 | 2507 | 929 |
| 948788 | 115212 | 115227 | CGGGAACAGGAATCAG | 13 | 2555 | 2570 | 930 |
| 948789 | 115213 | 115228 | ACGGGAACAGGAATCA | 19 | 2556 | 2571 | 931 |
| 948790 | 115217 | 115232 | CCCCACGGGAACAGGA | 101 | 2560 | 2575 | 932 |
| 948791 | 115235 | 115250 | CGAGAAGGAGGCTGCT | 45 | 2578 | 2593 | 933 |
| 948792 | 115236 | 115251 | CCGAGAAGGAGGCTGC | 37 | 2579 | 2594 | 934 |
| 948793 | 115237 | 115252 | GCCGAGAAGGAGGCTG | 124 | 2580 | 2595 | 935 |
| 948794 | 115279 | 115294 | GCAAACACGCTCTGGG | 6 | 2622 | 2637 | 936 |
| 948795 | 115280 | 115295 | GGCAAACACGCTCTGG | 11 | 2623 | 2638 | 937 |
| 948796 | 115281 | 115296 | TGGCAAACACGCTCTG | 31 | 2624 | 2639 | 938 |
| 948797 | 115282 | 115297 | TTGGCAAACACGCTCT | 23 | 2625 | 2640 | 939 |
| 948798 | 115284 | 115299 | TGTTGGCAAACACGCT | 15 | 2627 | 2642 | 940 |
| 948799 | 115286 | 115301 | ACTGTTGGCAAACACG | 66 | 2629 | 2644 | 941 |
| 948800 | 115287 | 115302 | CACTGTTGGCAAACAC | 39 | 2630 | 2645 | 942 |
| 948801 | 115288 | 115303 | TCACTGTTGGCAAACA | 28 | 2631 | 2646 | 943 |
| 948802 | 115289 | 115304 | GTCACTGTTGGCAAAC | 17 | 2632 | 2647 | 944 |
| 948803 | 115290 | 115305 | GGTCACTGTTGGCAAA | 16 | 2633 | 2648 | 945 |
| 948804 | 115291 | 115306 | AGGTCACTGTTGGCAA | 9 | 2634 | 2649 | 946 |
| 948805 | 115293 | 115308 | AGAGGTCACTGTTGGC | 3 | 2636 | 2651 | 947 |
| 948806 | 115294 | 115309 | AAGAGGTCACTGTTGG | 7 | 2637 | 2652 | 948 |
| 948807 | 115295 | 115310 | GAAGAGGTCACTGTTG | 19 | 2638 | 2653 | 949 |
| 948808 | 115297 | 115312 | GGGAAGAGGTCACTGT | 13 | 2640 | 2655 | 950 |
| 948809 | 115321 | 115336 | CGAGATGGGATCTGAG | 33 | 2664 | 2679 | 951 |
| 948810 | 115322 | 115337 | CCGAGATGGGATCTGA | 18 | 2665 | 2680 | 952 |
| 948811 | 115323 | 115338 | GCCGAGATGGGATCTG | 28 | 2666 | 2681 | 953 |
| 948812 | 115327 | 115342 | ACTGGCCGAGATGGGA | 13 | 2670 | 2685 | 954 |
| 948813 | 115328 | 115343 | AACTGGCCGAGATGGG | 20 | 2671 | 2686 | 955 |
| 948814 | 115330 | 115345 | CGAACTGGCCGAGATG | 27 | 2673 | 2688 | 956 |
| 948815 | 115331 | 115346 | CCGAACTGGCCGAGAT | 46 | 2674 | 2689 | 957 |
| 948816 | 115333 | 115348 | ATCCGAACTGGCCGAG | 35 | 2676 | 2691 | 958 |
| 948817 | 115334 | 115349 | GATCCGAACTGGCCGA | 105 | 2677 | 2692 | 959 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948818 | 115991 | 116006 | GCCGGCTGGGCGCAGC | 124 | 2735 | 2750 | 960 |
| 948819 | 116000 | 116015 | TAATGGTGGGCCGGCT | 83 | 2744 | 2759 | 961 |
| 948820 | 116002 | 116017 | GATAATGGTGGGCCGG | 96 | 2746 | 2761 | 962 |
| 948821 | 116003 | 116018 | GGATAATGGTGGGCCG | 73 | 2747 | 2762 | 963 |
| 948822 | 116004 | 116019 | CGGATAATGGTGGGCC | 41 | 2748 | 2763 | 964 |
| 948823 | 116014 | 116029 | CTCGGCTGGGCGGATA | 109 | 2758 | 2773 | 965 |
| 948824 | 116023 | 116038 | CAGGGATGGCTCGGCT | 48 | 2767 | 2782 | 966 |
| 948825 | 116028 | 116043 | TCGAGCAGGGATGGCT | 84 | 2772 | 2787 | 967 |
| 948826 | 116029 | 116044 | GTCGAGCAGGGATGGC | 135 | 2773 | 2788 | 968 |
| 948827 | 116034 | 116049 | GCCTAGTCGAGCAGGG | 84 | 2778 | 2793 | 969 |
| 948828 | 116055 | 116070 | CGAGAGCACGCCCCCC | 37 | 2799 | 2814 | 970 |
| 948829 | 116058 | 116073 | CCCCGAGAGCACGCCC | 73 | 2802 | 2817 | 971 |
| 948830 | 116092 | 116107 | ACTGAAGCTCCTGCGC | 75 | 2836 | 2851 | 972 |
| 948831 | 116109 | 116124 | GCGGAGGGCCCCAGAC | 94 | 2853 | 2868 | 973 |
| 948832 | 116163 | 116178 | GTTAAGGAAGAGGCCA | 27 | 2907 | 2922 | 974 |
| 948833 | 116210 | 116225 | TGCGGTGTCCAGCCAG | 42 | 2954 | 2969 | 975 |
| 948834 | 116212 | 116227 | AGTGCGGTGTCCAGCC | 24 | 2956 | 2971 | 976 |
| 948835 | 116213 | 116228 | CAGTGCGGTGTCCAGC | 9 | 2957 | 2972 | 977 |
| 948836 | 116214 | 116229 | GCAGTGCGGTGTCCAG | 11 | 2958 | 2973 | 978 |
| 948837 | 116216 | 116231 | GCGCAGTGCGGTGTCC | 60 | 2960 | 2975 | 979 |
| 948838 | 116217 | 116232 | TGCGCAGTGCGGTGTC | 58 | 2961 | 2976 | 980 |
| 948839 | 116221 | 116236 | CCTTTGCGCAGTGCGG | 57 | 2965 | 2980 | 981 |
| 948840 | 116222 | 116237 | CCCTTTGCGCAGTGCG | 21 | 2966 | 2981 | 982 |
| 948841 | 116224 | 116239 | GCCCCTTTGCGCAGTG | 104 | 2968 | 2983 | 983 |
| 948842 | 116225 | 116240 | GGCCCCTTTGCGCAGT | 98 | 2969 | 2984 | 984 |
| 948843 | 116261 | 116276 | GTGCAACACCCCAGCG | 58 | 3005 | 3020 | 985 |
| 948844 | 116266 | 116281 | CCAAAGTGCAACACCC | 31 | 3010 | 3025 | 986 |
| 948845 | 116267 | 116282 | CCCAAAGTGCAACACC | 82 | 3011 | 3026 | 987 |
| 948846 | 116288 | 116303 | TGCCACCCTGAGACTC | 62 | 3032 | 3047 | 988 |
| 948847 | 116310 | 116325 | TCAAGGGTTCTGGTCC | 10 | 3054 | 3069 | 989 |
| 948848 | 116311 | 116326 | GTCAAGGGTTCTGGTC | 28 | 3055 | 3070 | 990 |
| 948849 | 116313 | 116328 | GTGTCAAGGGTTCTGG | 8 | 3057 | 3072 | 991 |
| 948850 | 116315 | 116330 | TGGTGTCAAGGGTTCT | 6 | 3059 | 3074 | 992 |
| 948851 | 116316 | 116331 | ATGGTGTCAAGGGTTC | 5 | 3060 | 3075 | 993 |
| 948852 | 116317 | 116332 | GATGGTGTCAAGGGTT | 6 | 3061 | 3076 | 994 |
| 948853 | 116319 | 116334 | AGGATGGTGTCAAGGG | 13 | 3063 | 3078 | 995 |
| 948854 | 116320 | 116335 | CAGGATGGTGTCAAGG | 11 | 3064 | 3079 | 996 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948855 | 116321 | 116336 | TCAGGATGGTGTCAAG | 13 | 3065 | 3080 | 997 |
| 948856 | 116323 | 116338 | ATTCAGGATGGTGTCA | 13 | 3067 | 3082 | 998 |
| 948857 | 116325 | 116340 | TCATTCAGGATGGTGT | 20 | 3069 | 3084 | 999 |
| 948858 | 116327 | 116342 | CCTCATTCAGGATGGT | 82 | 3071 | 3086 | 1000 |
| 948859 | 116351 | 116366 | GTAGAGTCCCCCCCAG | 22 | 3095 | 3110 | 1001 |
| 948860 | 116353 | 116368 | TGGTAGAGTCCCCCCC | 44 | 3097 | 3112 | 1002 |
| 948861 | 116354 | 116369 | TTGGTAGAGTCCCCCC | 19 | 3098 | 3113 | 1003 |
| 948862 | 116355 | 116370 | CTTGGTAGAGTCCCCC | 9 | 3099 | 3114 | 1004 |
| 948863 | 116357 | 116372 | ACCTTGGTAGAGTCCC | 4 | 3101 | 3116 | 1005 |
| 948864 | 116358 | 116373 | GACCTTGGTAGAGTCC | 94 | 3102 | 3117 | 1006 |
| 948865 | 116361 | 116376 | GAAGACCTTGGTAGAG | 6 | 3105 | 3120 | 1007 |
| 948866 | 116363 | 116378 | AAGAAGACCTTGGTAG | 17 | 3107 | 3122 | 1008 |
| 948867 | 116364 | 116379 | CAAGAAGACCTTGGTA | 60 | 3108 | 3123 | 1009 |
| 948868 | 116365 | 116380 | CCAAGAAGACCTTGGT | 62 | 3109 | 3124 | 1010 |
| 948869 | 116366 | 116381 | CCCAAGAAGACCTTGG | 70 | 3110 | 3125 | 1011 |
| 948870 | 116367 | 116382 | GCCCAAGAAGACCTTG | 60 | 3111 | 3126 | 1012 |
| 948871 | 116384 | 116399 | CTACATGGGCTTTCCC | 85 | 3128 | 3143 | 1013 |
| 948872 | 116386 | 116401 | CCCTACATGGGCTTTC | 98 | 3130 | 3145 | 1014 |
| 948873 | 116399 | 116414 | TATAGAAGGCCTGCCC | 100 | 3143 | 3158 | 1015 |
| 948874 | 116401 | 116416 | CTTATAGAAGGCCTGC | 20 | 3145 | 3160 | 1016 |
| 948875 | 116402 | 116417 | ACTTATAGAAGGCCTG | 25 | 3146 | 3161 | 1017 |
| 948876 | 116403 | 116418 | CACTTATAGAAGGCCT | 34 | 3147 | 3162 | 1018 |
| 948877 | 116405 | 116420 | CGCACTTATAGAAGGC | 57 | 3149 | 3164 | 1019 |
| 948878 | 116406 | 116421 | CCGCACTTATAGAAGG | 83 | 3150 | 3165 | 1020 |
| 948879 | 116450 | 116465 | CCCTGCACCCCAGCAA | 128 | 3194 | 3209 | 1021 |
| 948880 | 116454 | 116469 | ATACCCCTGCACCCCA | 18 | 3198 | 3213 | 1022 |
| 948881 | 116456 | 116471 | ATATACCCCTGCACCC | 45 | 3200 | 3215 | 1023 |
| 948882 | 116457 | 116472 | GATATACCCCTGCACC | 11 | 3201 | 3216 | 1024 |
| 948883 | 116458 | 116473 | TGATATACCCCTGCAC | 13 | 3202 | 3217 | 1025 |
| 948884 | 116459 | 116474 | TTGATATACCCCTGCA | 9 | 3203 | 3218 | 1026 |
| 948885 | 116460 | 116475 | GTTGATATACCCCTGC | 4 | 3204 | 3219 | 1027 |
| 948886 | 116465 | 116480 | GGGAAGTTGATATACC | 14 | 3209 | 3224 | 1028 |
| 948887 | 116466 | 116481 | TGGGAAGTTGATATAC | 20 | 3210 | 3225 | 1029 |
| 948888 | 116468 | 116483 | AATGGGAAGTTGATAT | 59 | 3212 | 3227 | 1030 |
| 948889 | 116469 | 116484 | TAATGGGAAGTTGATA | 49 | 3213 | 3228 | 1031 |
| 948890 | 116470 | 116485 | CTAATGGGAAGTTGAT | 15 | 3214 | 3229 | 1032 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948891 | 116472 | 116487 | TGCTAATGGGAAGTTG | 12 | 3216 | 3231 | 1033 |
| 948892 | 116473 | 116488 | CTGCTAATGGGAAGTT | 4 | 3217 | 3232 | 1034 |
| 948893 | 116475 | 116490 | TCCTGCTAATGGGAAG | 2 | 3219 | 3234 | 1035 |
| 948894 | 116476 | 116491 | CTCCTGCTAATGGGAA | 86 | 3220 | 3235 | 1036 |
| 948895 | 116479 | 116494 | GAGCTCCTGCTAATGG | 94 | 3223 | 3238 | 1037 |
| 948896 | 116498 | 116513 | GGCCAGGCTTGCCGCT | 99 | 3242 | 3257 | 1038 |
| 948897 | 116512 | 116527 | TACCGAGCCCACTGGG | 103 | 3256 | 3271 | 1039 |
| 948898 | 116515 | 116530 | CACTACCGAGCCCACT | 82 | 3259 | 3274 | 1040 |
| 948899 | 116517 | 116532 | GGCACTACCGAGCCCA | 64 | 3261 | 3276 | 1041 |
| 948900 | 116520 | 116535 | CTGGGCACTACCGAGC | 92 | 3264 | 3279 | 1042 |
| 948901 | 116525 | 116540 | GCCAGCTGGGCACTAC | 149 | 3269 | 3284 | 1043 |
| 948902 | 116526 | 116541 | TGCCAGCTGGGCACTA | 130 | 3270 | 3285 | 1044 |
| 948903 | 116539 | 116554 | TACACCTCAGGCCTGC | 28 | 3283 | 3298 | 1045 |
| 948904 | 116540 | 116555 | GTACACCTCAGGCCTG | 98 | 3284 | 3299 | 1046 |
| 948905 | 116542 | 116557 | ATGTACACCTCAGGCC | 77 | 3286 | 3301 | 1047 |
| 948906 | 116543 | 116558 | TATGTACACCTCAGGC | 9 | 3287 | 3302 | 1048 |
| 948907 | 116545 | 116560 | ACTATGTACACCTCAG | 5 | 3289 | 3304 | 1049 |
| 948908 | 116546 | 116561 | GACTATGTACACCTCA | 16 | 3290 | 3305 | 1050 |
| 948909 | 116548 | 116563 | AGGACTATGTACACCT | 125 | 3292 | 3307 | 1051 |
| 948910 | 116549 | 116564 | AAGGACTATGTACACC | 5 | 3293 | 3308 | 1052 |
| 948911 | 116551 | 116566 | GGAAGGACTATGTACA | 11 | 3295 | 3310 | 1053 |
| 948912 | 116552 | 116567 | GGGAAGGACTATGTAC | 28 | 3296 | 3311 | 1054 |
| 948913 | 116553 | 116568 | CGGGAAGGACTATGTA | 16 | 3297 | 3312 | 1055 |
| 948914 | 116554 | 116569 | CCGGGAAGGACTATGT | 60 | 3298 | 3313 | 1056 |
| 948915 | 116555 | 116570 | GCCGGGAAGGACTATG | 40 | 3299 | 3314 | 1057 |
| 948916 | 116560 | 116575 | ATATGGCCGGGAAGGA | 21 | 3304 | 3319 | 1058 |
| 948917 | 116562 | 116577 | TAATATGGCCGGGAAG | 2 | 3306 | 3321 | 1059 |
| 948918 | 116563 | 116578 | TTAATATGGCCGGGAA | 9 | 3307 | 3322 | 1060 |
| 948919 | 116564 | 116579 | GTTAATATGGCCGGGA | 16 | 3308 | 3323 | 1061 |
| 948920 | 116566 | 116581 | TGGTTAATATGGCCGG | 37 | 3310 | 3325 | 1062 |
| 948921 | 116567 | 116582 | GTGGTTAATATGGCCG | 45 | 3311 | 3326 | 1063 |
| 948922 | 116568 | 116583 | TGTGGTTAATATGGCC | 10 | 3312 | 3327 | 1064 |
| 948923 | 116570 | 116585 | TGTGTGGTTAATATGG | 3 | 3314 | 3329 | 1065 |
| 948924 | 116571 | 116586 | CTGTGTGGTTAATATG | 4 | 3315 | 3330 | 1066 |
| 948925 | 116572 | 116587 | GCTGTGTGGTTAATAT | 7 | 3316 | 3331 | 1067 |
| 948926 | 116574 | 116589 | AGGCTGTGTGGTTAAT | 3 | 3318 | 3333 | 1068 |
| 948927 | 116618 | 116633 | GGCCTAGCAAAGGCAC | 118 | 3362 | 3377 | 1069 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948928 | 116631 | 116646 | GCCAACGGCTCCGGGC | 119 | 3375 | 3390 | 1070 |
| 948929 | 116637 | 116652 | GCCCGGGCCAACGGCT | 96 | 3381 | 3396 | 1071 |
| 948930 | 116645 | 116660 | CAAGGCCGGCCCGGGC | 131 | 3389 | 3404 | 1072 |
| 948931 | 116647 | 116662 | GGCAAGGCCGGCCCGG | 104 | 3391 | 3406 | 1073 |
| 948932 | 116652 | 116667 | AATAGGGCAAGGCCGG | 65 | 3396 | 3411 | 1074 |
| 948933 | 116653 | 116668 | GAATAGGGCAAGGCCG | 126 | 3397 | 3412 | 1075 |
| 948934 | 116654 | 116669 | GGAATAGGGCAAGGCC | 22 | 3398 | 3413 | 1076 |
| 948935 | 116656 | 116671 | GAGGAATAGGGCAAGG | 7 | 3400 | 3415 | 1077 |
| 948936 | 116657 | 116672 | AGAGGAATAGGGCAAG | 4 | 3401 | 3416 | 1078 |
| 948937 | 116658 | 116673 | GAGAGGAATAGGGCAA | 6 | 3402 | 3417 | 1079 |
| 948938 | 116660 | 116675 | AGGAGAGGAATAGGGC | 8 | 3404 | 3419 | 1080 |
| 948939 | 116705 | 116720 | ACATAGCCCAAGCCCA | 54 | 3449 | 3464 | 1081 |
| 948940 | 116706 | 116721 | CACATAGCCCAAGCCC | 72 | 3450 | 3465 | 1082 |
| 948941 | 116707 | 116722 | CCACATAGCCCAAGCC | 90 | 3451 | 3466 | 1083 |
| 948942 | 116709 | 116724 | ACCCACATAGCCCAAG | 71 | 3453 | 3468 | 1084 |
| 948943 | 116767 | 116782 | ACCCATCAGGGAGGCA | 93 | 3511 | 3526 | 1085 |
| 948944 | 116790 | 116805 | CAGAGAGAGGCCGCCC | 43 | 3534 | 3549 | 1086 |
| 948945 | 116793 | 116808 | CCTCAGAGAGAGGCCG | 134 | 3537 | 3552 | 1087 |
| 948946 | 116814 | 116829 | AGCGAGGAGTGGGTGA | 43 | 3558 | 3573 | 1088 |
| 948947 | 116817 | 116832 | CTGAGCGAGGAGTGGG | 57 | 3561 | 3576 | 1089 |
| 948948 | 116818 | 116833 | ACTGAGCGAGGAGTGG | 34 | 3562 | 3577 | 1090 |
| 948949 | 116820 | 116835 | AAACTGAGCGAGGAGT | 64 | 3564 | 3579 | 1091 |
| 948950 | 116821 | 116836 | CAAACTGAGCGAGGAG | 7 | 3565 | 3580 | 1092 |
| 948951 | 116823 | 116838 | GTCAAACTGAGCGAGG | 5 | 3567 | 3582 | 1093 |
| 948952 | 116824 | 116839 | GGTCAAACTGAGCGAG | 5 | 3568 | 3583 | 1094 |
| 948953 | 116825 | 116840 | TGGTCAAACTGAGCGA | 9 | 3569 | 3584 | 1095 |
| 948954 | 116827 | 116842 | AGTGGTCAAACTGAGC | 5 | 3571 | 3586 | 1096 |
| 948955 | 116828 | 116843 | CAGTGGTCAAACTGAG | 64 | 3572 | 3587 | 1097 |
| 948956 | 116829 | 116844 | ACAGTGGTCAAACTGA | 73 | 3573 | 3588 | 1098 |
| 948957 | 116830 | 116845 | TACAGTGGTCAAACTG | 69 | 3574 | 3589 | 1099 |
| 948958 | 116831 | 116846 | TTACAGTGGTCAAACT | 34 | 3575 | 3590 | 1100 |
| 948959 | 116833 | 116848 | ACTTACAGTGGTCAAA | 17 | 3577 | 3592 | 1101 |
| 948960 | 116834 | 116849 | CACTTACAGTGGTCAA | 11 | 3578 | 3593 | 1102 |
| 948961 | 116835 | 116850 | GCACTTACAGTGGTCA | 4 | 3579 | 3594 | 1103 |
| 948962 | 116836 | 116851 | GGCACTTACAGTGGTC | 45 | 3580 | 3595 | 1104 |
| 948963 | 116837 | 116852 | AGGCACTTACAGTGGT | 5 | 3581 | 3596 | 1105 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 948964 | 116841 | 116856 | GTGCAGGCACTTACAG | 43 | 3585 | 3600 | 1106 |
| 948965 | 116844 | 116859 | AGAGTGCAGGCACTTA | 7 | 3588 | 3603 | 1107 |
| 948966 | 116846 | 116861 | ACAGAGTGCAGGCACT | 8 | 3590 | 3605 | 1108 |
| 948967 | 116847 | 116862 | TACAGAGTGCAGGCAC | 12 | 3591 | 3606 | 1109 |
| 948968 | 116848 | 116863 | ATACAGAGTGCAGGCA | 6 | 3592 | 3607 | 1110 |
| 948969 | 116850 | 116865 | GAATACAGAGTGCAGG | 6 | 3594 | 3609 | 1111 |
| 948970 | 116851 | 116866 | AGAATACAGAGTGCAG | 2 | 3595 | 3610 | 1112 |
| 948971 | 116852 | 116867 | TAGAATACAGAGTGCA | 1 | 3596 | 3611 | 1113 |
| 948972 | 116854 | 116869 | AATAGAATACAGAGTG | 6 | 3598 | 3613 | 1114 |
| 948973 | 3394 | 3409 | GCTCACCGGCCCACGA | 72 | N/A | N/A | 1115 |
| 948974 | 3500 | 3515 | CGCGGGCACGCAAGCG | 144 | N/A | N/A | 1116 |
| 948975 | 3607 | 3622 | CGTGACACCGCCCCTG | 71 | N/A | N/A | 1117 |
| 948976 | 3715 | 3730 | ATCTACCCCAGACCCA | 63 | N/A | N/A | 1118 |
| 948977 | 3725 | 3740 | CAGAAGAGGGATCTAC | 99 | N/A | N/A | 1119 |
| 948978 | 3776 | 3791 | CAATAGATATCTAGAT | 144 | N/A | N/A | 1120 |
| 948979 | 3778 | 3793 | CCCAATAGATATCTAG | 59 | N/A | N/A | 1121 |
| 948980 | 3815 | 3830 | AGATACAAGAACAAGC | 67 | N/A | N/A | 1122 |
| 948981 | 3934 | 3949 | AGCTAGCCAGACAGCA | 146 | N/A | N/A | 1123 |
| 948982 | 4010 | 4025 | CAACAGAGGGACTGCT | 85 | N/A | N/A | 1124 |
| 948983 | 4035 | 4050 | ACAGTAGAGGCCAGCT | 96 | N/A | N/A | 1125 |
| 948984 | 4130 | 4145 | CGGAAGAGAGGAGCCA | 84 | N/A | N/A | 1126 |
| 948985 | 4135 | 4150 | TCACACGGAAGAGAGG | 63 | N/A | N/A | 1127 |
| 948986 | 4142 | 4157 | GAAGAATTCACACGGA | 50 | N/A | N/A | 1128 |
| 948987 | 4262 | 4277 | GTCCAAACCTCCTCCT | 63 | N/A | N/A | 1129 |
| 948988 | 4315 | 4330 | TCCTGAAGTAAGGTAC | 96 | N/A | N/A | 1130 |
| 948989 | 4326 | 4341 | TCGGAAAGGAATCCTG | 40 | N/A | N/A | 1131 |
| 948990 | 4371 | 4386 | AATTTGTAGGCTGTAG | 21 | N/A | N/A | 1132 |
| 948991 | 4388 | 4403 | TCCAAAGGAGGGCCCC | 140 | N/A | N/A | 1133 |
| 948992 | 4476 | 4491 | CACCGCGGCTTCTCAA | 38 | N/A | N/A | 1134 |
| 948993 | 4624 | 4639 | GAGAAGTGGCCGCCCA | 75 | N/A | N/A | 1135 |
| 948994 | 4649 | 4664 | CCACAAATGAGTAGTT | 49 | N/A | N/A | 1136 |
| 948995 | 4730 | 4745 | CATTATCCCTTGACAA | 115 | N/A | N/A | 1137 |
| 948996 | 4742 | 4757 | ATCAAGAAGGGACATT | 85 | N/A | N/A | 1138 |
| 948997 | 4838 | 4853 | GGTGATCACAGTCCCT | 72 | N/A | N/A | 1139 |
| 948998 | 4938 | 4953 | AGAGACAAGGTAGCAA | 45 | N/A | N/A | 1140 |
| 948999 | 4950 | 4965 | AGGCAATGAGCTAGAG | 39 | N/A | N/A | 1141 |
| 949000 | 5049 | 5064 | GAAGATGGTCACTCAA | 47 | N/A | N/A | 1142 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949001 | 5051 | 5066 | AGGAAGATGGTCACTC | 32 | N/A | N/A | 1143 |
| 949002 | 5162 | 5177 | GTCAACCAAGACTTAG | 48 | N/A | N/A | 1144 |
| 949003 | 5545 | 5560 | TAGAATGGCATCTTGT | 28 | N/A | N/A | 1145 |
| 949004 | 5710 | 5725 | CCGGATCTGGTTCTGT | 88 | N/A | N/A | 1146 |
| 949005 | 5810 | 5825 | AACCAGCCAGATAAAC | 94 | N/A | N/A | 1147 |
| 949006 | 5872 | 5887 | GCTTAAGTGTGTAACG | 8 | N/A | N/A | 1148 |
| 949007 | 5873 | 5888 | GGCTTAAGTGTGTAAC | 10 | N/A | N/A | 1149 |
| 949008 | 5898 | 5913 | GATTATAGCAATGCCT | 22 | N/A | N/A | 1150 |
| 949009 | 5940 | 5955 | GCTCAGCTATCTGAGC | 107 | N/A | N/A | 1151 |
| 949010 | 6074 | 6089 | CCAGACACCATGGTAG | 33 | N/A | N/A | 1152 |
| 949011 | 6150 | 6165 | ATATAATGAGCAACTC | 47 | N/A | N/A | 1153 |
| 949012 | 6174 | 6189 | GTGAGACTCGGTGTAA | 10 | N/A | N/A | 1154 |
| 949013 | 6298 | 6313 | GTGGTAACGCGCGCCT | 41 | N/A | N/A | 1155 |
| 949014 | 6455 | 6470 | AATACTCTTAACGAGG | 95 | N/A | N/A | 1156 |
| 949015 | 6556 | 6571 | ACCTTATCTCTTACAC | 63 | N/A | N/A | 1157 |
| 949016 | 6697 | 6712 | TCCAGGCTCGGCGCAA | 83 | N/A | N/A | 1158 |
| 949017 | 6752 | 6767 | AGCTATAGGGCTGAAC | 129 | N/A | N/A | 1159 |
| 949018 | 6816 | 6831 | CGCAGGTAAAACAAAA | 38 | N/A | N/A | 1160 |
| 949019 | 6817 | 6832 | ACGCAGGTAAAACAAA | 56 | N/A | N/A | 1161 |
| 949020 | 6821 | 6836 | AGCTACGCAGGTAAAA | 66 | N/A | N/A | 1162 |
| 949021 | 6824 | 6839 | AAAAGCTACGCAGGTA | 27 | N/A | N/A | 1163 |
| 949022 | 6870 | 6885 | CCGGATATTGACTGGA | 46 | N/A | N/A | 1164 |
| 949023 | 6891 | 6906 | TGTCTTAGAGCCACAA | 131 | N/A | N/A | 1165 |
| 949024 | 6906 | 6921 | CTCTATAGATCTGAGT | 123 | N/A | N/A | 1166 |
| 949025 | 6918 | 6933 | GACAACTCAGAACTCT | 93 | N/A | N/A | 1167 |
| 949026 | 7031 | 7046 | TACCACCCTCAGCTTA | 69 | N/A | N/A | 1168 |
| 949027 | 7131 | 7146 | CGCCAGGTGAAACTGA | 86 | N/A | N/A | 1169 |
| 949028 | 7155 | 7170 | CCACAAGGGACAAAGG | 89 | N/A | N/A | 1170 |
| 949029 | 7170 | 7185 | TCGAAGCCATTACTGC | 89 | N/A | N/A | 1171 |
| 949030 | 7248 | 7263 | TGCTAGGGAGTAGTGG | 47 | N/A | N/A | 1172 |
| 949031 | 7273 | 7288 | GCAAAATGATCTAGGC | 26 | N/A | N/A | 1173 |
| 949032 | 7328 | 7343 | CCGCAGACAAGCCAGG | 99 | N/A | N/A | 1174 |
| 949033 | 7351 | 7366 | CCAAAGTTCTATCTGC | 15 | N/A | N/A | 1175 |
| 949034 | 7395 | 7410 | TGACAAGGGTCAAGAG | 91 | N/A | N/A | 1176 |
| 949035 | 7400 | 7415 | CTAAATGACAAGGGTC | 22 | N/A | N/A | 1177 |
| 949036 | 7402 | 7417 | GGCTAAATGACAAGGG | 47 | N/A | N/A | 1178 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949037 | 7645 | 7660 | GTATAAGACCCTATCT | 83 | N/A | N/A | 1179 |
| 949038 | 7849 | 7864 | ATTTGAGGCGAGGAGG | 58 | N/A | N/A | 1180 |
| 949050 | 8567 | 8582 | TTTTAAAGAAGACGGG | 51 | N/A | N/A | 1181 |
| 949051 | 8584 | 8599 | TGCTATTATAACTCCT | 15 | N/A | N/A | 1182 |
| 949052 | 8671 | 8686 | GAACAACACCTAATGT | 47 | N/A | N/A | 1183 |
| 949053 | 8675 | 8690 | GAACGAACAACACCTA | 8 | N/A | N/A | 1184 |
| 949054 | 8678 | 8693 | AATGAACGAACAACAC | 22 | N/A | N/A | 1185 |
| 949055 | 8705 | 8720 | AGTAAAAGTACTCAGG | 8 | N/A | N/A | 1186 |
| 949056 | 8740 | 8755 | TGGTAACTTGCTCAGG | 16 | N/A | N/A | 1187 |
| 949057 | 8773 | 8788 | GCTGAAAGGCCAGCTC | 83 | N/A | N/A | 1188 |
| 949058 | 8949 | 8964 | CTACAGGTGTCACCAT | 100 | N/A | N/A | 1189 |
| 949059 | 9093 | 9108 | ACTTATCGCCTTTTTT | 11 | N/A | N/A | 1190 |
| 949061 | 9613 | 9628 | CTCCACTGGCCTGCTA | 4 | N/A | N/A | 1191 |
| 949062 | 9724 | 9739 | AGGGACAGCAGTAGCG | 69 | N/A | N/A | 1192 |
| 949063 | 9830 | 9845 | AGAAAAATGGCACGGG | 41 | N/A | N/A | 1193 |
| 949064 | 9883 | 9898 | TAAAAACGCAGCTGGA | 79 | N/A | N/A | 1194 |
| 949065 | 9971 | 9986 | TGCACTGGTGCAGCAC | 115 | N/A | N/A | 1195 |
| 949066 | 10072 | 10087 | GGCTCTAAACTAATAA | 143 | N/A | N/A | 1196 |
| 949067 | 10260 | 10275 | TCGGGATTCACTATGT | 28 | N/A | N/A | 1197 |
| 949068 | 10379 | 10394 | CGCTTACTGCAAGTTC | 40 | N/A | N/A | 1198 |
| 949069 | 10481 | 10496 | CCTAACCGAGCCTTGC | 78 | N/A | N/A | 1199 |
| 949070 | 10675 | 10690 | ACAACAATTTGCTACG | 45 | N/A | N/A | 1200 |
| 949071 | 10677 | 10692 | TCACAACAATTTGCTA | 23 | N/A | N/A | 1201 |
| 949072 | 11266 | 11281 | TGACACCAAACTGAGC | 92 | N/A | N/A | 1202 |
| 949073 | 11356 | 11371 | AAAGAAACTAAGGCCG | 87 | N/A | N/A | 1203 |
| 949074 | 11384 | 11399 | TAATGATGAGTTCCTT | 14 | N/A | N/A | 1204 |
| 949075 | 11392 | 11407 | CAACAGAGTAATGATG | 54 | N/A | N/A | 1205 |
| 949076 | 11496 | 11511 | CGATATTTCAGGATCT | 88 | N/A | N/A | 1206 |
| 949077 | 11597 | 11612 | CTCATCACCGTACACA | 9 | N/A | N/A | 1207 |
| 949078 | 11881 | 11896 | CCCTATCATTGGTTTT | 55 | N/A | N/A | 1208 |
| 949079 | 11984 | 11999 | TAACAGGTCTTGTGCA | 55 | N/A | N/A | 1209 |
| 949080 | 12093 | 12108 | ACGATTCACATGTGGG | 11 | N/A | N/A | 1210 |
| 949081 | 12141 | 12156 | AACCTAATCCCCAAAC | 104 | N/A | N/A | 1211 |
| 949082 | 12195 | 12210 | AGCACTTGGACAGCCT | 36 | N/A | N/A | 1212 |
| 949083 | 12200 | 12215 | GAAAAAGCACTTGGAC | 31 | N/A | N/A | 1213 |
| 949084 | 12214 | 12229 | CAATAAGTAACTCTGA | 52 | N/A | N/A | 1214 |
| 949085 | 12318 | 12333 | ATCTACAACTGTCCCC | 25 | N/A | N/A | 1215 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949086 | 12555 | 12570 | AATAATGAGACCCCAC | 145 | N/A | N/A | 1216 |
| 949087 | 12667 | 12682 | TAAATCTAACCTAGGC | 126 | N/A | N/A | 1217 |
| 949088 | 12778 | 12793 | CAGAAGTTTGGCAGAT | 5 | N/A | N/A | 1218 |
| 949089 | 12788 | 12803 | TCAAATCGGGCAGAAG | 22 | N/A | N/A | 1219 |
| 949090 | 12858 | 12873 | AAATTACGGTTTACAT | 71 | N/A | N/A | 1220 |
| 949091 | 12859 | 12874 | TAAATTACGGTTTACA | 20 | N/A | N/A | 1221 |
| 949092 | 12878 | 12893 | TTGTAGTTGGCAATCC | 12 | N/A | N/A | 1222 |
| 949093 | 12892 | 12907 | GGCTTAATTACAGCTT | 86 | N/A | N/A | 1223 |
| 949094 | 12901 | 12916 | CACAATAAGGGCTTAA | 10 | N/A | N/A | 1224 |
| 949095 | 12902 | 12917 | ACACAATAAGGGCTTA | 10 | N/A | N/A | 1225 |
| 949096 | 12947 | 12962 | CCCTATAAATATCTCA | 23 | N/A | N/A | 1226 |
| 949097 | 13037 | 13052 | ACGCACCCGGAAGCAG | 71 | N/A | N/A | 1227 |
| 949098 | 13140 | 13155 | AAACAGTCATCCAGCT | 105 | N/A | N/A | 1228 |
| 949099 | 13208 | 13223 | TGGCACACGGTGATTC | 57 | N/A | N/A | 1229 |
| 949100 | 13215 | 13230 | GCACATGTGGCACACG | 27 | N/A | N/A | 1230 |
| 949101 | 13273 | 13288 | AGGGATGCTAAGAGCA | 69 | N/A | N/A | 1231 |
| 949102 | 13281 | 13296 | TATAAAGCAGGGATGC | 117 | N/A | N/A | 1232 |
| 949103 | 13391 | 13406 | CCATATGTGTGGCTCT | 21 | N/A | N/A | 1233 |
| 949104 | 13520 | 13535 | GCATATCCAAAGCCAC | 38 | N/A | N/A | 1234 |
| 949105 | 13635 | 13650 | CATTTAACTGTTCACC | 28 | N/A | N/A | 1235 |
| 949106 | 13812 | 13827 | CGACAGACAAGTACCA | 46 | N/A | N/A | 1236 |
| 949107 | 13952 | 13967 | GCATACAGCCTTTTTT | 38 | N/A | N/A | 1237 |
| 949108 | 13953 | 13968 | CGCATACAGCCTTTTT | 15 | N/A | N/A | 1238 |
| 949109 | 13955 | 13970 | ACCGCATACAGCCTTT | 9 | N/A | N/A | 1239 |
| 949110 | 13956 | 13971 | CACCGCATACAGCCTT | 46 | N/A | N/A | 1240 |
| 949111 | 13959 | 13974 | AACCACCGCATACAGC | 50 | N/A | N/A | 1241 |
| 949112 | 13961 | 13976 | TGAACCACCGCATACA | 40 | N/A | N/A | 1242 |
| 949113 | 14262 | 14277 | TGCAACCTTCAAGTAA | 94 | N/A | N/A | 1243 |
| 949114 | 14390 | 14405 | GCAAACCGCTTCTCAC | 74 | N/A | N/A | 1244 |
| 949115 | 14492 | 14507 | CCCCAAGTCCTGGCGG | 99 | N/A | N/A | 1245 |
| 949116 | 14629 | 14644 | GAAAAGTCGGCATTCC | 74 | N/A | N/A | 1246 |
| 949117 | 14757 | 14772 | TGACAGTGGTGCTCCC | 66 | N/A | N/A | 1247 |
| 949118 | 15000 | 15015 | TGGCATGTGGTTGTTG | 26 | N/A | N/A | 1248 |
| 949119 | 15165 | 15180 | AACAAATATATGCACG | 20 | N/A | N/A | 1249 |
| 949120 | 15370 | 15385 | TCGCACCTCGGGATTC | 92 | N/A | N/A | 1250 |
| 949121 | 15507 | 15522 | GTGAAATTCACTCCAT | 40 | N/A | N/A | 1251 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949122 | 15612 | 15627 | GGAAGATGTCCTTGCT | 49 | N/A | N/A | 1252 |
| 949123 | 15643 | 15658 | ATAGATGGAGCAAATC | 77 | N/A | N/A | 1253 |
| 949124 | 15647 | 15662 | TTATATAGATGGAGCA | 32 | N/A | N/A | 1254 |
| 949125 | 15708 | 15723 | ACGCAGATAGACACCC | 53 | N/A | N/A | 1255 |
| 949126 | 15712 | 15727 | GCCAACGCAGATAGAC | 93 | N/A | N/A | 1256 |
| 949127 | 15777 | 15792 | TGCCATACAGGGCCTC | 116 | N/A | N/A | 1257 |
| 949128 | 15859 | 15874 | GAAAGAGCAGTGGTGC | 73 | N/A | N/A | 1258 |
| 949129 | 15973 | 15988 | GGGCATGGAGGTGTCA | 90 | N/A | N/A | 1259 |
| 949130 | 16025 | 16040 | CGCGAAAGTGTGTCAC | 64 | N/A | N/A | 1260 |
| 949131 | 16117 | 16132 | TATCACCCAGCAGGCA | 75 | N/A | N/A | 1261 |
| 949132 | 16275 | 16290 | GGCCAGCTGGTAGGCC | 114 | N/A | N/A | 1262 |
| 949134 | 16714 | 16729 | GTCAAGCTGAGCCAGT | 52 | N/A | N/A | 1263 |
| 949135 | 16815 | 16830 | ACAGAAGCCGGGCTTC | 127 | N/A | N/A | 1264 |
| 949136 | 16926 | 16941 | ATCAATTTTCACCCAG | 19 | N/A | N/A | 1265 |
| 949137 | 16930 | 16945 | GTGCATCAATTTTCAC | 127 | N/A | N/A | 1266 |
| 949138 | 17244 | 17259 | AAAGAGTTTAAGGGCG | 57 | N/A | N/A | 1267 |
| 949139 | 17282 | 17297 | CCACAACGAGTAAACA | 15 | N/A | N/A | 1268 |
| 949140 | 17615 | 17630 | GGACAGGGTGAATTGT | 62 | N/A | N/A | 1269 |
| 949141 | 17723 | 17738 | AGTCACACCTAGAAAT | 32 | N/A | N/A | 1270 |
| 949142 | 17758 | 17773 | GACTTATAGGCTCACT | 12 | N/A | N/A | 1271 |
| 949143 | 17763 | 17778 | TACTAGACTTATAGGC | 26 | N/A | N/A | 1272 |
| 949144 | 17765 | 17780 | GTTACTAGACTTATAG | 19 | N/A | N/A | 1273 |
| 949145 | 17766 | 17781 | TGTTACTAGACTTATA | 40 | N/A | N/A | 1274 |
| 949146 | 17834 | 17849 | ATATAGCAGGGACCTG | 70 | N/A | N/A | 1275 |
| 949147 | 17838 | 17853 | CTAAATATAGCAGGGA | 36 | N/A | N/A | 1276 |
| 949148 | 17840 | 17855 | CACTAAATATAGCAGG | 24 | N/A | N/A | 1277 |
| 949149 | 18278 | 18293 | TTTGAGCCCGAGAGGG | 46 | N/A | N/A | 1278 |
| 949150 | 18486 | 18501 | TTATTTCTAGGCAGGG | 13 | N/A | N/A | 1279 |
| 949151 | 18524 | 18539 | GTAAATTTGAAGCTTA | 144 | N/A | N/A | 1280 |
| 949152 | 18583 | 18598 | AATTAGAGGACACTGG | 19 | N/A | N/A | 1281 |
| 949153 | 18665 | 18680 | GCTTTAACTCCTAGAC | 61 | N/A | N/A | 1282 |
| 949154 | 19040 | 19055 | GTATACCAAGGTTAAT | 56 | N/A | N/A | 1283 |
| 949155 | 19050 | 19065 | CTTAATAGTAGTATAC | 96 | N/A | N/A | 1284 |
| 949156 | 19458 | 19473 | CACACGAGGTCTCACT | 44 | N/A | N/A | 1285 |
| 949157 | 19461 | 19476 | CTACACACGAGGTCTC | 72 | N/A | N/A | 1286 |
| 949158 | 19663 | 19678 | TACATTCTGGCTTTGG | 12 | N/A | N/A | 1287 |
| 949159 | 19763 | 19778 | TCTCAGTATGTATACT | 12 | N/A | N/A | 1288 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949160 | 19814 | 19829 | TGTCCAGTCCTAAGAC | 101 | N/A | N/A | 1289 |
| 949161 | 19816 | 19831 | AATGTCCAGTCCTAAG | 81 | N/A | N/A | 1290 |
| 949162 | 19817 | 19832 | CAATGTCCAGTCCTAA | 19 | N/A | N/A | 1291 |
| 949163 | 19818 | 19833 | GCAATGTCCAGTCCTA | 4 | N/A | N/A | 1292 |
| 949164 | 19820 | 19835 | ATGCAATGTCCAGTCC | 13 | N/A | N/A | 1293 |
| 949165 | 19821 | 19836 | GATGCAATGTCCAGTC | 70 | N/A | N/A | 1294 |
| 949166 | 19822 | 19837 | AGATGCAATGTCCAGT | 13 | N/A | N/A | 1295 |
| 949167 | 19824 | 19839 | CTAGATGCAATGTCCA | 12 | N/A | N/A | 1296 |
| 949168 | 19843 | 19858 | GCTTAAGGAGATCCGA | 17 | N/A | N/A | 1297 |
| 949169 | 19844 | 19859 | GGCTTAAGGAGATCCG | 85 | N/A | N/A | 1298 |
| 949170 | 19872 | 19887 | GGCTGAGTTGCTTCCC | 79 | N/A | N/A | 1299 |
| 949171 | 19935 | 19950 | TTCCAGATAAGCCCTA | 32 | N/A | N/A | 1300 |
| 949172 | 19986 | 20001 | CACCAATGGCCTTCTT | 42 | N/A | N/A | 1301 |
| 949173 | 20328 | 20343 | GAAGATGGCTGGACGA | 34 | N/A | N/A | 1302 |
| 949174 | 20330 | 20345 | CAGAAGATGGCTGGAC | 34 | N/A | N/A | 1303 |
| 949175 | 20378 | 20393 | CAATAATTTATCAGTC | 68 | N/A | N/A | 1304 |
| 949176 | 20440 | 20455 | GGGAAACCTAGCAAGC | 80 | N/A | N/A | 1305 |
| 949177 | 20487 | 20502 | CCCAAAGGATAGAGTA | 23 | N/A | N/A | 1306 |
| 949178 | 20735 | 20750 | TTACATGAGTCTAGGA | 50 | N/A | N/A | 1307 |
| 949179 | 20737 | 20752 | TATTACATGAGTCTAG | 68 | N/A | N/A | 1308 |
| 949180 | 20740 | 20755 | GATTATTACATGAGTC | 49 | N/A | N/A | 1309 |
| 949181 | 20748 | 20763 | GGCAAGAGGATTATTA | 53 | N/A | N/A | 1310 |
| 949182 | 20844 | 20859 | AGCAACTTTAGGGAGA | 5 | N/A | N/A | 1311 |
| 949183 | 20899 | 20914 | GAACAGACAGTTCAGG | 76 | N/A | N/A | 1312 |
| 949184 | 20947 | 20962 | AAGATATGTGGTTTTG | 35 | N/A | N/A | 1313 |
| 949185 | 21341 | 21356 | GAGCATCACCAGCCCA | 127 | N/A | N/A | 1314 |
| 949186 | 21403 | 21418 | TAGAAATGAGTGGGCG | 116 | N/A | N/A | 1315 |
| 949187 | 21416 | 21431 | AGCTACAGCAATATAG | 43 | N/A | N/A | 1316 |
| 949188 | 21449 | 21464 | ACTCACATGGCCTGAT | 81 | N/A | N/A | 1317 |
| 949189 | 21491 | 21506 | CTAGACTAGACAAAAC | 91 | N/A | N/A | 1318 |
| 949190 | 21514 | 21529 | ATATATATGTGGAGGC | 4 | N/A | N/A | 1319 |
| 949191 | 21561 | 21576 | CTAATACACAATGATC | 34 | N/A | N/A | 1320 |
| 949192 | 21591 | 21606 | CAAAAAACTAATACCG | 105 | N/A | N/A | 1321 |
| 949193 | 21698 | 21713 | AACCAGTACCAGCTGG | 98 | N/A | N/A | 1322 |
| 949194 | 21758 | 21773 | AGAAACTGTACTGGTC | 25 | N/A | N/A | 1323 |
| 949195 | 21845 | 21860 | GGATATTCTTAACAGG | 26 | N/A | N/A | 1324 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949196 | 21854 | 21869 | AGCTAGGAAGGATATT | 83 | N/A | N/A | 1325 |
| 949197 | 22009 | 22024 | AAGTATGCGCTGCCAT | 38 | N/A | N/A | 1326 |
| 949198 | 22018 | 22033 | TGGGACTGTAAGTATG | 63 | N/A | N/A | 1327 |
| 949199 | 22133 | 22148 | GGATATAGGGTCTCCC | 138 | N/A | N/A | 1328 |
| 949200 | 22243 | 22258 | CATGAGGTAGGACAGC | 54 | N/A | N/A | 1329 |
| 949201 | 22251 | 22266 | GAAAAAGCCATGAGGT | 100 | N/A | N/A | 1330 |
| 949202 | 22301 | 22316 | CCACAGGGTTATCTGG | 119 | N/A | N/A | 1331 |
| 949203 | 22345 | 22360 | AAGGAGGCTTTTAAGC | 92 | N/A | N/A | 1332 |
| 949204 | 22446 | 22461 | AGGAATGACAAGTGGT | 17 | N/A | N/A | 1333 |
| 949205 | 22466 | 22481 | CGCATAGGTGGAACAA | 58 | N/A | N/A | 1334 |
| 949206 | 22478 | 22493 | CAAGAAACCAAACGCA | 81 | N/A | N/A | 1335 |
| 949207 | 22638 | 22653 | AATATACGGGCATGTT | 82 | N/A | N/A | 1336 |
| 949208 | 22639 | 22654 | AAATATACGGGCATGT | 110 | N/A | N/A | 1337 |
| 949209 | 22641 | 22656 | AAAAATATACGGGCAT | 104 | N/A | N/A | 1338 |
| 949210 | 22643 | 22658 | ACAAAAATATACGGGC | 67 | N/A | N/A | 1339 |
| 949211 | 22644 | 22659 | TACAAAAATATACGGG | 33 | N/A | N/A | 1340 |
| 949212 | 22780 | 22795 | TCAAACAAATAGGCCG | 86 | N/A | N/A | 1341 |
| 949213 | 22862 | 22877 | ATGCAAGGGACTGCGC | 66 | N/A | N/A | 1342 |
| 949214 | 22883 | 22898 | ACCTATCGCATGCCAG | 17 | N/A | N/A | 1343 |
| 949215 | 23000 | 23015 | GTTCAGGTCAGAGCCT | 51 | N/A | N/A | 1344 |
| 949216 | 23297 | 23312 | TCTCAATGAAAGTCTC | 10 | N/A | N/A | 1345 |
| 949217 | 23548 | 23563 | GTAACAACCGCTGGGA | 27 | N/A | N/A | 1346 |
| 949218 | 23555 | 23570 | TTAAAGAGTAACAACC | 75 | N/A | N/A | 1347 |
| 949219 | 23715 | 23730 | GCCCAGCTAACTAACT | 108 | N/A | N/A | 1348 |
| 949220 | 24040 | 24055 | GACTACAGTACAGGCG | 74 | N/A | N/A | 1349 |
| 949221 | 24201 | 24216 | AGAACAAGGGAACACG | 80 | N/A | N/A | 1350 |
| 949222 | 24210 | 24225 | CCCCATAGAAGAACAA | 138 | N/A | N/A | 1351 |
| 949223 | 24289 | 24304 | GATTAGGTATTATGGT | 12 | N/A | N/A | 1352 |
| 949224 | 24296 | 24311 | TCAAAAGGATTAGGTA | 25 | N/A | N/A | 1353 |
| 949225 | 24315 | 24330 | ATCCACTGAATAGTAT | 32 | N/A | N/A | 1354 |
| 949226 | 24364 | 24379 | CTACAAAATCAGATAG | 91 | N/A | N/A | 1355 |
| 949227 | 24438 | 24453 | GACATTAGTGGCTTCC | 35 | N/A | N/A | 1356 |
| 949228 | 24561 | 24576 | AACCAGCATGGATGAA | 87 | N/A | N/A | 1357 |
| 949229 | 24782 | 24797 | TGCAACCTTGCCCCCC | 11 | N/A | N/A | 1358 |
| 949230 | 24934 | 24949 | TAGTATTCAAAAAACG | 80 | N/A | N/A | 1359 |
| 949231 | 25044 | 25059 | CAAATTAAATACACCC | 62 | N/A | N/A | 1360 |
| 949232 | 25058 | 25073 | GAATACTATTCTAACA | 118 | N/A | N/A | 1361 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949233 | 25210 | 25225 | CACCACAATTTGCTCT | 63 | N/A | N/A | 1362 |
| 949234 | 25305 | 25320 | TCAGAAAAGGAGGGTA | 109 | N/A | N/A | 1363 |
| 949235 | 25321 | 25336 | TTCCACTTCAAGAACC | 87 | N/A | N/A | 1364 |
| 949236 | 25696 | 25711 | TGTAAGCAACTGTATT | 49 | N/A | N/A | 1365 |
| 949237 | 25788 | 25803 | TGAGAAGATATGCTGA | 26 | N/A | N/A | 1366 |
| 949238 | 25822 | 25837 | AACCTATGTATCAAAG | 87 | N/A | N/A | 1367 |
| 949239 | 25925 | 25940 | CAAAGTAGTTCCTCCA | 34 | N/A | N/A | 1368 |
| 949240 | 25927 | 25942 | TACAAAGTAGTTCCTC | 68 | N/A | N/A | 1369 |
| 949241 | 26042 | 26057 | CCCAAGAGTAAAATAC | 105 | N/A | N/A | 1370 |
| 949242 | 26084 | 26099 | ACGAAACCAATAAGAC | 104 | N/A | N/A | 1371 |
| 949243 | 26090 | 26105 | GAAAATACGAAACCAA | 99 | N/A | N/A | 1372 |
| 949244 | 26133 | 26148 | TAATAATGGATGGAAC | 84 | N/A | N/A | 1373 |
| 949245 | 26155 | 26170 | TGGTATCAGGCAAGAA | 35 | N/A | N/A | 1374 |
| 949246 | 27033 | 27048 | CATGATGCTGCAATCA | 97 | N/A | N/A | 1375 |
| 949247 | 27177 | 27192 | CACAAGCCTGCGGACC | 110 | N/A | N/A | 1376 |
| 949248 | 27191 | 27206 | GAGCATAGCAGACACA | 65 | N/A | N/A | 1377 |
| 949249 | 27254 | 27269 | GGCAACATCACTCTAA | 62 | N/A | N/A | 1378 |
| 949250 | 27289 | 27304 | CAAAGAGCCTTGGCAC | 111 | N/A | N/A | 1379 |
| 949251 | 27390 | 27405 | CAGGACTAGTTCACTA | 78 | N/A | N/A | 1380 |
| 949252 | 27473 | 27488 | ATGAAATTGGGATAAC | 60 | N/A | N/A | 1381 |
| 949253 | 27509 | 27524 | ATGAAGGCTGCCACTT | 103 | N/A | N/A | 1382 |
| 949254 | 27575 | 27590 | AGCAAGATCATTGGGT | 65 | N/A | N/A | 1383 |
| 949255 | 27634 | 27649 | GGAAACCTTGGACTCC | 91 | N/A | N/A | 1384 |
| 949256 | 27761 | 27776 | GTCTATTGGCACACAG | 38 | N/A | N/A | 1385 |
| 949257 | 27775 | 27790 | GATTAAGTCATCCGGT | 70 | N/A | N/A | 1386 |
| 949258 | 27872 | 27887 | GGGCACTGCACAAAGC | 86 | N/A | N/A | 1387 |
| 949259 | 27975 | 27990 | AGTCAGCGGAGACTGA | 98 | N/A | N/A | 1388 |
| 949260 | 28212 | 28227 | CGGCAAAAGAAGCTGG | 133 | N/A | N/A | 1389 |
| 949261 | 28320 | 28335 | AGCTAGAGCATCAGCT | 122 | N/A | N/A | 1390 |
| 949262 | 28971 | 28986 | CTGGAAACAGTCTCGC | 29 | N/A | N/A | 1391 |
| 949263 | 29116 | 29131 | AGCCGAAGTGTAGTGG | 51 | N/A | N/A | 1392 |
| 949264 | 29258 | 29273 | GGCCAAGTCTCCCATC | 117 | N/A | N/A | 1393 |
| 949265 | 29370 | 29385 | CCGGACCCGTTCTTGA | 85 | N/A | N/A | 1394 |
| 949266 | 29501 | 29516 | AGGTAGTGACCTCCAG | 114 | N/A | N/A | 1395 |
| 949267 | 29557 | 29572 | ACCCACAGTCTGCATT | 97 | N/A | N/A | 1396 |
| 949268 | 29591 | 29606 | GCCCAAGTGAACTAGA | 94 | N/A | N/A | 1397 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949269 | 29625 | 29640 | ATGTATGGATTTCCAG | 62 | N/A | N/A | 1398 |
| 949270 | 29642 | 29657 | TTACAGGGTGGTCAGC | 82 | N/A | N/A | 1399 |
| 949271 | 29721 | 29736 | GTAAAACGGTTGTGGT | 30 | N/A | N/A | 1400 |
| 949272 | 29739 | 29754 | CAACAGGTGTCCTGCT | 64 | N/A | N/A | 1401 |
| 949273 | 29842 | 29857 | TGTCATCCTAACTGCT | 57 | N/A | N/A | 1402 |
| 949274 | 29943 | 29958 | AGAAACTGGCCGGCCC | 132 | N/A | N/A | 1403 |
| 949275 | 30052 | 30067 | TTTATAGTCTCCAACG | 34 | N/A | N/A | 1404 |
| 949276 | 30178 | 30193 | ACGGACTGGATTATGC | 27 | N/A | N/A | 1405 |
| 949277 | 30248 | 30263 | GGCTAAATCAATCTTG | 60 | N/A | N/A | 1406 |
| 949278 | 30282 | 30297 | CGATAATGACCTAAAT | 84 | N/A | N/A | 1407 |
| 949279 | 30283 | 30298 | CCGATAATGACCTAAA | 8 | N/A | N/A | 1408 |
| 949280 | 30406 | 30421 | GAATATCAACACCTTG | 35 | N/A | N/A | 1409 |
| 949281 | 30508 | 30523 | AGTGATATGCTGCCTA | 39 | N/A | N/A | 1410 |
| 949282 | 30705 | 30720 | GGTTTATTTGCACCTC | 39 | N/A | N/A | 1411 |
| 949283 | 30830 | 30845 | TACCAGGGACTCAACT | 111 | N/A | N/A | 1412 |
| 949284 | 30933 | 30948 | GGCCAGACATTGCTGT | 142 | N/A | N/A | 1413 |
| 949285 | 31273 | 31288 | CACATTGGTGGTCAAG | 98 | N/A | N/A | 1414 |
| 949286 | 31373 | 31388 | CTCATAACATTTGACG | 45 | N/A | N/A | 1415 |
| 949287 | 31708 | 31723 | AAAAAAGCCGGCACGG | 120 | N/A | N/A | 1416 |
| 949288 | 32027 | 32042 | AAAATTGGTTGAGTGC | 40 | N/A | N/A | 1417 |
| 949289 | 32161 | 32176 | GTAAAACTCAGGCTGA | 81 | N/A | N/A | 1418 |
| 949290 | 32192 | 32207 | CAAAAGAGAACATTCG | 64 | N/A | N/A | 1419 |
| 949291 | 32264 | 32279 | TGTTATGTGGGAATGA | 35 | N/A | N/A | 1420 |
| 949292 | 32420 | 32435 | AGGGACACAACAGGCT | 85 | N/A | N/A | 1421 |
| 949293 | 32560 | 32575 | CACAATCCACTCCTGG | 100 | N/A | N/A | 1422 |
| 949294 | 32561 | 32576 | CCACAATCCACTCCTG | 83 | N/A | N/A | 1423 |
| 949295 | 32615 | 32630 | TTGCAGAACAATGGGC | 105 | N/A | N/A | 1424 |
| 949296 | 32697 | 32712 | GCGCAGGGTCCCGTAT | 95 | N/A | N/A | 1425 |
| 949297 | 32719 | 32734 | TATTAGAGTGGCAGCC | 86 | N/A | N/A | 1426 |
| 949298 | 32799 | 32814 | TGCCACTCACAACTGG | 104 | N/A | N/A | 1427 |
| 949299 | 32852 | 32867 | CGCCATAGGAAGCTGC | 111 | N/A | N/A | 1428 |
| 949300 | 32895 | 32910 | GAGCAGGCGGGCAGCT | 82 | N/A | N/A | 1429 |
| 949301 | 32899 | 32914 | AACAGAGCAGGCGGGC | 92 | N/A | N/A | 1430 |
| 949302 | 32900 | 32915 | TAACAGAGCAGGCGGG | 103 | N/A | N/A | 1431 |
| 949303 | 32903 | 32918 | CATTAACAGAGCAGGC | 119 | N/A | N/A | 1432 |
| 949304 | 32904 | 32919 | GCATTAACAGAGCAGG | 46 | N/A | N/A | 1433 |
| 949305 | 33006 | 33021 | AGCCACATATGCCTCC | 91 | N/A | N/A | 1434 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949306 | 33148 | 33163 | TGTTATGGGCCCTCCT | 82 | N/A | N/A | 1435 |
| 949307 | 33277 | 33292 | TCCAAGGCTGTCAGCG | 106 | N/A | N/A | 1436 |
| 949308 | 33391 | 33406 | CACGAGGCTGCAGACC | 40 | N/A | N/A | 1437 |
| 949309 | 33454 | 33469 | CCGCAGGTAGGTGCCA | 56 | N/A | N/A | 1438 |
| 949310 | 33488 | 33503 | GCCCAAGCCTTACAGT | 117 | N/A | N/A | 1439 |
| 949311 | 33512 | 33527 | AGCCATTGGTCACCCA | 43 | N/A | N/A | 1440 |
| 949312 | 33618 | 33633 | CCGCACCCACCTCAGG | 132 | N/A | N/A | 1441 |
| 949313 | 33644 | 33659 | CACCAATGAGGCAGAC | 69 | N/A | N/A | 1442 |
| 949314 | 33725 | 33740 | GTGGACTGAGGTTCAG | 101 | N/A | N/A | 1443 |
| 949315 | 33826 | 33841 | CTCTAACCCCATCTCG | 81 | N/A | N/A | 1444 |
| 949316 | 33927 | 33942 | TCGGCAGGAGCCCACA | 108 | N/A | N/A | 1445 |
| 949317 | 34028 | 34043 | CCATATGCTCAGCACA | 30 | N/A | N/A | 1446 |
| 949318 | 34029 | 34044 | ACCATATGCTCAGCAC | 45 | N/A | N/A | 1447 |
| 949319 | 34159 | 34174 | GATAAGCCCACAGAGG | 107 | N/A | N/A | 1448 |
| 949320 | 34164 | 34179 | CAACAGATAAGCCCAC | 83 | N/A | N/A | 1449 |
| 949321 | 34281 | 34296 | ACAGACCACAAGGCTC | 65 | N/A | N/A | 1450 |
| 949322 | 34283 | 34298 | GAACAGACCACAAGGC | 82 | N/A | N/A | 1451 |
| 949323 | 34407 | 34422 | CAGGAAGGCGGTAGGG | 92 | N/A | N/A | 1452 |
| 949324 | 34539 | 34554 | TGGGAGGACACTTCCA | 121 | N/A | N/A | 1453 |
| 949325 | 34546 | 34561 | CATGAAATGGGAGGAC | 9 | N/A | N/A | 1454 |
| 949326 | 34561 | 34576 | ACTGACTTGGCCATCC | 68 | N/A | N/A | 1455 |
| 949327 | 34654 | 34669 | CCAGACTGTGGAGCCA | 35 | N/A | N/A | 1456 |
| 949328 | 34763 | 34778 | GCCAAGACTTCTGCAC | 129 | N/A | N/A | 1457 |
| 949329 | 34873 | 34888 | GCCTACCTGGCCATGG | 119 | N/A | N/A | 1458 |
| 949330 | 34995 | 35010 | GCTGACCGGGTTCCCC | 148 | N/A | N/A | 1459 |
| 949331 | 35150 | 35165 | TCCTATCCATGGGCCC | 93 | N/A | N/A | 1460 |
| 949332 | 35178 | 35193 | TACTATTGCATCATTT | 33 | N/A | N/A | 1461 |
| 949333 | 35385 | 35400 | CCCTAGTGAACTTCCC | 38 | N/A | N/A | 1462 |
| 949334 | 35541 | 35556 | GCAAACCTCAGTCTCG | 39 | N/A | N/A | 1463 |
| 949335 | 35921 | 35936 | GCACAATTAAGTAGTT | 36 | N/A | N/A | 1464 |
| 949336 | 35950 | 35965 | GCATAGAGTAGGGCTG | 55 | N/A | N/A | 1465 |
| 949337 | 35955 | 35970 | CCAAAGCATAGAGTAG | 57 | N/A | N/A | 1466 |
| 949338 | 35956 | 35971 | CCCAAAGCATAGAGTA | 62 | N/A | N/A | 1467 |
| 949339 | 36021 | 36036 | CCCATCTGAGCTGTGT | 79 | N/A | N/A | 1468 |
| 949340 | 36170 | 36185 | TCGAATGACATTTCCT | 65 | N/A | N/A | 1469 |
| 949341 | 36211 | 36226 | AGTAAGACAGGGTAAC | 136 | N/A | N/A | 1470 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949342 | 36311 | 36326 | GTGCACCCAGGCTGCC | 105 | N/A | N/A | 1471 |
| 949343 | 36420 | 36435 | TTCCAGCCTCCGTCAT | 90 | N/A | N/A | 1472 |
| 949344 | 36531 | 36546 | CCTAAGGGTTTTCTGG | 109 | N/A | N/A | 1473 |
| 949345 | 36532 | 36547 | CCCTAAGGGTTTTCTG | 144 | N/A | N/A | 1474 |
| 949346 | 36570 | 36585 | CCAGAAGTCTCCTAGG | 108 | N/A | N/A | 1475 |
| 949347 | 36647 | 36662 | CTAAAAGTTCCCAGAC | 86 | N/A | N/A | 1476 |
| 949348 | 36757 | 36772 | GGAGACGCAGCTCTCA | 103 | N/A | N/A | 1477 |
| 949349 | 36892 | 36907 | GGACAAGCACCCCTCT | 26 | N/A | N/A | 1478 |
| 949350 | 36996 | 37011 | CCCGACCCCGGCCAAT | 96 | N/A | N/A | 1479 |
| 949351 | 37100 | 37115 | GTTCACTACAGACATC | 71 | N/A | N/A | 1480 |
| 949352 | 37105 | 37120 | TTCTAGTTCACTACAG | 92 | N/A | N/A | 1481 |
| 949353 | 37243 | 37258 | CATAGTACCCCACACA | 56 | N/A | N/A | 1482 |
| 949354 | 37300 | 37315 | TTGTAGTGTGGAATAT | 40 | N/A | N/A | 1483 |
| 949355 | 37364 | 37379 | CGCCCAAGAGAACACA | 104 | N/A | N/A | 1484 |
| 949356 | 37481 | 37496 | CTCCACTTTGTGTCTG | 58 | N/A | N/A | 1485 |
| 949357 | 37583 | 37598 | GCCTTCTGAGCAAACA | 90 | N/A | N/A | 1486 |
| 949358 | 37726 | 37741 | AAAATGGGTCTGCTGG | 18 | N/A | N/A | 1487 |
| 949359 | 37730 | 37745 | CATTAAAATGGGTCTG | 56 | N/A | N/A | 1488 |
| 949360 | 37843 | 37858 | ACCTTAAGTTTCTTGT | 70 | N/A | N/A | 1489 |
| 949361 | 37896 | 37911 | TGCAATGGAGTCCAAA | 65 | N/A | N/A | 1490 |
| 949362 | 37970 | 37985 | CCTTAAGTTTTTTGGT | 132 | N/A | N/A | 1491 |
| 949363 | 38144 | 38159 | TCATGATTATTAACCT | 29 | N/A | N/A | 1492 |
| 949364 | 38160 | 38175 | AGGCATTGAGAACTTT | 77 | N/A | N/A | 1493 |
| 949365 | 38190 | 38205 | AGCTATTCAACACTGA | 65 | N/A | N/A | 1494 |
| 949366 | 38206 | 38221 | CATTAGAGTAGCTAAT | 141 | N/A | N/A | 1495 |
| 949367 | 38246 | 38261 | TTGAATTCCGCATCAT | 86 | N/A | N/A | 1496 |
| 949368 | 38313 | 38328 | AACAAAACAGGACCCG | 108 | N/A | N/A | 1497 |
| 949369 | 38353 | 38368 | GAAGAAAGTCTGTACT | 86 | N/A | N/A | 1498 |
| 949370 | 38488 | 38503 | TTGTAGTGATCAGTTT | 54 | N/A | N/A | 1499 |
| 949371 | 38588 | 38603 | ATCCATGCTGCTATGC | 63 | N/A | N/A | 1500 |
| 949372 | 38688 | 38703 | TTGCACAACAAAGAGC | 90 | N/A | N/A | 1501 |
| 949373 | 38948 | 38963 | GATATATTGCTGGGCA | 72 | N/A | N/A | 1502 |
| 949374 | 38949 | 38964 | AGATATATTGCTGGGC | 44 | N/A | N/A | 1503 |
| 949375 | 39017 | 39032 | ACCTAAGGAAGCTGAC | 72 | N/A | N/A | 1504 |
| 949376 | 39062 | 39077 | TTAAAGCCCAGCAACA | 93 | N/A | N/A | 1505 |
| 949377 | 39088 | 39103 | ACGAAAAATTCAGATC | 104 | N/A | N/A | 1506 |
| 949378 | 39089 | 39104 | GACGAAAAATTCAGAT | 83 | N/A | N/A | 1507 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949379 | 39124 | 39139 | ACAGAATTGTTACAAC | 104 | N/A | N/A | 1508 |
| 949380 | 39156 | 39171 | GTACAGGGTGGACATT | 90 | N/A | N/A | 1509 |
| 949381 | 39162 | 39177 | ACAAAAGTACAGGGTG | 66 | N/A | N/A | 1510 |
| 949382 | 39163 | 39178 | TACAAAAGTACAGGGT | 86 | N/A | N/A | 1511 |
| 949383 | 39164 | 39179 | ATACAAAAGTACAGGG | 54 | N/A | N/A | 1512 |
| 949384 | 39195 | 39210 | AGTCAAGGAGAACATG | 63 | N/A | N/A | 1513 |
| 949385 | 39529 | 39544 | TTGTAGTGGGTCACGC | 53 | N/A | N/A | 1514 |
| 949386 | 39644 | 39659 | CATGATTGCGCCGTTG | 17 | N/A | N/A | 1515 |
| 949387 | 39745 | 39760 | GTAATTCACTGCGGAT | 32 | N/A | N/A | 1516 |
| 949388 | 39877 | 39892 | AAACTTGCAGCAGTGG | 67 | N/A | N/A | 1517 |
| 949389 | 39981 | 39996 | AAATGGACTAGAAGGG | 59 | N/A | N/A | 1518 |
| 949390 | 40014 | 40029 | AGATAGAAATCAGGGC | 47 | N/A | N/A | 1519 |
| 949391 | 40058 | 40073 | TCACAGGGTGGACTTG | 53 | N/A | N/A | 1520 |
| 949392 | 40089 | 40104 | GTAGACACATGTCCTT | 49 | N/A | N/A | 1521 |
| 949393 | 40195 | 40210 | GACTACAGTCTGTTCG | 96 | N/A | N/A | 1522 |
| 949394 | 40295 | 40310 | AACACAGGAGCAGCAT | 87 | N/A | N/A | 1523 |
| 949395 | 40306 | 40321 | AACGATAAAACAACAC | 70 | N/A | N/A | 1524 |
| 949396 | 40409 | 40424 | ACTGAATCACCAGCAG | 99 | N/A | N/A | 1525 |
| 949397 | 40837 | 40852 | GCCTTTACTTAAGATA | 3 | N/A | N/A | 1526 |
| 949398 | 40961 | 40976 | ACGCAGTGTCTCAGGT | 125 | N/A | N/A | 1527 |
| 949399 | 41061 | 41076 | CACAAGTAGCCTTGGC | 107 | N/A | N/A | 1528 |
| 949400 | 41107 | 41122 | TCACAGTGGACACCAG | 85 | N/A | N/A | 1529 |
| 949401 | 41162 | 41177 | TGACAGACCCCAAAGT | 121 | N/A | N/A | 1530 |
| 949402 | 41234 | 41249 | GAACAAGCTACATCAA | 100 | N/A | N/A | 1531 |
| 949403 | 41266 | 41281 | TGGAGAGGGTTCTCTG | 94 | N/A | N/A | 1532 |
| 949404 | 41272 | 41287 | GATAATTGGAGAGGGT | 84 | N/A | N/A | 1533 |
| 949405 | 41393 | 41408 | GCGAACCTTTCTCACT | 57 | N/A | N/A | 1534 |
| 949406 | 41447 | 41462 | AAACAGGATACGAGAC | 74 | N/A | N/A | 1535 |
| 949407 | 41451 | 41466 | GCACAAACAGGATACG | 86 | N/A | N/A | 1536 |
| 949408 | 41497 | 41512 | TAATCCCTTTCCGTCA | 92 | N/A | N/A | 1537 |
| 949409 | 41604 | 41619 | TGTCTTCGAGCCACAC | 99 | N/A | N/A | 1538 |
| 949410 | 41708 | 41723 | CCCTACAGACACTTGC | 101 | N/A | N/A | 1539 |
| 949411 | 41814 | 41829 | CCGTAGGCAGATTCCA | 62 | N/A | N/A | 1540 |
| 949412 | 41862 | 41877 | GCGAAACCAGAGAGAT | 88 | N/A | N/A | 1541 |
| 949413 | 41863 | 41878 | GGCGAAACCAGAGAGA | 86 | N/A | N/A | 1542 |
| 949414 | 41962 | 41977 | AGCTTTTAAACCCCCC | 87 | N/A | N/A | 1543 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949415 | 41984 | 41999 | AGCCAGATTATTAACA | 58 | N/A | N/A | 1544 |
| 949416 | 42064 | 42079 | GATGAGGAGGCTGGTC | 78 | N/A | N/A | 1545 |
| 949417 | 42169 | 42184 | ACGAAGACCCCCCAGG | 163 | N/A | N/A | 1546 |
| 949418 | 42203 | 42218 | CATGAGAAAAGGGATC | 97 | N/A | N/A | 1547 |
| 949419 | 42249 | 42264 | CAACAAGTCAGCCCAA | 100 | N/A | N/A | 1548 |
| 949420 | 42252 | 42267 | ACACAACAAGTCAGCC | 78 | N/A | N/A | 1549 |
| 949421 | 42254 | 42269 | CTACACAACAAGTCAG | 28 | N/A | N/A | 1550 |
| 949422 | 42318 | 42333 | TTCTAGCCCGTCAGCC | 90 | N/A | N/A | 1551 |
| 949423 | 42434 | 42449 | TTCCAGAAGACCTGTT | 143 | N/A | N/A | 1552 |
| 949424 | 42507 | 42522 | TAGCACTACAATCATT | 71 | N/A | N/A | 1553 |
| 949425 | 42544 | 42559 | AACGAGACAGCATCCT | 64 | N/A | N/A | 1554 |
| 949426 | 42577 | 42592 | GCAATTGGTACTGTAC | 101 | N/A | N/A | 1555 |
| 949427 | 42584 | 42599 | ACACAGGGCAATTGGT | 144 | N/A | N/A | 1556 |
| 949428 | 42727 | 42742 | TCGAACTCAACCTCAG | 70 | N/A | N/A | 1557 |
| 949429 | 42860 | 42875 | TGCCTCGGGTTCAAGC | 64 | N/A | N/A | 1558 |
| 949430 | 42983 | 42998 | TGAAAGGTTCTAGGCA | 64 | N/A | N/A | 1559 |
| 949431 | 42984 | 42999 | GTGAAAGGTTCTAGGC | 57 | N/A | N/A | 1560 |
| 949432 | 43017 | 43032 | TCGAAAGGAAATTCTG | 89 | N/A | N/A | 1561 |
| 949433 | 43028 | 43043 | ACATTAAAGGCTCGAA | 43 | N/A | N/A | 1562 |
| 949434 | 43030 | 43045 | GTACATTAAAGGCTCG | 59 | N/A | N/A | 1563 |
| 949435 | 43050 | 43065 | GTAGAAACAGTGGGCT | 61 | N/A | N/A | 1564 |
| 949436 | 43094 | 43109 | GTACACTCAGAAAGGA | 91 | N/A | N/A | 1565 |
| 949437 | 43141 | 43156 | GTGAATACACCAGGAT | 76 | N/A | N/A | 1566 |
| 949438 | 43194 | 43209 | ACTCAGGCACAACCAC | 123 | N/A | N/A | 1567 |
| 949439 | 43864 | 43879 | CGACAGAGCTGTTTAA | 47 | N/A | N/A | 1568 |
| 949440 | 43884 | 43899 | GCGGAATGTAAATTAC | 40 | N/A | N/A | 1569 |
| 949441 | 43918 | 43933 | CTAAAGACCACTAATT | 122 | N/A | N/A | 1570 |
| 949442 | 43920 | 43935 | GACTAAAGACCACTAA | 53 | N/A | N/A | 1571 |
| 949443 | 44005 | 44020 | GTACAGAGCCATGACT | 113 | N/A | N/A | 1572 |
| 949444 | 44161 | 44176 | TAAAGCCTGGACAAG | 77 | N/A | N/A | 1573 |
| 949445 | 44199 | 44214 | TACATCTGGACTATGG | 23 | N/A | N/A | 1574 |
| 949446 | 44271 | 44286 | GATACCTGGATGTGGG | 80 | N/A | N/A | 1575 |
| 949447 | 44336 | 44351 | GACAAAATAGGATGTG | 88 | N/A | N/A | 1576 |
| 949448 | 44351 | 44366 | AGGAAAGTTATTGATG | 63 | N/A | N/A | 1577 |
| 949449 | 44356 | 44371 | ATACGAGGAAAGTTAT | 112 | N/A | N/A | 1578 |
| 949450 | 44359 | 44374 | AAAATACGAGGAAAGT | 80 | N/A | N/A | 1579 |
| 949451 | 44362 | 44377 | GGTAAAATACGAGGAA | 23 | N/A | N/A | 1580 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949452 | 44375 | 44390 | CCACATGTATATGGGT | 85 | N/A | N/A | 1581 |
| 949453 | 44426 | 44441 | CCATACCCAGGAGATC | 57 | N/A | N/A | 1582 |
| 949454 | 44509 | 44524 | AACCATTTCCCTCTGG | 58 | N/A | N/A | 1583 |
| 949455 | 44624 | 44639 | GGCGACCTCAGCAAAG | 85 | N/A | N/A | 1584 |
| 949456 | 44732 | 44747 | AAGGAAGTCCCTGTGA | 106 | N/A | N/A | 1585 |
| 949457 | 44851 | 44866 | GGCAACCACACATCCA | 79 | N/A | N/A | 1586 |
| 949458 | 44953 | 44968 | ACTGAGCCGTTTTTCA | 42 | N/A | N/A | 1587 |
| 949459 | 45279 | 45294 | CCGAAGTGAGAGGGTC | 88 | N/A | N/A | 1588 |
| 949460 | 45364 | 45379 | CAAAATCGGGTTATCT | 66 | N/A | N/A | 1589 |
| 949461 | 45365 | 45380 | GCAAAATCGGGTTATC | 38 | N/A | N/A | 1590 |
| 949462 | 45412 | 45427 | AAGGATGGATGTGTCA | 18 | N/A | N/A | 1591 |
| 949463 | 45503 | 45518 | TGACATGCGGGAATGA | 40 | N/A | N/A | 1592 |
| 949464 | 45523 | 45538 | AGTAGAAACTGGGACG | 43 | N/A | N/A | 1593 |
| 949465 | 45570 | 45585 | AGCTATAAAACCAGCC | 106 | N/A | N/A | 1594 |
| 949466 | 45603 | 45618 | TACAAAAGAGTATAGC | 70 | N/A | N/A | 1595 |
| 949467 | 45705 | 45720 | CACCACTGCACGGCCT | 97 | N/A | N/A | 1596 |
| 949468 | 45850 | 45865 | AACATAACCCCCATCT | 88 | N/A | N/A | 1597 |
| 949469 | 45957 | 45972 | AGCAATGGTAGAGGGC | 113 | N/A | N/A | 1598 |
| 949470 | 46279 | 46294 | GCAATGGTGGCCGGGC | 96 | N/A | N/A | 1599 |
| 949471 | 46323 | 46338 | TTCAACAGGCTGGGTC | 44 | N/A | N/A | 1600 |
| 949472 | 46330 | 46345 | TACTATATTCAACAGG | 18 | N/A | N/A | 1601 |
| 949473 | 46344 | 46359 | CCACACATAGGCCATA | 35 | N/A | N/A | 1602 |
| 949474 | 46382 | 46397 | ATACACTGAGATCAGG | 50 | N/A | N/A | 1603 |
| 949475 | 46431 | 46446 | GCTGGGATATACGCCC | 98 | N/A | N/A | 1604 |
| 949476 | 46505 | 46520 | ACGGAGACCCTTACCT | 129 | N/A | N/A | 1605 |
| 949477 | 46528 | 46543 | TTGCAGATTAGCAGGG | 35 | N/A | N/A | 1606 |
| 949478 | 46560 | 46575 | ACAAACTGAGTGTTGA | 73 | N/A | N/A | 1607 |
| 949479 | 46562 | 46577 | ACACAAACTGAGTGTT | 78 | N/A | N/A | 1608 |
| 949480 | 46577 | 46592 | CGCAAGAAGACATTAA | 54 | N/A | N/A | 1609 |
| 949481 | 46666 | 46681 | GGCAGCATGGCTAAGC | 75 | N/A | N/A | 1610 |
| 949482 | 46764 | 46779 | ACGAAAGTGAGGAGTC | 66 | N/A | N/A | 1611 |
| 949483 | 46766 | 46781 | GGACGAAAGTGAGGAG | 15 | N/A | N/A | 1612 |
| 949484 | 46863 | 46878 | TACGAAATAGCAGAGC | 17 | N/A | N/A | 1613 |
| 949485 | 46885 | 46900 | GCCCATTGGCCCATCG | 154 | N/A | N/A | 1614 |
| 949486 | 47094 | 47109 | GATCACCCGCCACTGT | 105 | N/A | N/A | 1615 |
| 949487 | 47352 | 47367 | CACCAGGGACTCATTA | 124 | N/A | N/A | 1616 |

TABLE 3-continued

| | | | DNM2 mRNA Expression | | | |
|---|---|---|---|---|---|---|
| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949488 | 47466 | 47481 | ACACAGTGGTGGTCCC | 59 | N/A | N/A | 1617 |
| 949489 | 47517 | 47532 | TGCTTTAAGGCTAACA | 82 | N/A | N/A | 1618 |
| 949490 | 47599 | 47614 | GGCCTGCGCTCTGTGC | 87 | N/A | N/A | 1619 |
| 949491 | 47700 | 47715 | TGCCCTAAGGCAAGTG | 91 | N/A | N/A | 1620 |
| 949492 | 47797 | 47812 | CAACAGCCACAGGATC | 77 | N/A | N/A | 1621 |
| 949493 | 47803 | 47818 | TTCCACCAACAGCCAC | 25 | N/A | N/A | 1622 |
| 949494 | 47924 | 47939 | AACTATGCATCCACCT | 122 | N/A | N/A | 1623 |
| 949495 | 47927 | 47942 | TGCAACTATGCATCCA | 130 | N/A | N/A | 1624 |
| 949496 | 48220 | 48235 | GGCTAGGTGGTGTGCG | 116 | N/A | N/A | 1625 |
| 949497 | 48501 | 48516 | GAGATTGGAGCCTGGT | 33 | N/A | N/A | 1626 |
| 949498 | 48506 | 48521 | AATAAGAGATTGGAGC | 89 | N/A | N/A | 1627 |
| 949499 | 48507 | 48522 | CAATAAGAGATTGGAG | 69 | N/A | N/A | 1628 |
| 949500 | 48508 | 48523 | GCAATAAGAGATTGGA | 13 | N/A | N/A | 1629 |
| 949501 | 48622 | 48637 | GTGAATCCAACAGACA | 70 | N/A | N/A | 1630 |
| 949502 | 48748 | 48763 | CAACATGCCTTCCAGT | 124 | N/A | N/A | 1631 |
| 949503 | 48869 | 48884 | TGCCACTCCCTATCCC | 79 | N/A | N/A | 1632 |
| 949504 | 48972 | 48987 | GCTTAATGCCTTGCCT | 128 | N/A | N/A | 1633 |
| 949505 | 49052 | 49067 | CCGCAATGTGTTCATT | 42 | N/A | N/A | 1634 |
| 949506 | 49095 | 49110 | GTATACCCCACAAGGC | 73 | N/A | N/A | 1635 |
| 949507 | 49171 | 49186 | GTAAAGGGTGGCAGCC | 84 | N/A | N/A | 1636 |
| 949508 | 49196 | 49211 | AGTCACTTTAACAAGT | 57 | N/A | N/A | 1637 |
| 949509 | 49218 | 49233 | GCTACCAAGGCACAGA | 72 | N/A | N/A | 1638 |
| 949510 | 49265 | 49280 | CATGGCCACGATGGCA | 92 | N/A | N/A | 1639 |
| 949511 | 49297 | 49312 | GAAGAGACAGCATACC | 69 | N/A | N/A | 1640 |
| 949512 | 49403 | 49418 | AGTTATGGTTCACTGG | 29 | N/A | N/A | 1641 |
| 949513 | 49511 | 49526 | ACTCAGAGTTTACGGG | 91 | N/A | N/A | 1642 |
| 949514 | 49613 | 49628 | TTCCGGTGAGCACACC | 49 | N/A | N/A | 1643 |
| 949515 | 49770 | 49785 | GAATCAGGAGGGAGAT | 101 | N/A | N/A | 1644 |
| 949516 | 49888 | 49903 | GGCAAGTGACCAGGTG | 55 | N/A | N/A | 1645 |
| 949517 | 49896 | 49911 | ACGAAGGCGGCAAGTG | 6 | N/A | N/A | 1646 |
| 949518 | 50269 | 50284 | GCAGAGAGAGTCCATT | 38 | N/A | N/A | 1647 |
| 949519 | 50271 | 50286 | GCGCAGAGAGAGTCCA | 116 | N/A | N/A | 1648 |
| 949520 | 50402 | 50417 | GCCCAGTAGGCAAGAA | 117 | N/A | N/A | 1649 |
| 949521 | 50423 | 50438 | AAGTAACCCCCATCAC | 94 | N/A | N/A | 1650 |
| 949522 | 50491 | 50506 | CTAGATACAAGGCTGC | 62 | N/A | N/A | 1651 |
| 949523 | 50510 | 50525 | CGCCAGCTTGGTCTGC | 70 | N/A | N/A | 1652 |
| 949524 | 50597 | 50612 | ACGCAAATATCTCCCA | 41 | N/A | N/A | 1653 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949525 | 50612 | 50627 | CTAATCCGAGGCAATA | 59 | N/A | N/A | 1654 |
| 949526 | 50654 | 50669 | GCACACAACACTTCCC | 41 | N/A | N/A | 1655 |
| 949527 | 50713 | 50728 | GGCAGGATCCACTCAT | 111 | N/A | N/A | 1656 |
| 949528 | 50818 | 50833 | AGGAGAGGAGATCTGC | 87 | N/A | N/A | 1657 |
| 949529 | 50847 | 50862 | ACACAATGACGAGGCT | 27 | N/A | N/A | 1658 |
| 949530 | 50945 | 50960 | TGTTAGTCTCAGGGAA | 54 | N/A | N/A | 1659 |
| 949531 | 50961 | 50976 | ACAAACACGGCTCAGC | 77 | N/A | N/A | 1660 |
| 949532 | 51078 | 51093 | CGACACCCAGCTCCGG | 95 | N/A | N/A | 1661 |
| 949533 | 51207 | 51222 | TTGAAATGCCCAGGTC | 37 | N/A | N/A | 1662 |
| 949534 | 51318 | 51333 | TTCAAAGGAGCTTGTG | 100 | N/A | N/A | 1663 |
| 949535 | 51433 | 51448 | TGCAAGCTGCCACCTT | 79 | N/A | N/A | 1664 |
| 949536 | 51496 | 51511 | TGCTAAACAGTCAATC | 62 | N/A | N/A | 1665 |
| 949537 | 51544 | 51559 | AACCTAGGAGGACATC | 62 | N/A | N/A | 1666 |
| 949538 | 51660 | 51675 | CCCTACTGAAGCTGGA | 71 | N/A | N/A | 1667 |
| 949539 | 51787 | 51802 | AATCACGCTGCCAAGG | 112 | N/A | N/A | 1668 |
| 949540 | 51890 | 51905 | TCAGAGAGGTTCGCAG | 57 | N/A | N/A | 1669 |
| 949541 | 51993 | 52008 | CGGCAAACTGCAAAGC | 67 | N/A | N/A | 1670 |
| 949542 | 52114 | 52129 | CAACAAGCCACTGAGC | 108 | N/A | N/A | 1671 |
| 949543 | 52204 | 52219 | TAACAATCCACTGGCC | 116 | N/A | N/A | 1672 |
| 949544 | 52243 | 52258 | GCTCAAGTGCTGGAGA | 89 | N/A | N/A | 1673 |
| 949545 | 52494 | 52509 | CAAGATCCTACATGTA | 79 | N/A | N/A | 1674 |
| 949546 | 52597 | 52612 | TAAAAGCTTCCACCAG | 119 | N/A | N/A | 1675 |
| 949547 | 52610 | 52625 | CCCAATAGAGGTTTAA | 100 | N/A | N/A | 1676 |
| 949548 | 52802 | 52817 | TCTCATACTTCGGCCT | 111 | N/A | N/A | 1677 |
| 949549 | 52918 | 52933 | CAACAGAGGTTTTTG | 67 | N/A | N/A | 1678 |
| 949550 | 52944 | 52959 | GTGAAAGTAAATGCTG | 48 | N/A | N/A | 1679 |
| 949551 | 53030 | 53045 | AACAGAACCACACCAG | 216 | N/A | N/A | 1680 |
| 949552 | 53066 | 53081 | CCAGAAAACCGTTTCT | 93 | N/A | N/A | 1681 |
| 949553 | 53509 | 53524 | ATGCAGGCTGGGAACC | 88 | N/A | N/A | 1682 |
| 949554 | 53548 | 53563 | TGCCAGACTTTGGAGC | 92 | N/A | N/A | 1683 |
| 949555 | 53611 | 53626 | CCCAAGTCCGCCCAGT | 90 | N/A | N/A | 1684 |
| 949556 | 53712 | 53727 | CTGAATCTAGGTGTCT | 54 | N/A | N/A | 1685 |
| 949557 | 53847 | 53862 | CTTGAATGTCCATGCC | 60 | N/A | N/A | 1686 |
| 949558 | 53863 | 53878 | ATATAGAGAGCTTTAC | 104 | N/A | N/A | 1687 |
| 949559 | 53866 | 53881 | CTAATATAGAGAGCTT | 51 | N/A | N/A | 1688 |
| 949560 | 53867 | 53882 | TCTAATATAGAGAGCT | 78 | N/A | N/A | 1689 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949561 | 53909 | 53924 | CCCCATAACACTTACT | 98 | N/A | N/A | 1690 |
| 949562 | 54006 | 54021 | AGCTACTCTCTCAAGT | 53 | N/A | N/A | 1691 |
| 949563 | 54011 | 54026 | GGGCAAGCTACTCTCT | 126 | N/A | N/A | 1692 |
| 949564 | 54127 | 54142 | AGCTACGGTCTGAGCA | 114 | N/A | N/A | 1693 |
| 949565 | 54237 | 54252 | AGTCAGAGGGCCTGCC | 58 | N/A | N/A | 1694 |
| 949566 | 54341 | 54356 | GCTCACTTTGGATTGT | 48 | N/A | N/A | 1695 |
| 949567 | 54452 | 54467 | GTCTACAAAGCCCAGC | 67 | N/A | N/A | 1696 |
| 949568 | 54562 | 54577 | AAAGAGACCATCTCCC | 91 | N/A | N/A | 1697 |
| 949569 | 54673 | 54688 | GGGAAACACTCGGCCG | 142 | N/A | N/A | 1698 |
| 949570 | 54784 | 54799 | CAATGAGGACATCTGC | 59 | N/A | N/A | 1699 |
| 949571 | 54787 | 54802 | GGGCAATGAGGACATC | 54 | N/A | N/A | 1700 |
| 949572 | 54890 | 54905 | AGGAACTTCGCCTCTT | 112 | N/A | N/A | 1701 |
| 949573 | 54924 | 54939 | TCCTAAGCCAGATAGC | 49 | N/A | N/A | 1702 |
| 949574 | 55043 | 55058 | TCTAAGATCCCCATTT | 106 | N/A | N/A | 1703 |
| 949575 | 55144 | 55159 | TTTCACCGTCCCATCA | 72 | N/A | N/A | 1704 |
| 949576 | 55247 | 55262 | AATAACACAGCCATGC | 84 | N/A | N/A | 1705 |
| 949577 | 55348 | 55363 | ACCCACCCCGGAGATG | 100 | N/A | N/A | 1706 |
| 949578 | 55383 | 55398 | TAATAAGTCACACTGG | 47 | N/A | N/A | 1707 |
| 949579 | 55384 | 55399 | GTAATAAGTCACACTG | 107 | N/A | N/A | 1708 |
| 949580 | 55469 | 55484 | CTATGATCTATGATCA | 115 | N/A | N/A | 1709 |
| 949581 | 55678 | 55693 | TCCGTATAAGATGTGA | 34 | N/A | N/A | 1710 |
| 949582 | 56054 | 56069 | CTATTATCCAGCACTG | 56 | N/A | N/A | 1711 |
| 949583 | 56111 | 56126 | AGCTACTGTAGTGATG | 81 | N/A | N/A | 1712 |
| 949584 | 56167 | 56182 | TCGAATTTTCAGAGTA | 26 | N/A | N/A | 1713 |
| 949585 | 56229 | 56244 | ACGGAAGGTGGCTGCC | 61 | N/A | N/A | 1714 |
| 949586 | 56251 | 56266 | GCAAATATAAGGCATG | 60 | N/A | N/A | 1715 |
| 949587 | 56268 | 56283 | CACAGATTGAGGACAA | 47 | N/A | N/A | 1716 |
| 949588 | 56319 | 56334 | TGACAAGCAGTGTGGG | 48 | N/A | N/A | 1717 |
| 949589 | 56371 | 56386 | GGTATCTGAAAGTCAC | 9 | N/A | N/A | 1718 |
| 949590 | 56530 | 56545 | CCACAAGGTAGAGGGA | 154 | N/A | N/A | 1719 |
| 949591 | 56538 | 56553 | CAAGGAGCCCACAAGG | 114 | N/A | N/A | 1720 |
| 949592 | 56633 | 56648 | GCCCAAGTCCTTGTGG | 105 | N/A | N/A | 1721 |
| 949593 | 56691 | 56706 | GATTAAGGTGATGCTG | 61 | N/A | N/A | 1722 |
| 949594 | 56692 | 56707 | TGATTAAGGTGATGCT | 41 | N/A | N/A | 1723 |
| 949595 | 56734 | 56749 | AGGAAGCACCAGGATA | 23 | N/A | N/A | 1724 |
| 949596 | 56860 | 56875 | CATATTATGAATCCCC | 66 | N/A | N/A | 1725 |
| 949597 | 56863 | 56878 | TGACATATTATGAATC | 105 | N/A | N/A | 1726 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949598 | 56979 | 56994 | ATGACAAGGGTCTTGG | 17 | N/A | N/A | 1727 |
| 949599 | 57373 | 57388 | TAATGACCCAGGCTGG | 121 | N/A | N/A | 1728 |
| 949600 | 57619 | 57634 | GCCTACCGTGTGGCGA | 104 | N/A | N/A | 1729 |
| 949601 | 57654 | 57669 | CCAGAAACGGTCAGTG | 132 | N/A | N/A | 1730 |
| 949602 | 57722 | 57737 | TGTGAATGGGCACATG | 102 | N/A | N/A | 1731 |
| 949603 | 57840 | 57855 | CAAACAACTTCTTGGC | 82 | N/A | N/A | 1732 |
| 949604 | 57948 | 57963 | GAAGACTGGTTCTGGC | 60 | N/A | N/A | 1733 |
| 949605 | 57953 | 57968 | TTACAGAAGACTGGTT | 91 | N/A | N/A | 1734 |
| 949606 | 58891 | 58906 | GGCAAGGTGGCTAAAA | 123 | N/A | N/A | 1735 |
| 949607 | 58993 | 59008 | AGGAACCCATCATGGT | 95 | N/A | N/A | 1736 |
| 949608 | 59092 | 59107 | TGACAAGGTAGGTTTT | 57 | N/A | N/A | 1737 |
| 949609 | 59093 | 59108 | TTGACAAGGTAGGTTT | 25 | N/A | N/A | 1738 |
| 949610 | 59102 | 59117 | CAAAACTGGTTGACAA | 47 | N/A | N/A | 1739 |
| 949611 | 59104 | 59119 | TGCAAAACTGGTTGAC | 58 | N/A | N/A | 1740 |
| 949612 | 59272 | 59287 | GTGAAGTGCAGTAGCT | 88 | N/A | N/A | 1741 |
| 949613 | 59302 | 59317 | TAAGATAGAGGGTCTT | 35 | N/A | N/A | 1742 |
| 949614 | 59399 | 59414 | GCTAACAATTTAAGGA | 60 | N/A | N/A | 1743 |
| 949615 | 59741 | 59756 | CTGAGAGGCATACAAA | 66 | N/A | N/A | 1744 |
| 949616 | 59846 | 59861 | GGAGAAGAAGTGAGCC | 109 | N/A | N/A | 1745 |
| 949617 | 60067 | 60082 | ACAAATGGATGAGGCC | 129 | N/A | N/A | 1746 |
| 949618 | 60068 | 60083 | GACAAATGGATGAGGC | 54 | N/A | N/A | 1747 |
| 949619 | 60379 | 60394 | GACAAACAGATGAGGC | 74 | N/A | N/A | 1748 |
| 949620 | 60427 | 60442 | GAATAAATTTCAGCCC | 100 | N/A | N/A | 1749 |
| 949621 | 60483 | 60498 | TTCAATGGCACAGTTC | 73 | N/A | N/A | 1750 |
| 949622 | 60586 | 60601 | TCAGACTTGAGGATGT | 32 | N/A | N/A | 1751 |
| 949623 | 60639 | 60654 | GCACAAACAGGCCCGC | 99 | N/A | N/A | 1752 |
| 949624 | 60700 | 60715 | GTCAAGTTCAACACTG | 25 | N/A | N/A | 1753 |
| 949625 | 60903 | 60918 | GCTCAGGGTTACCTTG | 81 | N/A | N/A | 1754 |
| 949626 | 61033 | 61048 | AGGAAGTGCCATGTTC | 64 | N/A | N/A | 1755 |
| 949627 | 61134 | 61149 | TCCCACTCTGGCAACA | 79 | N/A | N/A | 1756 |
| 949628 | 61204 | 61219 | AGCTAGATGGGACCTA | 102 | N/A | N/A | 1757 |
| 949629 | 61255 | 61270 | GAAGTTCCCGTTCTGA | 47 | N/A | N/A | 1758 |
| 949630 | 61336 | 61351 | AAATAGACGATCTCAC | 87 | N/A | N/A | 1759 |
| 949631 | 61340 | 61355 | AGGGAAATAGACGATC | 96 | N/A | N/A | 1760 |
| 949632 | 61344 | 61359 | TCGAAGGGAAATAGAC | 101 | N/A | N/A | 1761 |
| 949633 | 61382 | 61397 | GTAGAAGGATCTGACT | 114 | N/A | N/A | 1762 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949634 | 61384 | 61399 | CAGTAGAAGGATCTGA | 123 | N/A | N/A | 1763 |
| 949635 | 61480 | 61495 | GTGAAGATCTCTGGTG | 88 | N/A | N/A | 1764 |
| 949636 | 61485 | 61500 | CCAGAGTGAAGATCTC | 119 | N/A | N/A | 1765 |
| 949637 | 61587 | 61602 | CTGCAGATCAACTGCT | 104 | N/A | N/A | 1766 |
| 949638 | 61636 | 61651 | CCACAAGTCATTCCAG | 71 | N/A | N/A | 1767 |
| 949639 | 61706 | 61721 | TTCCAGGACTACCTCT | 76 | N/A | N/A | 1768 |
| 949640 | 61813 | 61828 | GGCTTTGGGAAACCTC | 48 | N/A | N/A | 1769 |
| 949641 | 61839 | 61854 | TATTAAGGACAACCTC | 98 | N/A | N/A | 1770 |
| 949642 | 61840 | 61855 | TTATTAAGGACAACCT | 81 | N/A | N/A | 1771 |
| 949643 | 61842 | 61857 | TGTTATTAAGGACAAC | 125 | N/A | N/A | 1772 |
| 949644 | 61889 | 61904 | TGGCACACGGCAAATA | 96 | N/A | N/A | 1773 |
| 949645 | 61904 | 61919 | TCATAAGGGTGAGCCT | 70 | N/A | N/A | 1774 |
| 949646 | 61915 | 61930 | TCACAGGGTGGTCATA | 68 | N/A | N/A | 1775 |
| 949647 | 61937 | 61952 | GAAGATGGTCACAGCC | 51 | N/A | N/A | 1776 |
| 949648 | 61944 | 61959 | GTCGAATGAAGATGGT | 38 | N/A | N/A | 1777 |
| 949649 | 62105 | 62120 | GGCCTGAAAGAGCCCA | 112 | N/A | N/A | 1778 |
| 949650 | 62252 | 62267 | GATAAGGACCCCACCC | 108 | N/A | N/A | 1779 |
| 949651 | 62328 | 62343 | AAAGAAGGAGTTACGG | 88 | N/A | N/A | 1780 |
| 949652 | 62378 | 62393 | ACGAATGCATACAAAT | 72 | N/A | N/A | 1781 |
| 949653 | 62384 | 62399 | TGAAAAACGAATGCAT | 107 | N/A | N/A | 1782 |
| 949654 | 62491 | 62506 | CACCAGTGGCTGTCTG | 63 | N/A | N/A | 1783 |
| 949655 | 62887 | 62902 | TCATAATAGGCCGGGT | 61 | N/A | N/A | 1784 |
| 949656 | 62969 | 62984 | ATAATAACCACCGAAG | 45 | N/A | N/A | 1785 |
| 949657 | 62972 | 62987 | ATAATAATAACCACCG | 13 | N/A | N/A | 1786 |
| 949658 | 63350 | 63365 | CCTAGGATTTGTGTTA | 101 | N/A | N/A | 1787 |
| 949659 | 63667 | 63682 | GCCTAGGATTTATAGA | 96 | N/A | N/A | 1788 |
| 949660 | 63759 | 63774 | CCACAAATGAATGGTA | 72 | N/A | N/A | 1789 |
| 949661 | 63780 | 63795 | TGGGATGTGGTCTGGT | 98 | N/A | N/A | 1790 |
| 949662 | 63826 | 63841 | CTAATTACCAGCTAAC | 46 | N/A | N/A | 1791 |
| 949663 | 63880 | 63895 | ACTTAGGTTACTCCTA | 76 | N/A | N/A | 1792 |
| 949664 | 64255 | 64270 | AACTGCTGCTCCGATA | 53 | N/A | N/A | 1793 |
| 949665 | 64313 | 64328 | GGCTATAGGGCTGATA | 104 | N/A | N/A | 1794 |
| 949666 | 64366 | 64381 | AAATGCACCGCTCTGC | 137 | N/A | N/A | 1795 |
| 949667 | 64530 | 64545 | ACAGAATAAGACATCG | 55 | N/A | N/A | 1796 |
| 949668 | 64650 | 64665 | AGCAATCGCACATGCC | 92 | N/A | N/A | 1797 |
| 949669 | 64984 | 64999 | AGTAGATGCCAGAGGG | 54 | N/A | N/A | 1798 |
| 949670 | 65026 | 65041 | GGCTAAGCATGAAGGG | 96 | N/A | N/A | 1799 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949671 | 65086 | 65101 | ATCTATCTCAGACATC | 110 | N/A | N/A | 1800 |
| 949672 | 65109 | 65124 | CCAAGGTCTGAACTTT | 69 | N/A | N/A | 1801 |
| 949673 | 65111 | 65126 | AACCAAGGTCTGAACT | 125 | N/A | N/A | 1802 |
| 949674 | 65112 | 65127 | CAACCAAGGTCTGAAC | 110 | N/A | N/A | 1803 |
| 949675 | 65113 | 65128 | GCAACCAAGGTCTGAA | 31 | N/A | N/A | 1804 |
| 949676 | 65115 | 65130 | TGGCAACCAAGGTCTG | 67 | N/A | N/A | 1805 |
| 949677 | 65116 | 65131 | CTGGCAACCAAGGTCT | 120 | N/A | N/A | 1806 |
| 949678 | 65117 | 65132 | GCTGGCAACCAAGGTC | 156 | N/A | N/A | 1807 |
| 949679 | 65119 | 65134 | ATGCTGGCAACCAAGG | 40 | N/A | N/A | 1808 |
| 949680 | 65192 | 65207 | GAATTTAGCCCTGACA | 94 | N/A | N/A | 1809 |
| 949681 | 65208 | 65223 | AGCTAAACAGGGTTTT | 78 | N/A | N/A | 1810 |
| 949682 | 65343 | 65358 | GTCCAAGGGCAGCCGG | 100 | N/A | N/A | 1811 |
| 949683 | 65383 | 65398 | CCCCAAAGGCCCTTAG | 97 | N/A | N/A | 1812 |
| 949684 | 65458 | 65473 | GTGGACATCAGTGAGT | 53 | N/A | N/A | 1813 |
| 949685 | 65527 | 65542 | CTACAAGTGAGCTGAG | 6 | N/A | N/A | 1814 |
| 949686 | 65543 | 65558 | CAAAACGGGAGCAGGC | 83 | N/A | N/A | 1815 |
| 949687 | 65544 | 65559 | ACAAAACGGGAGCAGG | 51 | N/A | N/A | 1816 |
| 949688 | 65545 | 65560 | CACAAAACGGGAGCAG | 76 | N/A | N/A | 1817 |
| 949689 | 65583 | 65598 | AAAAAGGGTCCAGTGG | 91 | N/A | N/A | 1818 |
| 949690 | 65599 | 65614 | TCATTAGTACGCCAGG | 24 | N/A | N/A | 1819 |
| 949691 | 65686 | 65701 | CCCAACTGTGCTTTCC | 26 | N/A | N/A | 1820 |
| 949692 | 66037 | 66052 | TCACACACGGATTTTT | 73 | N/A | N/A | 1821 |
| 949693 | 66148 | 66163 | TTCTGCATTGCAGTGG | 26 | N/A | N/A | 1822 |
| 949694 | 66218 | 66233 | GTAAAAAGCATCTGGC | 83 | N/A | N/A | 1823 |
| 949695 | 66272 | 66287 | GCCAGAGTCACCATCA | 73 | N/A | N/A | 1824 |
| 949696 | 66327 | 66342 | TGCCAAGGTGAGGTCA | 91 | N/A | N/A | 1825 |
| 949697 | 66373 | 66388 | CGCCAGATCTCTCTTG | 104 | N/A | N/A | 1826 |
| 949698 | 66787 | 66802 | TGCCTACCATTGCACT | 86 | N/A | N/A | 1827 |
| 949699 | 66882 | 66897 | CGAGAAGGAGGTAGAA | 82 | N/A | N/A | 1828 |
| 949700 | 66890 | 66905 | AACTACACCGAGAAGG | 101 | N/A | N/A | 1829 |
| 949701 | 66895 | 66910 | TCCAAAACTACACCGA | 72 | N/A | N/A | 1830 |
| 949702 | 66973 | 66988 | ATCAAACGAGTATATT | 91 | N/A | N/A | 1831 |
| 949703 | 66974 | 66989 | TATCAAACGAGTATAT | 101 | N/A | N/A | 1832 |
| 949704 | 66987 | 67002 | AGCTAAAATCCACTAT | 110 | N/A | N/A | 1833 |
| 949705 | 66998 | 67013 | CAATAGGGAAGAGCTA | 57 | N/A | N/A | 1834 |
| 949706 | 66999 | 67014 | GCAATAGGGAAGAGCT | 117 | N/A | N/A | 1835 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949707 | 67000 | 67015 | AGCAATAGGGAAGAGC | 75 | N/A | N/A | 1836 |
| 949708 | 67377 | 67392 | ATCAAGACTCTGAATA | 86 | N/A | N/A | 1837 |
| 949709 | 67669 | 67684 | TTCAAAGATAGGTGAG | 32 | N/A | N/A | 1838 |
| 949710 | 67762 | 67777 | CATTAAGTATTTGGAG | 77 | N/A | N/A | 1839 |
| 949711 | 67770 | 67785 | AAGAGCAACATTAAGT | 111 | N/A | N/A | 1840 |
| 949712 | 67773 | 67788 | GCGAAGAGCAACATTA | 120 | N/A | N/A | 1841 |
| 949713 | 67793 | 67808 | TGCGAATGCACATGGC | 138 | N/A | N/A | 1842 |
| 949714 | 67803 | 67818 | ACACAGAGGGTGCGAA | 153 | N/A | N/A | 1843 |
| 949715 | 67805 | 67820 | CAACACAGAGGGTGCG | 47 | N/A | N/A | 1844 |
| 949716 | 67823 | 67838 | TAACATGTTACTCAGA | 75 | N/A | N/A | 1845 |
| 949717 | 67870 | 67885 | TCAAGTATAGAGATGG | 46 | N/A | N/A | 1846 |
| 949718 | 68110 | 68125 | AGTACCTGATTCAGCG | 147 | N/A | N/A | 1847 |
| 949719 | 68180 | 68195 | TGCCAGTGAGGATTGC | 56 | N/A | N/A | 1848 |
| 949720 | 68210 | 68225 | AAAACAAGTGCTGCTC | 77 | N/A | N/A | 1849 |
| 949721 | 68491 | 68506 | GAATCAAGTACATTTC | 77 | N/A | N/A | 1850 |
| 949722 | 68541 | 68556 | GTAATAGTAGCAGCAC | 29 | N/A | N/A | 1851 |
| 949723 | 68542 | 68557 | TGTAATAGTAGCAGCA | 20 | N/A | N/A | 1852 |
| 949724 | 68610 | 68625 | GTCTTCTGGGTAAATG | 30 | N/A | N/A | 1853 |
| 949725 | 68624 | 68639 | AGGCAATGCATACAGT | 25 | N/A | N/A | 1854 |
| 949726 | 68992 | 69007 | GAACGATAGGCCAGGC | 90 | N/A | N/A | 1855 |
| 949727 | 68999 | 69014 | AAGAAGAGAACGATAG | 67 | N/A | N/A | 1856 |
| 949728 | 69029 | 69044 | GTTTATGCACCATGTG | 20 | N/A | N/A | 1857 |
| 949729 | 69102 | 69117 | AAAACAGCGAGGAGGA | 90 | N/A | N/A | 1858 |
| 949730 | 69108 | 69123 | TGCTAGAAAACAGCGA | 109 | N/A | N/A | 1859 |
| 949731 | 69206 | 69221 | CAGGAACCTACTCTCG | 86 | N/A | N/A | 1860 |
| 949732 | 69213 | 69228 | ACAAGGACAGGAACCT | 97 | N/A | N/A | 1861 |
| 949733 | 69215 | 69230 | CTACAAGGACAGGAAC | 107 | N/A | N/A | 1862 |
| 949734 | 69361 | 69376 | CTAGACACTGACTTCC | 89 | N/A | N/A | 1863 |
| 949735 | 69486 | 69501 | GGCCAGCTGGACTTTT | 74 | N/A | N/A | 1864 |
| 949736 | 69589 | 69604 | TACTAGGGCACTTAAG | 149 | N/A | N/A | 1865 |
| 949737 | 69591 | 69606 | GATACTAGGGCACTTA | 69 | N/A | N/A | 1866 |
| 949738 | 69692 | 69707 | ACCAAGGGTCCCTGCC | 113 | N/A | N/A | 1867 |
| 949739 | 69781 | 69796 | TACAAAGTGTCTGGCG | 53 | N/A | N/A | 1868 |
| 949740 | 69782 | 69797 | ATACAAAGTGTCTGGC | 41 | N/A | N/A | 1869 |
| 949741 | 70034 | 70049 | GATTAGGAGACAAGCC | 87 | N/A | N/A | 1870 |
| 949742 | 70467 | 70482 | ATCCATTCTGGACAAC | 62 | N/A | N/A | 1871 |
| 949743 | 70664 | 70679 | CACTAGAGGATAGGCG | 118 | N/A | N/A | 1872 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949744 | 70759 | 70774 | GTAAAGCAGAGTTTGG | 25 | N/A | N/A | 1873 |
| 949745 | 70760 | 70775 | TGTAAAGCAGAGTTTG | 46 | N/A | N/A | 1874 |
| 949746 | 70766 | 70781 | GCAAAGTGTAAAGCAG | 53 | N/A | N/A | 1875 |
| 949747 | 70787 | 70802 | CCATAAAATCAGCCTA | 71 | N/A | N/A | 1876 |
| 949748 | 70897 | 70912 | AAAGAACTCGGGAGGT | 65 | N/A | N/A | 1877 |
| 949749 | 71020 | 71035 | TTAAGATCAAGAGATC | 115 | N/A | N/A | 1878 |
| 949750 | 71155 | 71170 | TCAAGATGAGCTCCCC | 65 | N/A | N/A | 1879 |
| 949751 | 71255 | 71270 | GTCCATCCAGACCACG | 119 | N/A | N/A | 1880 |
| 949752 | 71260 | 71275 | GGACAGTCCATCCAGA | 84 | N/A | N/A | 1881 |
| 949753 | 71369 | 71384 | GGAGACGGCACGGAGC | 81 | N/A | N/A | 1882 |
| 949754 | 71371 | 71386 | ACGGAGACGGCACGGA | 87 | N/A | N/A | 1883 |
| 949755 | 71473 | 71488 | ACCAAGGGCCAACACC | 70 | N/A | N/A | 1884 |
| 949756 | 71697 | 71712 | ACATACTGCAGCAGGG | 52 | N/A | N/A | 1885 |
| 949757 | 71797 | 71812 | AATCAATGAGTGGACG | 29 | N/A | N/A | 1886 |
| 949758 | 71827 | 71842 | ACGCAGAAGGCTTGCA | 87 | N/A | N/A | 1887 |
| 949759 | 71908 | 71923 | CCATTCTGAGCACTCC | 41 | N/A | N/A | 1888 |
| 949760 | 72021 | 72036 | TCTAAAGGAGGCTGTT | 82 | N/A | N/A | 1889 |
| 949761 | 72175 | 72190 | AGCCTAATTTTGCAAT | 133 | N/A | N/A | 1890 |
| 949762 | 72938 | 72953 | GGCCAACACTCATCTT | 128 | N/A | N/A | 1891 |
| 949763 | 73188 | 73203 | TGATATGCAGTGACAC | 75 | N/A | N/A | 1892 |
| 949764 | 73296 | 73311 | TCCCACACGGCTCCTG | 144 | N/A | N/A | 1893 |
| 949765 | 73415 | 73430 | GCACAACCTGCTCTAT | 80 | N/A | N/A | 1894 |
| 949766 | 73519 | 73534 | GAGCACCTGAGTCAGT | 91 | N/A | N/A | 1895 |
| 949767 | 73639 | 73654 | ACCAACCAAGTCATGG | 137 | N/A | N/A | 1896 |
| 949768 | 73653 | 73668 | AGCTAAGCAGCTGCAC | 133 | N/A | N/A | 1897 |
| 949769 | 73742 | 73757 | TTACAGGCCAAAAGCC | 88 | N/A | N/A | 1898 |
| 949770 | 73868 | 73883 | GAGGAGGCGGTGTCCT | 122 | N/A | N/A | 1899 |
| 949771 | 73954 | 73969 | CATAAAAGCACTCTGG | 87 | N/A | N/A | 1900 |
| 949772 | 73957 | 73972 | GAGCATAAAAGCACTC | 92 | N/A | N/A | 1901 |
| 949773 | 73970 | 73985 | GTCAAGGCTGTCTGAG | 56 | N/A | N/A | 1902 |
| 949774 | 74231 | 74246 | GCTGAATCTTGTGTTT | 47 | N/A | N/A | 1903 |
| 949775 | 74259 | 74274 | CACAACAACACTTCCT | 73 | N/A | N/A | 1904 |
| 949776 | 74351 | 74366 | CTTTAGAGGTGCAGAA | 53 | N/A | N/A | 1905 |
| 949777 | 74592 | 74607 | ATCCACTGAAGCCTCT | 50 | N/A | N/A | 1906 |
| 949778 | 74872 | 74887 | CTTAACAAGTAGTATT | 14 | N/A | N/A | 1907 |
| 949779 | 74874 | 74889 | GGCTTAACAAGTAGTA | 38 | N/A | N/A | 1908 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949780 | 74962 | 74977 | GGCAACTGGTTACAAA | 58 | N/A | N/A | 1909 |
| 949781 | 74967 | 74982 | TGCAAGGCAACTGGTT | 14 | N/A | N/A | 1910 |
| 949782 | 75001 | 75016 | CTCCATGGTGAGAGTG | 73 | N/A | N/A | 1911 |
| 949783 | 75055 | 75070 | GCTAAAGCAAGAAGGC | 87 | N/A | N/A | 1912 |
| 949784 | 75104 | 75119 | AGAAAGACCGCCCATG | 97 | N/A | N/A | 1913 |
| 949785 | 75219 | 75234 | GCGGAGACAGAAGGCT | 121 | N/A | N/A | 1914 |
| 949786 | 75320 | 75335 | AAGCATCGGTTAAGGC | 142 | N/A | N/A | 1915 |
| 949787 | 75846 | 75861 | CCCAAGTGGTGAGGCT | 74 | N/A | N/A | 1916 |
| 949788 | 76007 | 76022 | GTTCAGGCAGGCGGTT | 53 | N/A | N/A | 1917 |
| 949789 | 76107 | 76122 | AACAAGAGACCTTGTC | 47 | N/A | N/A | 1918 |
| 949790 | 76211 | 76226 | GATCAGGCTACTCAGG | 116 | N/A | N/A | 1919 |
| 949791 | 76415 | 76430 | TCATAGCCAATATAAC | 42 | N/A | N/A | 1920 |
| 949792 | 76430 | 76445 | TATCACAGGGTGTGCT | 67 | N/A | N/A | 1921 |
| 949793 | 76487 | 76502 | TCGGAATGTACTCTTA | 23 | N/A | N/A | 1922 |
| 949794 | 76518 | 76533 | GAATTCGGGTTGAATC | 107 | N/A | N/A | 1923 |
| 949795 | 76636 | 76651 | GACAAAGCACACCTGG | 81 | N/A | N/A | 1924 |
| 949796 | 76637 | 76652 | GGACAAAGCACACCTG | 100 | N/A | N/A | 1925 |
| 949797 | 76731 | 76746 | CACTAAACTAATGACA | 98 | N/A | N/A | 1926 |
| 949798 | 76734 | 76749 | TAGCACTAAACTAATG | 88 | N/A | N/A | 1927 |
| 949799 | 76737 | 76752 | GCATAGCACTAAACTA | 83 | N/A | N/A | 1928 |
| 949800 | 76739 | 76754 | AGGCATAGCACTAAAC | 80 | N/A | N/A | 1929 |
| 949801 | 76744 | 76759 | AGCAAAGGCATAGCAC | 91 | N/A | N/A | 1930 |
| 949802 | 76764 | 76779 | ACCAAACCAGGACCAA | 57 | N/A | N/A | 1931 |
| 949803 | 77124 | 77139 | GTTAATGCTTCACCTG | 25 | N/A | N/A | 1932 |
| 949804 | 77125 | 77140 | GGTTAATGCTTCACCT | 104 | N/A | N/A | 1933 |
| 949805 | 77175 | 77190 | GTAAAGGGTGTGCACA | 10 | N/A | N/A | 1934 |
| 949806 | 77224 | 77239 | AGGCAAGCACAAGCTG | 115 | N/A | N/A | 1935 |
| 949807 | 77245 | 77260 | CCTTCATACCCCAACT | 97 | N/A | N/A | 1936 |
| 949808 | 77343 | 77358 | TACTGAAGTACCTGGG | 102 | N/A | N/A | 1937 |
| 949809 | 77421 | 77436 | TCCTAAGCATTCCTAA | 113 | N/A | N/A | 1938 |
| 949810 | 77450 | 77465 | GTAGGATGATCTTGTT | 27 | N/A | N/A | 1939 |
| 949811 | 77458 | 77473 | GTAAAAAGTAGGATG | 68 | N/A | N/A | 1940 |
| 949812 | 77502 | 77517 | CCTTAAAAAGAGTCTC | 75 | N/A | N/A | 1941 |
| 949813 | 77561 | 77576 | GCTCATCTAATGGACA | 46 | N/A | N/A | 1942 |
| 949814 | 77634 | 77649 | GGCGAGACAGAGTAAG | 12 | N/A | N/A | 1943 |
| 949815 | 77894 | 77909 | TATACTGGACACGGTG | 96 | N/A | N/A | 1944 |
| 949816 | 77895 | 77910 | ATATACTGGACACGGT | 88 | N/A | N/A | 1945 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID: 2 Stop Site | SEQ ID NO |
|---|---|---|---|---|---|---|---|
| 949817 | 77897 | 77912 | ATATATACTGGACACG | 36 | N/A | N/A | 1946 |
| 949818 | 78035 | 78050 | GTTTTATTGGCCGGGT | 20 | N/A | N/A | 1947 |
| 949819 | 78144 | 78159 | AGTCACTGATCCTAAA | 74 | N/A | N/A | 1948 |
| 949820 | 78149 | 78164 | CAAGAAGTCACTGATC | 69 | N/A | N/A | 1949 |
| 949821 | 78222 | 78237 | ACAAAATGGGTTGAGG | 38 | N/A | N/A | 1950 |
| 949822 | 78223 | 78238 | TACAAAATGGGTTGAG | 50 | N/A | N/A | 1951 |
| 949823 | 78262 | 78277 | GGACAGGACTTTGCCC | 119 | N/A | N/A | 1952 |
| 949824 | 78348 | 78363 | CCACAATTCAGGTGGC | 122 | N/A | N/A | 1953 |
| 949825 | 78366 | 78381 | GGAAAGGTAGCCACTT | 64 | N/A | N/A | 1954 |
| 949826 | 78470 | 78485 | GCCCACTTATTCCTCC | 120 | N/A | N/A | 1955 |
| 949827 | 78561 | 78576 | CCAAATTCAAGAGCTC | 45 | N/A | N/A | 1956 |
| 949828 | 78611 | 78626 | TACCATTTTCAGCAG | 25 | N/A | N/A | 1957 |
| 949829 | 78678 | 78693 | TCAAAACGGAGGTTTC | 20 | N/A | N/A | 1958 |
| 949830 | 78711 | 78726 | GACCATCCTATGAGGA | 106 | N/A | N/A | 1959 |
| 949831 | 78878 | 78893 | GACCAGAGACGGGAGG | 58 | N/A | N/A | 1960 |
| 949832 | 78949 | 78964 | GCCTAGAGGTAGGAGC | 64 | N/A | N/A | 1961 |
| 949833 | 78961 | 78976 | CCACAAGTTCAGGCCT | 107 | N/A | N/A | 1962 |
| 949834 | 79024 | 79039 | TCAAAGCTGAGTGTCA | 25 | N/A | N/A | 1963 |
| 949835 | 79143 | 79158 | TGCTAGGGACATCTTC | 17 | N/A | N/A | 1964 |
| 949836 | 79212 | 79227 | GTATATATCAGCTCAG | 30 | N/A | N/A | 1965 |
| 949837 | 79225 | 79240 | ACATAAGGATGTTGTA | 126 | N/A | N/A | 1966 |
| 949838 | 79243 | 79258 | ATCCATGTTCAGTTTC | 13 | N/A | N/A | 1967 |
| 949839 | 79330 | 79345 | CGGAAAAAGAAGTCCC | 154 | N/A | N/A | 1968 |
| 949840 | 79375 | 79390 | TTCAAGCAAATCACAC | 96 | N/A | N/A | 1969 |
| 949841 | 79794 | 79809 | TCAGTATGCACCACCA | 6 | N/A | N/A | 1970 |
| 949842 | 79870 | 79885 | AAGCATGACATGACAC | 16 | N/A | N/A | 1971 |
| 949843 | 80250 | 80265 | CAGAATATTTAACTCG | 26 | N/A | N/A | 1972 |
| 949844 | 80347 | 80362 | GACAAACCAAGCACAT | 107 | N/A | N/A | 1973 |
| 949845 | 80435 | 80450 | GTGGAACTTGCCTGAC | 86 | N/A | N/A | 1974 |
| 949846 | 80542 | 80557 | TCCAAGAGCCCTCTTA | 11 | N/A | N/A | 1975 |
| 949847 | 80662 | 80677 | CCTATTTGATCAGGAG | 137 | N/A | N/A | 1976 |
| 949848 | 80759 | 80774 | TGATTCAGTGCCGCCC | 7 | N/A | N/A | 1977 |
| 949849 | 80769 | 80784 | CCCAAAACCCTGATTC | 17 | N/A | N/A | 1978 |
| 949850 | 80805 | 80820 | TCACGAGGAAGCCATG | 54 | N/A | N/A | 1979 |
| 949851 | 80870 | 80885 | GGCGATGGAAGGGCAG | 57 | N/A | N/A | 1980 |
| 949852 | 80981 | 80996 | TTTCATTGGCCCTGGC | 62 | N/A | N/A | 1981 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949853 | 80987 | 81002 | CAGCAATTTCATTGGC | 63 | N/A | N/A | 1982 |
| 949854 | 81187 | 81202 | TACCTTACTGGTACAC | 67 | N/A | N/A | 1983 |
| 949855 | 81200 | 81215 | GCCGAGGGAGCAATAC | 102 | N/A | N/A | 1984 |
| 949856 | 81201 | 81216 | TGCCGAGGGAGCAATA | 49 | N/A | N/A | 1985 |
| 949857 | 81288 | 81303 | GAAAAGGCACCAGTGG | 39 | N/A | N/A | 1986 |
| 949858 | 81306 | 81321 | CACAAAGCGATATGGG | 7 | N/A | N/A | 1987 |
| 949859 | 81411 | 81426 | GTGCATCTGTCTGGCC | 79 | N/A | N/A | 1988 |
| 949860 | 81445 | 81460 | TGCTAGGCTTGGTATC | 95 | N/A | N/A | 1989 |
| 949861 | 81530 | 81545 | CAGCAGTTGACGCGGG | 127 | N/A | N/A | 1990 |
| 949862 | 81635 | 81650 | CCGGAGCTGAGGGACA | 117 | N/A | N/A | 1991 |
| 949863 | 81738 | 81753 | AAAAATGGGCTGCCCC | 103 | N/A | N/A | 1992 |
| 949864 | 81740 | 81755 | CCAAAAATGGGCTGCC | 90 | N/A | N/A | 1993 |
| 949865 | 81752 | 81767 | GACTAAGTGGATCCAA | 2 | N/A | N/A | 1994 |
| 949866 | 81769 | 81784 | GCGCATAGAGGCACTG | 56 | N/A | N/A | 1995 |
| 949867 | 81845 | 81860 | AACCAGGCCCGCGGCG | 90 | N/A | N/A | 1996 |
| 949868 | 81909 | 81924 | GCGCAAGCACAGACTG | 109 | N/A | N/A | 1997 |
| 949869 | 81953 | 81968 | GCAGAAATTCCCTGGC | 92 | N/A | N/A | 1998 |
| 949870 | 82004 | 82019 | AGCTTAAGCAGCAAAT | 111 | N/A | N/A | 1999 |
| 949871 | 82041 | 82056 | TTTGGACTGTTTTCCC | 8 | N/A | N/A | 2000 |
| 949872 | 82043 | 82058 | TGTTTGGACTGTTTTC | 2 | N/A | N/A | 2001 |
| 949873 | 82044 | 82059 | CTGTTTGGACTGTTTT | 1 | N/A | N/A | 2002 |
| 949874 | 82045 | 82060 | CCTGTTTGGACTGTTT | 1 | N/A | N/A | 2003 |
| 949875 | 82047 | 82062 | AACCTGTTTGGACTGT | 4 | N/A | N/A | 2004 |
| 949876 | 82048 | 82063 | CAACCTGTTTGGACTG | 5 | N/A | N/A | 2005 |
| 949877 | 82050 | 82065 | TCCAACCTGTTTGGAC | 27 | N/A | N/A | 2006 |
| 949878 | 82052 | 82067 | TTTCCAACCTGTTTGG | 44 | N/A | N/A | 2007 |
| 949879 | 82053 | 82068 | TTTTCCAACCTGTTTG | 17 | N/A | N/A | 2008 |
| 949880 | 82054 | 82069 | GTTTTCCAACCTGTTT | 4 | N/A | N/A | 2009 |
| 949881 | 82084 | 82099 | ATGTCCATGACACCTG | 17 | N/A | N/A | 2010 |
| 949882 | 82085 | 82100 | CATGTCCATGACACCT | 39 | N/A | N/A | 2011 |
| 949883 | 82087 | 82102 | TTCATGTCCATGACAC | 30 | N/A | N/A | 2012 |
| 949884 | 82089 | 82104 | CATTCATGTCCATGAC | 13 | N/A | N/A | 2013 |
| 949885 | 82091 | 82106 | AACATTCATGTCCATG | 51 | N/A | N/A | 2014 |
| 949886 | 82154 | 82169 | TACAGAAGGGCCACGG | 6 | N/A | N/A | 2015 |
| 949887 | 82155 | 82170 | TTACAGAAGGGCCACG | 10 | N/A | N/A | 2016 |
| 949888 | 82259 | 82274 | GATTAGTCCATGCATG | 99 | N/A | N/A | 2017 |
| 949889 | 82308 | 82323 | ACACACGCAGGACAGG | 85 | N/A | N/A | 2018 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949890 | 82361 | 82376 | GGTCATGCGGAGGGCA | 41 | N/A | N/A | 2019 |
| 949891 | 82509 | 82524 | TGTTACCTTCTCGGCA | 19 | N/A | N/A | 2020 |
| 949892 | 82529 | 82544 | GCGGAGATGAGAACAA | 13 | N/A | N/A | 2021 |
| 949893 | 82619 | 82634 | CTGGTAGGCGGAAGGG | 77 | N/A | N/A | 2022 |
| 949894 | 82632 | 82647 | CTCTAAGTGACAACTG | 18 | N/A | N/A | 2023 |
| 949895 | 82720 | 82735 | AACAAAGGCTGACCGC | 85 | N/A | N/A | 2024 |
| 949896 | 82827 | 82842 | GATGATGTGTTTCCTG | 1 | N/A | N/A | 2025 |
| 949897 | 82836 | 82851 | GGCTATACAGATGATG | 7 | N/A | N/A | 2026 |
| 949898 | 82948 | 82963 | AACCAGACCTCATGCA | 22 | N/A | N/A | 2027 |
| 949899 | 82953 | 82968 | AACTTAACCAGACCTC | 12 | N/A | N/A | 2028 |
| 949900 | 82994 | 83009 | CGCCAAATGCCCCCAC | 29 | N/A | N/A | 2029 |
| 949901 | 83049 | 83064 | GATAGGAACTCCTTGC | 48 | N/A | N/A | 2030 |
| 949902 | 83051 | 83066 | TCGATAGGAACTCCTT | 96 | N/A | N/A | 2031 |
| 949903 | 83124 | 83139 | CTGAAGGGCCTCGCCA | 119 | N/A | N/A | 2032 |
| 949904 | 83183 | 83198 | TGCCATGCAGGGCTTC | 74 | N/A | N/A | 2033 |
| 949905 | 83283 | 83298 | GTGGACCGGAGACAGC | 125 | N/A | N/A | 2034 |
| 949906 | 83399 | 83414 | TAGAAAATGCGGAGGG | 91 | N/A | N/A | 2035 |
| 949907 | 83424 | 83439 | CGGGAAGCAACATGAA | 77 | N/A | N/A | 2036 |
| 949908 | 83429 | 83444 | TGGCACGGGAAGCAAC | 87 | N/A | N/A | 2037 |
| 949909 | 83464 | 83479 | GAACAAGCAGAGTGGT | 51 | N/A | N/A | 2038 |
| 949910 | 83566 | 83581 | GGCCAGTACCTGGTCC | 103 | N/A | N/A | 2039 |
| 949911 | 83622 | 83637 | GAACAGTACACTTGAC | 90 | N/A | N/A | 2040 |
| 949912 | 83627 | 83642 | GCACAGAACAGTACAC | 100 | N/A | N/A | 2041 |
| 949942 | 83908 | 83923 | GGTTGACTACAAAGGG | 5 | N/A | N/A | 2042 |
| 949943 | 83909 | 83924 | AGGTTGACTACAAAGG | 3 | N/A | N/A | 2043 |
| 949944 | 83911 | 83926 | AGAGGTTGACTACAAA | 4 | N/A | N/A | 2044 |
| 949945 | 83912 | 83927 | GAGAGGTTGACTACAA | 2 | N/A | N/A | 2045 |
| 949946 | 83914 | 83929 | TTGAGAGGTTGACTAC | 66 | N/A | N/A | 2046 |
| 949947 | 83916 | 83931 | TTTTGAGAGGTTGACT | 21 | N/A | N/A | 2047 |
| 949948 | 83918 | 83933 | GTTTTTGAGAGGTTGA | 2 | N/A | N/A | 2048 |
| 949949 | 83919 | 83934 | GGTTTTTGAGAGGTTG | 3 | N/A | N/A | 2049 |
| 949950 | 83920 | 83935 | GGGTTTTTGAGAGGTT | 5 | N/A | N/A | 2050 |
| 949951 | 83922 | 83937 | GTGGGTTTTTGAGAGG | 17 | N/A | N/A | 2051 |
| 949952 | 83923 | 83938 | TGTGGGTTTTTGAGAG | 25 | N/A | N/A | 2052 |
| 949953 | 83924 | 83939 | CTGTGGGTTTTTGAGA | 38 | N/A | N/A | 2053 |
| 949954 | 83926 | 83941 | GCCTGTGGGTTTTTGA | 24 | N/A | N/A | 2054 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949955 | 84164 | 84179 | CCATAACTTACTGAAG | 69 | N/A | N/A | 2055 |
| 949956 | 84276 | 84291 | GTAGGATAGGGAGCGG | 31 | N/A | N/A | 2056 |
| 949957 | 84379 | 84394 | TCCCAAATGCAGACGC | 38 | N/A | N/A | 2057 |
| 949958 | 84397 | 84412 | ACAAACAACACGCTTG | 88 | N/A | N/A | 2058 |
| 949959 | 84399 | 84414 | CAACAAACAACACGCT | 88 | N/A | N/A | 2059 |
| 949960 | 84687 | 84702 | AATTAGGTGGGTAAAG | 64 | N/A | N/A | 2060 |
| 949961 | 84860 | 84875 | GCCTTTGCAAGAAAGC | 94 | N/A | N/A | 2061 |
| 949962 | 85204 | 85219 | GGTTTCAACAAACAGT | 11 | N/A | N/A | 2062 |
| 949963 | 85243 | 85258 | AACAAAGTGACATAGC | 8 | N/A | N/A | 2063 |
| 949964 | 85260 | 85275 | GGAGAGGGACCATTTT | 94 | N/A | N/A | 2064 |
| 949965 | 85323 | 85338 | AATCAAAACTGGGCGC | 100 | N/A | N/A | 2065 |
| 949966 | 85335 | 85350 | AGCAATTGGCCAAATC | 55 | N/A | N/A | 2066 |
| 949967 | 85362 | 85377 | GGCATAGGTGGACTGG | 21 | N/A | N/A | 2067 |
| 949968 | 85379 | 85394 | AGCTACAGCAGCTATG | 83 | N/A | N/A | 2068 |
| 949969 | 85438 | 85453 | CTTACCAACAGTAACA | 67 | N/A | N/A | 2069 |
| 949970 | 85541 | 85556 | GGCTGGTTTAGTAAGG | 75 | N/A | N/A | 2070 |
| 949971 | 85608 | 85623 | GGGCAAGGCACTCGGA | 54 | N/A | N/A | 2071 |
| 949972 | 85618 | 85633 | GAATAAAGTAGGGCAA | 44 | N/A | N/A | 2072 |
| 949973 | 85681 | 85696 | CGTCACTGGACTCCCC | 75 | N/A | N/A | 2073 |
| 949974 | 85784 | 85799 | CCAGGATGAAGTTGGT | 94 | N/A | N/A | 2074 |
| 949975 | 85876 | 85891 | ATCAAGCTAGAAAGGT | 19 | N/A | N/A | 2075 |
| 949976 | 85880 | 85895 | AGCTATCAAGCTAGAA | 82 | N/A | N/A | 2076 |
| 949977 | 85884 | 85899 | CTCAAGCTATCAAGCT | 120 | N/A | N/A | 2077 |
| 949978 | 85946 | 85961 | CCAATTATGAACACTA | 7 | N/A | N/A | 2078 |
| 949979 | 85984 | 85999 | GTTCAAAGTGTTGCAT | 9 | N/A | N/A | 2079 |
| 949980 | 86329 | 86344 | AGCCACTGCCTTGTAT | 74 | N/A | N/A | 2080 |
| 949981 | 86547 | 86562 | AATCATAGCCTCAAAC | 85 | N/A | N/A | 2081 |
| 949982 | 86551 | 86566 | GAACAATCATAGCCTC | 14 | N/A | N/A | 2082 |
| 949983 | 86933 | 86948 | AATAATGTGCAGTTGT | 14 | N/A | N/A | 2083 |
| 949984 | 87041 | 87056 | CCCCAAGGTCTGGAGT | 104 | N/A | N/A | 2084 |
| 949985 | 87160 | 87175 | TCCCAGACAGGAGAAC | 80 | N/A | N/A | 2085 |
| 949986 | 87349 | 87364 | ACCTACTTGGCAAACC | 128 | N/A | N/A | 2086 |
| 949987 | 87359 | 87374 | CTCTAAAAGTACCTAC | 127 | N/A | N/A | 2087 |
| 949988 | 87456 | 87471 | CGACAGAGACTGTCTG | 130 | N/A | N/A | 2088 |
| 949989 | 87574 | 87589 | CTAAACTAACCATGGG | 79 | N/A | N/A | 2089 |
| 949990 | 87595 | 87610 | GAACATAGCACTGCCC | 3 | N/A | N/A | 2090 |
| 949991 | 87597 | 87612 | CTGAACATAGCACTGC | 3 | N/A | N/A | 2091 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949992 | 87598 | 87613 | TCTGAACATAGCACTG | 9 | N/A | N/A | 2092 |
| 949993 | 87680 | 87695 | GCACACTGGTCGCTAA | 43 | N/A | N/A | 2093 |
| 949994 | 87782 | 87797 | TTGAAGCTAGGGAGAC | 85 | N/A | N/A | 2094 |
| 949995 | 87817 | 87832 | ACGGAAGGTTCTGGTT | 69 | N/A | N/A | 2095 |
| 949996 | 87880 | 87895 | GCACACTGAATCGACA | 23 | N/A | N/A | 2096 |
| 949997 | 87882 | 87897 | ACGCACACTGAATCGA | 43 | N/A | N/A | 2097 |
| 949998 | 87893 | 87908 | TGCCTGAGACCACGCA | 152 | N/A | N/A | 2098 |
| 949999 | 88002 | 88017 | TACCAGCGGCACCACC | 72 | N/A | N/A | 2099 |
| 950000 | 88014 | 88029 | AGCGAGAGGGCATACC | 30 | N/A | N/A | 2100 |
| 950001 | 88119 | 88134 | CACTACACCTTAACGC | 70 | N/A | N/A | 2101 |
| 950002 | 88226 | 88241 | CTCTAGAGGCCCTCCC | 98 | N/A | N/A | 2102 |
| 950003 | 88271 | 88286 | CACCGATAAATGTTGT | 27 | N/A | N/A | 2103 |
| 950004 | 88308 | 88323 | CAGCACGGAACAGATC | 51 | N/A | N/A | 2104 |
| 950005 | 88397 | 88412 | AGGGACTTCGGCTCAT | 120 | N/A | N/A | 2105 |
| 950006 | 88497 | 88512 | GCAAACCAAAGATGGG | 47 | N/A | N/A | 2106 |
| 950007 | 88619 | 88634 | GGTAAGTGGGAAGGCC | 73 | N/A | N/A | 2107 |
| 950008 | 88766 | 88781 | CCCCGTAGCTCTTCAG | 24 | N/A | N/A | 2108 |
| 950009 | 88878 | 88893 | TTTAAGGACTCCACCT | 86 | N/A | N/A | 2109 |
| 950010 | 88992 | 89007 | TGGCATCACCTGACTT | 99 | N/A | N/A | 2110 |
| 950011 | 89116 | 89131 | ATCCAAAATCCTCCCC | 43 | N/A | N/A | 2111 |
| 950012 | 89192 | 89207 | TCAAATAGCAGCCCAC | 38 | N/A | N/A | 2112 |
| 950013 | 89231 | 89246 | CCTAAGGGCCTCCTGG | 102 | N/A | N/A | 2113 |
| 950014 | 89335 | 89350 | CACAAGAAGGATTTTC | 2 | N/A | N/A | 2114 |
| 950015 | 89459 | 89474 | CAGCAATCGACCCACC | 31 | N/A | N/A | 2115 |
| 950016 | 89560 | 89575 | GCTGAGATTACGCACC | 38 | N/A | N/A | 2116 |
| 950017 | 89706 | 89721 | CTTATCTGGGCTATTT | 7 | N/A | N/A | 2117 |
| 950018 | 89719 | 89734 | TATTATAGGGCTTCTT | 20 | N/A | N/A | 2118 |
| 950019 | 89813 | 89828 | GAAAGTAGGCTTCTGT | 6 | N/A | N/A | 2119 |
| 950020 | 89966 | 89981 | TGTTACTTATCCATCA | 7 | N/A | N/A | 2120 |
| 950021 | 89980 | 89995 | CAACATATATCTCCTG | 8 | N/A | N/A | 2121 |
| 950022 | 90075 | 90090 | ACAAATCCCACTATAT | 58 | N/A | N/A | 2122 |
| 950023 | 90081 | 90096 | GCATAGACAAATCCCA | 3 | N/A | N/A | 2123 |
| 950024 | 90175 | 90190 | CGACAGGGTGTGTTTC | 6 | N/A | N/A | 2124 |
| 950025 | 90197 | 90212 | AAATTTAGAGGACATC | 38 | N/A | N/A | 2125 |
| 950026 | 90276 | 90291 | AGCCATCCAGTCTTAG | 38 | N/A | N/A | 2126 |
| 950027 | 90541 | 90556 | CTCAAGTAGTTCCCCT | 12 | N/A | N/A | 2127 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950028 | 90642 | 90657 | CACTAGAATCCCGGAG | 18 | N/A | N/A | 2128 |
| 950029 | 90673 | 90688 | ACTTACTAAAGCGCAG | 24 | N/A | N/A | 2129 |
| 950030 | 90722 | 90737 | AGTAAATGTATCTGGT | 3 | N/A | N/A | 2130 |
| 950031 | 90754 | 90769 | GCGCAAGGGAAACGGC | 97 | N/A | N/A | 2131 |
| 950032 | 90804 | 90819 | TGAGCAGCCACAGGTA | 31 | N/A | N/A | 2132 |
| 950033 | 90806 | 90821 | AGTGAGCAGCCACAGG | 45 | N/A | N/A | 2133 |
| 950034 | 90807 | 90822 | AAGTGAGCAGCCACAG | 83 | N/A | N/A | 2134 |
| 950035 | 90808 | 90823 | CAAGTGAGCAGCCACA | 27 | N/A | N/A | 2135 |
| 950036 | 90810 | 90825 | ACCAAGTGAGCAGCCA | 14 | N/A | N/A | 2136 |
| 950037 | 90812 | 90827 | GGACCAAGTGAGCAGC | 54 | N/A | N/A | 2137 |
| 950038 | 90837 | 90852 | GCGAATGTGGCCGTTC | 64 | N/A | N/A | 2138 |
| 950039 | 90889 | 90904 | GAACAGACAGGGTTCA | 97 | N/A | N/A | 2139 |
| 950040 | 90978 | 90993 | CGGGAGACTGCAGAGG | 44 | N/A | N/A | 2140 |
| 950041 | 91083 | 91098 | AGCAGATGGCCTGGTA | 18 | N/A | N/A | 2141 |
| 950042 | 91189 | 91204 | ACATAGGGCCTTCTGG | 38 | N/A | N/A | 2142 |
| 950043 | 91226 | 91241 | AGCCAAGAGTCAAGTT | 36 | N/A | N/A | 2143 |
| 950044 | 91384 | 91399 | CATGAGCCCACCACTC | 120 | N/A | N/A | 2144 |
| 950045 | 91538 | 91553 | CTCCTAACATGCTAGA | 75 | N/A | N/A | 2145 |
| 950046 | 91825 | 91840 | CGCTCAAGGGAAAAAT | 25 | N/A | N/A | 2146 |
| 950047 | 91934 | 91949 | TCCCAAGCTCCCCTGA | 51 | N/A | N/A | 2147 |
| 950048 | 92034 | 92049 | GATACAGCCGTTCATA | 11 | N/A | N/A | 2148 |
| 950049 | 92059 | 92074 | TAATAAGGTACTGAAG | 54 | N/A | N/A | 2149 |
| 950050 | 92634 | 92649 | ACGAAGCTAGGAGGCG | 108 | N/A | N/A | 2150 |
| 950051 | 92635 | 92650 | CACGAAGCTAGGAGGC | 35 | N/A | N/A | 2151 |
| 950052 | 92814 | 92829 | GCATGATAATCCCAGC | 98 | N/A | N/A | 2152 |
| 950053 | 93110 | 93125 | AGCCGCCCAGGCCAGA | 96 | N/A | N/A | 2153 |
| 950054 | 93183 | 93198 | GCAGAAATTTTGCGAA | 35 | N/A | N/A | 2154 |
| 950055 | 93185 | 93200 | AGGCAGAAATTTTGCG | 48 | N/A | N/A | 2155 |
| 950056 | 93235 | 93250 | GGTGGAGTCCCCGCCC | 165 | N/A | N/A | 2156 |
| 950057 | 93248 | 93263 | GTGCAAGGTACATGGT | 11 | N/A | N/A | 2157 |
| 950058 | 93303 | 93318 | CGCAAAAATAAATCAT | 83 | N/A | N/A | 2158 |
| 950059 | 93304 | 93319 | GCGCAAAAATAAATCA | 105 | N/A | N/A | 2159 |
| 950060 | 93322 | 93337 | ATGTATTACCTACGGC | 7 | N/A | N/A | 2160 |
| 950061 | 93383 | 93398 | CATATTCATGGTGTTA | 10 | N/A | N/A | 2161 |
| 950062 | 93496 | 93511 | AGAGATGGAAGGGACG | 89 | N/A | N/A | 2162 |
| 950063 | 93586 | 93601 | CCACACTAAGCATGTA | 38 | N/A | N/A | 2163 |
| 950064 | 93600 | 93615 | TCTAATGTTTGCTACC | 7 | N/A | N/A | 2164 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950065 | 93601 | 93616 | CTCTAATGTTTGCTAC | 4 | N/A | N/A | 2165 |
| 950066 | 93612 | 93627 | ACCACTAGATTCTCTA | 56 | N/A | N/A | 2166 |
| 950067 | 93648 | 93663 | GAACAGGGAATATTAG | 79 | N/A | N/A | 2167 |
| 950068 | 93744 | 93759 | TTATACCCAGGGCAAC | 37 | N/A | N/A | 2168 |
| 950069 | 93854 | 93869 | TAAGTATTTGCCATCC | 6 | N/A | N/A | 2169 |
| 950070 | 93908 | 93923 | GCTTAAGCGAGATCTT | 42 | N/A | N/A | 2170 |
| 950071 | 93921 | 93936 | GAATTCTGGTCTGGCT | 26 | N/A | N/A | 2171 |
| 950072 | 93958 | 93973 | CATAGGAGATAGAAGG | 4 | N/A | N/A | 2172 |
| 950073 | 93960 | 93975 | TGCATAGGAGATAGAA | 34 | N/A | N/A | 2173 |
| 950074 | 94019 | 94034 | CACAAGAGGGCAAGAT | 36 | N/A | N/A | 2174 |
| 950075 | 94050 | 94065 | TGCTAGATCAACTAGC | 7 | N/A | N/A | 2175 |
| 950076 | 94058 | 94073 | GCAAAGAGTGCTAGAT | 89 | N/A | N/A | 2176 |
| 950077 | 94060 | 94075 | AGGCAAAGAGTGCTAG | 78 | N/A | N/A | 2177 |
| 950078 | 94065 | 94080 | GCACAAGGCAAAGAGT | 89 | N/A | N/A | 2178 |
| 950079 | 94078 | 94093 | TGCTAGAGGAGCGGCA | 114 | N/A | N/A | 2179 |
| 950080 | 94153 | 94168 | CTATAGAACAGGAGTG | 15 | N/A | N/A | 2180 |
| 950081 | 94155 | 94170 | TGCTATAGAACAGGAG | 9 | N/A | N/A | 2181 |
| 950082 | 94164 | 94179 | AGCCACATCTGCTATA | 89 | N/A | N/A | 2182 |
| 950083 | 94176 | 94191 | CCTTAATCACTTAGCC | 7 | N/A | N/A | 2183 |
| 950084 | 94200 | 94215 | TATCATATAGGGAGAA | 16 | N/A | N/A | 2184 |
| 950085 | 94215 | 94230 | GCATAGAGAAGAGGGT | 6 | N/A | N/A | 2185 |
| 950086 | 94270 | 94285 | GACAAGAGGCAGCATC | 7 | N/A | N/A | 2186 |
| 950087 | 94333 | 94348 | TCACAGGCCAAGGATA | 81 | N/A | N/A | 2187 |
| 950088 | 94371 | 94386 | TGGCAGGAAACGGTGC | 42 | N/A | N/A | 2188 |
| 950089 | 94450 | 94465 | GCAAATATGATTCATC | 1 | N/A | N/A | 2189 |
| 950090 | 94481 | 94496 | AAGGAGGTGTTACCCA | 60 | N/A | N/A | 2190 |
| 950091 | 94581 | 94596 | CTATGAGTAGCAGGCT | 3 | N/A | N/A | 2191 |
| 950092 | 94652 | 94667 | GTCCAAGTGTAAGAGC | 12 | N/A | N/A | 2192 |
| 950093 | 94695 | 94710 | GCAAAAGGGAGCCCCT | 69 | N/A | N/A | 2193 |
| 950094 | 94696 | 94711 | AGCAAAAGGGAGCCCC | 88 | N/A | N/A | 2194 |
| 950095 | 94770 | 94785 | TGCCAGAAGAGCCCCG | 84 | N/A | N/A | 2195 |
| 950096 | 94791 | 94806 | CTACAAGAAAGACCCT | 30 | N/A | N/A | 2196 |
| 950097 | 94805 | 94820 | TAGGATCGGCTCAGCT | 18 | N/A | N/A | 2197 |
| 950098 | 94810 | 94825 | TGGCATAGGATCGGCT | 54 | N/A | N/A | 2198 |
| 950099 | 94920 | 94935 | GAACACATGAGGAACC | 24 | N/A | N/A | 2199 |
| 950100 | 94977 | 94992 | GTACAAGGGAGAAGCA | 100 | N/A | N/A | 2200 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950101 | 95047 | 95062 | GGCCACGCTCATGACG | 97 | N/A | N/A | 2201 |
| 950102 | 95086 | 95101 | GTAGAGATGGGAACCA | 4 | N/A | N/A | 2202 |
| 950103 | 95155 | 95170 | AAGCAGGGATCCTCTG | 114 | N/A | N/A | 2203 |
| 950104 | 95189 | 95204 | GCGGTATGGGTGGCAG | 106 | N/A | N/A | 2204 |
| 950105 | 95227 | 95242 | GGCTAGGGTGCACAGT | 60 | N/A | N/A | 2205 |
| 950106 | 95278 | 95293 | CTTAGAAGGAAGTAGG | 100 | N/A | N/A | 2206 |
| 950107 | 95378 | 95393 | CCGTTAGCCATCCACC | 73 | N/A | N/A | 2207 |
| 950108 | 95416 | 95431 | CCCTAGGGAGCTGCAA | 112 | N/A | N/A | 2208 |
| 950109 | 95443 | 95458 | CCACACGGGTTCAGAG | 43 | N/A | N/A | 2209 |
| 950110 | 95496 | 95511 | GCACACCAAGCCTTGG | 63 | N/A | N/A | 2210 |
| 950111 | 95645 | 95660 | AGGGATGTGCCCGCAC | 87 | N/A | N/A | 2211 |
| 950112 | 95745 | 95760 | TGACAACCAGGTGAGG | 24 | N/A | N/A | 2212 |
| 950113 | 95854 | 95869 | TGGGAATGCCTCCATT | 95 | N/A | N/A | 2213 |
| 950114 | 95954 | 95969 | AGCCCTGTGAGGTCA | 66 | N/A | N/A | 2214 |
| 950115 | 96079 | 96094 | GTACAGACTTATCCCT | 28 | N/A | N/A | 2215 |
| 950116 | 96081 | 96096 | GGGTACAGACTTATCC | 95 | N/A | N/A | 2216 |
| 950117 | 96178 | 96193 | GGCTAAAGAGTACCCA | 63 | N/A | N/A | 2217 |
| 950118 | 96181 | 96196 | GGTGGCTAAAGAGTAC | 23 | N/A | N/A | 2218 |
| 950119 | 96298 | 96313 | GACTACCCCGACCCAC | 71 | N/A | N/A | 2219 |
| 950120 | 96399 | 96414 | GCACGGCACGGCAGGA | 24 | N/A | N/A | 2220 |
| 950121 | 96523 | 96538 | ACGCACAGGGCGGCCT | 111 | N/A | N/A | 2221 |
| 950122 | 96527 | 96542 | AGGCACGCACAGGGCG | 83 | N/A | N/A | 2222 |
| 950123 | 96646 | 96661 | CTAACGGCAGGCAGCC | 71 | N/A | N/A | 2223 |
| 950124 | 96752 | 96767 | CATCAGGGTTTCAGGC | 11 | N/A | N/A | 2224 |
| 950125 | 96860 | 96875 | GGCTAGGGTCAAAGGT | 21 | N/A | N/A | 2225 |
| 950126 | 96977 | 96992 | GCCCATGGGAGGAGTC | 80 | N/A | N/A | 2226 |
| 950127 | 97078 | 97093 | GAAACCAACATGAGGC | 20 | N/A | N/A | 2227 |
| 950128 | 97149 | 97164 | CGCAATAGAGACACCT | 32 | N/A | N/A | 2228 |
| 950129 | 97221 | 97236 | GAACCTCGCTCCGTGC | 165 | N/A | N/A | 2229 |
| 950130 | 97453 | 97468 | AGTGACTGAGTTCTGC | 22 | N/A | N/A | 2230 |
| 950131 | 97809 | 97824 | GGTTACGGTTGTTTTT | 26 | N/A | N/A | 2231 |
| 950132 | 97855 | 97870 | GTACAATGTAAGCCTT | 3 | N/A | N/A | 2232 |
| 950133 | 97920 | 97935 | TGCTAGTGACTCCATC | 27 | N/A | N/A | 2233 |
| 950134 | 98046 | 98061 | AGTGATGGAACCCCGG | 48 | N/A | N/A | 2234 |
| 950135 | 98098 | 98113 | CGCAGATAGAAAAACT | 26 | N/A | N/A | 2235 |
| 950136 | 98099 | 98114 | TCGCAGATAGAAAAAC | 60 | N/A | N/A | 2236 |
| 950137 | 98150 | 98165 | GCACACTGTGGCCAAG | 70 | N/A | N/A | 2237 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950138 | 98259 | 98274 | AGTGAACGAGTCCCTC | 84 | N/A | N/A | 2238 |
| 950139 | 98353 | 98368 | TTCTACATAGGACCAT | 13 | N/A | N/A | 2239 |
| 950140 | 98399 | 98414 | AAACATCACAGGGACC | 43 | N/A | N/A | 2240 |
| 950141 | 98508 | 98523 | TCAGAAGAGAGGACCT | 42 | N/A | N/A | 2241 |
| 950142 | 98643 | 98658 | AGACACAGGGTAATGC | 35 | N/A | N/A | 2242 |
| 950143 | 98866 | 98881 | CAACAATGCAACAACG | 15 | N/A | N/A | 2243 |
| 950144 | 99310 | 99325 | CGCCAGATTAATTTTG | 46 | N/A | N/A | 2244 |
| 950145 | 99477 | 99492 | AACAATTGTCTGGTGT | 85 | N/A | N/A | 2245 |
| 950146 | 99478 | 99493 | CAACAATTGTCTGGTG | 63 | N/A | N/A | 2246 |
| 950147 | 99481 | 99496 | TAACAACAATTGTCTG | 20 | N/A | N/A | 2247 |
| 950148 | 99493 | 99508 | TAAGACTATAGTTAAC | 63 | N/A | N/A | 2248 |
| 950149 | 99519 | 99534 | CAACAGAAGAGTAGGG | 26 | N/A | N/A | 2249 |
| 950150 | 99522 | 99537 | GTTCAACAGAAGAGTA | 25 | N/A | N/A | 2250 |
| 950151 | 99626 | 99641 | GATAAATACTAGAGGC | 45 | N/A | N/A | 2251 |
| 950152 | 99810 | 99825 | GATCAGGGCCATAGAA | 79 | N/A | N/A | 2252 |
| 950153 | 99823 | 99838 | CAAGAAACGGGTTGAT | 71 | N/A | N/A | 2253 |
| 950154 | 99830 | 99845 | AATTAAGCAAGAAACG | 114 | N/A | N/A | 2254 |
| 950155 | 99893 | 99908 | CAACAAGCTATCACAC | 92 | N/A | N/A | 2255 |
| 950156 | 99912 | 99927 | CTGGACCGCATCAGAG | 92 | N/A | N/A | 2256 |
| 950157 | 99924 | 99939 | TTGAAAGCCAACCTGG | 105 | N/A | N/A | 2257 |
| 950158 | 100015 | 100030 | TAACACAGCCATGGCT | 123 | N/A | N/A | 2258 |
| 950159 | 100020 | 100035 | CCACATAACACAGCCA | 28 | N/A | N/A | 2259 |
| 950160 | 100125 | 100140 | TTGCAGCACAGGGTCA | 56 | N/A | N/A | 2260 |
| 950161 | 100161 | 100176 | GGCAACAGGAGACGCG | 62 | N/A | N/A | 2261 |
| 950162 | 100227 | 100242 | AGAGGCTACATGGTGA | 60 | N/A | N/A | 2262 |
| 950163 | 100328 | 100343 | GAAACAACCAATATCC | 58 | N/A | N/A | 2263 |
| 950164 | 100399 | 100414 | CACGAAGGGTTGACAC | 101 | N/A | N/A | 2264 |
| 950165 | 100435 | 100450 | GGCCAGAGTCCTGACT | 98 | N/A | N/A | 2265 |
| 950166 | 100535 | 100550 | GTTACCAGGACAAAAC | 126 | N/A | N/A | 2266 |
| 950167 | 100670 | 100685 | TGCCATCCCAGGGACC | 105 | N/A | N/A | 2267 |
| 950168 | 100782 | 100797 | CTACAGAGCATTCCCC | 89 | N/A | N/A | 2268 |
| 950169 | 100811 | 100826 | TGCCAGCAAGTCCCCA | 80 | N/A | N/A | 2269 |
| 950170 | 100929 | 100944 | GCCAAGAGGCCCGCCT | 171 | N/A | N/A | 2270 |
| 950171 | 101038 | 101053 | ACCCGAATAGCAAGCG | 54 | N/A | N/A | 2271 |
| 950172 | 101155 | 101170 | GAGCATGGGCCCGCAG | 139 | N/A | N/A | 2272 |
| 950173 | 101255 | 101270 | GATGATCCTTTCACCC | 90 | N/A | N/A | 2273 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950174 | 101362 | 101377 | CACCACCCTGGGTTTA | 132 | N/A | N/A | 2274 |
| 950175 | 101483 | 101498 | GCAGACCACGCCTGGC | 44 | N/A | N/A | 2275 |
| 950176 | 101603 | 101618 | TGCAAGGCGGAAAGAG | 95 | N/A | N/A | 2276 |
| 950177 | 101718 | 101733 | GGCATTCCCACCCAGG | 84 | N/A | N/A | 2277 |
| 950178 | 101808 | 101823 | GAAAACTAGACTTGCA | 31 | N/A | N/A | 2278 |
| 950179 | 101810 | 101825 | CTGAAAACTAGACTTG | 44 | N/A | N/A | 2279 |
| 950180 | 101850 | 101865 | GAAAAACACGAAGGGC | 86 | N/A | N/A | 2280 |
| 950181 | 101951 | 101966 | TCATTACGGCCGGCGC | 109 | N/A | N/A | 2281 |
| 950182 | 102059 | 102074 | CTAACTTGGGTGGTGG | 43 | N/A | N/A | 2282 |
| 950183 | 102159 | 102174 | AGATATTGATGTCTTG | 7 | N/A | N/A | 2283 |
| 950184 | 102264 | 102279 | GCAGAGGGAGCCCCGA | 90 | N/A | N/A | 2284 |
| 950185 | 102314 | 102329 | TCGCATAGAAGATTCG | 38 | N/A | N/A | 2285 |
| 950186 | 102365 | 102380 | CGGCAGGTGAGTGTCA | 30 | N/A | N/A | 2286 |
| 950187 | 102465 | 102480 | GACTACCTGTTCAGGA | 112 | N/A | N/A | 2287 |
| 950188 | 102585 | 102600 | GAAGAGTGGTGGTTTC | 80 | N/A | N/A | 2288 |
| 950189 | 102639 | 102654 | TGCGAGCCGGCCCCAG | 61 | N/A | N/A | 2289 |
| 950190 | 102716 | 102731 | CACGATCCCAAACCCT | 79 | N/A | N/A | 2290 |
| 950191 | 102830 | 102845 | TGCCGGCACGCACGCG | 135 | N/A | N/A | 2291 |
| 950192 | 102935 | 102950 | CAGCAGGGCCAAGTAA | 61 | N/A | N/A | 2292 |
| 950193 | 103102 | 103117 | GGTAACACAGGGCCTG | 119 | N/A | N/A | 2293 |
| 950207 | 103286 | 103301 | GAGCATAGGAAGAGGG | 27 | N/A | N/A | 2294 |
| 950208 | 103302 | 103317 | GCAAAGAAGTAGGGCA | 81 | N/A | N/A | 2295 |
| 950209 | 103323 | 103338 | GATTAGCCTGCCAGGC | 20 | N/A | N/A | 2296 |
| 950210 | 103425 | 103440 | CCTCATCTATCCAAGG | 99 | N/A | N/A | 2297 |
| 950211 | 103552 | 103567 | GGCACATGGGCTCAGC | 119 | N/A | N/A | 2298 |
| 950212 | 103672 | 103687 | CTCCAAGTTCAGGAGC | 119 | N/A | N/A | 2299 |
| 950213 | 103832 | 103847 | CGCAAGCCACAGCAGG | 101 | N/A | N/A | 2300 |
| 950214 | 103971 | 103986 | ACTCACCCAGTGATGT | 111 | N/A | N/A | 2301 |
| 950215 | 104100 | 104115 | GTTCAGGAAGCACCAA | 20 | N/A | N/A | 2302 |
| 950216 | 104276 | 104291 | AGCCTTACTCCCTTTC | 34 | N/A | N/A | 2303 |
| 950217 | 104326 | 104341 | CGCTTTAGGACATCTT | 63 | N/A | N/A | 2304 |
| 950218 | 104410 | 104425 | TAGGAGTGAGTTACCT | 102 | N/A | N/A | 2305 |
| 950219 | 104458 | 104473 | CACGAAGTGAATGGAA | 13 | N/A | N/A | 2306 |
| 950220 | 104486 | 104501 | ACGCACAACACAACTG | 63 | N/A | N/A | 2307 |
| 950221 | 104560 | 104575 | TGCCACTGGACTGACT | 69 | N/A | N/A | 2308 |
| 950222 | 104606 | 104621 | GACCTAGGTGCCTGAC | 27 | N/A | N/A | 2309 |
| 950223 | 104678 | 104693 | ACTCTACCCGCACCCT | 96 | N/A | N/A | 2310 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950224 | 104783 | 104798 | CTCCATGATGCTCCCT | 63 | N/A | N/A | 2311 |
| 950225 | 104895 | 104910 | GTGTAGCATGCGCCAC | 124 | N/A | N/A | 2312 |
| 950226 | 104953 | 104968 | GGGAAAAGAGTCACCC | 113 | N/A | N/A | 2313 |
| 950227 | 105113 | 105128 | CTTCACCCCGAGCCAT | 90 | N/A | N/A | 2314 |
| 950228 | 105248 | 105263 | CGGGAAGCATCCCTGG | 114 | N/A | N/A | 2315 |
| 950229 | 105253 | 105268 | CAGCACGGGAAGCATC | 53 | N/A | N/A | 2316 |
| 950230 | 105366 | 105381 | TGCAAGCACCTGAGCC | 99 | N/A | N/A | 2317 |
| 950231 | 105479 | 105494 | CCCTATGGGTTCTGGC | 78 | N/A | N/A | 2318 |
| 950232 | 105561 | 105576 | TCACAATTGGTGCCTT | 16 | N/A | N/A | 2319 |
| 950233 | 105622 | 105637 | CCCCACCTCGGCCAAT | 59 | N/A | N/A | 2320 |
| 950234 | 105668 | 105683 | CTAAATGGAGCTCTTG | 64 | N/A | N/A | 2321 |
| 950235 | 105671 | 105686 | GGCCTAAATGGAGCTC | 79 | N/A | N/A | 2322 |
| 950236 | 105727 | 105742 | CATCACACTCCTCGAT | 96 | N/A | N/A | 2323 |
| 950237 | 105864 | 105879 | ATGTACTGTGAGCTTC | 12 | N/A | N/A | 2324 |
| 950238 | 106002 | 106017 | GCTAATCCCTGACTCA | 37 | N/A | N/A | 2325 |
| 950239 | 106118 | 106133 | ACTCAGCTGGAGTTGG | 63 | N/A | N/A | 2326 |
| 950240 | 106174 | 106189 | GACAAATGGGTCTCGA | 124 | N/A | N/A | 2327 |
| 950241 | 106213 | 106228 | GCCTAGAAGAGCTATG | 97 | N/A | N/A | 2328 |
| 950242 | 106218 | 106233 | GGCAAGCCTAGAAGAG | 95 | N/A | N/A | 2329 |
| 950243 | 106269 | 106284 | AGGCACACGGCTCAGG | 55 | N/A | N/A | 2330 |
| 950244 | 106276 | 106291 | GTACAGGAGGCACACG | 82 | N/A | N/A | 2331 |
| 950245 | 106340 | 106355 | TACTACTCTGGGTTTC | 53 | N/A | N/A | 2332 |
| 950246 | 106457 | 106472 | GAACATGCAGGGCCTG | 13 | N/A | N/A | 2333 |
| 950247 | 106838 | 106853 | AAGAAGTAGAAGTCGG | 36 | N/A | N/A | 2334 |
| 950248 | 106946 | 106961 | GGATGAGGTTGTGTGG | 82 | N/A | N/A | 2335 |
| 950249 | 107060 | 107075 | ACGCACATTTTCCTGT | 59 | N/A | N/A | 2336 |
| 950250 | 107115 | 107130 | TGCTAAACAGTGCTTG | 76 | N/A | N/A | 2337 |
| 950251 | 107478 | 107493 | AAAGTTTAGGCATGGT | 22 | N/A | N/A | 2338 |
| 950252 | 107673 | 107688 | CGTCAATACTAAAATA | 119 | N/A | N/A | 2339 |
| 950253 | 108115 | 108130 | GCCCGAATGTGTTTTG | 72 | N/A | N/A | 2340 |
| 950254 | 108434 | 108449 | CACCAGAACTTTATTA | 92 | N/A | N/A | 2341 |
| 950255 | 108584 | 108599 | GGCAAGTGTCTGAGTT | 17 | N/A | N/A | 2342 |
| 950256 | 108685 | 108700 | TCTGACTGATCAGGAA | 85 | N/A | N/A | 2343 |
| 950257 | 108748 | 108763 | GCACAAGCTTGACCCT | 92 | N/A | N/A | 2344 |
| 950258 | 108970 | 108985 | GAAAATGACCTGTCCT | 92 | N/A | N/A | 2345 |
| 950259 | 109080 | 109095 | CCGTGAGGGAACTTTC | 69 | N/A | N/A | 2346 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950260 | 109124 | 109139 | AAGCAAGTGGGACCCC | 79 | N/A | N/A | 2347 |
| 950261 | 109129 | 109144 | GAACAAAGCAAGTGGG | 62 | N/A | N/A | 2348 |
| 950262 | 109183 | 109198 | GGCCAAGGGTGGCCAT | 143 | N/A | N/A | 2349 |
| 950263 | 109205 | 109220 | CGGCAAGGCATTTTAA | 88 | N/A | N/A | 2350 |
| 950264 | 109407 | 109422 | TTTAAGCGATCTCCTG | 31 | N/A | N/A | 2351 |
| 950265 | 109408 | 109423 | GTTTAAGCGATCTCCT | 39 | N/A | N/A | 2352 |
| 950266 | 109516 | 109531 | ACCCAACCTTGGGACA | 75 | N/A | N/A | 2353 |
| 950267 | 109576 | 109591 | CCCAAAGGATCTGCCC | 101 | N/A | N/A | 2354 |
| 950268 | 109649 | 109664 | TGCCTGGGTATGTTTG | 76 | N/A | N/A | 2355 |
| 950269 | 109910 | 109925 | AGATAGGCCTGCTTGC | 70 | N/A | N/A | 2356 |
| 950270 | 109914 | 109929 | CACCAGATAGGCCTGC | 74 | N/A | N/A | 2357 |
| 950271 | 110212 | 110227 | ACTCACATTGTTGATC | 92 | N/A | N/A | 2358 |
| 950272 | 110607 | 110622 | CTCTAGGCTTACCACA | 53 | N/A | N/A | 2359 |
| 950273 | 110885 | 110900 | GCCTAGGGTGCCTGGC | 105 | N/A | N/A | 2360 |
| 950274 | 110899 | 110914 | TACAAACAGGTATGGC | 20 | N/A | N/A | 2361 |
| 950275 | 110900 | 110915 | CTACAAACAGGTATGG | 46 | N/A | N/A | 2362 |
| 950276 | 111043 | 111058 | TCAAATTTGTTGTTGC | 14 | N/A | N/A | 2363 |
| 950277 | 111093 | 111108 | CCAAAGAGGATGGCCG | 66 | N/A | N/A | 2364 |
| 950278 | 111150 | 111165 | AGTTAGTGGACTTGAT | 37 | N/A | N/A | 2365 |
| 950279 | 111166 | 111181 | CTGCAGTGTTCACTCC | 64 | N/A | N/A | 2366 |
| 950280 | 111195 | 111210 | GCCTAAGTTAATTCAG | 88 | N/A | N/A | 2367 |
| 950281 | 111339 | 111354 | GCAACCAGGGTAAACG | 94 | N/A | N/A | 2368 |
| 950282 | 111471 | 111486 | ACTGAAGAGGAGCCCA | 57 | N/A | N/A | 2369 |
| 950283 | 111548 | 111563 | GCCAAAGGCCTGATAC | 96 | N/A | N/A | 2370 |
| 950284 | 111581 | 111596 | GGTTTATAAAGCTTCC | 35 | N/A | N/A | 2371 |
| 950285 | 111781 | 111796 | TCTTACCTCGGTCTTC | 66 | N/A | N/A | 2372 |
| 950286 | 111872 | 111887 | TGAAAGAGGTTCCTGC | 36 | N/A | N/A | 2373 |
| 950287 | 111910 | 111925 | GTTGACATTCATATAC | 68 | N/A | N/A | 2374 |
| 950288 | 112131 | 112146 | TGAGAATGGGAGCAAC | 39 | N/A | N/A | 2375 |
| 950289 | 112147 | 112162 | GAACACTGATCACTAC | 32 | N/A | N/A | 2376 |
| 950290 | 112174 | 112189 | AAACATACCAGGACAC | 39 | N/A | N/A | 2377 |
| 950291 | 112192 | 112207 | TCCTATCGGTATATGA | 139 | N/A | N/A | 2378 |
| 950292 | 112222 | 112237 | TCATAGCAGAAGAACC | 28 | N/A | N/A | 2379 |
| 950293 | 112260 | 112275 | TAAACTTGCAGGGTCA | 9 | N/A | N/A | 2380 |
| 950294 | 112267 | 112282 | CTAAAAGTAAACTTGC | 98 | N/A | N/A | 2381 |
| 950295 | 112360 | 112375 | TCCCATCTTTGGCTGC | 37 | N/A | N/A | 2382 |
| 950296 | 112902 | 112917 | TCCTACTGGATACAGA | 58 | N/A | N/A | 2383 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 950299 | 113293 | 113308 | GCCAATCCTGTTATAT | 97 | N/A | N/A | 2384 |
| 950300 | 113614 | 113629 | GCAGAATAATCCTGTT | 77 | N/A | N/A | 2385 |
| 950301 | 113616 | 113631 | TGGCAGAATAATCCTG | 69 | N/A | N/A | 2386 |
| 950302 | 113780 | 113795 | GTTGACACCATGCTTG | 14 | N/A | N/A | 2387 |
| 950303 | 113923 | 113938 | CCCCAGACTTTTTTGA | 101 | N/A | N/A | 2388 |
| 950304 | 114269 | 114284 | AACCAGGCTTCCGGAC | 83 | N/A | N/A | 2389 |
| 950305 | 114450 | 114465 | AGCTGTAGGGCTGGCT | 61 | N/A | N/A | 2390 |
| 950306 | 114637 | 114652 | TCTGGCCACGCCTTGC | 93 | N/A | N/A | 2391 |
| 950307 | 114737 | 114752 | CCTTAAGGAACTCCAT | 109 | N/A | N/A | 2392 |
| 950308 | 114843 | 114858 | CCTAATATCTCTAGGG | 82 | N/A | N/A | 2393 |
| 950309 | 115000 | 115015 | GCGCAGTGGGATCCTC | 178 | N/A | N/A | 2394 |
| 950310 | 115042 | 115057 | TGCCAGAACCTGAGGT | 96 | N/A | N/A | 2395 |
| 950311 | 115081 | 115096 | ATACAGATGGAGTAGG | 63 | N/A | N/A | 2396 |
| 950312 | 115423 | 115438 | ACAGGAGGAGAGACCC | 58 | N/A | N/A | 2397 |
| 950313 | 115497 | 115512 | CCAAATAGGGATGAGG | 87 | N/A | N/A | 2398 |
| 950314 | 115504 | 115519 | TCGCAAGCCAAATAGG | 29 | N/A | N/A | 2399 |
| 950315 | 115538 | 115553 | GAACAAGCCTCTTGGC | 142 | N/A | N/A | 2400 |
| 950316 | 115640 | 115655 | GCCCAGTGTGAGGGTT | 102 | N/A | N/A | 2401 |
| 950317 | 115795 | 115810 | CATCAACTCGCCTGCT | 101 | N/A | N/A | 2402 |
| 950318 | 115915 | 115930 | CCGGGAGCAAGAGGCA | 160 | N/A | N/A | 2403 |
| 951323 | 3692 | 3707 | CCAGATGGCAGACTTC | 19 | N/A | N/A | 2404 |
| 951324 | 3772 | 3787 | AGATATCTAGATGGCC | 111 | N/A | N/A | 2405 |
| 951325 | 3773 | 3788 | TAGATATCTAGATGGC | 63 | N/A | N/A | 2406 |
| 951326 | 3774 | 3789 | ATAGATATCTAGATGG | 52 | N/A | N/A | 2407 |
| 951327 | 3884 | 3899 | CCAAATGGTGGTGGCA | 84 | N/A | N/A | 2408 |
| 951328 | 4373 | 4388 | CCAATTTGTAGGCTGT | 9 | N/A | N/A | 2409 |
| 951329 | 4487 | 4502 | ACAGATGGGCACACCG | 91 | N/A | N/A | 2410 |
| 951330 | 4647 | 4662 | ACAAATGAGTAGTTCC | 6 | N/A | N/A | 2411 |
| 951331 | 4668 | 4683 | TCATTTGGCAGCCACA | 41 | N/A | N/A | 2412 |
| 951332 | 4670 | 4685 | TATCATTTGGCAGCCA | 77 | N/A | N/A | 2413 |
| 951333 | 4673 | 4688 | TGTTATCATTTGGCAG | 13 | N/A | N/A | 2414 |
| 951334 | 4767 | 4782 | CCTTACTTGGGATTCA | 64 | N/A | N/A | 2415 |
| 951335 | 4792 | 4807 | ATGATAACACAGCCTC | 47 | N/A | N/A | 2416 |
| 951336 | 4793 | 4808 | GATGATAACACAGCCT | 46 | N/A | N/A | 2417 |
| 951337 | 4795 | 4810 | GGGATGATAACACAGC | 104 | N/A | N/A | 2418 |
| 951338 | 4917 | 4932 | GAGATTTGTGCTGCTT | 16 | N/A | N/A | 2419 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951339 | 5744 | 5759 | GTAAGTAAGCACTTTT | 45 | N/A | N/A | 2420 |
| 951340 | 5899 | 5914 | GGATTATAGCAATGCC | 12 | N/A | N/A | 2421 |
| 951341 | 5970 | 5985 | TCACTTTACAGCCTCC | 9 | N/A | N/A | 2422 |
| 951342 | 6124 | 6139 | GGATTCTAGGAGGTCG | 36 | N/A | N/A | 2423 |
| 951343 | 6458 | 6473 | ATTAATACTCTTAACG | 57 | N/A | N/A | 2424 |
| 951344 | 6738 | 6753 | ACTAACTGGGCTGTTC | 53 | N/A | N/A | 2425 |
| 951345 | 6740 | 6755 | GAACTAACTGGGCTGT | 40 | N/A | N/A | 2426 |
| 951346 | 6857 | 6872 | GGAAATCTAACACTGG | 7 | N/A | N/A | 2427 |
| 951347 | 6908 | 6923 | AACTCTATAGATCTGA | 101 | N/A | N/A | 2428 |
| 951348 | 6959 | 6974 | AGACATGGTGGAACCA | 81 | N/A | N/A | 2429 |
| 951349 | 7117 | 7132 | GATTACAACAACAGCC | 76 | N/A | N/A | 2430 |
| 951350 | 7175 | 7190 | TGAAATCGAAGCCATT | 95 | N/A | N/A | 2431 |
| 951351 | 7399 | 7414 | TAAATGACAAGGGTCA | 83 | N/A | N/A | 2432 |
| 951352 | 7942 | 7957 | GCTATTATAACTTGTA | 8 | N/A | N/A | 2433 |
| 951353 | 8568 | 8583 | ATTTTAAAGAAGACGG | 42 | N/A | N/A | 2434 |
| 951354 | 8583 | 8598 | GCTATTATAACTCCTA | 11 | N/A | N/A | 2435 |
| 951355 | 8616 | 8631 | CACTTAATCCCTATTC | 74 | N/A | N/A | 2436 |
| 951356 | 9095 | 9110 | ATACTTATCGCCTTTT | 5 | N/A | N/A | 2437 |
| 951357 | 9099 | 9114 | CATCATACTTATCGCC | 6 | N/A | N/A | 2438 |
| 951358 | 9144 | 9159 | TCCAACTGTGATCTCT | 8 | N/A | N/A | 2439 |
| 951359 | 10032 | 10047 | CCAAGGAACACATCAC | 25 | N/A | N/A | 2440 |
| 951360 | 10064 | 10079 | ACTAATAAGATCTGTT | 97 | N/A | N/A | 2441 |
| 951361 | 10131 | 10146 | TGCAATTTGTCTTTGC | 78 | N/A | N/A | 2442 |
| 951362 | 10136 | 10151 | CAAGATGCAATTTGTC | 3 | N/A | N/A | 2443 |
| 951363 | 10700 | 10715 | CGAGATCACAAATGCT | 41 | N/A | N/A | 2444 |
| 951364 | 11386 | 11401 | AGTAATGATGAGTTCC | 3 | N/A | N/A | 2445 |
| 951365 | 11416 | 11431 | CACTGATAGGCACTCC | 8 | N/A | N/A | 2446 |
| 951366 | 11553 | 11568 | ATTACTTGTTTGCAGC | 8 | N/A | N/A | 2447 |
| 951367 | 11556 | 11571 | CCAATTACTTGTTTGC | 8 | N/A | N/A | 2448 |
| 951368 | 11572 | 11587 | TAAATAACTCTCACGG | 25 | N/A | N/A | 2449 |
| 951369 | 11573 | 11588 | GTAAATAACTCTCACG | 86 | N/A | N/A | 2450 |
| 951370 | 11575 | 11590 | GTGTAAATAACTCTCA | 10 | N/A | N/A | 2451 |
| 951371 | 11922 | 11937 | GTTGATAGTCGGTTGT | 4 | N/A | N/A | 2452 |
| 951372 | 11960 | 11975 | GGTCATTAAAGATTCT | 4 | N/A | N/A | 2453 |
| 951373 | 11990 | 12005 | GGTACCTAACAGGTCT | 93 | N/A | N/A | 2454 |
| 951374 | 12062 | 12077 | GTCTTTCCGGTCTTTT | 4 | N/A | N/A | 2455 |
| 951375 | 12148 | 12163 | GATTATAAACCTAATC | 121 | N/A | N/A | 2456 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951376 | 12215 | 12230 | TCAATAAGTAACTCTG | 11 | N/A | N/A | 2457 |
| 951377 | 12216 | 12231 | GTCAATAAGTAACTCT | 140 | N/A | N/A | 2458 |
| 951378 | 12237 | 12252 | ACCTATCAAGGGCTGT | 27 | N/A | N/A | 2459 |
| 951379 | 12244 | 12259 | GTTATGAACCTATCAA | 20 | N/A | N/A | 2460 |
| 951380 | 12245 | 12260 | TGTTATGAACCTATCA | 47 | N/A | N/A | 2461 |
| 951381 | 12850 | 12865 | GTTTACATGATGTTCT | 7 | N/A | N/A | 2462 |
| 951382 | 12860 | 12875 | GTAAATTACGGTTTAC | 122 | N/A | N/A | 2463 |
| 951383 | 12861 | 12876 | AGTAAATTACGGTTTA | 14 | N/A | N/A | 2464 |
| 951384 | 12890 | 12905 | CTTAATTACAGCTTGT | 6 | N/A | N/A | 2465 |
| 951385 | 12934 | 12949 | TCATTATTGGCTTGGA | 41 | N/A | N/A | 2466 |
| 951386 | 12935 | 12950 | CTCATTATTGGCTTGG | 4 | N/A | N/A | 2467 |
| 951387 | 12971 | 12986 | CCTTTATTCAGATTGT | 3 | N/A | N/A | 2468 |
| 951388 | 13136 | 13151 | AGTCATCCAGCTCCCG | 54 | N/A | N/A | 2469 |
| 951389 | 13167 | 13182 | ATAAATGTCCAGCAGC | 44 | N/A | N/A | 2470 |
| 951390 | 13169 | 13184 | TCATAAATGTCCAGCA | 63 | N/A | N/A | 2471 |
| 951391 | 13170 | 13185 | ATCATAAATGTCCAGC | 32 | N/A | N/A | 2472 |
| 951392 | 13392 | 13407 | GCCATATGTGTGGCTC | 65 | N/A | N/A | 2473 |
| 951393 | 13487 | 13502 | TGTAATCTTGGCCCAG | 83 | N/A | N/A | 2474 |
| 951394 | 13521 | 13536 | TGCATATCCAAAGCCA | 83 | N/A | N/A | 2475 |
| 951395 | 14442 | 14457 | CCACATGTGAAGCAGC | 21 | N/A | N/A | 2476 |
| 951396 | 14476 | 14491 | GGCTATTCCACTGCAG | 99 | N/A | N/A | 2477 |
| 951397 | 14694 | 14709 | TCTGTAATGGTTTCCC | 5 | N/A | N/A | 2478 |
| 951398 | 14808 | 14823 | TGTACCTAAGTACAGA | 97 | N/A | N/A | 2479 |
| 951399 | 14824 | 14839 | TCTATAGGTACCAGCA | 50 | N/A | N/A | 2480 |
| 951400 | 15508 | 15523 | AGTGAAATTCACTCCA | 47 | N/A | N/A | 2481 |
| 951401 | 15651 | 15666 | CTCTTTATATAGATGG | 58 | N/A | N/A | 2482 |
| 951402 | 16748 | 16763 | AGAGATACATCAACCC | 35 | N/A | N/A | 2483 |
| 951403 | 17836 | 17851 | AAATATAGCAGGGACC | 51 | N/A | N/A | 2484 |
| 951404 | 17839 | 17854 | ACTAAATATAGCAGGG | 30 | N/A | N/A | 2485 |
| 951405 | 17842 | 17857 | GGCACTAAATATAGCA | 71 | N/A | N/A | 2486 |
| 951406 | 19042 | 19057 | TAGTATACCAAGGTTA | 11 | N/A | N/A | 2487 |
| 951407 | 19043 | 19058 | GTAGTATACCAAGGTT | 6 | N/A | N/A | 2488 |
| 951408 | 19760 | 19775 | CAGTATGTATACTTCC | 2 | N/A | N/A | 2489 |
| 951409 | 19761 | 19776 | TCAGTATGTATACTTC | 86 | N/A | N/A | 2490 |
| 951410 | 20345 | 20360 | TCCTGATAAGATTCAC | 17 | N/A | N/A | 2491 |
| 951411 | 20392 | 20407 | TCAGTTATCACTGTCA | 31 | N/A | N/A | 2492 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951412 | 20458 | 20473 | ACTAGTAACTTTCCAG | 37 | N/A | N/A | 2493 |
| 951413 | 20741 | 20756 | GGATTATTACATGAGT | 11 | N/A | N/A | 2494 |
| 951414 | 20743 | 20758 | GAGGATTATTACATGA | 29 | N/A | N/A | 2495 |
| 951415 | 20864 | 20879 | GCCAACTAATTCCAGA | 46 | N/A | N/A | 2496 |
| 951416 | 21512 | 21527 | ATATATGTGGAGGCAA | 10 | N/A | N/A | 2497 |
| 951417 | 21513 | 21528 | TATATATGTGGAGGCA | 104 | N/A | N/A | 2498 |
| 951418 | 21515 | 21530 | AATATATATGTGGAGG | 4 | N/A | N/A | 2499 |
| 951419 | 21654 | 21669 | CACTATTGGCACACCA | 115 | N/A | N/A | 2500 |
| 951420 | 21655 | 21670 | ACACTATTGGCACACC | 122 | N/A | N/A | 2501 |
| 951421 | 21656 | 21671 | AACACTATTGGCACAC | 111 | N/A | N/A | 2502 |
| 951422 | 21840 | 21855 | TTCTTAACAGGCTCCC | 41 | N/A | N/A | 2503 |
| 951423 | 22010 | 22025 | TAAGTATGCGCTGCCA | 31 | N/A | N/A | 2504 |
| 951424 | 22134 | 22149 | AGGATATAGGGTCTCC | 97 | N/A | N/A | 2505 |
| 951425 | 22135 | 22150 | AAGGATATAGGGTCTC | 37 | N/A | N/A | 2506 |
| 951426 | 22212 | 22227 | GAACATCATGGAGCCT | 33 | N/A | N/A | 2507 |
| 951427 | 23308 | 23323 | TTTGATACTGATCTCA | 18 | N/A | N/A | 2508 |
| 951428 | 24284 | 24299 | GGTATTATGGTATGTG | 2 | N/A | N/A | 2509 |
| 951429 | 24285 | 24300 | AGGTATTATGGTATGT | 2 | N/A | N/A | 2510 |
| 951430 | 24396 | 24411 | TCATATGTATGGGTTT | 4 | N/A | N/A | 2511 |
| 951431 | 24398 | 24413 | CTTCATATGTATGGGT | 10 | N/A | N/A | 2512 |
| 951432 | 25701 | 25716 | ATAGATGTAAGCAACT | 51 | N/A | N/A | 2513 |
| 951433 | 25709 | 25724 | GGAAATTCATAGATGT | 113 | N/A | N/A | 2514 |
| 951434 | 25740 | 25755 | ACTTATGGATGCAGCT | 52 | N/A | N/A | 2515 |
| 951435 | 25741 | 25756 | AACTTATGGATGCAGC | 39 | N/A | N/A | 2516 |
| 951436 | 26160 | 26175 | AGCATTGGTATCAGGC | 35 | N/A | N/A | 2517 |
| 951437 | 26168 | 26183 | TGGATATCAGCATTGG | 17 | N/A | N/A | 2518 |
| 951438 | 26173 | 26188 | ATGGATGGATATCAGC | 41 | N/A | N/A | 2519 |
| 951439 | 26180 | 26195 | TTCAATCATGGATGGA | 72 | N/A | N/A | 2520 |
| 951440 | 27070 | 27085 | GGAATACTTGCAGCTA | 41 | N/A | N/A | 2521 |
| 951441 | 27071 | 27086 | AGGAATACTTGCAGCT | 11 | N/A | N/A | 2522 |
| 951442 | 27224 | 27239 | CAACATGGCACTCCCT | 64 | N/A | N/A | 2523 |
| 951443 | 27231 | 27246 | TCTGATGCAACATGGC | 12 | N/A | N/A | 2524 |
| 951444 | 27569 | 27584 | ATCATTGGGTGAAGAC | 43 | N/A | N/A | 2525 |
| 951445 | 27762 | 27777 | GGTCTATTGGCACACA | 32 | N/A | N/A | 2526 |
| 951446 | 27776 | 27791 | AGATTAAGTCATCCGG | 90 | N/A | N/A | 2527 |
| 951447 | 27777 | 27792 | GAGATTAAGTCATCCG | 61 | N/A | N/A | 2528 |
| 951448 | 27778 | 27793 | AGAGATTAAGTCATCC | 73 | N/A | N/A | 2529 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951449 | 28228 | 28243 | GCAAATGCTAGCTGCA | 142 | N/A | N/A | 2530 |
| 951450 | 29274 | 29289 | CGCTCTAATGTCCTGA | 11 | N/A | N/A | 2531 |
| 951451 | 29308 | 29323 | TGGATATCCAGACCCA | 97 | N/A | N/A | 2532 |
| 951452 | 29321 | 29336 | GCAGATCCTGCCTTGG | 92 | N/A | N/A | 2533 |
| 951453 | 29584 | 29599 | TGAACTAGAGGCAGGC | 29 | N/A | N/A | 2534 |
| 951454 | 29585 | 29600 | GTGAACTAGAGGCAGG | 19 | N/A | N/A | 2535 |
| 951455 | 29974 | 29989 | TGTAACTTTCAGCAGT | 25 | N/A | N/A | 2536 |
| 951456 | 29999 | 30014 | TGTGATTGCAGGCCAG | 13 | N/A | N/A | 2537 |
| 951457 | 30053 | 30068 | TTTTATAGTCTCCAAC | 140 | N/A | N/A | 2538 |
| 951458 | 30107 | 30122 | TGTATGGACAGCAGGC | 13 | N/A | N/A | 2539 |
| 951459 | 30108 | 30123 | GTGTATGGACAGCAGG | 10 | N/A | N/A | 2540 |
| 951460 | 30242 | 30257 | ATCAATCTTGGGAGCT | 39 | N/A | N/A | 2541 |
| 951461 | 30246 | 30261 | CTAAATCAATCTTGGG | 40 | N/A | N/A | 2542 |
| 951462 | 30348 | 30363 | ATATTAATGCAGTGGT | 4 | N/A | N/A | 2543 |
| 951463 | 30349 | 30364 | CATATTAATGCAGTGG | 14 | N/A | N/A | 2544 |
| 951464 | 30350 | 30365 | ACATATTAATGCAGTG | 66 | N/A | N/A | 2545 |
| 951465 | 30407 | 30422 | AGAATATCAACACCTT | 69 | N/A | N/A | 2546 |
| 951466 | 30408 | 30423 | TAGAATATCAACACCT | 61 | N/A | N/A | 2547 |
| 951467 | 30426 | 30441 | TTATCTAACAGTCCCA | 45 | N/A | N/A | 2548 |
| 951468 | 30429 | 30444 | CATTTATCTAACAGTC | 104 | N/A | N/A | 2549 |
| 951469 | 30509 | 30524 | TAGTGATATGCTGCCT | 22 | N/A | N/A | 2550 |
| 951470 | 30852 | 30867 | CACAATCCTGGCTATC | 56 | N/A | N/A | 2551 |
| 951471 | 30931 | 30946 | CCAGACATTGCTGTCG | 108 | N/A | N/A | 2552 |
| 951472 | 31367 | 31382 | ACATTTGACGGTTTGA | 15 | N/A | N/A | 2553 |
| 951473 | 32256 | 32271 | GGGAATGATGCCACCT | 110 | N/A | N/A | 2554 |
| 951474 | 32270 | 32285 | CCAATCTGTTATGTGG | 23 | N/A | N/A | 2555 |
| 951475 | 32336 | 32351 | TGGAATCCAGTATTTC | 103 | N/A | N/A | 2556 |
| 951476 | 32498 | 32513 | AGGAATCCTGCAGCTC | 108 | N/A | N/A | 2557 |
| 951477 | 32722 | 32737 | TCCTATTAGAGTGGCA | 49 | N/A | N/A | 2558 |
| 951478 | 32905 | 32920 | AGCATTAACAGAGCAG | 92 | N/A | N/A | 2559 |
| 951479 | 33017 | 33032 | GGCTTTACTCCAGCCA | 104 | N/A | N/A | 2560 |
| 951480 | 33518 | 33533 | AACAATAGCCATTGGT | 107 | N/A | N/A | 2561 |
| 951481 | 34302 | 34317 | TGTTTATTTACCGTTT | 3 | N/A | N/A | 2562 |
| 951482 | 35180 | 35195 | AGTACTATTGCATCAT | 28 | N/A | N/A | 2563 |
| 951483 | 36041 | 36056 | TCACATACAGACCCCA | 59 | N/A | N/A | 2564 |
| 951484 | 36073 | 36088 | CTAAATGTCACTTAGC | 40 | N/A | N/A | 2565 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951485 | 36087 | 36102 | GGAACTAACACATGCT | 23 | N/A | N/A | 2566 |
| 951486 | 36362 | 36377 | GAAATCTACCTACTCC | 105 | N/A | N/A | 2567 |
| 951487 | 36363 | 36378 | TGAAATCTACCTACTC | 121 | N/A | N/A | 2568 |
| 951488 | 36617 | 36632 | GGCACCAACATTCACC | 96 | N/A | N/A | 2569 |
| 951489 | 36660 | 36675 | TCCGATTTTGCTTCTA | 10 | N/A | N/A | 2570 |
| 951490 | 36665 | 36680 | ACTTATCCGATTTTGC | 23 | N/A | N/A | 2571 |
| 951491 | 36809 | 36824 | TGTTATTCCGAACAGT | 43 | N/A | N/A | 2572 |
| 951492 | 36911 | 36926 | TCTCATGGCGACTGGC | 77 | N/A | N/A | 2573 |
| 951493 | 36948 | 36963 | GGAATAAAGGCTCTCG | 22 | N/A | N/A | 2574 |
| 951494 | 37009 | 37024 | TTAGATTGTATGACCC | 9 | N/A | N/A | 2575 |
| 951495 | 37194 | 37209 | GGCTTTGTTAGATGCC | 107 | N/A | N/A | 2576 |
| 951496 | 37246 | 37261 | ATTCATAGTACCCCAC | 62 | N/A | N/A | 2577 |
| 951497 | 37304 | 37319 | GTATTTGTAGTGTGGA | 110 | N/A | N/A | 2578 |
| 951498 | 37305 | 37320 | GGTATTTGTAGTGTGG | 10 | N/A | N/A | 2579 |
| 951499 | 37446 | 37461 | GACAATGGTGATGCCC | 62 | N/A | N/A | 2580 |
| 951500 | 37566 | 37581 | ATCTTAGGCAGACCCT | 42 | N/A | N/A | 2581 |
| 951501 | 37570 | 37585 | ACACATCTTAGGCAGA | 14 | N/A | N/A | 2582 |
| 951502 | 37729 | 37744 | ATTAAAATGGGTCTGC | 77 | N/A | N/A | 2583 |
| 951503 | 37750 | 37765 | CATTTAACCATGACAG | 31 | N/A | N/A | 2584 |
| 951504 | 37751 | 37766 | CCATTTAACCATGACA | 32 | N/A | N/A | 2585 |
| 951505 | 37971 | 37986 | ACCTTAAGTTTTTTGG | 118 | N/A | N/A | 2586 |
| 951506 | 38196 | 38211 | GCTAATAGCTATTCAA | 39 | N/A | N/A | 2587 |
| 951507 | 38225 | 38240 | CGCATTACTGAGTTCA | 12 | N/A | N/A | 2588 |
| 951508 | 38335 | 38350 | GTGACTAAGACAACCA | 40 | N/A | N/A | 2589 |
| 951509 | 38538 | 38553 | AGACATGTAACTCCCT | 39 | N/A | N/A | 2590 |
| 951510 | 38540 | 38555 | CTAGACATGTAACTCC | 72 | N/A | N/A | 2591 |
| 951511 | 38592 | 38607 | GCCTATCCATGCTGCT | 105 | N/A | N/A | 2592 |
| 951512 | 39123 | 39138 | CAGAATTGTTACAACC | 47 | N/A | N/A | 2593 |
| 951513 | 39140 | 39155 | CCATTAAAATTTGCCC | 30 | N/A | N/A | 2594 |
| 951514 | 39141 | 39156 | TCCATTAAAATTTGCC | 44 | N/A | N/A | 2595 |
| 951515 | 39233 | 39248 | TTAACTATATCTAACT | 73 | N/A | N/A | 2596 |
| 951516 | 39236 | 39251 | CGATTAACTATATCTA | 87 | N/A | N/A | 2597 |
| 951517 | 39547 | 39562 | ATTTATGCGATTGGCC | 88 | N/A | N/A | 2598 |
| 951518 | 39548 | 39563 | GATTTATGCGATTGGC | 17 | N/A | N/A | 2599 |
| 951519 | 39549 | 39564 | AGATTTATGCGATTGG | 11 | N/A | N/A | 2600 |
| 951520 | 39555 | 39570 | TGTTTAAGATTTATGC | 41 | N/A | N/A | 2601 |
| 951521 | 39748 | 39763 | AAAGTAATTCACTGCG | 81 | N/A | N/A | 2602 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951522 | 40198 | 40213 | ATGGACTACAGTCTGT | 110 | N/A | N/A | 2603 |
| 951523 | 40275 | 40290 | TGCAATCACAGACATC | 93 | N/A | N/A | 2604 |
| 951524 | 41080 | 41095 | GTATTAACCTCATGAA | 93 | N/A | N/A | 2605 |
| 951525 | 41081 | 41096 | GGTATTAACCTCATGA | 68 | N/A | N/A | 2606 |
| 951526 | 41125 | 41140 | GTCTTTCCGTCACAGT | 40 | N/A | N/A | 2607 |
| 951527 | 41273 | 41288 | GGATAATTGGAGAGGG | 94 | N/A | N/A | 2608 |
| 951528 | 41274 | 41289 | GGGATAATTGGAGAGG | 68 | N/A | N/A | 2609 |
| 951529 | 42072 | 42087 | GGGATTATGATGAGGA | 3 | N/A | N/A | 2610 |
| 951530 | 42327 | 42342 | GATGATGGGTTCTAGC | 85 | N/A | N/A | 2611 |
| 951531 | 42355 | 42370 | GGGAGATGTGCTCTTT | 49 | N/A | N/A | 2612 |
| 951532 | 42381 | 42396 | GTATTACCCAGTGGCT | 62 | N/A | N/A | 2613 |
| 951533 | 42382 | 42397 | TGTATTACCCAGTGGC | 15 | N/A | N/A | 2614 |
| 951534 | 42387 | 42402 | GGGAATGTATTACCCA | 131 | N/A | N/A | 2615 |
| 951535 | 42501 | 42516 | TACAATCATTCCCAGC | 89 | N/A | N/A | 2616 |
| 951536 | 42506 | 42521 | AGCACTACAATCATTC | 82 | N/A | N/A | 2617 |
| 951537 | 42569 | 42584 | TACTGTACAGCTGTGC | 8 | N/A | N/A | 2618 |
| 951538 | 42578 | 42593 | GGCAATTGGTACTGTA | 121 | N/A | N/A | 2619 |
| 951539 | 42599 | 42614 | GAAAATTTGTACAGGA | 55 | N/A | N/A | 2620 |
| 951540 | 43029 | 43044 | TACATTAAAGGCTCGA | 44 | N/A | N/A | 2621 |
| 951541 | 43843 | 43858 | GTACATATCCTGGCCG | 32 | N/A | N/A | 2622 |
| 951542 | 43871 | 43886 | TACTATTCGACAGAGC | 31 | N/A | N/A | 2623 |
| 951543 | 43873 | 43888 | ATTACTATTCGACAGA | 36 | N/A | N/A | 2624 |
| 951544 | 43876 | 43891 | TAAATTACTATTCGAC | 45 | N/A | N/A | 2625 |
| 951545 | 43877 | 43892 | GTAAATTACTATTCGA | 63 | N/A | N/A | 2626 |
| 951546 | 43878 | 43893 | TGTAAATTACTATTCG | 19 | N/A | N/A | 2627 |
| 951547 | 44416 | 44431 | GAGATCAACACATTTC | 57 | N/A | N/A | 2628 |
| 951548 | 44701 | 44716 | AGAAATTACTCTTGCG | 116 | N/A | N/A | 2629 |
| 951549 | 44902 | 44917 | TCCAATGACAGCCCAG | 26 | N/A | N/A | 2630 |
| 951550 | 44914 | 44929 | GTGAATTCAATGTCCA | 11 | N/A | N/A | 2631 |
| 951551 | 44929 | 44944 | ACACATGTGGAACACG | 80 | N/A | N/A | 2632 |
| 951552 | 45353 | 45368 | TATCTATAACACATGA | 44 | N/A | N/A | 2633 |
| 951553 | 45356 | 45371 | GGTTATCTATAACACA | 23 | N/A | N/A | 2634 |
| 951554 | 45446 | 45461 | GTCTTTATTGCATGGG | 8 | N/A | N/A | 2635 |
| 951555 | 45569 | 45584 | GCTATAAAACCAGCCA | 101 | N/A | N/A | 2636 |
| 951556 | 45590 | 45605 | AGCATTGGATTGAGCA | 89 | N/A | N/A | 2637 |
| 951557 | 46280 | 46295 | AGCAATGGTGGCCGGG | 109 | N/A | N/A | 2638 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951558 | 46328 | 46343 | CTATATTCAACAGGCT | 24 | N/A | N/A | 2639 |
| 951559 | 46329 | 46344 | ACTATATTCAACAGGC | 61 | N/A | N/A | 2640 |
| 951560 | 46335 | 46350 | GGCCATACTATATTCA | 102 | N/A | N/A | 2641 |
| 951561 | 46428 | 46443 | GGGATATACGCCCACC | 8 | N/A | N/A | 2642 |
| 951562 | 46590 | 46605 | TATTTAAAAGGGCCGC | 23 | N/A | N/A | 2643 |
| 951563 | 46591 | 46606 | GTATTTAAAAGGGCCG | 97 | N/A | N/A | 2644 |
| 951564 | 46861 | 46876 | CGAAATAGCAGAGCTC | 75 | N/A | N/A | 2645 |
| 951565 | 46961 | 46976 | TCTATAGTGACTCTCA | 9 | N/A | N/A | 2646 |
| 951566 | 46962 | 46977 | TTCTATAGTGACTCTC | 6 | N/A | N/A | 2647 |
| 951567 | 47624 | 47639 | GTTCATCCGGGTCAGG | 36 | N/A | N/A | 2648 |
| 951568 | 47926 | 47941 | GCAACTATGCATCCAC | 141 | N/A | N/A | 2649 |
| 951569 | 48813 | 48828 | GAACATGGCAGCCAGT | 82 | N/A | N/A | 2650 |
| 951570 | 48973 | 48988 | TGCTTAATGCCTTGCC | 82 | N/A | N/A | 2651 |
| 951571 | 49051 | 49066 | CGCAATGTGTTCATTT | 27 | N/A | N/A | 2652 |
| 951572 | 49192 | 49207 | ACTTTAACAAGTCCCG | 36 | N/A | N/A | 2653 |
| 951573 | 49193 | 49208 | CACTTTAACAAGTCCC | 23 | N/A | N/A | 2654 |
| 951574 | 49227 | 49242 | ACAGATGAAGCTACCA | 27 | N/A | N/A | 2655 |
| 951575 | 49443 | 49458 | GGTTATGGTCTTAGGT | 16 | N/A | N/A | 2656 |
| 951576 | 49674 | 49689 | TCGATTTGATTCTGAG | 84 | N/A | N/A | 2657 |
| 951577 | 50575 | 50590 | GACAAATTGCCACTGG | 54 | N/A | N/A | 2658 |
| 951578 | 50595 | 50610 | GCAAATATCTCCCAGT | 19 | N/A | N/A | 2659 |
| 951579 | 50845 | 50860 | ACAATGACGAGGCTGG | 25 | N/A | N/A | 2660 |
| 951580 | 50979 | 50994 | TCAAATCCCATCAGGA | 90 | N/A | N/A | 2661 |
| 951581 | 51714 | 51729 | TGTACTTGCGGGTTTT | 42 | N/A | N/A | 2662 |
| 951582 | 51790 | 51805 | AGCAATCACGCTGCCA | 99 | N/A | N/A | 2663 |
| 951583 | 51798 | 51813 | AGTCATCCAGCAATCA | 43 | N/A | N/A | 2664 |
| 951584 | 51810 | 51825 | ATTAATCTGGGCAGTC | 38 | N/A | N/A | 2665 |
| 951585 | 51811 | 51826 | GATTAATCTGGGCAGT | 67 | N/A | N/A | 2666 |
| 951586 | 51816 | 51831 | TAAAGGATTAATCTGG | 48 | N/A | N/A | 2667 |
| 951587 | 51977 | 51992 | ATTTTGATAGCTCCAC | 33 | N/A | N/A | 2668 |
| 951588 | 51979 | 51994 | GCATTTTGATAGCTCC | 17 | N/A | N/A | 2669 |
| 951589 | 52601 | 52616 | GGTTTAAAAGCTTCCA | 98 | N/A | N/A | 2670 |
| 951590 | 52938 | 52953 | GTAAATGCTGAATGCC | 34 | N/A | N/A | 2671 |
| 951591 | 53084 | 53099 | GGATATGGACAGCAGG | 17 | N/A | N/A | 2672 |
| 951592 | 53085 | 53100 | AGGATATGGACAGCAG | 15 | N/A | N/A | 2673 |
| 951593 | 53553 | 53568 | TCACATGCCAGACTTT | 100 | N/A | N/A | 2674 |
| 951594 | 53781 | 53796 | CACACTCACGCATGTT | 102 | N/A | N/A | 2675 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951595 | 53852 | 53867 | TTTACCTTGAATGTCC | 46 | N/A | N/A | 2676 |
| 951596 | 54009 | 54024 | GCAAGCTACTCTCTCA | 88 | N/A | N/A | 2677 |
| 951597 | 54160 | 54175 | TCAATACCTGCACAGG | 42 | N/A | N/A | 2678 |
| 951598 | 54161 | 54176 | GTCAATACCTGCACAG | 80 | N/A | N/A | 2679 |
| 951599 | 54177 | 54192 | TGTATGAGGACTCAGA | 42 | N/A | N/A | 2680 |
| 951600 | 54189 | 54204 | ATCATAACAGGCTGTA | 28 | N/A | N/A | 2681 |
| 951601 | 54190 | 54205 | CATCATAACAGGCTGT | 94 | N/A | N/A | 2682 |
| 951602 | 54199 | 54214 | TAAAATGCGCATCATA | 51 | N/A | N/A | 2683 |
| 951603 | 54255 | 54270 | GTAATGAGCTCAGTCT | 45 | N/A | N/A | 2684 |
| 951604 | 55117 | 55132 | GAAACTACGGCACTCT | 121 | N/A | N/A | 2685 |
| 951605 | 55385 | 55400 | GGTAATAAGTCACACT | 103 | N/A | N/A | 2686 |
| 951606 | 55528 | 55543 | GATTAATATCGGCTGA | 44 | N/A | N/A | 2687 |
| 951607 | 55530 | 55545 | TGGATTAATATCGGCT | 24 | N/A | N/A | 2688 |
| 951608 | 55531 | 55546 | ATGGATTAATATCGGC | 9 | N/A | N/A | 2689 |
| 951609 | 56236 | 56251 | GTTCATCACGGAAGGT | 120 | N/A | N/A | 2690 |
| 951610 | 56274 | 56289 | CCGAATCACAGATTGA | 71 | N/A | N/A | 2691 |
| 951611 | 56324 | 56339 | GTAATTGACAAGCAGT | 16 | N/A | N/A | 2692 |
| 951612 | 56327 | 56342 | TAAGTAATTGACAAGC | 29 | N/A | N/A | 2693 |
| 951613 | 56387 | 56402 | GTATATAAGACCCGGG | 65 | N/A | N/A | 2694 |
| 951614 | 56388 | 56403 | TGTATATAAGACCCGG | 86 | N/A | N/A | 2695 |
| 951615 | 56389 | 56404 | GTGTATATAAGACCCG | 53 | N/A | N/A | 2696 |
| 951616 | 56390 | 56405 | AGTGTATATAAGACCC | 41 | N/A | N/A | 2697 |
| 951617 | 56459 | 56474 | GACTATTCAAGAGGGC | 70 | N/A | N/A | 2698 |
| 951618 | 56567 | 56582 | TCTCATGGCACTCACT | 42 | N/A | N/A | 2699 |
| 951619 | 56617 | 56632 | ATTCATGGTCCACCAG | 101 | N/A | N/A | 2700 |
| 951620 | 56685 | 56700 | GGTGATGCTGCAGAGC | 36 | N/A | N/A | 2701 |
| 951621 | 56725 | 56740 | CAGGATACATCACCCA | 128 | N/A | N/A | 2702 |
| 951622 | 56858 | 56873 | TATTATGAATCCCCCT | 90 | N/A | N/A | 2703 |
| 951623 | 56859 | 56874 | ATATTATGAATCCCCC | 100 | N/A | N/A | 2704 |
| 951624 | 56861 | 56876 | ACATATTATGAATCCC | 52 | N/A | N/A | 2705 |
| 951625 | 57375 | 57390 | AGTAATGACCCAGGCT | 74 | N/A | N/A | 2706 |
| 951626 | 57642 | 57657 | AGTGATGGGTCCCCAC | 94 | N/A | N/A | 2707 |
| 951627 | 57738 | 57753 | GTGAATATCAACTGTT | 41 | N/A | N/A | 2708 |
| 951628 | 57916 | 57931 | GCAGATCTGGCTGCCT | 71 | N/A | N/A | 2709 |
| 951629 | 58905 | 58920 | AGGATATTTGGCTGGG | 70 | N/A | N/A | 2710 |
| 951630 | 59003 | 59018 | ACTTATCGCAAGGAAC | 71 | N/A | N/A | 2711 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951631 | 59075 | 59090 | GCGATATACCTTTCTG | 26 | N/A | N/A | 2712 |
| 951632 | 59076 | 59091 | TGCGATATACCTTTCT | 19 | N/A | N/A | 2713 |
| 951633 | 59174 | 59189 | TGAATGACAGGTGTGT | 124 | N/A | N/A | 2714 |
| 951634 | 59346 | 59361 | TACAATCACAATTGCT | 47 | N/A | N/A | 2715 |
| 951635 | 60402 | 60417 | GCCAATACCAAAGAAC | 96 | N/A | N/A | 2716 |
| 951636 | 60469 | 60484 | TCTAAATCAGGACAGT | 86 | N/A | N/A | 2717 |
| 951637 | 61124 | 61139 | GCAACATGGGCACTGC | 100 | N/A | N/A | 2718 |
| 951638 | 61190 | 61205 | TAAGATCGCATCTGGG | 93 | N/A | N/A | 2719 |
| 951639 | 61274 | 61289 | AGCTATCTGGGTTAGG | 105 | N/A | N/A | 2720 |
| 951640 | 61338 | 61353 | GGAAATAGACGATCTC | 68 | N/A | N/A | 2721 |
| 951641 | 61460 | 61475 | CCAATTTGGGCATCAA | 102 | N/A | N/A | 2722 |
| 951642 | 61461 | 61476 | GCCAATTTGGGCATCA | 102 | N/A | N/A | 2723 |
| 951643 | 61530 | 61545 | GTTATATGTGTGGCAT | 35 | N/A | N/A | 2724 |
| 951644 | 61531 | 61546 | TGTTATATGTGTGGCA | 40 | N/A | N/A | 2725 |
| 951645 | 61532 | 61547 | GTGTTATATGTGTGGC | 9 | N/A | N/A | 2726 |
| 951646 | 61680 | 61695 | GCTAAAATTCCACTCT | 96 | N/A | N/A | 2727 |
| 951647 | 61796 | 61811 | CGTAAACATGATTCCT | 20 | N/A | N/A | 2728 |
| 951648 | 61841 | 61856 | GTTATTAAGGACAACC | 120 | N/A | N/A | 2729 |
| 951649 | 61857 | 61872 | CGTTATTGTCATTTGT | 46 | N/A | N/A | 2730 |
| 951650 | 61943 | 61958 | TCGAATGAAGATGGTC | 30 | N/A | N/A | 2731 |
| 951651 | 62255 | 62270 | AATGATAAGGACCCCA | 63 | N/A | N/A | 2732 |
| 951652 | 62257 | 62272 | GTAATGATAAGGACCC | 66 | N/A | N/A | 2733 |
| 951653 | 62258 | 62273 | AGTAATGATAAGGACC | 80 | N/A | N/A | 2734 |
| 951654 | 62398 | 62413 | GTTAATTGTGCACTTG | 15 | N/A | N/A | 2735 |
| 951655 | 62399 | 62414 | TGTTAATTGTGCACTT | 80 | N/A | N/A | 2736 |
| 951656 | 62400 | 62415 | GTGTTAATTGTGCACT | 109 | N/A | N/A | 2737 |
| 951657 | 62526 | 62541 | AGTTATAAACCCTGGG | 11 | N/A | N/A | 2738 |
| 951658 | 63805 | 63820 | ACAATAATTGGCCAAA | 86 | N/A | N/A | 2739 |
| 951659 | 63829 | 63844 | GATCTAATTACCAGCT | 128 | N/A | N/A | 2740 |
| 951660 | 63881 | 63896 | TACTTAGGTTACTCCT | 49 | N/A | N/A | 2741 |
| 951661 | 64400 | 64415 | GACAATGGGTCAACGC | 67 | N/A | N/A | 2742 |
| 951662 | 65042 | 65057 | TGCTCTAAATGACTGC | 96 | N/A | N/A | 2743 |
| 951663 | 65090 | 65105 | CCACATCTATCTCAGA | 112 | N/A | N/A | 2744 |
| 951664 | 65141 | 65156 | AATATCTCAGCAGTGC | 54 | N/A | N/A | 2745 |
| 951665 | 65142 | 65157 | CAATATCTCAGCAGTG | 126 | N/A | N/A | 2746 |
| 951666 | 65354 | 65369 | GGCCTAACAGTGTCCA | 105 | N/A | N/A | 2747 |
| 951667 | 65601 | 65616 | AGTCATTAGTACGCCA | 46 | N/A | N/A | 2748 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID: 2 Stop Site | SEQ ID NO |
|---|---|---|---|---|---|---|---|
| 951668 | 66403 | 66418 | GTCTTGTGGGATGTGA | 66 | N/A | N/A | 2749 |
| 951669 | 66821 | 66836 | TCAATACACACTGTTG | 85 | N/A | N/A | 2750 |
| 951670 | 66828 | 66843 | GGATAATTCAATACAC | 41 | N/A | N/A | 2751 |
| 951671 | 67824 | 67839 | ATAACATGTTACTCAG | 71 | N/A | N/A | 2752 |
| 951672 | 67825 | 67840 | CATAACATGTTACTCA | 87 | N/A | N/A | 2753 |
| 951673 | 67827 | 67842 | GTCATAACATGTTACT | 76 | N/A | N/A | 2754 |
| 951674 | 67828 | 67843 | TGTCATAACATGTTAC | 102 | N/A | N/A | 2755 |
| 951675 | 67840 | 67855 | GGCACTCACAGCTGTC | 119 | N/A | N/A | 2756 |
| 951676 | 68164 | 68179 | AGCTGTTGTGCAGTGC | 73 | N/A | N/A | 2757 |
| 951677 | 68238 | 68253 | GCTAAATGTGGACTGA | 28 | N/A | N/A | 2758 |
| 951678 | 68623 | 68638 | GGCAATGCATACAGTC | 44 | N/A | N/A | 2759 |
| 951679 | 68650 | 68665 | GTTATTAACCCCCTGT | 44 | N/A | N/A | 2760 |
| 951680 | 69011 | 69026 | TCAATTACTTACAAGA | 62 | N/A | N/A | 2761 |
| 951681 | 69030 | 69045 | TGTTTATGCACCATGT | 57 | N/A | N/A | 2762 |
| 951682 | 69227 | 69242 | GAATTATGCCTTCTAC | 25 | N/A | N/A | 2763 |
| 951683 | 69652 | 69667 | GTCTATGTGGGCTGCC | 80 | N/A | N/A | 2764 |
| 951684 | 69735 | 69750 | ATCTATGGCATGGAGC | 82 | N/A | N/A | 2765 |
| 951685 | 69737 | 69752 | ACATCTATGGCATGGA | 75 | N/A | N/A | 2766 |
| 951686 | 71409 | 71424 | ACAGATAAATCAAGCC | 50 | N/A | N/A | 2767 |
| 951687 | 71450 | 71465 | CACTATGCGGCCACCA | 93 | N/A | N/A | 2768 |
| 951688 | 71699 | 71714 | GTACATACTGCAGCAG | 113 | N/A | N/A | 2769 |
| 951689 | 71700 | 71715 | GGTACATACTGCAGCA | 107 | N/A | N/A | 2770 |
| 951690 | 71857 | 71872 | GCGAATGCCATGCTTA | 82 | N/A | N/A | 2771 |
| 951691 | 71968 | 71983 | GACATTTAACACACTA | 7 | N/A | N/A | 2772 |
| 951692 | 73303 | 73318 | GGCTTAATCCCACACG | 97 | N/A | N/A | 2773 |
| 951693 | 73694 | 73709 | GAATTTGGGATTGTGG | 21 | N/A | N/A | 2774 |
| 951694 | 73828 | 73843 | TCATGCATGGCACTGT | 102 | N/A | N/A | 2775 |
| 951695 | 73956 | 73971 | AGCATAAAAGCACTCT | 74 | N/A | N/A | 2776 |
| 951696 | 74038 | 74053 | GCTATGAATTTCCTCC | 10 | N/A | N/A | 2777 |
| 951697 | 74039 | 74054 | GGCTATGAATTTCCTC | 115 | N/A | N/A | 2778 |
| 951698 | 74365 | 74380 | TGCTATGACCCTCACT | 82 | N/A | N/A | 2779 |
| 951699 | 75020 | 75035 | ACAGATAACAGTGGCG | 24 | N/A | N/A | 2780 |
| 951700 | 75136 | 75151 | GTAATTCCCGTTCTCT | 16 | N/A | N/A | 2781 |
| 951701 | 75145 | 75160 | TCTATTACCGTAATTC | 23 | N/A | N/A | 2782 |
| 951702 | 75247 | 75262 | TACATGAACAGTCTGT | 50 | N/A | N/A | 2783 |
| 951703 | 75327 | 75342 | AACTTACAAGCATCGG | 91 | N/A | N/A | 2784 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951704 | 75329 | 75344 | TGAACTTACAAGCATC | 94 | N/A | N/A | 2785 |
| 951705 | 75417 | 75432 | ATCAATTTTAAACACG | 31 | N/A | N/A | 2786 |
| 951706 | 75765 | 75780 | ACAAATACATGAGGTC | 32 | N/A | N/A | 2787 |
| 951707 | 75894 | 75909 | GTATTATTCCCAGCTA | 77 | N/A | N/A | 2788 |
| 951708 | 75895 | 75910 | TGTATTATTCCCAGCT | 102 | N/A | N/A | 2789 |
| 951709 | 76435 | 76450 | GAGAATATCACAGGGT | 10 | N/A | N/A | 2790 |
| 951710 | 76448 | 76463 | TGTAATCAGTCAAGAG | 18 | N/A | N/A | 2791 |
| 951711 | 76550 | 76565 | GACAATTGTGACCGGC | 88 | N/A | N/A | 2792 |
| 951712 | 76568 | 76583 | CACAATCAGAGCATTC | 34 | N/A | N/A | 2793 |
| 951713 | 76593 | 76608 | TGATTTACAGGCCCAA | 37 | N/A | N/A | 2794 |
| 951714 | 76594 | 76609 | GTGATTTACAGGCCCA | 50 | N/A | N/A | 2795 |
| 951715 | 76725 | 76740 | ACTAATGACAGACAAC | 27 | N/A | N/A | 2796 |
| 951716 | 76728 | 76743 | TAAACTAATGACAGAC | 92 | N/A | N/A | 2797 |
| 951717 | 76775 | 76790 | TTGAATTGTGGACCAA | 60 | N/A | N/A | 2798 |
| 951718 | 77126 | 77141 | AGGTTAATGCTTCACC | 54 | N/A | N/A | 2799 |
| 951719 | 77303 | 77318 | TCAAATGGTGACCACT | 112 | N/A | N/A | 2800 |
| 951720 | 77432 | 77447 | CGTTTTAGTTTTCCTA | 14 | N/A | N/A | 2801 |
| 951721 | 77538 | 77553 | GTAATAACATGTGTCG | 45 | N/A | N/A | 2802 |
| 951722 | 77539 | 77554 | GGTAATAACATGTGTC | 27 | N/A | N/A | 2803 |
| 951723 | 77570 | 77585 | TAAACAATTGCTCATC | 59 | N/A | N/A | 2804 |
| 951724 | 78076 | 78091 | GGTAATTCTGCAAAGA | 29 | N/A | N/A | 2805 |
| 951725 | 78080 | 78095 | TAATGGTAATTCTGCA | 43 | N/A | N/A | 2806 |
| 951726 | 78082 | 78097 | ACTAATGGTAATTCTG | 50 | N/A | N/A | 2807 |
| 951727 | 78166 | 78181 | TTAGATCTCATTACCT | 71 | N/A | N/A | 2808 |
| 951728 | 78206 | 78221 | GTAACAACATCTACCT | 88 | N/A | N/A | 2809 |
| 951729 | 78207 | 78222 | GGTAACAACATCTACC | 3 | N/A | N/A | 2810 |
| 951730 | 78387 | 78402 | TGATTTACAGGATGCT | 15 | N/A | N/A | 2811 |
| 951731 | 78388 | 78403 | TTGATTTACAGGATGC | 8 | N/A | N/A | 2812 |
| 951732 | 78539 | 78554 | GCAAATGCTGGCTACG | 85 | N/A | N/A | 2813 |
| 951733 | 78546 | 78561 | CCCAATGGCAAATGCT | 66 | N/A | N/A | 2814 |
| 951734 | 78848 | 78863 | GGCACTACCTTCACCA | 109 | N/A | N/A | 2815 |
| 951735 | 79046 | 79061 | TCATATTGTTCTGCCC | 15 | N/A | N/A | 2816 |
| 951736 | 79047 | 79062 | TTCATATTGTTCTGCC | 11 | N/A | N/A | 2817 |
| 951737 | 79077 | 79092 | GGCTTTTGTCAGAGGA | 8 | N/A | N/A | 2818 |
| 951738 | 79153 | 79168 | TTCAATGACATGCTAG | 19 | N/A | N/A | 2819 |
| 951739 | 79209 | 79224 | TATATCAGCTCAGTGC | 75 | N/A | N/A | 2820 |
| 951740 | 79211 | 79226 | TATATATCAGCTCAGT | 66 | N/A | N/A | 2821 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951741 | 79214 | 79229 | TTGTATATATCAGCTC | 37 | N/A | N/A | 2822 |
| 951742 | 79229 | 79244 | TCATACATAAGGATGT | 91 | N/A | N/A | 2823 |
| 951743 | 79398 | 79413 | GCTCATTGTAAACAGT | 20 | N/A | N/A | 2824 |
| 951744 | 79462 | 79477 | TGCATTTGGTCTTGCT | 118 | N/A | N/A | 2825 |
| 951745 | 79799 | 79814 | GACTATCAGTATGCAC | 118 | N/A | N/A | 2826 |
| 951746 | 79845 | 79860 | CATCATATTGGTGGGA | 11 | N/A | N/A | 2827 |
| 951747 | 80265 | 80280 | GCTATATTCACAAGGC | 70 | N/A | N/A | 2828 |
| 951748 | 80266 | 80281 | GGCTATATTCACAAGG | 39 | N/A | N/A | 2829 |
| 951749 | 80520 | 80535 | AACGATTAGGGACTCA | 4 | N/A | N/A | 2830 |
| 951750 | 80663 | 80678 | CCCTATTTGATCAGGA | 117 | N/A | N/A | 2831 |
| 951751 | 80845 | 80860 | GCAACTACCTTTGTTA | 17 | N/A | N/A | 2832 |
| 951752 | 80986 | 81001 | AGCAATTTCATTGGCC | 105 | N/A | N/A | 2833 |
| 951753 | 81192 | 81207 | AGCAATACCTTACTGG | 46 | N/A | N/A | 2834 |
| 951754 | 81436 | 81451 | TGGTATCAGGGTCCCA | 130 | N/A | N/A | 2835 |
| 951755 | 81663 | 81678 | CATGATGTCGCTGGCA | 41 | N/A | N/A | 2836 |
| 951756 | 81741 | 81756 | TCCAAAAATGGGCTGC | 28 | N/A | N/A | 2837 |
| 951757 | 82016 | 82031 | TCTAATCGAAGAAGCT | 99 | N/A | N/A | 2838 |
| 951758 | 82262 | 82277 | TCTGATTAGTCCATGC | 40 | N/A | N/A | 2839 |
| 951759 | 82535 | 82550 | ACAAATGCGGAGATGA | 41 | N/A | N/A | 2840 |
| 951761 | 82653 | 82668 | GCCAATGCAAGGTGGC | 119 | N/A | N/A | 2841 |
| 951762 | 82803 | 82818 | TGTTTTGGTGCTGGCT | 99 | N/A | N/A | 2842 |
| 951763 | 82880 | 82895 | TGGAATGGTTACTCTC | 3 | N/A | N/A | 2843 |
| 951764 | 82920 | 82935 | ATCTTCTGCAGTGTGG | 2 | N/A | N/A | 2844 |
| 951765 | 83070 | 83085 | GGTATCTGGGCCATCA | 101 | N/A | N/A | 2845 |
| 951766 | 83419 | 83434 | AGCAACATGAACCACA | 26 | N/A | N/A | 2846 |
| 951767 | 84425 | 84440 | GTAATCAAGGCAGCAA | 7 | N/A | N/A | 2847 |
| 951768 | 85210 | 85225 | AGCTCTGGTTTCAACA | 82 | N/A | N/A | 2848 |
| 951769 | 85217 | 85232 | TTAATTAAGCTCTGGT | 12 | N/A | N/A | 2849 |
| 951770 | 85218 | 85233 | CTTAATTAAGCTCTGG | 22 | N/A | N/A | 2850 |
| 951771 | 85220 | 85235 | GGCTTAATTAAGCTCT | 67 | N/A | N/A | 2851 |
| 951772 | 85238 | 85253 | AGTGACATAGCAAGCA | 7 | N/A | N/A | 2852 |
| 951773 | 85417 | 85432 | AAGAATCAGACTCTTC | 110 | N/A | N/A | 2853 |
| 951774 | 85726 | 85741 | CATTTATAACAGGCA | 82 | N/A | N/A | 2854 |
| 951775 | 85727 | 85742 | CCATTTATAACAGGCC | 94 | N/A | N/A | 2855 |
| 951776 | 85844 | 85859 | GGCTTATGAGTCCACT | 91 | N/A | N/A | 2856 |
| 951777 | 85973 | 85988 | TGCATTAAAACTGCGA | 87 | N/A | N/A | 2857 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951778 | 86550 | 86565 | AACAATCATAGCCTCA | 114 | N/A | N/A | 2858 |
| 951779 | 86582 | 86597 | AACTTACTGTCTCCCA | 37 | N/A | N/A | 2859 |
| 951780 | 86937 | 86952 | GTTTAATAATGTGCAG | 40 | N/A | N/A | 2860 |
| 951781 | 86938 | 86953 | GGTTTAATAATGTGCA | 11 | N/A | N/A | 2861 |
| 951782 | 86939 | 86954 | GGGTTTAATAATGTGC | 27 | N/A | N/A | 2862 |
| 951783 | 87671 | 87686 | TCGCTAAAGGCTCTGA | 10 | N/A | N/A | 2863 |
| 951784 | 87858 | 87873 | TGAAATCAGGGCTCCC | 31 | N/A | N/A | 2864 |
| 951785 | 88030 | 88045 | CTCTATCACAGGGCCC | 92 | N/A | N/A | 2865 |
| 951786 | 88032 | 88047 | TGCTCTATCACAGGGC | 30 | N/A | N/A | 2866 |
| 951787 | 88258 | 88273 | TGTATCTGGTGACTCC | 5 | N/A | N/A | 2867 |
| 951788 | 88270 | 88285 | ACCGATAAATGTTGTA | 65 | N/A | N/A | 2868 |
| 951789 | 88634 | 88649 | TATAGTAACAGCTGGG | 73 | N/A | N/A | 2869 |
| 951790 | 88637 | 88652 | CAGTATAGTAACAGCT | 94 | N/A | N/A | 2870 |
| 951791 | 88638 | 88653 | TCAGTATAGTAACAGC | 41 | N/A | N/A | 2871 |
| 951792 | 88880 | 88895 | TGTTTAAGGACTCCAC | 28 | N/A | N/A | 2872 |
| 951793 | 88887 | 88902 | GACAATTTGTTTAAGG | 5 | N/A | N/A | 2873 |
| 951794 | 89152 | 89167 | GATCTAATCAGAAGCA | 29 | N/A | N/A | 2874 |
| 951795 | 89558 | 89573 | TGAGATTACGCACCAC | 5 | N/A | N/A | 2875 |
| 951796 | 89718 | 89733 | ATTATAGGGCTTCTTA | 30 | N/A | N/A | 2876 |
| 951797 | 89720 | 89735 | TTATTATAGGGCTTCT | 8 | N/A | N/A | 2877 |
| 951798 | 89721 | 89736 | TTTATTATAGGGCTTC | 1 | N/A | N/A | 2878 |
| 951799 | 89722 | 89737 | GTTTATTATAGGGCTT | 1 | N/A | N/A | 2879 |
| 951800 | 89746 | 89761 | AGTGATATTCCCAACA | 19 | N/A | N/A | 2880 |
| 951801 | 89977 | 89992 | CATATATCTCCTGTTA | 20 | N/A | N/A | 2881 |
| 951802 | 89999 | 90014 | TCATATCACCACTTGC | 29 | N/A | N/A | 2882 |
| 951803 | 90003 | 90018 | ACAATCATATCACCAC | 6 | N/A | N/A | 2883 |
| 951804 | 90004 | 90019 | GACAATCATATCACCA | 3 | N/A | N/A | 2884 |
| 951805 | 90058 | 90073 | TTATATGTGGACACCT | 34 | N/A | N/A | 2885 |
| 951806 | 90059 | 90074 | TTTATATGTGGACACC | 10 | N/A | N/A | 2886 |
| 951807 | 90139 | 90154 | CACAATCCCAGATCTC | 7 | N/A | N/A | 2887 |
| 951808 | 90161 | 90176 | TCTATAAGGTTCCTTA | 14 | N/A | N/A | 2888 |
| 951809 | 90165 | 90180 | TGTTTCTATAAGGTTC | 3 | N/A | N/A | 2889 |
| 951810 | 90199 | 90214 | CCAAATTTAGAGGACA | 46 | N/A | N/A | 2890 |
| 951811 | 90222 | 90237 | ACATATCTTGCATGAC | 4 | N/A | N/A | 2891 |
| 951812 | 90264 | 90279 | TTAGACATCAGACTGT | 76 | N/A | N/A | 2892 |
| 951813 | 90267 | 90282 | GTCTTAGACATCAGAC | 115 | N/A | N/A | 2893 |
| 951814 | 90706 | 90721 | TCAATTGAGGCTTCTA | 7 | N/A | N/A | 2894 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951815 | 90716 | 90731 | TGTATCTGGTTCAATT | 11 | N/A | N/A | 2895 |
| 951816 | 90721 | 90736 | GTAAATGTATCTGGTT | 2 | N/A | N/A | 2896 |
| 951817 | 91071 | 91086 | GGTACTGAGGCTGTGG | 28 | N/A | N/A | 2897 |
| 951818 | 91117 | 91132 | CAGAATTATCAATTCC | 145 | N/A | N/A | 2898 |
| 951819 | 91174 | 91189 | GGTGGGTAAAATGTGC | 63 | N/A | N/A | 2899 |
| 951820 | 91191 | 91206 | GCACATAGGGCCTTCT | 79 | N/A | N/A | 2900 |
| 951821 | 91909 | 91924 | GACAATGTAGTTTCCA | 2 | N/A | N/A | 2901 |
| 951822 | 91939 | 91954 | AACTATCCCAAGCTCC | 10 | N/A | N/A | 2902 |
| 951823 | 91945 | 91960 | GGCTTCAACTATCCCA | 39 | N/A | N/A | 2903 |
| 951824 | 92037 | 92052 | ATTGATACAGCCGTTC | 8 | N/A | N/A | 2904 |
| 951825 | 92827 | 92842 | ATGATAAAGGCTGGCA | 21 | N/A | N/A | 2905 |
| 951826 | 92828 | 92843 | AATGATAAAGGCTGGC | 127 | N/A | N/A | 2906 |
| 951827 | 93169 | 93184 | AAGATTATGGTTTCCT | 4 | N/A | N/A | 2907 |
| 951828 | 93170 | 93185 | GAAGATTATGGTTTCC | 6 | N/A | N/A | 2908 |
| 951829 | 93241 | 93256 | GTACATGGTGGAGTCC | 83 | N/A | N/A | 2909 |
| 951830 | 93321 | 93336 | TGTATTACCTACGGCA | 6 | N/A | N/A | 2910 |
| 951831 | 93392 | 93407 | GCTATTAATCATATTC | 18 | N/A | N/A | 2911 |
| 951832 | 93572 | 93587 | TACTTACCAGGATCTC | 24 | N/A | N/A | 2912 |
| 951833 | 93746 | 93761 | ACTTATACCCAGGGCA | 7 | N/A | N/A | 2913 |
| 951834 | 93747 | 93762 | GACTTATACCCAGGGC | 81 | N/A | N/A | 2914 |
| 951835 | 93923 | 93938 | ATGAATTCTGGTCTGG | 2 | N/A | N/A | 2915 |
| 951836 | 94043 | 94058 | TCAACTAGCCATGTCT | 25 | N/A | N/A | 2916 |
| 951837 | 94169 | 94184 | CACTTAGCCACATCTG | 5 | N/A | N/A | 2917 |
| 951838 | 94174 | 94189 | TTAATCACTTAGCCAC | 8 | N/A | N/A | 2918 |
| 951839 | 94177 | 94192 | ACCTTAATCACTTAGC | 5 | N/A | N/A | 2919 |
| 951840 | 94182 | 94197 | ACAATACCTTAATCAC | 7 | N/A | N/A | 2920 |
| 951841 | 94284 | 94299 | CAATTTATCTGGAGGA | 8 | N/A | N/A | 2921 |
| 951842 | 94350 | 94365 | TCAATTAGTGTTGCCT | 119 | N/A | N/A | 2922 |
| 951843 | 94351 | 94366 | ATCAATTAGTGTTGCC | 5 | N/A | N/A | 2923 |
| 951844 | 94423 | 94438 | GTCAATCGACTGGTAC | 41 | N/A | N/A | 2924 |
| 951845 | 94446 | 94461 | ATATGATTCATCTCGG | 2 | N/A | N/A | 2925 |
| 951846 | 94447 | 94462 | AATATGATTCATCTCG | 2 | N/A | N/A | 2926 |
| 951847 | 94583 | 94598 | AGCTATGAGTAGCAGG | 18 | N/A | N/A | 2927 |
| 951848 | 94885 | 94900 | GCCAACTAATTCCTCC | 31 | N/A | N/A | 2928 |
| 951849 | 96000 | 96015 | GCCATTCACGGGCTGC | 104 | N/A | N/A | 2929 |
| 951850 | 96084 | 96099 | CAAGGGTACAGACTTA | 152 | N/A | N/A | 2930 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951851 | 96224 | 96239 | GGCTGGATGTGAGTGC | 63 | N/A | N/A | 2931 |
| 951852 | 96650 | 96665 | ACAACTAACGGCAGGC | 17 | N/A | N/A | 2932 |
| 951853 | 96755 | 96770 | ACACATCAGGGTTTCA | 56 | N/A | N/A | 2933 |
| 951854 | 97483 | 97498 | TCCTAATGGTGACTCA | 40 | N/A | N/A | 2934 |
| 951855 | 97854 | 97869 | TACAATGTAAGCCTTT | 7 | N/A | N/A | 2935 |
| 951856 | 98522 | 98537 | GTATTTCAAAGTAGTC | 4 | N/A | N/A | 2936 |
| 951857 | 98652 | 98667 | GGTTTTAATAGACACA | 6 | N/A | N/A | 2937 |
| 951858 | 98653 | 98668 | GGGTTTTAATAGACAC | 53 | N/A | N/A | 2938 |
| 951859 | 99483 | 99498 | GTTAACAACAATTGTC | 60 | N/A | N/A | 2939 |
| 951860 | 99712 | 99727 | ACAGATCTTGCATGTT | 84 | N/A | N/A | 2940 |
| 951861 | 99888 | 99903 | AGCTATCACACAGAAG | 95 | N/A | N/A | 2941 |
| 951862 | 100033 | 100048 | GCAAATCCATTGCCCA | 78 | N/A | N/A | 2942 |
| 951863 | 100171 | 100186 | GTGTTAAGGTGGCAAC | 43 | N/A | N/A | 2943 |
| 951864 | 100222 | 100237 | CTACATGGTGATGGGT | 20 | N/A | N/A | 2944 |
| 951865 | 100285 | 100300 | GTTAGCTGGACTCACA | 89 | N/A | N/A | 2945 |
| 951866 | 100375 | 100390 | CAATATCCTGGTGACT | 36 | N/A | N/A | 2946 |
| 951867 | 100514 | 100529 | ACACATGCAGTGAGCC | 60 | N/A | N/A | 2947 |
| 951868 | 101384 | 101399 | TGTATGGTGGCTCAGC | 26 | N/A | N/A | 2948 |
| 951869 | 101385 | 101400 | TTGTATGGTGGCTCAG | 44 | N/A | N/A | 2949 |
| 951870 | 101796 | 101811 | TGCAATGCTGCCAGGC | 72 | N/A | N/A | 2950 |
| 951871 | 102161 | 102176 | AGAGATATTGATGTCT | 51 | N/A | N/A | 2951 |
| 951872 | 102425 | 102440 | GCACATTGGTTAGGCT | 93 | N/A | N/A | 2952 |
| 951873 | 102445 | 102460 | CTCAATGTGTACAGTA | 22 | N/A | N/A | 2953 |
| 951874 | 102885 | 102900 | TGGAACTGTTTACAGT | 10 | N/A | N/A | 2954 |
| 951875 | 102926 | 102941 | CAAGTAACTGAGTCAC | 7 | N/A | N/A | 2955 |
| 951876 | 103421 | 103436 | ATCTATCCAAGGAGGA | 93 | N/A | N/A | 2956 |
| 951877 | 103897 | 103912 | TCAGTTCACGGATCCC | 42 | N/A | N/A | 2957 |
| 951878 | 104120 | 104135 | TGCTTTCTAAGGTTGG | 14 | N/A | N/A | 2958 |
| 951879 | 104441 | 104456 | TTTTATCTGGGCTCCA | 39 | N/A | N/A | 2959 |
| 951880 | 104447 | 104462 | TGGAACTTTTATCTGG | 17 | N/A | N/A | 2960 |
| 951881 | 104452 | 104467 | GTGAATGGAACTTTTA | 5 | N/A | N/A | 2961 |
| 951882 | 104843 | 104858 | TGTATATGAGCCCATC | 99 | N/A | N/A | 2962 |
| 951883 | 105539 | 105554 | TCATATCCATGCCCAC | 31 | N/A | N/A | 2963 |
| 951884 | 105559 | 105574 | ACAATTGGTGCCTTTC | 14 | N/A | N/A | 2964 |
| 951885 | 105560 | 105575 | CACAATTGGTGCCTTT | 20 | N/A | N/A | 2965 |
| 951886 | 105730 | 105745 | GGACATCACACTCCTC | 100 | N/A | N/A | 2966 |
| 951887 | 105777 | 105792 | CGCAATGGTGACTGCC | 114 | N/A | N/A | 2967 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951888 | 105791 | 105806 | TGAAATACCATCCACG | 40 | N/A | N/A | 2968 |
| 951889 | 105793 | 105808 | CTTGAAATACCATCCA | 19 | N/A | N/A | 2969 |
| 951890 | 106015 | 106030 | GCCTTTACTGACAGCT | 71 | N/A | N/A | 2970 |
| 951891 | 106173 | 106188 | ACAAATGGGTCTCGAG | 101 | N/A | N/A | 2971 |
| 951892 | 106195 | 106210 | GGTTTTCACGGCCAGC | 44 | N/A | N/A | 2972 |
| 951893 | 106203 | 106218 | GCTATGAAGGTTTTCA | 10 | N/A | N/A | 2973 |
| 951894 | 106204 | 106219 | AGCTATGAAGGTTTTC | 20 | N/A | N/A | 2974 |
| 951895 | 106233 | 106248 | TGTCATATGGCCAGGG | 17 | N/A | N/A | 2975 |
| 951896 | 106295 | 106310 | TAATATTGTCACCCTC | 93 | N/A | N/A | 2976 |
| 951897 | 106296 | 106311 | ATAATATTGTCACCCT | 29 | N/A | N/A | 2977 |
| 951898 | 106351 | 106366 | GTTTTTGCAGCTACTA | 9 | N/A | N/A | 2978 |
| 951899 | 106371 | 106386 | ACTATCAACCATCTTA | 20 | N/A | N/A | 2979 |
| 951900 | 106391 | 106406 | GGACTTAATTTACACA | 12 | N/A | N/A | 2980 |
| 951901 | 106392 | 106407 | TGGACTTAATTTACAC | 30 | N/A | N/A | 2981 |
| 951902 | 106404 | 106419 | GATACTAAAGTCTGGA | 11 | N/A | N/A | 2982 |
| 951903 | 107100 | 107115 | GCAGATGGTGGTCTAC | 69 | N/A | N/A | 2983 |
| 951904 | 109198 | 109213 | GCATTTTAATATTGGG | 31 | N/A | N/A | 2984 |
| 951905 | 109409 | 109424 | GGTTTAAGCGATCTCC | 46 | N/A | N/A | 2985 |
| 951906 | 109955 | 109970 | CCAATAACTGACCTCA | 72 | N/A | N/A | 2986 |
| 951907 | 109956 | 109971 | ACCAATAACTGACCTC | 54 | N/A | N/A | 2987 |
| 951908 | 111211 | 111226 | AGTTATTCTGATGCCA | 3 | N/A | N/A | 2988 |
| 951909 | 111349 | 111364 | GGGTATGGTTGCAACC | 92 | N/A | N/A | 2989 |
| 951910 | 111384 | 111399 | TCATTAGGACACAGCG | 20 | N/A | N/A | 2990 |
| 951911 | 111385 | 111400 | ATCATTAGGACACAGC | 6 | N/A | N/A | 2991 |
| 951912 | 111494 | 111509 | TACTATCAGTACAGCT | 83 | N/A | N/A | 2992 |
| 951913 | 111496 | 111511 | GATACTATCAGTACAG | 42 | N/A | N/A | 2993 |
| 951914 | 111499 | 111514 | GGAGATACTATCAGTA | 115 | N/A | N/A | 2994 |
| 951915 | 111500 | 111515 | TGGAGATACTATCAGT | 27 | N/A | N/A | 2995 |
| 951916 | 112149 | 112164 | GTGAACACTGATCACT | 86 | N/A | N/A | 2996 |
| 951917 | 112185 | 112200 | GGTATATGAGGAAACA | 18 | N/A | N/A | 2997 |
| 951918 | 112208 | 112223 | CCGTATATGTCTCCGA | 8 | N/A | N/A | 2998 |
| 951919 | 112209 | 112224 | ACCGTATATGTCTCCG | 7 | N/A | N/A | 2999 |
| 951920 | 112293 | 112308 | GGCAATTGTCTCTCTT | 47 | N/A | N/A | 3000 |
| 951921 | 112316 | 112331 | TGTATAAGCTCACTTT | 40 | N/A | N/A | 3001 |
| 951922 | 112318 | 112333 | CATGTATAAGCTCACT | 105 | N/A | N/A | 3002 |
| 951923 | 112320 | 112335 | AGCATGTATAAGCTCA | 36 | N/A | N/A | 3003 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 951924 | 112369 | 112384 | ATAATTATGTCCCATC | 24 | N/A | N/A | 3004 |
| 951925 | 112370 | 112385 | GATAATTATGTCCCAT | 5 | N/A | N/A | 3005 |
| 951926 | 112371 | 112386 | GGATAATTATGTCCCA | 61 | N/A | N/A | 3006 |
| 951927 | 112372 | 112387 | TGGATAATTATGTCCC | 102 | N/A | N/A | 3007 |
| 951928 | 112373 | 112388 | ATGGATAATTATGTCC | 105 | N/A | N/A | 3008 |
| 951929 | 112950 | 112965 | ACTACTAGTTTCTGTT | 91 | N/A | N/A | 3009 |
| 951930 | 112951 | 112966 | CACTACTAGTTTCTGT | 37 | N/A | N/A | 3010 |
| 951931 | 113712 | 113727 | GGTTATGAGATTCTTA | 4 | N/A | N/A | 3011 |
| 951932 | 113713 | 113728 | TGGTTATGAGATTCTT | 5 | N/A | N/A | 3012 |
| 951933 | 114474 | 114489 | TTTATTCACAGGGTCC | 29 | N/A | N/A | 3013 |
| 951934 | 114476 | 114491 | TATTTATTCACAGGGT | 28 | N/A | N/A | 3014 |
| 951935 | 114477 | 114492 | GTATTTATTCACAGGG | 18 | N/A | N/A | 3015 |
| 951936 | 114510 | 114525 | GCCAATGGAAGGCACC | 129 | N/A | N/A | 3016 |
| 951937 | 114524 | 114539 | TCCATTTGGGCTGTGC | 86 | N/A | N/A | 3017 |
| 951938 | 114750 | 114765 | TGCGATATCCTCCCCT | 15 | N/A | N/A | 3018 |
| 951939 | 115717 | 115732 | GAGAATAAAGCCTGGC | 80 | N/A | N/A | 3019 |
| 908415 | 83669 83757 83845 | 83684 83772 83860 | GATTGAGGTAAGGGTT | 20 | N/A N/A N/A | N/A N/A N/A | 3020 |
| 908426 | 83689 83777 83865 | 83704 83792 83880 | ACGGAACCGCTCTGTA | 88 | N/A N/A N/A | N/A N/A N/A | 509 |
| 908428 | 83691 83779 83867 | 83706 83794 83882 | TGACGGAACCGCTCTG | 73 | N/A N/A N/A | N/A N/A N/A | 511 |
| 908507 | 103213 103251 | 103228 103266 | AGCAGAGCATAGGAGA | 20 | N/A N/A | N/A N/A | 590 |
| 949039 | 7946 8587 | 7961 8602 | AAGTGCTATTATAACT | 100 | N/A N/A | N/A N/A | 3021 |
| 949040 | 7947 8588 | 7962 8603 | GAAGTGCTATTATAAC | 8 | N/A N/A | N/A N/A | 3022 |
| 949041 | 7948 8589 | 7963 8604 | AGAAGTGCTATTATAA | 6 | N/A N/A | N/A N/A | 3023 |
| 949042 | 7949 8590 | 7964 8605 | AAGAAGTGCTATTATA | 15 | N/A N/A | N/A N/A | 3024 |
| 949043 | 7950 8591 | 7965 8606 | AAAGAAGTGCTATTAT | 37 | N/A N/A | N/A N/A | 3025 |
| 949044 | 7951 8592 | 7966 8607 | GAAAGAAGTGCTATTA | 19 | N/A N/A | N/A N/A | 3026 |
| 949045 | 7952 8593 | 7967 8608 | GGAAAGAAGTGCTATT | 20 | N/A N/A | N/A N/A | 3027 |
| 949046 | 7953 8594 | 7968 8609 | GGGAAAGAAGTGCTAT | 36 | N/A N/A | N/A N/A | 3028 |
| 949047 | 7954 8595 | 7969 8610 | AGGGAAAGAAGTGCTA | 64 | N/A N/A | N/A N/A | 3029 |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949048 | 7955 | 7970 | AAGGGAAAGAAGTGCT | 22 | N/A | N/A | 3030 |
|  | 8596 | 8611 |  |  | N/A | N/A |  |
| 949049 | 7956 | 7971 | AAAGGGAAAGAAGTGC | 21 | N/A | N/A | 3031 |
|  | 8597 | 8612 |  |  | N/A | N/A |  |
| 949060 | 9158 | 9173 | TAAAATGTACCCCCTC | 42 | N/A | N/A | 3032 |
|  | 9478 | 9493 |  |  | N/A | N/A |  |
| 949133 | 16330 | 16345 | GAAAAGAACAACCTGG | 21 | N/A | N/A | 3033 |
|  | 16655 | 16670 |  |  | N/A | N/A |  |
| 949913 | 83642 | 83657 | TGCAGCTGTCAGCATG | 61 | N/A | N/A | 3034 |
|  | 83730 | 83745 |  |  | N/A | N/A |  |
|  | 83818 | 83833 |  |  | N/A | N/A |  |
| 949914 | 83643 | 83658 | ATGCAGCTGTCAGCAT | 113 | N/A | N/A | 3035 |
|  | 83731 | 83746 |  |  | N/A | N/A |  |
|  | 83819 | 83834 |  |  | N/A | N/A |  |
| 949915 | 83644 | 83659 | TATGCAGCTGTCAGCA | 59 | N/A | N/A | 3036 |
|  | 83732 | 83747 |  |  | N/A | N/A |  |
|  | 83820 | 83835 |  |  | N/A | N/A |  |
| 949916 | 83645 | 83660 | ATATGCAGCTGTCAGC | 16 | N/A | N/A | 3037 |
|  | 83733 | 83748 |  |  | N/A | N/A |  |
|  | 83821 | 83836 |  |  | N/A | N/A |  |
| 949917 | 83648 | 83663 | GCCATATGCAGCTGTC | 13 | N/A | N/A | 3038 |
|  | 83736 | 83751 |  |  | N/A | N/A |  |
|  | 83824 | 83839 |  |  | N/A | N/A |  |
| 949918 | 83652 | 83667 | CTTTGCCATATGCAGC | 8 | N/A | N/A | 3039 |
|  | 83740 | 83755 |  |  | N/A | N/A |  |
|  | 83828 | 83843 |  |  | N/A | N/A |  |
| 949919 | 83653 | 83668 | ACTTTGCCATATGCAG | 15 | N/A | N/A | 3040 |
|  | 83741 | 83756 |  |  | N/A | N/A |  |
|  | 83829 | 83844 |  |  | N/A | N/A |  |
| 949920 | 83654 | 83669 | TACTTTGCCATATGCA | 4 | N/A | N/A | 3041 |
|  | 83742 | 83757 |  |  | N/A | N/A |  |
|  | 83830 | 83845 |  |  | N/A | N/A |  |
| 949921 | 83655 | 83670 | TTACTTTGCCATATGC | 1 | N/A | N/A | 3042 |
|  | 83743 | 83758 |  |  | N/A | N/A |  |
|  | 83831 | 83846 |  |  | N/A | N/A |  |
| 949922 | 83656 | 83671 | GTTACTTTGCCATATG | 4 | N/A | N/A | 3043 |
|  | 83744 | 83759 |  |  | N/A | N/A |  |
|  | 83832 | 83847 |  |  | N/A | N/A |  |
| 949923 | 83657 | 83672 | GGTTACTTTGCCATAT | 8 | N/A | N/A | 3044 |
|  | 83745 | 83760 |  |  | N/A | N/A |  |
|  | 83833 | 83848 |  |  | N/A | N/A |  |
| 949924 | 83668 | 83683 | ATTGAGGTAAGGGTTA | 4 | N/A | N/A | 3045 |
|  | 83756 | 83771 |  |  | N/A | N/A |  |
|  | 83844 | 83859 |  |  | N/A | N/A |  |
| 949925 | 83675 | 83690 | TATCTTGATTGAGGTA | 6 | N/A | N/A | 3046 |
|  | 83763 | 83778 |  |  | N/A | N/A |  |
|  | 83851 | 83866 |  |  | N/A | N/A |  |
| 949926 | 83676 | 83691 | GTATCTTGATTGAGGT | 2 | N/A | N/A | 3047 |
|  | 83764 | 83779 |  |  | N/A | N/A |  |
|  | 83852 | 83867 |  |  | N/A | N/A |  |
| 949927 | 83677 | 83692 | TGTATCTTGATTGAGG | 1 | N/A | N/A | 3048 |
|  | 83765 | 83780 |  |  | N/A | N/A |  |
|  | 83853 | 83868 |  |  | N/A | N/A |  |

TABLE 3-continued

DNM2 mRNA Expression

| Compound Number | SEQ ID: 1 Start Site | SEQ ID: 1 Stop Site | Sequence | Dynamin2 (% Control) | SEQ ID: 2 Start Site | SEQ ID 2: Stop Site | SEQ ID NO |
|---|---|---|---|---|---|---|---|
| 949928 | 83678 | 83693 | CTGTATCTTGATTGAG | 4 | N/A | N/A | 3049 |
|  | 83766 | 83781 |  |  | N/A | N/A |  |
|  | 83854 | 83869 |  |  | N/A | N/A |  |
| 949929 | 83682 | 83697 | CGCTCTGTATCTTGAT | 2 | N/A | N/A | 3050 |
|  | 83770 | 83785 |  |  | N/A | N/A |  |
|  | 83858 | 83873 |  |  | N/A | N/A |  |
| 949930 | 83683 | 83698 | CCGCTCTGTATCTTGA | 9 | N/A | N/A | 3051 |
|  | 83771 | 83786 |  |  | N/A | N/A |  |
|  | 83859 | 83874 |  |  | N/A | N/A |  |
| 949931 | 83700 | 83715 | TTTAGGAGGTGACGGA | 6 | N/A | N/A | 3052 |
|  | 83788 | 83803 |  |  | N/A | N/A |  |
|  | 83876 | 83891 |  |  | N/A | N/A |  |
| 949932 | 83701 | 83716 | TTTTAGGAGGTGACGG | 7 | N/A | N/A | 3053 |
|  | 83789 | 83804 |  |  | N/A | N/A |  |
|  | 83877 | 83892 |  |  | N/A | N/A |  |
| 949933 | 83702 | 83717 | ATTTTAGGAGGTGACG | 17 | N/A | N/A | 3054 |
|  | 83878 | 83893 |  |  | N/A | N/A |  |
| 949934 | 83703 | 83718 | GATTTTAGGAGGTGAC | 15 | N/A | N/A | 3055 |
|  | 83879 | 83894 |  |  | N/A | N/A |  |
| 949935 | 83704 | 83719 | GGATTTTAGGAGGTGA | 6 | N/A | N/A | 3056 |
|  | 83880 | 83895 |  |  | N/A | N/A |  |
| 949936 | 83705 | 83720 | GGGATTTTAGGAGGTG | 15 | N/A | N/A | 3057 |
|  | 83881 | 83896 |  |  | N/A | N/A |  |
| 949937 | 83706 | 83721 | AGGGATTTTAGGAGGT | 8 | N/A | N/A | 3058 |
|  | 83882 | 83897 |  |  | N/A | N/A |  |
| 949938 | 83707 | 83722 | CAGGGATTTTAGGAGG | 12 | N/A | N/A | 3059 |
|  | 83883 | 83898 |  |  | N/A | N/A |  |
| 949939 | 83708 | 83723 | ACAGGGATTTTAGGAG | 18 | N/A | N/A | 3060 |
|  | 83884 | 83899 |  |  | N/A | N/A |  |
| 949940 | 83728 | 83743 | CAGCTGTCAGCATGAT | 63 | N/A | N/A | 3061 |
|  | 83816 | 83831 |  |  | N/A | N/A |  |
| 949941 | 83729 | 83744 | GCAGCTGTCAGCATGA | 67 | N/A | N/A | 3062 |
|  | 83817 | 83832 |  |  | N/A | N/A |  |
| 950194 | 103191 | 103206 | CGGTGGCCATGGAGGG | 67 | N/A | N/A | 3063 |
|  | 103229 | 103244 |  |  | N/A | N/A |  |
|  | 103267 | 103282 |  |  | N/A | N/A |  |
| 950195 | 103192 | 103207 | CCGGTGGCCATGGAGG | 98 | N/A | N/A | 3064 |
|  | 103230 | 103245 |  |  | N/A | N/A |  |
|  | 103268 | 103283 |  |  | N/A | N/A |  |
| 950196 | 103193 | 103208 | CCCGGTGGCCATGGAG | 91 | N/A | N/A | 3065 |
|  | 103231 | 103246 |  |  | N/A | N/A |  |
|  | 103269 | 103284 |  |  | N/A | N/A |  |
| 950197 | 103194 | 103209 | GCCCGGTGGCCATGGA | 122 | N/A | N/A | 3066 |
|  | 103232 | 103247 |  |  | N/A | N/A |  |
|  | 103270 | 103285 |  |  | N/A | N/A |  |
| 950198 | 103195 | 103210 | GGCCCGGTGGCCATGG | 106 | N/A | N/A | 3067 |
|  | 103233 | 103248 |  |  | N/A | N/A |  |
|  | 103271 | 103286 |  |  | N/A | N/A |  |
| 950199 | 103196 | 103211 | GGGCCCGGTGGCCATG | 125 | N/A | N/A | 3068 |
|  | 103234 | 103249 |  |  | N/A | N/A |  |
|  | 103272 | 103287 |  |  | N/A | N/A |  |
| 950200 | 103210 | 103225 | AGAGCATAGGAGAGGG | 20 | N/A | N/A | 3069 |
|  | 103248 | 103263 |  |  | N/A | N/A |  |

TABLE 3-continued

DNM2 mRNA Expression

| Compound Number | SEQ ID: 1 Start Site | SEQ ID: 1 Stop Site | Sequence | Dynamin2 (% Control) | SEQ ID 2 Start Site | SEQ ID 2: Stop Site | SEQ ID NO |
|---|---|---|---|---|---|---|---|
| 950201 | 103212 103250 | 103227 103265 | GCAGAGCATAGGAGAG | 21 | N/A N/A | N/A N/A | 3070 |
| 950202 | 103214 103252 | 103229 103267 | GAGCAGAGCATAGGAG | 23 | N/A N/A | N/A N/A | 3071 |
| 950203 | 103215 103253 | 103230 103268 | GGAGCAGAGCATAGGA | 22 | N/A N/A | N/A N/A | 3072 |
| 950204 | 103217 103255 | 103232 103270 | AGGGAGCAGAGCATAG | 53 | N/A N/A | N/A N/A | 3073 |
| 950205 | 103219 103257 | 103234 103272 | GGAGGGAGCAGAGCAT | 50 | N/A N/A | N/A N/A | 3074 |
| 950206 | 103221 103259 | 103236 103274 | ATGGAGGGAGCAGAGC | 53 | N/A N/A | N/A N/A | 3075 |
| 950297 | 113289 113606 | 113304 113621 | ATCCTGTTATATCTTT | 3 | N/A N/A | N/A N/A | 3076 |
| 950298 | 113290 113607 | 113305 113622 | AATCCTGTTATATCTT | 2 | N/A N/A | N/A N/A | 3077 |

Each modified oligonucleotide listed in the table below is 100% complementary to human DNM2 nucleic acid sequence GENBANK Number NM_001005361.2. (SEQ ID No: 3 (. As shown below, modified oligonucleotides complementary to human DNM2 inhibited human DNM2 mRNA expression.

TABLE 4

DNM2 mRNA Expression

| Compound Number | SEQ ID: 3 Start Site | SEQ ID: 3 Stop Site | Sequence | Dynamin2 (% Control) | SEQ ID NO |
|---|---|---|---|---|---|
| 948482 | 1735 | 1750 | CACCAGGATCTCCCCC | 30 | 3078 |
| 948483 | 1738 | 1753 | GATCACCAGGATCTCC | 101 | 3079 |
| 948509 | 1511 | 1526 | GCTTCTCGGCACACTT | 27 | 3080 |
| 948510 | 1512 | 1527 | AGCTTCTCGGCACACT | 48 | 3081 |
| 948511 | 1514 | 1529 | TGAGCTTCTCGGCACA | 111 | 3082 |
| 948512 | 1520 | 1535 | AGGAACTGAGCTTCTC | 39 | 3083 |
| 948513 | 1521 | 1536 | TAGGAACTGAGCTTCT | 37 | 3084 |

Example 3: Effect of Modified Oligonucleotides Complementary to Dynamin 2 In Vitro Modified oligonucleotides complementary to dynamin 2 (DNM2) nucleic acid were designed and tested for their effect on dynamin 2 mRNA in vitro. The modified oligonucleotides were tested in a series of experiments that had similar culture conditions.

A431 cells cultured at a density of 10,000 cells per well were treated with only 500 nM of modified oligonucleotide via free uptake or no modified oligonucleotide for untreated controls. After approximately 24 hours, RNA was isolated from the cells and DNM2 mRNA levels were measured by quantitative real-time PCR as described in Example 1.

The modified oligonucleotides described in the tables below each have a 3-10-3 cEt gapmer motif, wherein the central gap segment contains ten 2'-deoxynucleosides and is flanked by wing segments on the 3' and 5' ends, each containing three cEt nucleosides. Each modified oligonucleotide listed in the tables below is 100% complementary to human DNM2 nucleic acid sequence GENBANK Number NC_000019.10, truncated from 10715001 to 1083500 (SEQ ID NO: 1) and/or GENBANK Number NM_004945.3 (SEQ ID NO: 2). As shown below, modified oligonucleotides complementary to human DNM2 inhibited human DNM2 mRNA expression.

TABLE 5

DNM2 mRNA Expression

| Compound Number | SEQ ID: 1 Start Site | SEQ ID: 1 Stop Site | Sequence | DNM2 (% Control) | SEQ ID: 2 Start Site | SEQ ID 2: Stop Site | SEQ ID NO |
|---|---|---|---|---|---|---|---|
| 694824 | 57496 | 57511 | TTTTGGACTTGCAGTG | 25 | 443 | 458 | 3085 |
| 695171 | 82451 | 82466 | ACACACTTCAAACTCG | 30 | N/A | N/A | 13 |

TABLE 5-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 695171 | 82451 | 82466 | ACACACTTCAAACTCG | 26 | N/A | N/A | 13 |
| 695171 | 82451 | 82466 | ACACACTTCAAACTCG | 28 | N/A | N/A | 13 |
| 695171 | 82451 | 82466 | ACACACTTCAAACTCG | 31 | N/A | N/A | 13 |
| 695171 | 82451 | 82466 | ACACACTTCAAACTCG | 27 | N/A | N/A | 13 |
| 695171 | 82451 | 82466 | ACACACTTCAAACTCG | 42 | N/A | N/A | 13 |
| 695171 | 82451 | 82466 | ACACACTTCAAACTCG | 37 | N/A | N/A | 13 |
| 695171 | 82451 | 82466 | ACACACTTCAAACTCG | 29 | N/A | N/A | 13 |
| 951371 | 11922 | 11937 | GTTGATAGTCGGTTGT | 9 | N/A | N/A | 2452 |
| 951371 | 11922 | 11937 | GTTGATAGTCGGTTGT | 8 | N/A | N/A | 2452 |
| 951371 | 11922 | 11937 | GTTGATAGTCGGTTGT | 7 | N/A | N/A | 2452 |
| 951371 | 11922 | 11937 | GTTGATAGTCGGTTGT | 7 | N/A | N/A | 2452 |
| 951371 | 11922 | 11937 | GTTGATAGTCGGTTGT | 7 | N/A | N/A | 2452 |
| 951371 | 11922 | 11937 | GTTGATAGTCGGTTGT | 10 | N/A | N/A | 2452 |
| 951371 | 11922 | 11937 | GTTGATAGTCGGTTGT | 19 | N/A | N/A | 2452 |
| 951371 | 11922 | 11937 | GTTGATAGTCGGTTGT | 9 | N/A | N/A | 2452 |
| 988378 | 82447 | 82462 | ACTTCAAACTCGGCTC | 24 | N/A | N/A | 3086 |
| 988379 | 81166 | 81181 | AACTGTATTGATTAGC | 20 | 1492 | 1507 | 3087 |
| 988380 | 116569 | 116584 | GTGTGGTTAATATGGC | 2 | 3313 | 3328 | 3088 |
| 988381 | 116853 | 116868 | ATAGAATACAGAGTGC | 19 | 3597 | 3612 | 3089 |
| 988382 | 11917 | 11932 | TAGTCGGTTGTCTGGA | 21 | N/A | N/A | 3090 |
| 988383 | 11919 | 11934 | GATAGTCGGTTGTCTG | 37 | N/A | N/A | 3091 |
| 988384 | 11920 | 11935 | TGATAGTCGGTTGTCT | 67 | N/A | N/A | 3092 |
| 988385 | 11921 | 11936 | TTGATAGTCGGTTGTC | 26 | N/A | N/A | 3093 |
| 988386 | 11923 | 11938 | AGTTGATAGTCGGTTG | 3 | N/A | N/A | 3094 |
| 988387 | 11924 | 11939 | GAGTTGATAGTCGGTT | 5 | N/A | N/A | 3095 |
| 988388 | 11925 | 11940 | CGAGTTGATAGTCGGT | 9 | N/A | N/A | 3096 |
| 988389 | 11927 | 11942 | AGCGAGTTGATAGTCG | 42 | N/A | N/A | 3097 |
| 988390 | 24283 | 24298 | GTATTATGGTATGTGA | 14 | N/A | N/A | 3098 |
| 988391 | 24286 | 24301 | TAGGTATTATGGTATG | 20 | N/A | N/A | 3099 |
| 988392 | 24287 | 24302 | TTAGGTATTATGGTAT | 31 | N/A | N/A | 3100 |
| 988393 | 24288 | 24303 | ATTAGGTATTATGGTA | 29 | N/A | N/A | 3101 |
| 988394 | 24290 | 24305 | GGATTAGGTATTATGG | 6 | N/A | N/A | 3102 |
| 988395 | 82040 | 82055 | TTGGACTGTTTTCCCC | 39 | N/A | N/A | 3103 |
| 988396 | 82042 | 82057 | GTTTGGACTGTTTTCC | 7 | N/A | N/A | 3104 |
| 988397 | 82824 | 82839 | GATGTGTTTCCTGTGT | 2 | N/A | N/A | 3105 |
| 988398 | 82825 | 82840 | TGATGTGTTTCCTGTG | 3 | N/A | N/A | 3106 |

TABLE 5-continued

DNM2 mRNA Expression

| Compound Number | SEQ ID: 1 Start Site | SEQ ID: 1 Stop Site | Sequence | DNM2 (% Control) | SEQ ID: 2 Start Site | SEQ ID: 2 Stop Site | SEQ ID NO |
|---|---|---|---|---|---|---|---|
| 988399 | 82826 | 82841 | ATGATGTGTTTCCTGT | 5 | N/A | N/A | 3107 |
| 988400 | 82828 | 82843 | AGATGATGTGTTTCCT | 4 | N/A | N/A | 3108 |
| 988401 | 82829 | 82844 | CAGATGATGTGTTTCC | 4 | N/A | N/A | 3109 |
| 988402 | 82830 | 82845 | ACAGATGATGTGTTTC | 7 | N/A | N/A | 3110 |
| 988403 | 82832 | 82847 | ATACAGATGATGTGTT | 99 | N/A | N/A | 3111 |
| 988404 | 83917 | 83932 | TTTTTGAGAGGTTGAC | 19 | N/A | N/A | 3112 |
| 988405 | 89716 | 89731 | TATAGGGCTTCTTATC | 61 | N/A | N/A | 3113 |
| 988406 | 89717 | 89732 | TTATAGGGCTTCTTAT | 64 | N/A | N/A | 3114 |
| 988407 | 89723 | 89738 | AGTTTATTATAGGGCT | 8 | N/A | N/A | 3115 |
| 988408 | 89724 | 89739 | AAGTTTATTATAGGGC | 13 | N/A | N/A | 3116 |
| 988409 | 89725 | 89740 | TAAGTTTATTATAGGG | 25 | N/A | N/A | 3117 |
| 988410 | 89726 | 89741 | GTAAGTTTATTATAGG | 24 | N/A | N/A | 3118 |
| 988411 | 89727 | 89742 | AGTAAGTTTATTATAG | 96 | N/A | N/A | 3119 |
| 988412 | 90717 | 90732 | ATGTATCTGGTTCAAT | 34 | N/A | N/A | 3120 |
| 988413 | 90718 | 90733 | AATGTATCTGGTTCAA | 11 | N/A | N/A | 3121 |
| 988414 | 90719 | 90734 | AAATGTATCTGGTTCA | 8 | N/A | N/A | 3122 |
| 988415 | 90720 | 90735 | TAAATGTATCTGGTTC | 11 | N/A | N/A | 3123 |
| 988416 | 90723 | 90738 | AAGTAAATGTATCTGG | 15 | N/A | N/A | 3124 |
| 988417 | 90724 | 90739 | CAAGTAAATGTATCTG | 51 | N/A | N/A | 3125 |
| 988418 | 90725 | 90740 | ACAAGTAAATGTATCT | 45 | N/A | N/A | 3126 |
| 988419 | 90726 | 90741 | AACAAGTAAATGTATC | 109 | N/A | N/A | 3127 |
| 988420 | 93918 | 93933 | TTCTGGTCTGGCTTAA | 16 | N/A | N/A | 3128 |
| 988421 | 93920 | 93935 | AATTCTGGTCTGGCTT | 45 | N/A | N/A | 3129 |
| 988422 | 93922 | 93937 | TGAATTCTGGTCTGGC | 7 | N/A | N/A | 3130 |
| 988423 | 93924 | 93939 | AATGAATTCTGGTCTG | 30 | N/A | N/A | 3131 |
| 988424 | 93925 | 93940 | GAATGAATTCTGGTCT | 80 | N/A | N/A | 3132 |
| 988425 | 93926 | 93941 | AGAATGAATTCTGGTC | 20 | N/A | N/A | 3133 |
| 988426 | 93928 | 93943 | CAAGAATGAATTCTGG | 74 | N/A | N/A | 3134 |

Example 4: Dose Response of Modified Oligonucleotides Complementary to Dynamin 2 In Vitro Selected oligonucleotides listed in the Examples above were tested at various doses via free uptake in A431 cells. Cells were cultured at a density of 10,000 cells per well and treated with 62.5, 250, 1,000, or 4,000 nM of modified oligonucleotide, as specified in the table below. After a treatment period of approximately 48 hours, total RNA was isolated and analyzed by RT-PCR with primer probe set RTS36027 (described in Example 1), normalized with ribogreen. As illustrated in the tables below, DNM2 mRNA expression was inhibited in a dose-dependent manner by modified oligonucleotides complementary to DNM2.

TABLE 6

DNM2 mRNA Expression

| Compound Number | DNM2 expression (% control) | | | | $IC_{50}$ (μM) |
|---|---|---|---|---|---|
| | 62.5 nM | 250 nM | 1,000 nM | 4,000 nM | |
| 694838 | 31 | 12 | 5 | 3 | <0.1 |
| 695171 | 74 | 28 | 11 | 4 | 0.1 |
| 695171 | 83 | 33 | 11 | 5 | 0.2 |

TABLE 6-continued

DNM2 mRNA Expression

| Compound Number | DNM2 expression (% control) | | | | IC$_{50}$ (µM) |
|---|---|---|---|---|---|
| | 62.5 nM | 250 nM | 1,000 nM | 4,000 nM | |
| 695171 | 57 | 25 | 7 | 3 | 0.1 |
| 695171 | 59 | 24 | 9 | 4 | 0.1 |
| 695171 | 51 | 17 | 9 | 4 | <0.1 |
| 695171 | 57 | 28 | 10 | 4 | 0.1 |
| 907945 | 38 | 10 | 5 | 3 | <0.1 |
| 907946 | 70 | 36 | 17 | 11 | 0.2 |
| 907947 | 48 | 28 | 9 | 6 | <0.1 |
| 907948 | 51 | 22 | 9 | 5 | <0.1 |
| 907949 | 77 | 43 | 16 | 6 | 0.2 |
| 907966 | 53 | 30 | 15 | 8 | <0.1 |
| 907967 | 32 | 10 | 6 | 4 | <0.1 |
| 907968 | 65 | 30 | 14 | 8 | 0.1 |
| 907969 | 19 | 6 | 3 | 2 | <0.1 |
| 907970 | 20 | 5 | 3 | 2 | <0.1 |
| 907971 | 59 | 30 | 17 | 12 | 0.1 |
| 907972 | 72 | 36 | 18 | 17 | 0.2 |
| 907975 | 35 | 15 | 7 | 4 | <0.1 |
| 907979 | 55 | 26 | 14 | 10 | <0.1 |
| 907983 | 39 | 16 | 9 | 8 | <0.1 |
| 907998 | 40 | 13 | 6 | 4 | <0.1 |
| 908000 | 71 | 42 | 19 | 11 | 0.2 |
| 908011 | 53 | 24 | 13 | 9 | <0.1 |
| 908013 | 52 | 25 | 13 | 7 | <0.1 |
| 908025 | 69 | 31 | 13 | 6 | 0.1 |
| 908027 | 38 | 13 | 5 | 2 | <0.1 |
| 908028 | 80 | 51 | 22 | 9 | 0.3 |
| 908029 | 83 | 43 | 19 | 9 | 0.3 |
| 908031 | 44 | 13 | 4 | 2 | <0.1 |
| 908033 | 52 | 18 | 8 | 5 | <0.1 |
| 908034 | 63 | 29 | 13 | 8 | 0.1 |
| 908035 | 26 | 6 | 2 | 1 | <0.1 |
| 908036 | 71 | 39 | 20 | 11 | 0.2 |
| 908037 | 26 | 9 | 3 | 1 | <0.1 |
| 908041 | 49 | 19 | 6 | 3 | <0.1 |
| 908043 | 28 | 15 | 10 | 8 | <0.1 |
| 908044 | 43 | 17 | 7 | 3 | <0.1 |
| 908047 | 54 | 28 | 15 | 9 | <0.1 |
| 908049 | 49 | 15 | 6 | 3 | <0.1 |
| 908052 | 53 | 21 | 7 | 4 | <0.1 |
| 908055 | 69 | 36 | 19 | 12 | 0.2 |
| 908056 | 54 | 23 | 9 | 6 | <0.1 |
| 908059 | 35 | 11 | 3 | 2 | <0.1 |
| 908061 | 27 | 7 | 2 | 1 | <0.1 |
| 908068 | 72 | 41 | 21 | 10 | 0.2 |
| 908070 | 64 | 35 | 15 | 9 | 0.1 |
| 908085 | 68 | 33 | 18 | 11 | 0.1 |
| 908098 | 61 | 28 | 12 | 10 | 0.1 |
| 908102 | 42 | 28 | 17 | 11 | <0.1 |
| 908104 | 44 | 23 | 12 | 8 | <0.1 |
| 908107 | 51 | 25 | 11 | 7 | <0.1 |
| 908135 | 46 | 23 | 14 | 14 | <0.1 |
| 908138 | 50 | 24 | 11 | 6 | <0.1 |
| 908146 | 58 | 33 | 19 | 15 | 0.1 |
| 908147 | 37 | 18 | 10 | 6 | <0.1 |
| 908148 | 42 | 15 | 7 | 5 | <0.1 |
| 908154 | 28 | 9 | 3 | 2 | <0.1 |
| 908164 | 65 | 31 | 16 | 10 | 0.1 |
| 908166 | 44 | 18 | 9 | 5 | <0.1 |
| 908167 | 62 | 28 | 16 | 12 | 0.1 |
| 908177 | 69 | 37 | 15 | 7 | 0.2 |
| 908178 | 52 | 22 | 6 | 4 | <0.1 |
| 908179 | 47 | 18 | 7 | 4 | <0.1 |
| 908183 | 58 | 34 | 15 | 11 | 0.1 |
| 908184 | 56 | 24 | 11 | 8 | <0.1 |
| 908201 | 26 | 13 | 5 | 4 | <0.1 |
| 908213 | 37 | 13 | 5 | 3 | <0.1 |
| 908214 | 57 | 37 | 17 | 12 | 0.1 |
| 908215 | 63 | 30 | 12 | 6 | 0.1 |
| 908217 | 32 | 10 | 3 | 2 | <0.1 |
| 908232 | 58 | 26 | 6 | 3 | 0.1 |
| 908255 | 64 | 28 | 13 | 9 | 0.1 |
| 908267 | 48 | 28 | 12 | 8 | 0.1 |
| 908355 | 83 | 62 | 42 | 26 | 0.6 |
| 908389 | 43 | 16 | 5 | 3 | <0.1 |
| 908392 | 12 | 3 | 1 | 1 | <0.1 |
| 908396 | 57 | 19 | 6 | 3 | <0.1 |
| 908401 | 26 | 6 | 2 | 1 | <0.1 |
| 908404 | 58 | 29 | 15 | 8 | 0.1 |
| 908405 | 49 | 26 | 9 | 4 | <0.1 |
| 908407 | 70 | 30 | 12 | 5 | 0.1 |
| 908408 | 18 | 2 | 1 | 1 | <0.1 |
| 908409 | 67 | 33 | 13 | 5 | 0.1 |
| 908410 | 71 | 36 | 15 | 7 | 0.2 |
| 908412 | 58 | 24 | 10 | 6 | 0.1 |
| 908413 | 33 | 8 | 2 | 1 | <0.1 |
| 908414 | 25 | 6 | 3 | 2 | <0.1 |
| 908415 | 40 | 11 | 4 | 3 | <0.1 |
| 908416 | 42 | 13 | 4 | 1 | <0.1 |
| 908417 | 26 | 5 | 2 | 1 | <0.1 |
| 908418 | 63 | 33 | 11 | 4 | 0.1 |
| 908419 | 50 | 11 | 4 | 2 | <0.1 |
| 908420 | 17 | 3 | 1 | 1 | <0.1 |
| 908421 | 23 | 4 | 1 | 1 | <0.1 |
| 908422 | 51 | 16 | 5 | 3 | <0.1 |
| 908424 | 57 | 22 | 9 | 7 | <0.1 |
| 908425 | 57 | 38 | 20 | 12 | 0.1 |
| 908434 | 54 | 20 | 8 | 3 | <0.1 |
| 908436 | 71 | 40 | 17 | 8 | 0.2 |
| 908439 | 38 | 9 | 2 | 2 | <0.1 |
| 908440 | 25 | 6 | 3 | 3 | <0.1 |
| 908441 | 33 | 6 | 2 | 1 | <0.1 |
| 908442 | 32 | 9 | 3 | 1 | <0.1 |
| 908443 | 56 | 17 | 5 | 2 | <0.1 |
| 908444 | 31 | 7 | 2 | 1 | <0.1 |
| 908448 | 78 | 44 | 13 | 8 | 0.2 |
| 908449 | 47 | 20 | 7 | 4 | <0.1 |
| 908451 | 45 | 14 | 6 | 5 | <0.1 |
| 908475 | 66 | 29 | 12 | 5 | 0.1 |
| 908506 | 34 | 9 | 4 | 3 | <0.1 |
| 908507 | 67 | 39 | 16 | 10 | 0.1 |
| 908508 | 52 | 30 | 14 | 10 | <0.1 |

Example 5: Dose Response of Modified Oligonucleotides Complementary to Dynamin 2 In Vitro Selected oligonucleotides listed in the Examples above were tested via free uptake at various doses in A431 cells. Cells were cultured at a density of 10,000 cells per well and treated with 31.25, 125, 500, or 2,000 nM of modified oligonucleotide, as specified in the tables below. After approximately 48 hours, total RNA was isolated and analyzed by RT-PCR with primer probe set RTS36027 (described in Example 1), normalized with ribogreen. As illustrated in the tables below, DNM2 mRNA expression was inhibited in a dose-dependent manner by modified oligonucleotides complementary to DNM2.

TABLE 7

DNM2 mRNA Expression

| Compound Number | DNM2 expression (% control) | | | | IC50 (µM) |
|---|---|---|---|---|---|
| | 31.25 nM | 125 nM | 500 nM | 2,000 nM | |
| 695015 | 105 | 94 | 89 | 94 | >2.0 |
| 695170 | 62 | 30 | 13 | 5 | 0.05 |
| 695171 | 72 | 33 | 11 | 4 | 0.07 |
| 695171 | 70 | 33 | 10 | 3 | 0.1 |
| 695171 | 70 | 35 | 14 | 6 | 0.1 |
| 695171 | 58 | 22 | 9 | 2 | <0.03 |

TABLE 7-continued

DNM2 mRNA Expression

| Compound Number | DNM2 expression (% control) | | | | IC50 (μM) |
|---|---|---|---|---|---|
| | 31.25 nM | 125 nM | 500 nM | 2,000 nM | |
| 695171 | 71 | 36 | 12 | 4 | 0.08 |
| 695171 | 70 | 32 | 11 | 4 | 0.07 |
| 695171 | 74 | 36 | 12 | 4 | 0.08 |
| 695171 | 71 | 31 | 10 | 3 | 0.07 |
| 695171 | 73 | 36 | 14 | 4 | 0.08 |
| 695171 | 73 | 36 | 17 | 7 | 0.09 |
| 695171 | 54 | 27 | 10 | 3 | <0.03 |
| 695171 | 69 | 33 | 10 | 5 | 0.06 |
| 695171 | 74 | 35 | 12 | 4 | 0.08 |
| 695171 | 81 | 40 | 14 | 4 | 0.11 |
| 695171 | 79 | 40 | 14 | 5 | 0.11 |
| 695171 | 77 | 38 | 14 | 5 | 0.10 |
| 695171 | 72 | 37 | 13 | 5 | 0.08 |
| 695171 | 71 | 34 | 11 | 4 | 0.07 |
| 695171 | 66 | 43 | 11 | 5 | 0.08 |
| 695171 | 68 | 33 | 11 | 4 | 0.06 |
| 695171 | 63 | 29 | 12 | 5 | 0.05 |
| 948488 | 79 | 33 | 12 | 4 | 0.09 |
| 948489 | 53 | 17 | 5 | 1 | <0.03 |
| 948490 | 25 | 5 | 1 | 0 | <0.03 |
| 948492 | 67 | 32 | 9 | 4 | 0.06 |
| 948496 | 72 | 43 | 15 | 6 | 0.09 |
| 948505 | 67 | 36 | 12 | 5 | 0.07 |
| 948506 | 58 | 16 | 5 | 2 | <0.03 |
| 948507 | 80 | 30 | 9 | 3 | 0.1 |
| 948508 | 63 | 26 | 7 | 3 | 0.0 |
| 948521 | 79 | 35 | 19 | 13 | 0.11 |
| 948524 | 70 | 43 | 19 | 9 | 0.09 |
| 948525 | 75 | 47 | 19 | 7 | 0.12 |
| 948526 | 73 | 35 | 12 | 7 | 0.08 |
| 948527 | 62 | 31 | 14 | 9 | 0.05 |
| 948528 | 64 | 29 | 11 | 20 | 0.04 |
| 948538 | 104 | 95 | 96 | 91 | >2.0 |
| 948549 | 71 | 38 | 16 | 11 | 0.08 |
| 948556 | 36 | 11 | 4 | 3 | <0.03 |
| 948557 | 23 | 8 | 4 | 3 | <0.03 |
| 948558 | 68 | 29 | 14 | 10 | 0.06 |
| 948559 | 48 | 16 | 7 | 5 | <0.03 |
| 948560 | 24 | 7 | 3 | 2 | <0.03 |
| 948562 | 69 | 26 | 10 | 5 | 0.06 |
| 948568 | 57 | 26 | 11 | 7 | <0.03 |
| 948575 | 73 | 39 | 20 | 10 | 0.1 |
| 948587 | 43 | 14 | 7 | 4 | <0.03 |
| 948589 | 66 | 21 | 11 | 9 | 0.04 |
| 948590 | 53 | 35 | 16 | 10 | 0.03 |
| 948602 | 39 | 15 | 7 | 5 | <0.03 |
| 948604 | 42 | 17 | 7 | 4 | <0.03 |
| 948608 | 54 | 18 | 6 | 4 | <0.03 |
| 948622 | 79 | 47 | 22 | 10 | 0.13 |
| 948629 | 51 | 13 | 6 | 2 | <0.03 |
| 948630 | 67 | 33 | 13 | 5 | 0.06 |
| 948631 | 46 | 14 | 5 | 3 | <0.03 |
| 948632 | 42 | 12 | 5 | 2 | <0.03 |
| 948633 | 57 | 21 | 8 | 6 | <0.03 |
| 948646 | 63 | 58 | 23 | 10 | 0.11 |
| 948654 | 68 | 40 | 13 | 4 | 0.08 |
| 948656 | 69 | 40 | 22 | 13 | 0.09 |
| 948660 | 47 | 11 | 2 | 1 | <0.03 |
| 948661 | 80 | 41 | 14 | 4 | 0.11 |
| 948662 | 63 | 38 | 16 | 8 | 0.06 |
| 948664 | 45 | 12 | 2 | 1 | <0.03 |
| 948665 | 64 | 25 | 7 | 3 | 0.04 |
| 948666 | 82 | 37 | 12 | 4 | 0.11 |
| 948673 | 33 | 9 | 3 | 2 | <0.03 |
| 948674 | 75 | 39 | 12 | 5 | 0.1 |
| 948675 | 43 | 8 | 2 | 0 | <0.03 |
| 948676 | 40 | 10 | 2 | 0 | <0.03 |
| 948677 | 53 | 11 | 2 | 1 | <0.03 |
| 948678 | 69 | 27 | 9 | 4 | 0.06 |
| 948684 | 61 | 29 | 11 | 4 | 0.04 |
| 948685 | 52 | 15 | 5 | 2 | <0.03 |
| 948686 | 24 | 8 | 2 | 1 | <0.03 |
| 948687 | 58 | 19 | 5 | 2 | <0.03 |
| 948689 | 73 | 26 | 17 | 8 | 0.07 |
| 948692 | 49 | 20 | 8 | 6 | <0.03 |
| 948693 | 71 | 40 | 18 | 10 | 0.09 |
| 948695 | 75 | 38 | 20 | 7 | 0.1 |
| 948700 | 63 | 25 | 7 | 3 | 0.04 |
| 948701 | 64 | 24 | 9 | 4 | 0.04 |
| 948702 | 60 | 25 | 6 | 1 | 0.04 |
| 948703 | 66 | 29 | 7 | 2 | 0.05 |
| 948707 | 69 | 24 | 7 | 3 | 0.05 |
| 948729 | 47 | 12 | 2 | 1 | <0.03 |
| 948731 | 67 | 33 | 11 | 4 | 0.06 |
| 948732 | 68 | 40 | 14 | 7 | 0.08 |
| 948735 | 22 | 9 | 2 | 2 | <0.03 |
| 948741 | 49 | 55 | 24 | 15 | 0.06 |
| 948752 | 64 | 31 | 12 | 5 | 0.05 |
| 948765 | 61 | 20 | 7 | 3 | 0.03 |
| 948766 | 78 | 43 | 18 | 7 | 0.11 |
| 948767 | 76 | 40 | 19 | 12 | 0.1 |
| 948768 | 67 | 35 | 17 | 12 | 0.1 |
| 948769 | 60 | 24 | 10 | 5 | 0.0 |
| 948788 | 57 | 27 | 13 | 10 | 0.03 |
| 948794 | 51 | 26 | 5 | 2 | <0.03 |
| 948804 | 42 | 18 | 8 | 5 | <0.03 |
| 948805 | 34 | 13 | 5 | 3 | <0.03 |
| 948806 | 16 | 18 | 7 | 5 | <0.03 |
| 948807 | 56 | 35 | 18 | 11 | 0.04 |
| 948812 | 77 | 40 | 20 | 11 | 0.11 |
| 948835 | 66 | 28 | 7 | 3 | 0.05 |
| 948836 | 52 | 27 | 11 | 6 | <0.03 |
| 948847 | 68 | 32 | 12 | 7 | 0.06 |
| 948849 | 43 | 13 | 6 | 5 | <0.03 |
| 948850 | 43 | 15 | 7 | 5 | <0.03 |
| 948851 | 45 | 16 | 5 | 3 | <0.03 |
| 948852 | 51 | 16 | 4 | 2 | <0.03 |
| 948853 | 84 | 32 | 9 | 5 | 0.10 |
| 948854 | 58 | 21 | 7 | 3 | <0.03 |
| 948855 | 56 | 30 | 12 | 6 | 0.03 |
| 948856 | 70 | 38 | 14 | 8 | 0.08 |
| 948862 | 55 | 26 | 10 | 4 | <0.03 |
| 948863 | 43 | 8 | 2 | 2 | <0.03 |
| 948865 | 57 | 24 | 10 | 6 | <0.03 |
| 948880 | 84 | 46 | 26 | 14 | 0.16 |
| 948882 | 66 | 36 | 19 | 8 | 0.07 |
| 948883 | 81 | 62 | 29 | 16 | 0.21 |
| 948884 | 59 | 25 | 9 | 4 | 0.03 |
| 948885 | 53 | 18 | 6 | 4 | <0.03 |
| 948891 | 96 | 52 | 24 | 12 | 0.20 |
| 948892 | 54 | 24 | 7 | 4 | <0.03 |
| 948893 | 93 | 84 | 59 | 44 | 1.24 |
| 948906 | 81 | 46 | 19 | 9 | 0.13 |
| 948907 | 65 | 25 | 8 | 4 | 0.05 |
| 948910 | 62 | 22 | 8 | 4 | 0.0 |
| 948911 | 48 | 16 | 10 | 4 | <0.03 |
| 948917 | 81 | 57 | 30 | 19 | 0.20 |
| 948918 | 69 | 36 | 14 | 6 | 0.07 |
| 948922 | 64 | 32 | 12 | 6 | 0.05 |
| 948923 | 30 | 8 | 4 | 3 | <0.03 |
| 948924 | 32 | 11 | 3 | 2 | <0.03 |
| 948925 | 58 | 27 | 9 | 6 | 0.03 |
| 948926 | 109 | 94 | 105 | 111 | >2.0 |
| 948935 | 38 | 17 | 6 | 3 | <0.03 |
| 948936 | 47 | 12 | 4 | 2 | <0.03 |
| 948937 | 48 | 21 | 7 | 3 | <0.03 |
| 948938 | 49 | 19 | 8 | 5 | <0.03 |
| 948950 | 54 | 27 | 8 | 3 | <0.03 |
| 948951 | 32 | 13 | 5 | 3 | <0.03 |
| 948952 | 46 | 13 | 4 | 2 | <0.03 |
| 948953 | 69 | 41 | 14 | 7 | 0.08 |
| 948954 | 43 | 15 | 8 | 4 | <0.03 |
| 948960 | 41 | 14 | 8 | 7 | <0.03 |
| 948961 | 48 | 17 | 6 | 3 | <0.03 |
| 948963 | 51 | 23 | 8 | 4 | <0.03 |
| 948965 | 96 | 77 | 53 | 28 | 0.57 |
| 948966 | 63 | 32 | 11 | 4 | 0.05 |
| 948967 | 71 | 38 | 13 | 6 | 0.08 |

TABLE 7-continued

DNM2 mRNA Expression

| Compound Number | DNM2 expression (% control) | | | | IC50 (µM) |
|---|---|---|---|---|---|
| | 31.25 nM | 125 nM | 500 nM | 2,000 nM | |
| 948968 | 60 | 29 | 9 | 3 | 0.04 |
| 948969 | 47 | 18 | 6 | 4 | <0.03 |
| 948970 | 31 | 9 | 3 | 2 | <0.03 |
| 948971 | 34 | 9 | 2 | 2 | <0.03 |
| 948972 | 72 | 32 | 9 | 3 | 0.07 |
| 949006 | 79 | 53 | 19 | 8 | 0.1 |
| 949007 | 84 | 37 | 9 | 6 | 0.1 |
| 949012 | 81 | 38 | 17 | 10 | 0.11 |
| 949040 | 80 | 36 | 11 | 4 | 0.10 |
| 949041 | 101 | 50 | 14 | 5 | 0.18 |
| 949051 | 74 | 45 | 16 | 8 | 0.10 |
| 949053 | 89 | 54 | 18 | 5 | 0.2 |
| 949055 | 68 | 24 | 8 | 4 | 0.0 |
| 949059 | 73 | 40 | 15 | 5 | 0.09 |
| 949061 | 109 | 99 | 83 | 73 | >2.0 |
| 949077 | 82 | 47 | 15 | 5 | 0.1 |
| 949080 | 48 | 20 | 7 | 5 | <0.03 |
| 949088 | 73 | 24 | 8 | 3 | 0.06 |
| 949092 | 66 | 24 | 13 | 14 | 0.05 |
| 949094 | 79 | 48 | 17 | 6 | 0.13 |
| 949095 | 90 | 66 | 19 | 6 | 0.20 |
| 949109 | 95 | 55 | 26 | 13 | 0.22 |
| 949139 | 72 | 47 | 24 | 11 | 0.12 |
| 949158 | 54 | 20 | 10 | 8 | <0.03 |
| 949159 | 75 | 40 | 15 | 25 | 0.10 |
| 949163 | 52 | 15 | 4 | 2 | <0.03 |
| 949164 | 42 | 30 | 15 | 10 | <0.03 |
| 949167 | 78 | 39 | 17 | 21 | 0.11 |
| 949168 | 67 | 36 | 19 | 12 | 0.07 |
| 949182 | 65 | 27 | 8 | 4 | 0.05 |
| 949190 | 57 | 15 | 3 | 2 | <0.03 |
| 949216 | 74 | 42 | 14 | 5 | 0.10 |
| 949223 | 87 | 28 | 16 | 6 | 0.1 |
| 949229 | 125 | 101 | 92 | 78 | >2.0 |
| 949279 | 85 | 41 | 15 | 5 | 0.12 |
| 949325 | 98 | 112 | 86 | 75 | >2.0 |
| 949397 | 94 | 96 | 100 | 106 | >2.0 |
| 949483 | 71 | 43 | 21 | 11 | 0.10 |
| 949500 | 78 | 56 | 24 | 10 | 0.16 |
| 949517 | 103 | 98 | 97 | 80 | >2.0 |
| 949589 | 111 | 89 | 57 | 42 | 1.06 |
| 949685 | 101 | 82 | 58 | 40 | 0.99 |
| 949778 | 90 | 55 | 20 | 9 | 0.18 |
| 949805 | 106 | 88 | 66 | 48 | 1.73 |
| 949814 | 59 | 51 | 22 | 8 | 0.08 |
| 949841 | 87 | 46 | 11 | 4 | 0.13 |
| 949846 | 48 | 30 | 11 | 7 | <0.03 |
| 949848 | 57 | 18 | 4 | 2 | <0.03 |
| 949858 | 66 | 23 | 10 | 6 | 0.04 |
| 949865 | 61 | 11 | 3 | 1 | <0.03 |
| 949871 | 70 | 26 | 7 | 3 | 0.1 |
| 949872 | 47 | 13 | 3 | 1 | <0.03 |
| 949873 | 45 | 10 | 2 | 1 | <0.03 |
| 949874 | 14 | 3 | 1 | 0 | <0.03 |
| 949875 | 54 | 23 | 5 | 2 | <0.03 |
| 949876 | 79 | 32 | 10 | 5 | 0.09 |
| 949880 | 52 | 20 | 6 | 3 | <0.03 |
| 949884 | 87 | 41 | 16 | 7 | 0.13 |
| 949886 | 62 | 22 | 6 | 3 | 0.04 |
| 949887 | 87 | 64 | 21 | 8 | 0.19 |
| 949892 | 83 | 49 | 22 | 13 | 0.2 |
| 949896 | 13 | 1 | 1 | 0 | <0.03 |
| 949897 | 67 | 32 | 15 | 7 | 0.06 |
| 949899 | 80 | 49 | 20 | 6 | 0.14 |
| 949917 | 80 | 48 | 22 | 10 | 0.1 |
| 949918 | 84 | 46 | 15 | 4 | 0.1 |
| 949920 | 59 | 20 | 3 | 2 | <0.03 |
| 949921 | 67 | 19 | 2 | 1 | 0.04 |
| 949922 | 56 | 21 | 6 | 2 | <0.03 |
| 949923 | 70 | 34 | 15 | 7 | 0.07 |
| 949924 | 112 | 106 | 5 | 2 | 0.31 |
| 949925 | 59 | 27 | 6 | 2 | 0.04 |
| 949926 | 44 | 7 | 1 | 1 | <0.03 |
| 949927 | 37 | 4 | 1 | 1 | <0.03 |
| 949928 | 68 | 20 | 4 | 2 | 0.04 |
| 949929 | 66 | 18 | 3 | 1 | 0.04 |
| 949930 | 61 | 30 | 10 | 4 | 0.04 |
| 949931 | 68 | 27 | 6 | 2 | 0.05 |
| 949932 | 72 | 31 | 6 | 2 | 0.07 |
| 949934 | 66 | 42 | 22 | 12 | 0.08 |
| 949935 | 52 | 20 | 8 | 6 | <0.03 |
| 949937 | 69 | 27 | 7 | 5 | 0.06 |
| 949938 | 66 | 35 | 14 | 5 | 0.06 |
| 949942 | 69 | 30 | 8 | 3 | 0.06 |
| 949943 | 52 | 21 | 6 | 2 | <0.03 |
| 949944 | 60 | 20 | 4 | 3 | 0.03 |
| 949945 | 54 | 16 | 5 | 3 | <0.03 |
| 949948 | 34 | 5 | 1 | 1 | <0.03 |
| 949949 | 46 | 10 | 2 | 1 | <0.03 |
| 949950 | 46 | 12 | 3 | 2 | <0.03 |
| 949962 | 70 | 34 | 16 | 9 | 0.1 |
| 949963 | 71 | 43 | 15 | 6 | 0.1 |
| 949978 | 65 | 35 | 9 | 2 | 0.06 |
| 949979 | 72 | 35 | 11 | 5 | 0.08 |
| 949983 | 89 | 66 | 25 | 12 | 0.23 |
| 949990 | 61 | 23 | 5 | 2 | 0.04 |
| 949991 | 55 | 21 | 5 | 1 | <0.03 |
| 949992 | 56 | 29 | 11 | 6 | 0.03 |
| 950014 | 60 | 28 | 8 | 3 | 0.04 |
| 950017 | 68 | 38 | 11 | 5 | 0.07 |
| 950019 | 52 | 20 | 8 | 5 | <0.03 |
| 950020 | 84 | 43 | 13 | 5 | 0.12 |
| 950021 | 80 | 46 | 15 | 6 | 0.12 |
| 950023 | 57 | 17 | 5 | 2 | <0.03 |
| 950024 | 51 | 17 | 7 | 5 | <0.03 |
| 950030 | 37 | 7 | 1 | 0 | <0.03 |
| 950048 | 57 | 40 | 16 | 6 | 0.05 |
| 950057 | 65 | 38 | 21 | 9 | 0.07 |
| 950060 | 26 | 16 | 3 | 2 | <0.03 |
| 950061 | 55 | 34 | 10 | 5 | 0.04 |
| 950064 | 74 | 32 | 11 | 4 | 0.08 |
| 950065 | 72 | 30 | 8 | 2 | 0.07 |
| 950069 | 68 | 31 | 8 | 4 | 0.06 |
| 950072 | 49 | 20 | 6 | 3 | <0.03 |
| 950075 | 87 | 38 | 13 | 5 | 0.12 |
| 950080 | 69 | 40 | 15 | 7 | 0.08 |
| 950081 | 60 | 28 | 8 | 4 | 0.04 |
| 950083 | 65 | 29 | 12 | 4 | 0.1 |
| 950085 | 53 | 14 | 6 | 4 | <0.03 |
| 950086 | 76 | 43 | 15 | 4 | 0.10 |
| 950089 | 46 | 10 | 2 | 1 | <0.03 |
| 950091 | 45 | 12 | 2 | 1 | <0.03 |
| 950092 | 80 | 42 | 14 | 8 | 0.11 |
| 950102 | 81 | 37 | 9 | 3 | 0.10 |
| 950124 | 69 | 31 | 14 | 8 | 0.06 |
| 950132 | 55 | 14 | 4 | 1 | <0.03 |
| 950139 | 87 | 59 | 24 | 9 | 0.19 |
| 950183 | 44 | 23 | 5 | 2 | <0.03 |
| 950219 | 84 | 37 | 18 | 11 | 0.12 |
| 950237 | 83 | 48 | 17 | 8 | 0.14 |
| 950246 | 76 | 33 | 15 | 7 | 0.09 |
| 951328 | 76 | 37 | 12 | 4 | 0.09 |
| 951330 | 76 | 40 | 13 | 5 | 0.10 |
| 951333 | 89 | 45 | 22 | 9 | 0.16 |
| 951340 | 74 | 42 | 15 | 6 | 0.10 |
| 951341 | 92 | 58 | 21 | 4 | 0.19 |
| 951346 | 49 | 22 | 4 | 3 | <0.03 |
| 951352 | 67 | 19 | 7 | 3 | 0.04 |
| 951354 | 67 | 36 | 12 | 6 | 0.07 |
| 951356 | 57 | 23 | 6 | 2 | <0.03 |
| 951357 | 62 | 35 | 10 | 4 | 0.05 |
| 951358 | 76 | 36 | 12 | 5 | 0.09 |
| 951362 | 53 | 15 | 3 | 1 | <0.03 |
| 951364 | 58 | 18 | 4 | 2 | <0.03 |
| 951365 | 78 | 47 | 16 | 6 | 0.12 |
| 951366 | 61 | 34 | 12 | 6 | 0.05 |
| 951367 | 69 | 28 | 8 | 4 | 0.06 |
| 951370 | 74 | 41 | 16 | 7 | 0.10 |

TABLE 7-continued

DNM2 mRNA Expression

| Compound Number | DNM2 expression (% control) | | | | IC50 (µM) |
|---|---|---|---|---|---|
| | 31.25 nM | 125 nM | 500 nM | 2,000 nM | |
| 951371 | 30 | 7 | 2 | 2 | <0.03 |
| 951372 | 61 | 21 | 6 | 4 | 0.03 |
| 951374 | 62 | 17 | 4 | 2 | 0.03 |
| 951376 | 67 | 47 | 15 | 5 | 0.09 |
| 951381 | 63 | 28 | 11 | 6 | 0.05 |
| 951384 | 63 | 27 | 6 | 2 | 0.05 |
| 951386 | 66 | 22 | 6 | 3 | 0.04 |
| 951387 | 68 | 20 | 3 | 1 | 0.04 |
| 951397 | 69 | 35 | 8 | 4 | 0.07 |
| 951406 | 73 | 52 | 19 | 9 | 0.12 |
| 951407 | 56 | 21 | 6 | 3 | <0.03 |
| 951408 | 47 | 15 | 3 | 1 | <0.03 |
| 951413 | 68 | 46 | 20 | 9 | 0.09 |
| 951416 | 63 | 42 | 17 | 7 | 0.07 |
| 951418 | 60 | 22 | 6 | 3 | 0.03 |
| 951428 | 28 | 4 | 1 | 1 | <0.03 |
| 951429 | 32 | 6 | 2 | 2 | <0.03 |
| 951430 | 59 | 25 | 6 | 2 | 0.03 |
| 951431 | 46 | 32 | 9 | 5 | <0.03 |
| 951441 | 100 | 82 | 67 | 42 | 1.33 |
| 951450 | 71 | 36 | 12 | 6 | 0.08 |
| 951458 | 63 | 32 | 15 | 10 | 0.05 |
| 951459 | 77 | 44 | 17 | 9 | 0.11 |
| 951462 | 74 | 28 | 6 | 2 | 0.07 |
| 951463 | 74 | 35 | 15 | 6 | 0.09 |
| 951481 | 91 | 47 | 26 | 13 | 0.18 |
| 951489 | 59 | 17 | 8 | 3 | <0.03 |
| 951494 | 64 | 32 | 10 | 5 | 0.05 |
| 951498 | 58 | 27 | 10 | 7 | 0.03 |
| 951519 | 60 | 32 | 8 | 3 | 0.05 |
| 951529 | 90 | 35 | 24 | 18 | 0.15 |
| 951537 | 103 | 101 | 105 | 168 | >2.0 |
| 951550 | 66 | 42 | 15 | 6 | 0.08 |
| 951554 | 83 | 36 | 10 | 5 | 0.10 |
| 951561 | 88 | 59 | 74 | 100 | >2.0 |
| 951565 | 65 | 38 | 13 | 4 | 0.07 |
| 951566 | 77 | 36 | 9 | 3 | 0.09 |
| 951608 | 73 | 25 | 8 | 4 | 0.06 |
| 951645 | 64 | 29 | 12 | 7 | 0.05 |
| 951657 | 107 | 91 | 64 | 62 | >2.0 |
| 951691 | 58 | 28 | 9 | 3 | 0.04 |
| 951696 | 58 | 19 | 9 | 5 | <0.03 |
| 951700 | 76 | 40 | 16 | 9 | 0.10 |
| 951709 | 52 | 25 | 9 | 6 | <0.03 |
| 951729 | 73 | 74 | 88 | 89 | >2.0 |
| 951731 | 70 | 34 | 10 | 4 | 0.07 |
| 951737 | 57 | 24 | 5 | 4 | <0.03 |
| 951746 | 68 | 31 | 17 | 11 | 0.06 |
| 951749 | 71 | 27 | 4 | 2 | 0.06 |
| 951763 | 44 | 11 | 4 | 2 | <0.03 |
| 951764 | 40 | 9 | 2 | 1 | <0.03 |
| 951767 | 87 | 48 | 16 | 5 | 0.14 |
| 951772 | 62 | 30 | 10 | 7 | 0.05 |
| 951781 | 95 | 42 | 15 | 7 | 0.15 |
| 951783 | 56 | 31 | 12 | 5 | 0.04 |
| 951787 | 53 | 20 | 7 | 4 | <0.03 |
| 951793 | 44 | 11 | 4 | 2 | <0.03 |
| 951795 | 64 | 24 | 7 | 3 | 0.04 |
| 951797 | 40 | 15 | 6 | 4 | <0.03 |
| 951798 | 31 | 5 | 1 | 1 | <0.03 |
| 951799 | 27 | 5 | 1 | 1 | <0.03 |
| 951803 | 67 | 29 | 9 | 4 | 0.06 |
| 951804 | 45 | 13 | 3 | 1 | <0.03 |
| 951806 | 65 | 43 | 15 | 7 | 0.07 |
| 951807 | 59 | 30 | 10 | 4 | 0.04 |
| 951808 | 69 | 46 | 18 | 6 | 0.10 |
| 951809 | 47 | 13 | 3 | 1 | <0.03 |
| 951811 | 57 | 22 | 7 | 3 | <0.03 |
| 951814 | 60 | 25 | 10 | 7 | 0.04 |
| 951815 | 58 | 37 | 15 | 7 | 0.05 |
| 951816 | 46 | 10 | 2 | 1 | <0.03 |
| 951821 | 41 | 14 | 4 | 2 | <0.03 |
| 951822 | 86 | 44 | 15 | 7 | 0.13 |
| 951824 | 67 | 23 | 5 | 3 | 0.05 |
| 951827 | 51 | 17 | 5 | 2 | <0.03 |
| 951828 | 63 | 23 | 9 | 4 | 0.04 |
| 951830 | 61 | 26 | 10 | 5 | 0.04 |
| 951833 | 59 | 39 | 9 | 4 | 0.05 |
| 951835 | 23 | 4 | 1 | 0 | <0.03 |
| 951837 | 53 | 16 | 4 | 1 | <0.03 |
| 951838 | 80 | 51 | 22 | 8 | 0.14 |
| 951839 | 56 | 25 | 8 | 2 | <0.03 |
| 951840 | 76 | 37 | 12 | 4 | 0.09 |
| 951841 | 69 | 27 | 11 | 2 | 0.06 |
| 951843 | 63 | 29 | 8 | 4 | 0.05 |
| 951845 | 39 | 9 | 3 | 1 | <0.03 |
| 951846 | 45 | 14 | 3 | 1 | <0.03 |
| 951855 | 87 | 65 | 19 | 5 | 0.19 |
| 951856 | 61 | 18 | 4 | 2 | <0.03 |
| 951857 | 57 | 27 | 7 | 2 | 0.03 |
| 951874 | 74 | 73 | 68 | 47 | >2.0 |
| 951875 | 66 | 33 | 10 | 4 | 0.06 |
| 951881 | 49 | 22 | 3 | 2 | <0.03 |
| 951893 | 53 | 26 | 10 | 5 | <0.03 |
| 951898 | 46 | 18 | 5 | 2 | <0.03 |
| 951902 | 61 | 34 | 13 | 7 | 0.05 |
| 951938 | 85 | 51 | 20 | 11 | 0.16 |

Example 6: Dose Response of Modified Oligonucleotides Complementary to Dynamin 2 In Vitro Selected oligonucleotides listed in the Examples above were tested at various doses via free uptake in A431 cells. Cells were cultured at a density of 10,000 cells per well and treated with 8, 40, 200, or 1,000 nM of modified oligonucleotide, as specified in the table below. After approximately 48 hours, total RNA was isolated and analyzed by RT-PCR with primer probe set RTS36027 (described in Example 1), normalized with GADPH. As illustrated in the tables below, DNM2 mRNA expression was inhibited in a dose-dependent manner by modified oligonucleotides complementary to DNM2.

TABLE 8

DNM2 mRNA Expression

| Compound Number | DNM2 expression (% control) | | | | IC50 (µM) |
|---|---|---|---|---|---|
| | 8 nM | 40 nM | 200 nM | 1,000 nM | |
| 695171 | 90 | 84 | 54 | 26 | 0.24 |
| 951371 | 105 | 67 | 25 | 9 | 0.10 |
| 951371 | 101 | 70 | 27 | 11 | 0.10 |
| 951371 | 109 | 63 | 16 | 4 | 0.08 |
| 951371 | 91 | 61 | 23 | 8 | 0.07 |
| 951371 | 94 | 78 | 25 | 9 | 0.10 |
| 951371 | 91 | 63 | 23 | 8 | 0.07 |
| 951371 | 59 | 66 | 23 | 8 | 0.04 |
| 951371 | 94 | 56 | 20 | 7 | 0.07 |
| 951371 | 88 | 67 | 26 | 10 | 0.08 |
| 988380 | 77 | 33 | 5 | 1 | 0.02 |
| 988386 | 93 | 70 | 21 | 6 | 0.08 |
| 988387 | 101 | 46 | 5 | 1 | 0.05 |
| 988388 | 97 | 80 | 39 | 11 | 0.13 |
| 988394 | 120 | 81 | 23 | 5 | 0.12 |
| 988396 | 113 | 87 | 30 | 9 | 0.14 |
| 988397 | 77 | 29 | 7 | 2 | 0.02 |
| 988398 | 86 | 46 | 11 | 3 | 0.04 |
| 988399 | 81 | 47 | 13 | 3 | 0.04 |
| 988400 | 88 | 54 | 15 | 3 | 0.05 |

TABLE 8-continued

DNM2 mRNA Expression

| Compound Number | DNM2 expression (% control) | | | | IC50 (μM) |
|---|---|---|---|---|---|
| | 8 nM | 40 nM | 200 nM | 1,000 nM | |
| 988401 | 98 | 65 | 16 | 6 | 0.07 |
| 988402 | 94 | 48 | 11 | 2 | 0.05 |
| 988407 | 99 | 77 | 30 | 8 | 0.11 |
| 988413 | 84 | 58 | 23 | 7 | 0.06 |
| 988414 | 95 | 73 | 23 | 6 | 0.09 |
| 988415 | 82 | 62 | 25 | 7 | 0.06 |
| 988422 | 91 | 60 | 17 | 7 | 0.06 |

Example 7: Dose Response of Modified Oligonucleotides Complementary to Dynamin 2 In Vitro Selected oligonucleotides listed in the Examples above were tested at various doses via free uptake in A431 cells. Cells were cultured at a density of 10,000 cells per well treated with 7.8, 31.25, 125, 500, or 2,000 nM of modified oligonucleotide, as specified in the tables below. After approximately 48 hours, total RNA was isolated and analyzed by RT-PCR with primer probe set RTS36027 (described in Example 1), normalized with GADPH. As illustrated in the tables below, DNM2 expression was inhibited in a dose-dependent manner by modified oligonucleotides complementary to DNM2.

TABLE 9

DNM2 mRNA Expression

| Compound Number | DNM2 expression (% control) | | | | | IC50 (μM) |
|---|---|---|---|---|---|---|
| | 7.8 nM | 31.25 nM | 125 nM | 500 nM | 2,000 nM | |
| 908166 | 106 | 97 | 57 | 28 | 16 | 0.22 |
| 908213 | 139 | 85 | 56 | 30 | 16 | 0.21 |
| 908408 | 98 | 80 | 33 | 7 | 2 | 0.08 |
| 908420 | 91 | 86 | 45 | 13 | 4 | 0.11 |
| 948660 | 105 | 90 | 51 | 13 | 2 | 0.14 |
| 948677 | 101 | 101 | 61 | 23 | 8 | 0.21 |
| 948951 | 97 | 79 | 35 | 14 | 8 | 0.09 |
| 949190 | 107 | 101 | 54 | 22 | 8 | 0.18 |
| 949865 | 94 | 80 | 40 | 16 | 7 | 0.10 |
| 949935 | 88 | 84 | 58 | 31 | 19 | 0.20 |
| 950023 | 89 | 75 | 45 | 13 | 4 | 0.09 |
| 950060 | 81 | 79 | 48 | 29 | 11 | 0.13 |
| 950089 | 84 | 79 | 53 | 18 | 5 | 0.12 |
| 950132 | 87 | 83 | 44 | 19 | 9 | 0.11 |
| 950183 | 88 | 83 | 58 | 35 | 15 | 0.21 |

TABLE 10

DNM2 mRNA Expression

| Compound Number | DNM2 expression (% control) | | | | | IC50 (μM) |
|---|---|---|---|---|---|---|
| | 7.8 nM | 31.25 nM | 125 nM | 500 nM | 2,000 nM | |
| 908408 | 98 | 80 | 34 | 10 | 2 | 0.08 |
| 951356 | 190 | 79 | 60 | 28 | 10 | 0.23 |
| 951362 | 97 | 85 | 63 | 30 | 11 | 0.21 |
| 951372 | 87 | 80 | 55 | 23 | 10 | 0.14 |
| 951431 | 100 | 90 | 68 | 38 | 21 | 0.31 |
| 951797 | 89 | 77 | 42 | 19 | 10 | 0.10 |
| 951798 | 89 | 58 | 23 | 6 | 1 | 0.04 |

TABLE 10-continued

DNM2 mRNA Expression

| Compound Number | DNM2 expression (% control) | | | | | IC50 (μM) |
|---|---|---|---|---|---|---|
| | 7.8 nM | 31.25 nM | 125 nM | 500 nM | 2,000 nM | |
| 951799 | 90 | 68 | 23 | 6 | 2 | 0.05 |
| 951816 | 100 | 77 | 38 | 10 | 3 | 0.09 |
| 951821 | 87 | 57 | 45 | 16 | 6 | 0.07 |
| 951827 | 94 | 79 | 45 | 17 | 5 | 0.11 |
| 951839 | 95 | 90 | 69 | 38 | 14 | 0.29 |
| 951845 | 92 | 71 | 31 | 8 | 2 | 0.06 |
| 951846 | 91 | 85 | 50 | 19 | 5 | 0.13 |
| 951856 | 97 | 86 | 54 | 22 | 7 | 0.15 |

Example 8: Dose Response of Modified Oligonucleotides Complementary to Dynamin 2 In Vitro Selected oligonucleotides listed in the Examples above were tested at various doses in HSMM cells (human myoblast, Lonza CC-2580). Cells were cultured at a density of 20,000 cells per well and transfected via electroporation with 7.8, 31.25, 125, 500, or 2,000 nM of modified oligonucleotide, as specified in the tables below. After approximately 16 hours, total RNA was isolated and analyzed by RT-PCR with primer probe set RTS36027 (described in Example 1), normalized with ribogreen. As illustrated in the tables below, DNM2 mRNA expression was inhibited in a dose-dependent manner by modified oligonucleotides complementary to DNM2.

TABLE 11

DNM2 mRNA Expression

| Compound Number | DNM2 expression (% control) | | | | | IC50 (μM) |
|---|---|---|---|---|---|---|
| | 7.8 nM | 31.25 nM | 125 nM | 500 nM | 2,000 nM | |
| 908166 | 104 | 95 | 98 | 66 | 42 | 1.29 |
| 908213 | 93 | 82 | 70 | 42 | 19 | 0.33 |
| 908408 | 111 | 100 | 74 | 38 | 17 | 0.36 |
| 908420 | 91 | 93 | 67 | 39 | 17 | 0.30 |
| 948660 | 88 | 86 | 83 | 42 | 15 | 0.40 |
| 948677 | 90 | 80 | 87 | 51 | 22 | 0.54 |
| 948951 | 88 | 74 | 57 | 31 | 12 | 0.16 |
| 949190 | 99 | 88 | 82 | 47 | 23 | 0.49 |
| 949865 | 132 | 106 | 92 | 39 | 19 | 0.50 |
| 949935 | 90 | 92 | 94 | 60 | 25 | 0.77 |
| 950023 | 113 | 97 | 86 | 40 | 15 | 0.43 |
| 950060 | 109 | 105 | 78 | 69 | 32 | 0.95 |
| 950089 | 111 | 102 | 80 | 54 | 21 | 0.58 |
| 950132 | 117 | 98 | 79 | 51 | 19 | 0.51 |
| 950183 | 95 | 110 | 84 | 59 | 23 | 0.70 |

TABLE 12

DNM2 mRNA Expression

| Compound Number | DNM2 expression (% control) | | | | | IC50 (μM) |
|---|---|---|---|---|---|---|
| | 7.8 nM | 31.25 nM | 125 nM | 500 nM | 2,000 nM | |
| 908408 | 98 | 102 | 81 | 55 | 20 | 0.58 |
| 951356 | 95 | 102 | 94 | 74 | 41 | 1.45 |
| 951362 | 95 | 67 | 85 | 56 | 29 | 0.62 |
| 951372 | 95 | 91 | 86 | 60 | 27 | 0.75 |

TABLE 12-continued

DNM2 mRNA Expression

| Compound Number | 7.8 nM nM | DNM2 expression (% control) | | | | IC50 (µM) |
| --- | --- | --- | --- | --- | --- | --- |
| | | 31.25 nM | 125 nM | 500 nM | 2,000 nM | |
| 951431 | 87 | 90 | 89 | 55 | 35 | 0.77 |
| 951797 | 94 | 94 | 98 | 72 | 41 | 1.40 |
| 951798 | 103 | 95 | 79 | 40 | 21 | 0.40 |
| 951799 | 104 | 100 | 81 | 47 | 20 | 0.50 |
| 951816 | 106 | 91 | 89 | 53 | 30 | 0.70 |
| 951821 | 122 | 106 | 66 | 32 | 22 | 0.32 |
| 951827 | 100 | 87 | 51 | 38 | 20 | 0.21 |
| 951839 | 123 | 94 | 99 | 72 | 31 | 1.17 |
| 951845 | 104 | 94 | 75 | 51 | 20 | 0.48 |
| 951846 | 112 | 91 | 80 | 59 | 27 | 0.69 |
| 951856 | 113 | 101 | 77 | 50 | 22 | 0.52 |

Example 9: Dose Response of Modified Oligonucleotides Complementary to Dynamin 2 In Vitro Selected oligonucleotides listed in the Examples above were tested at various doses in SkMC cells (human skeletal muscle, Lonza CC-2561). Cells were cultured at a density of 20,000 cells per well and transfected via electroporation with 7.8, 31.25, 125, 500, or 2,000 nM of modified oligonucleotide, as specified in the tables below. After approximately 16 hours, total RNA was isolated and analyzed by RT-PCR with primer probe set RTS36027 (described in Example 1), normalized with ribogreen. As illustrated in the tables below, DNM2 mRNA expression was inhibited in a dose-dependent manner by modified oligonucleotides complementary to DNM2.

TABLE 13

DNM2 mRNA Expression

| Compound Number | 7.8 nM nM | DNM2 expression (% control) | | | | IC50 (µM) |
| --- | --- | --- | --- | --- | --- | --- |
| | | 31.25 nM | 125 nM | 500 nM | 2,000 nM | |
| 908166 | 90 | 84 | 87 | 43 | 13 | 0.41 |
| 908213 | 101 | 79 | 59 | 21 | 5 | 0.15 |
| 908408 | 94 | 72 | 57 | 21 | 3 | 0.13 |
| 908420 | 84 | 72 | 53 | 9 | 4 | 0.10 |
| 948660 | 95 | 90 | 64 | 12 | 2 | 0.16 |
| 948677 | 88 | 77 | 58 | 15 | 4 | 0.13 |
| 948951 | 83 | 67 | 41 | 12 | 5 | 0.07 |
| 949190 | 103 | 84 | 61 | 16 | 4 | 0.16 |
| 949865 | 130 | 106 | 55 | 10 | 4 | 0.17 |
| 949935 | 118 | 100 | 86 | 33 | 7 | 0.36 |
| 950023 | 129 | 98 | 57 | 11 | 3 | 0.17 |
| 950060 | 101 | 103 | 72 | 26 | 5 | 0.26 |
| 950089 | 112 | 78 | 65 | 20 | 4 | 0.17 |
| 950132 | 115 | 93 | 53 | 14 | 3 | 0.15 |
| 950183 | 114 | 92 | 70 | 24 | 5 | 0.23 |

TABLE 14

DNM2 mRNA Expression

| Compound Number | 7.8 nM nM | DNM2 expression (% control) | | | | IC50 (µM) |
| --- | --- | --- | --- | --- | --- | --- |
| | | 31.25 nM | 125 nM | 500 nM | 2,000 nM | |
| 908408 | 91 | 80 | 46 | 10 | 3 | 0.10 |
| 951356 | 103 | 98 | 90 | 52 | 15 | 0.55 |

TABLE 14-continued

DNM2 mRNA Expression

| Compound Number | 7.8 nM nM | DNM2 expression (% control) | | | | IC50 (µM) |
| --- | --- | --- | --- | --- | --- | --- |
| | | 31.25 nM | 125 nM | 500 nM | 2,000 nM | |
| 951362 | 90 | 88 | 65 | 22 | 4 | 0.19 |
| 951372 | 99 | 88 | 65 | 16 | 4 | 0.18 |
| 951431 | 103 | 97 | 70 | 25 | 6 | 0.24 |
| 951797 | 102 | 94 | 69 | 25 | 7 | 0.23 |
| 951798 | 99 | 90 | 46 | 8 | 3 | 0.12 |
| 951799 | 101 | 90 | 49 | 12 | 3 | 0.13 |
| 951816 | 96 | 78 | 63 | 13 | 4 | 0.14 |
| 951821 | 104 | 79 | 47 | 12 | 3 | 0.11 |
| 951827 | 94 | 71 | 44 | 8 | 3 | 0.08 |
| 951839 | 114 | 103 | 76 | 32 | 6 | 0.32 |
| 951845 | 97 | 88 | 55 | 12 | 4 | 0.14 |
| 951846 | 90 | 86 | 41 | 18 | 4 | 0.11 |
| 951856 | 102 | 91 | 62 | 15 | 4 | 0.17 |

Example 10: Administration of Modified Oligonucleotides Complementary to Human Dynamin 2 to CD1 Mice CD1® mice (Charles River, Mass.) were treated with modified oligonucleotides selected from Examples above and evaluated for changes in the levels of various plasma chemistry markers. Groups of 6 week old male CD1 mice were injected subcutaneously once a week for 6 weeks with 50 mg/kg of a modified oligonucleotide listed in the tables below (50 mg/kg/week dose). Each group contained 4 mice. One control group of male CD1 mice was injected subcutaneously once a week for 6 weeks with PBS. Mice were sacrificed 48 hours after the last dose, and organs and plasma were harvested for further analysis.

Levels of transaminases, albumin, BUN, and billirubin were measured using an automated clinical chemistry analyzer (Hitachi Olympus AU400e, Melville, N.Y.). Kidney, liver, and spleen weights were also measured. The results, presented in the tables below, show that many of the modified oligonucleotides complementary to DNM2 were well tolerated in vivo.

TABLE 15

Levels of plasma markers

| | ALT (U/L) | AST (U/L) | Albumin (mg/dL) | BUN (mg/d) | Creatine (mg/dL) | T.Bil. (g/dL) |
| --- | --- | --- | --- | --- | --- | --- |
| PBS | 48 | 82 | 3.36 | 27.2 | 0.12 | 0.66 |
| 549144 | 72 | 68 | 3.23 | 23.6 | 0.12 | 0.47 |
| 908166 | 259 | 108 | 3.16 | 20.4 | 0.11 | 0.38 |
| 908213 | 93 | 85 | 2.95 | 23.9 | 0.10 | 0.34 |
| 908389 | 1073 | 636 | 3.17 | 22.7 | 0.09 | 0.55 |
| 908408 | 67 | 70 | 2.97 | 26.2 | 0.11 | 0.32 |
| 908415 | 286 | 209 | 2.60 | 26.2 | 0.10 | 0.28 |
| 908416 | 425 | 336 | 2.35 | 26.4 | 0.07 | 0.19 |
| 908420 | 105 | 144 | 2.50 | 26.5 | 0.06 | 0.38 |
| 948660 | 112 | 165 | 2.59 | 21.8 | 0.08 | 0.26 |
| 948673 | 225 | 263 | 2.15 | 27.2 | 0.04 | 0.82 |
| 948675 | 100 | 132 | 2.25 | 21.4 | 0.06 | 0.22 |
| 948677 | 65 | 91 | 2.32 | 17.7 | 0.05 | 0.21 |
| 948951 | 107 | 126 | 2.46 | 21.4 | 0.07 | 0.22 |
| 949158 | 713 | 608 | 2.99 | 18.6 | 0.01 | 0.27 |
| 949190 | 64 | 62 | 2.52 | 22.1 | 0.07 | 0.20 |
| 949865 | 45 | 58 | 2.62 | 23.2 | 0.06 | 0.22 |
| 949873 | 89 | 163 | 2.33 | 20.7 | 0.04 | 0.21 |
| 949874 | 1079 | 853 | 2.77 | 20.7 | 0.05 | 0.46 |
| 949935 | 98 | 81 | 2.63 | 22.9 | 0.07 | 0.20 |

TABLE 15-continued

Levels of plasma markers

|  | ALT (U/L) | AST (U/L) | Albumin (mg/dL) | BUN (mg/d) | Creatine (mg/dL) | T.Bil. (g/dL) |
|---|---|---|---|---|---|---|
| 950023 | 42 | 57 | 2.52 | 22.2 | 0.04 | 0.20 |
| 950030 | 59 | 77 | 2.44 | 20.6 | 0.05 | 0.21 |

TABLE 16

Levels of plasma markers

| Compound No. | ALT (U/L) | AST (U/L) | Albumin (mg/dL) | BUN (mg/d) | Creatine (mg/dL) | T.Bil. (g/dL) |
|---|---|---|---|---|---|---|
| PBS | 37 | 62 | 2.78 | 22.0 | 0.08 | 0.46 |
| 549144 | 64 | 79 | 2.64 | 24.0 | 0.08 | 0.29 |
| 950060 | 47 | 63 | 2.47 | 22.0 | 0.09 | 0.33 |
| 950089 | 40 | 56 | 2.65 | 21.0 | 0.10 | 0.22 |
| 950132 | 58 | 58 | 2.58 | 20.0 | 0.07 | 0.24 |
| 950183 | 49 | 62 | 2.38 | 21.0 | 0.06 | 0.29 |
| 951356 | 64 | 80 | 2.39 | 23.0 | 0.10 | 0.25 |
| 951362 | 60 | 63 | 2.74 | 22.0 | 0.09 | 0.18 |
| 951371 | 312 | 209 | 2.32 | 20.0 | 0.09 | 0.18 |
| 951372 | 59 | 99 | 2.54 | 25.0 | 0.07 | 0.21 |
| 951407 | 172 | 200 | 2.72 | 24.0 | 0.07 | 0.24 |
| 951431 | 64 | 80 | 2.48 | 23.0 | 0.08 | 0.22 |
| 951793 | 319 | 238 | 2.5 | 19.0 | 0.10 | 0.20 |
| 951797 | 41 | 63 | 2.6 | 24.0 | 0.11 | 0.26 |
| 951798 | 53 | 97 | 2.57 | 26.0 | 0.10 | 0.19 |
| 951799 | 44 | 97 | 2.44 | 25.0 | 0.08 | 0.19 |
| 951816 | 121 | 113 | 2.63 | 19.0 | 0.10 | 0.20 |
| 951821 | 79 | 80 | 2.39 | 23.0 | 0.07 | 0.17 |
| 951827 | 56 | 88 | 2.46 | 25.0 | 0.10 | 0.21 |
| 951839 | 45 | 50 | 2.52 | 23.0 | 0.08 | 0.20 |
| 951845 | 117 | 132 | 2.51 | 21.0 | 0.08 | 0.25 |
| 951846 | 35 | 47 | 2.59 | 21.0 | 0.10 | 0.21 |
| 951856 | 112 | 412 | 2.25 | 20.0 | 0.09 | 0.17 |

TABLE 17

Organ weights

|  | kidney (g) | liver (g) | spleen (g) |
|---|---|---|---|
| PBS | 0.55 | 1.9 | 0.09 |
| 549144 | 0.52 | 1.9 | 0.10 |
| 908166 | 0.48 | 2.0 | 0.08 |
| 908213 | 0.52 | 2.0 | 0.12 |
| 908389 | 0.54 | 2.6 | 0.14 |
| 908408 | 0.49 | 2.2 | 0.13 |
| 908415 | 0.51 | 2.2 | 0.12 |
| 908416 | 0.51 | 2.1 | 0.16 |
| 908420 | 0.52 | 2.0 | 0.13 |
| 948660 | 0.44 | 1.8 | 0.14 |
| 948673 | 0.51 | 3.9 | 0.62 |
| 948675 | 0.48 | 2.1 | 0.21 |
| 948677 | 0.54 | 2.0 | 0.15 |
| 948951 | 0.45 | 1.9 | 0.11 |
| 949158 | 0.59 | 2.3 | 0.18 |
| 949190 | 0.53 | 2.2 | 0.14 |
| 949865 | 0.53 | 2.1 | 0.14 |
| 949873 | 0.47 | 1.8 | 0.20 |
| 949874 | 0.52 | 2.3 | 0.16 |
| 949935 | 0.57 | 2.0 | 0.13 |
| 950023 | 0.53 | 1.9 | 0.16 |
| 950030 | 0.59 | 2.1 | 0.20 |

TABLE 18

Organ weights

| Compound No. | kidney (g) | liver (g) | spleen (g) |
|---|---|---|---|
| PBS | 0.57 | 2.1 | 0.11 |
| 549144 | 0.57 | 2.0 | 0.09 |
| 950060 | 0.57 | 2.3 | 0.12 |
| 950089 | 0.60 | 2.4 | 0.15 |
| 950132 | 0.59 | 2.3 | 0.16 |
| 950183 | 0.60 | 2.4 | 0.14 |
| 951356 | 0.57 | 2.4 | 0.19 |
| 951362 | 0.58 | 2.3 | 0.16 |
| 951371 | 0.51 | 2.7 | 0.16 |
| 951372 | 0.55 | 2.5 | 0.17 |
| 951407 | 0.53 | 2.2 | 0.17 |
| 951431 | 0.54 | 2.2 | 0.18 |
| 951793 | 0.55 | 2.6 | 0.17 |
| 951797 | 0.52 | 2.1 | 0.15 |
| 951798 | 0.57 | 2.4 | 0.18 |
| 951799 | 0.54 | 2.4 | 0.16 |
| 951816 | 0.50 | 2.4 | 0.16 |
| 951821 | 0.50 | 2.0 | 0.13 |
| 951827 | 0.47 | 1.8 | 0.13 |
| 951839 | 0.51 | 2.2 | 0.15 |
| 951845 | 0.55 | 2.0 | 0.17 |
| 951846 | 0.57 | 2.2 | 0.17 |
| 951856 | 0.60 | 2.5 | 0.19 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10865414B2). An electronic copy of the "Sequence Listing" will also be available from the USPTO upon request and payment of the fee set forth in 37 CFR 1.19(b)(3).

What is claimed:

1. A compound comprising a modified oligonucleotide consisting of 16 to 20 linked nucleosides and having a nucleobase sequence comprising at least 14 contiguous nucleobases of SEQ ID NO: 2879 or SEQ ID NO: 2123, wherein the modified oligonucleotide comprises at least one of a modified internucleoside linkage and a modified sugar moiety.

2. The compound of claim 1, wherein the nucleobase sequence comprises SEQ ID NO: 2879.

3. The compound of claim 1, wherein the nucleobase sequence comprises SEQ ID NO: 2123.

4. The compound of claim 1, wherein the nucleobase sequence is SEQ ID NO: 2879 or 2123.

5. The compound of claim 1, wherein the modified oligonucleotide comprises:
- a gap segment consisting of 8-12 linked 2'-deoxynucleosides;
- a 5' wing segment consisting of 1-7 linked nucleosides; and
- a 3' wing segment consisting of 1-7 linked nucleosides;
- wherein the gap segment is positioned between the 5' wing segment and the 3' wing segment and wherein the terminal nucleoside of each wing segment comprises a modified sugar.

6. The compound of claim 1, wherein the modified oligonucleotide comprises:
- a gap segment consisting of 10 linked 2'-deoxynucleosides;
- a 5' wing segment consisting of 3 linked nucleosides; and
- a 3' wing segment consisting of 3 linked nucleosides;
- wherein the gap segment is positioned between the 5' wing segment and the 3' wing segment; wherein each nucleoside of each wing segment comprises a cEt sugar moiety; wherein each internucleoside linkage is a phosphorothioate linkage; and wherein each cytosine is a 5-methylcytosine.

7. The compound of claim 1, wherein the modified internucleoside linkage is a phosphorothioate internucleoside linkage.

8. The compound of claim 1, wherein the modified sugar moiety is a bicyclic sugar.

9. The compound of claim 8, wherein the bicyclic sugar is selected from the group consisting of LNA, ENA, and cEt.

10. The compound of claim 1, wherein the modified oligonucleotide comprises at least one 5-methylcytosine.

11. The compound of claim 1, wherein the modified oligonucleotide is single-stranded.

12. The compound of claim 1, wherein the compound is a double-stranded compound.

13. The compound of claim 1, comprising a conjugate group.

14. The compound of claim 13, wherein the compound consists of the modified oligonucleotide and the conjugate group.

15. A modified oligonucleotide according to the following formula: Gks Tks Tks Tds Ads Tds Tds Ads Tds Ads Gds Gds Gds mCks Tks Tk; wherein,
- A=an adenine nucleobase,
- mC=a 5-methylcytosine nucleobase,
- G=a guanine nucleobase,
- T=a thymine nucleobase,
- k=a cEt sugar moiety,
- d=a 2'-deoxyribosyl sugar moiety, and
- s=a phosphorothioate internucleoside linkage.

16. A modified oligonucleotide, wherein the anion form of the modified oligonucleotide has the following chemical structure:

281 282
(SEQ ID NO: 2879)
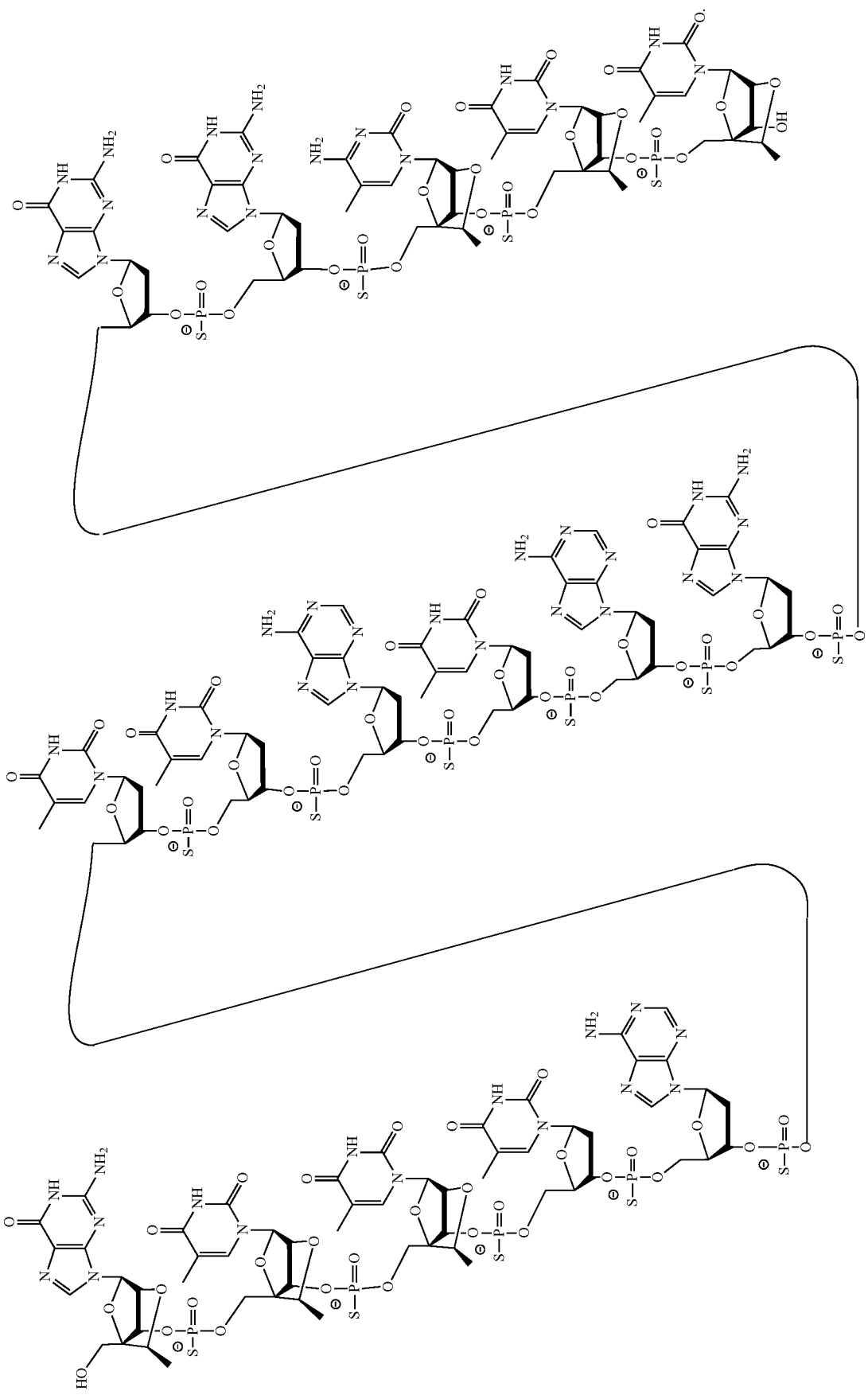

17. The modified oligonucleotide of claim 16, wherein the modified oligonucleotide is a salt.

18. The modified oligonucleotide of claim 17, wherein the cation of the salt is a sodium or a potassium.

19. A chirally enriched population of the compound of claim 1, wherein the population is enriched for compounds having a modified oligonucleotide comprising at least one particular phosphorothioate internucleoside linkage having a particular stereochemical configuration.

20. A pharmaceutical composition comprising the modified oligonucleotide of claim 16, and at least one pharmaceutically acceptable diluent or carrier.

21. A method of treating, preventing, or ameliorating centronuclear myopathy, Duchenne Muscular Dystrophy, or Charcot-Marie Tooth disease, the method comprising administering the compound of claim 1 to a subject with a mutation in at least one gene selected from among MTM1, BIN1, and DNM2.

22. An in vitro method of inhibiting expression of DNM2 in a cell comprising contacting the cell with compound comprising a single-stranded modified oligonucleotide that is 100% complementary to exon 10, intron 1, intron 11, intron 12, intron 13, intron 14, or the 3'-UTR of a DNM2 nucleic acid transcript, thereby inhibiting expression of DNM2 in the cell.

23. The in vitro method of claim 22, wherein the modified oligonucleotide consists of 16 to 20 linked nucleosides and has a nucleobase sequence comprising at least 14 contiguous nucleobases of SEQ ID NO: 2879 or SEQ ID NO: 2123, wherein the modified oligonucleotide comprises at least one of a modified internucleoside linkage and a modified sugar moiety.

24. The in vitro method of claim 22, wherein the modified oligonucleotide is according to the following formula: Gks Tks Tks Tds Ads Tds Tds Ads Tds Ads Gds Gds Gds mCks Tks Tk; wherein,
A=an adenine nucleobase,
mC=a 5-methylcytosine nucleobase,
G=a guanine nucleobase,
T=a thymine nucleobase,
k=a cEt sugar moiety,
d=a 2'-deoxyribosyl sugar moiety, and
s=a phosphorothioate internucleoside linkage.

25. The in vitro method of claim 22, wherein the anion form of the modified oligonucleotide has the following chemical structure:

287 288
(SEQ ID NO: 2879)
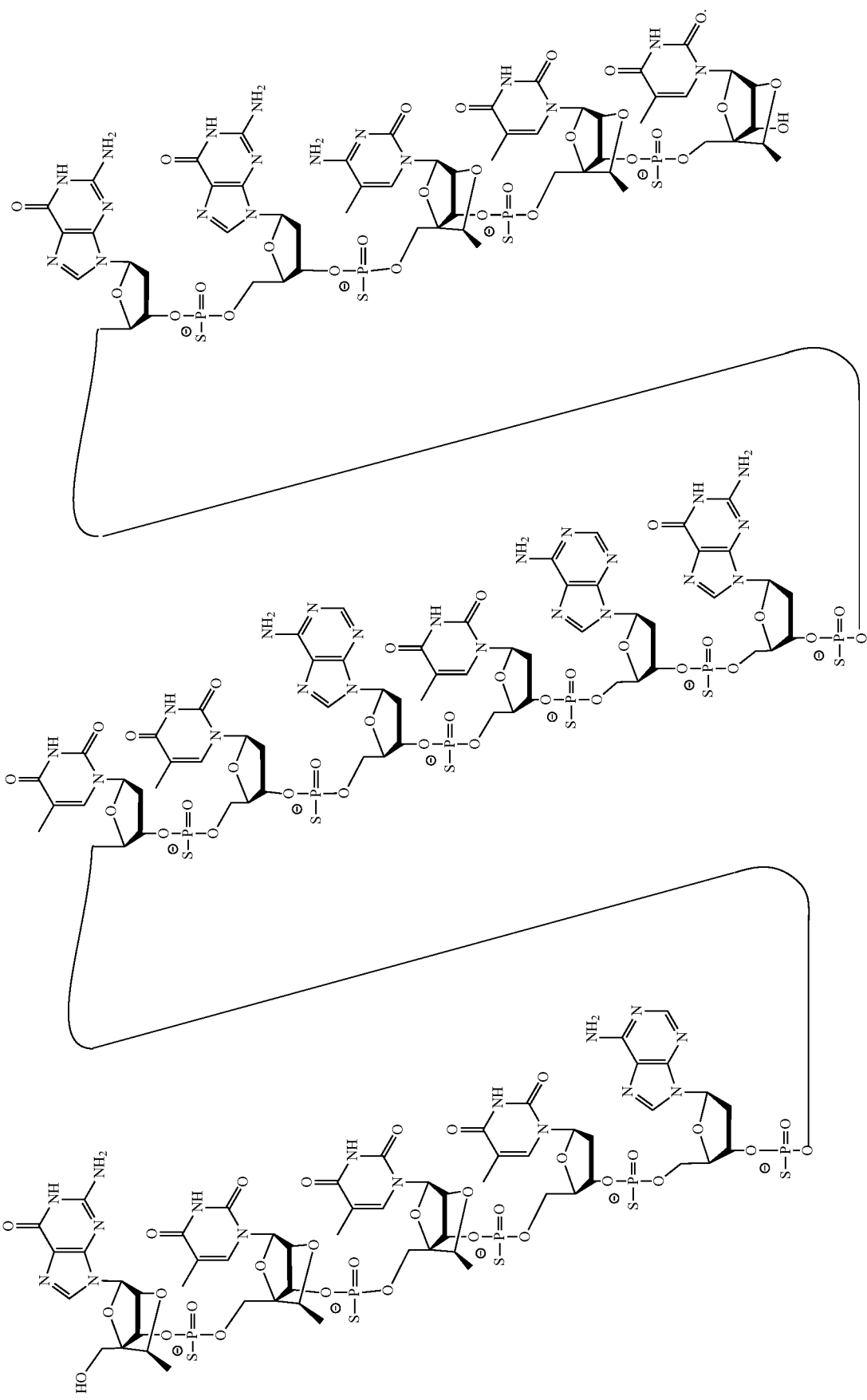

26. The in vitro method of claim 22, wherein the modified oligonucleotide has the following chemical structure:

293 294
(SEQ ID NO: 2879)
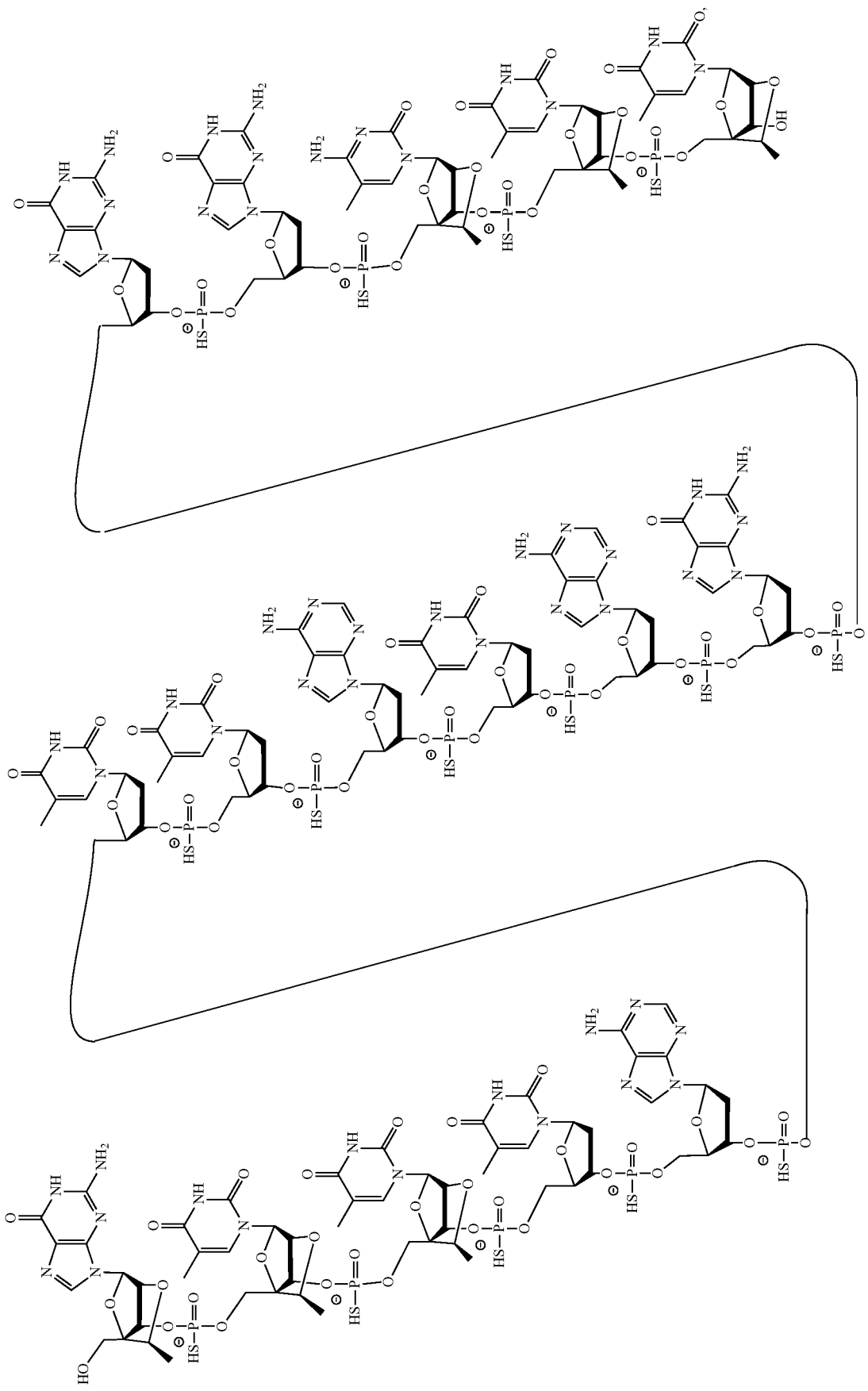

or a salt thereof.

27. The in vitro method of claim 22, wherein the modified oligonucleotide has the following chemical structure:

299 300
(SEQ ID NO: 2879)
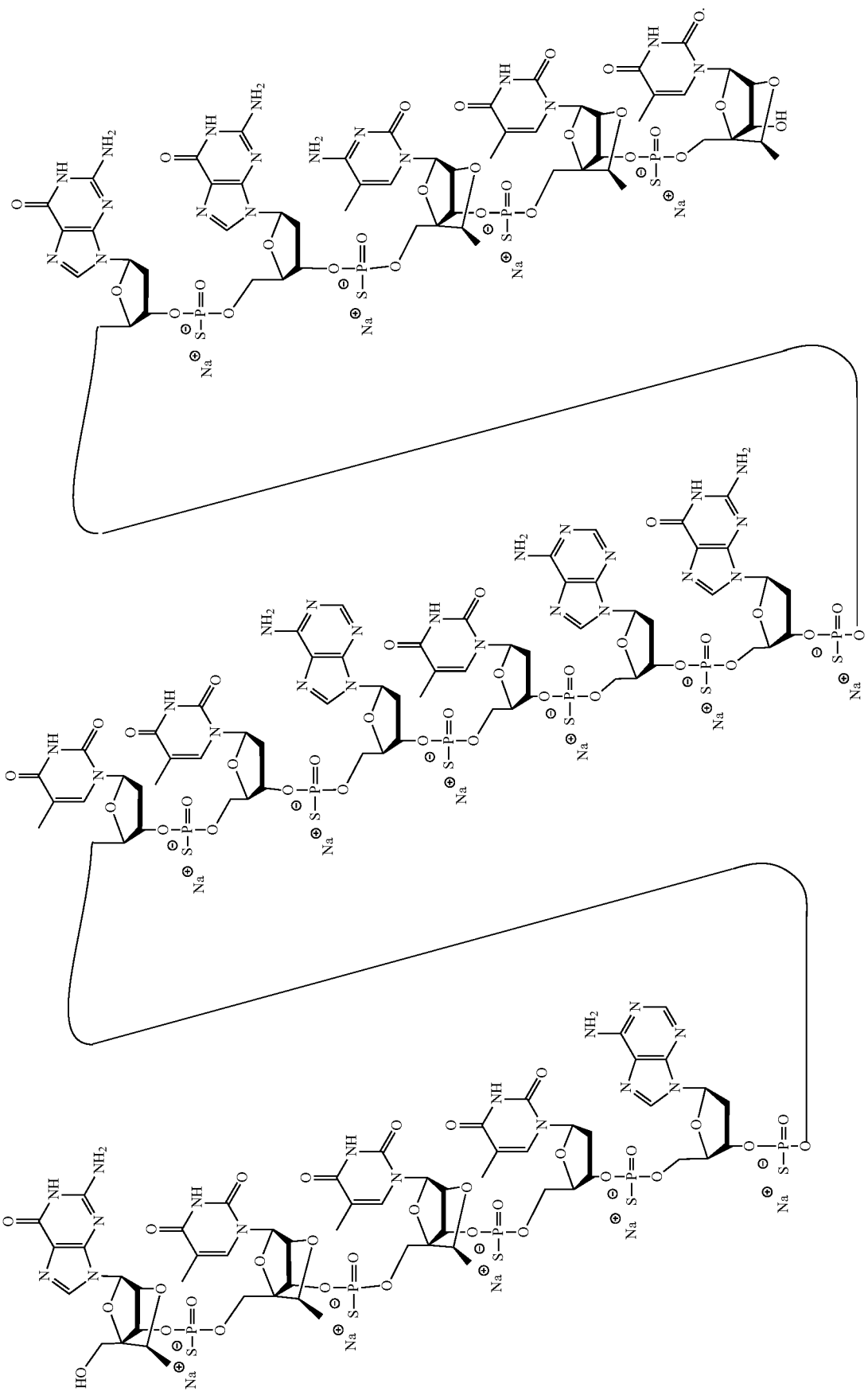

28. The pharmaceutical composition of claim 20, wherein the pharmaceutically acceptable diluent is phosphate buffered saline.

29. A chirally enriched population of the modified oligonucleotide of claim 15, wherein the population is enriched for modified oligonucleotides comprising at least one particular phosphorothioate internucleoside linkage having a particular stereochemical configuration.

30. A chirally enriched population of the modified oligonucleotide of claim 16, wherein the population is enriched for modified oligonucleotides comprising at least one particular phosphorothioate internucleoside linkage having a particular stereochemical configuration.

31. A pharmaceutical composition comprising the modified oligonucleotide of claim 15, and at least one pharmaceutically acceptable diluent or carrier.

32. The pharmaceutical composition of claim 31, wherein the pharmaceutically acceptable diluent is phosphate buffered saline.

33. A method of treating or ameliorating centronuclear myopathy, Duchenne Muscular Dystrophy, or Charcot-Marie Tooth disease, the method comprising administering the modified oligonucleotide of claim 15 to a subject with a mutation in at least one gene selected from among MTM1, BIN1, and DNM2.

34. A method of treating or ameliorating centronuclear myopathy, Duchenne Muscular Dystrophy, or Charcot-Marie Tooth disease, the method comprising administering the modified oligonucleotide of claim 16 to a subject with a mutation in at least one gene selected from among MTM1, BIN1, and DNM2.

35. The modified oligonucleotide of claim 15, comprising the modified oligonucleotide covalently linked to a conjugate group.

36. A modified oligonucleotide according to the following chemical structure:

305 306
(SEQ ID NO: 2879)
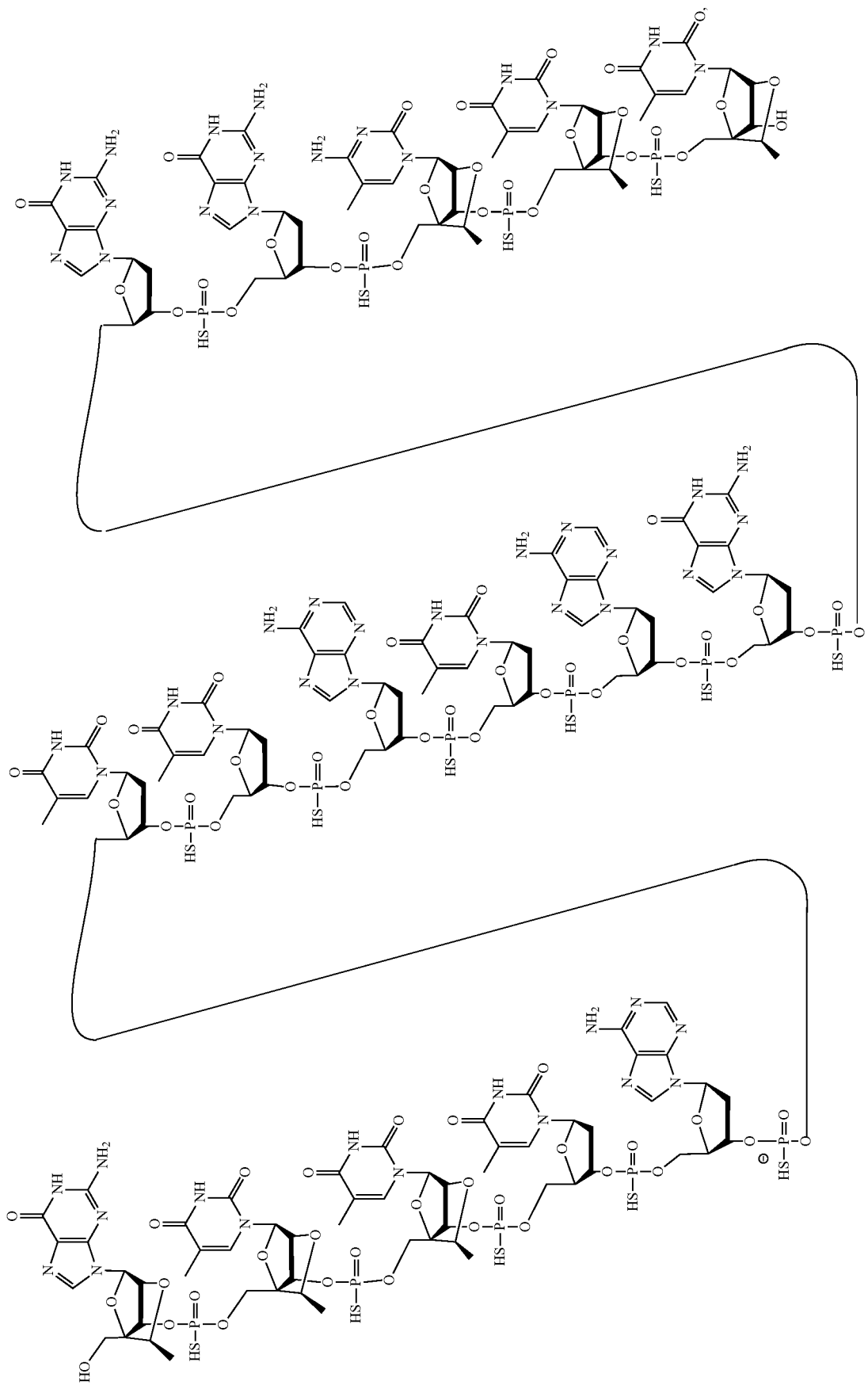

or a salt thereof.

37. The modified oligonucleotide of claim 36, which is the sodium salt or the potassium salt.

38. A chirally enriched population of the modified oligonucleotide of claim 36, wherein the population is enriched for modified oligonucleotides comprising at least one particular phosphorothioate internucleoside linkage having a particular stereochemical configuration.

39. A pharmaceutical composition comprising the modified oligonucleotide of claim 36 and at least one pharmaceutically acceptable diluent or carrier.

40. The pharmaceutical composition of claim 39, wherein the pharmaceutically acceptable diluent is phosphate buffered saline.

41. A method of treating or ameliorating centronuclear myopathy, Duchenne Muscular Dystrophy, or Charcot-Marie Tooth disease, the method comprising administering the modified oligonucleotide of claim 36 to a subject with a mutation in at least one gene selected from among MTM1, BIN1, and DNM2.

42. A modified oligonucleotide according to the following chemical structure:

311 312
(SEQ ID NO: 2879)
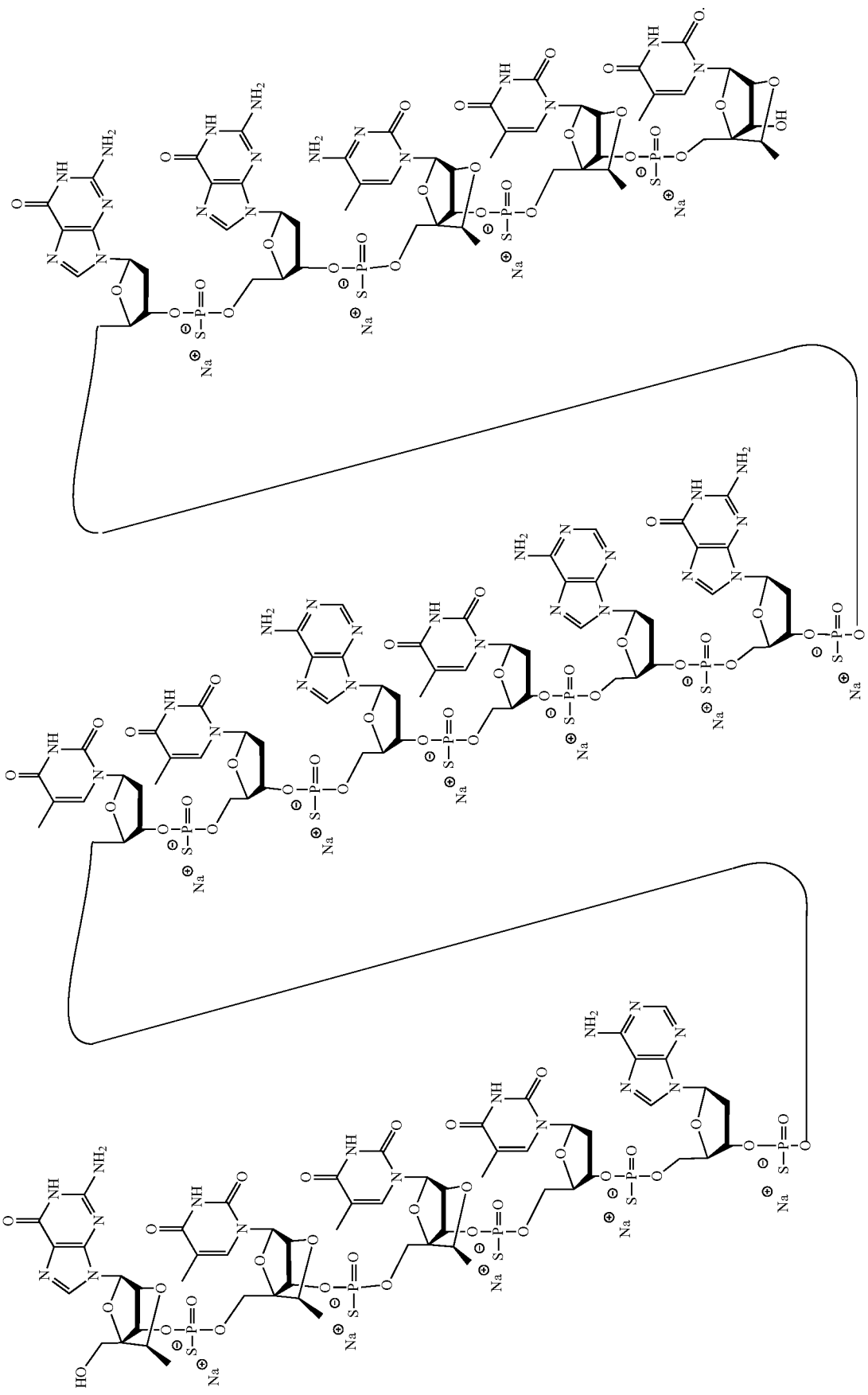

43. A chirally enriched population of the modified oligonucleotide of claim 42, wherein the population is enriched for modified oligonucleotides comprising at least one particular phosphorothioate internucleoside linkage having a particular stereochemical configuration.

44. A pharmaceutical composition comprising the modified oligonucleotide of claim 42 and at least one pharmaceutically acceptable diluent or carrier.

45. The pharmaceutical composition of claim 44, wherein the pharmaceutically acceptable diluent is phosphate buffered saline.

46. A method of treating or ameliorating centronuclear myopathy, Duchenne Muscular Dystrophy, or Charcot-Marie Tooth disease, the method comprising administering the modified oligonucleotide of claim 42 to a subject with a mutation in at least one gene selected from among MTM1, BIN1, and DNM2.

47. The pharmaceutical composition of claim 32, consisting essentially of the modified oligonucleotide and phosphate buffered saline.

48. The pharmaceutical composition of claim 40, consisting essentially of the modified oligonucleotide and phosphate buffered saline.

49. The pharmaceutical composition of claim 45, consisting essentially of the modified oligonucleotide and phosphate buffered saline.

* * * * *